US011485720B2

(12) United States Patent
Forte et al.

(10) Patent No.: US 11,485,720 B2
(45) Date of Patent: Nov. 1, 2022

(54) ANTI-INFECTIVE AGENTS

(71) Applicant: University of Dundee, Dundee (GB)

(72) Inventors: Barbara Forte, Dundee (GB); Neil Norcross, Dundee (GB); Chimed Jansen, Dundee (GB); Beatriz Baragana, Dundee (GB); Ian Gilbert, Dundee (GB); Laura Cleghorn, Dundee (GB); Susan Davis, Dundee (GB); Christopher Walpole, Quebec (CA)

(73) Assignee: UNIVERSITY OF DUNDEE, Dundee (GB)

( * ) Notice: Subject to any disclaimer, the term of this patent is extended or adjusted under 35 U.S.C. 154(b) by 0 days.

(21) Appl. No.: 17/069,448

(22) Filed: Oct. 13, 2020

(65) Prior Publication Data
US 2021/0101877 A1 Apr. 8, 2021

Related U.S. Application Data

(63) Continuation of application No. 16/311,829, filed as application No. PCT/GB2017/051809 on Jun. 20, 2017, now abandoned.

(30) Foreign Application Priority Data

Jun. 20, 2016 (GB) ..................................... 1610724

(51) Int. Cl.
*C07D 311/24* (2006.01)
*C07D 405/12* (2006.01)
*C07D 407/12* (2006.01)
*A61P 33/02* (2006.01)

(52) U.S. Cl.
CPC ............ *C07D 311/24* (2013.01); *A61P 33/02* (2018.01); *C07D 405/12* (2013.01); *C07D 407/12* (2013.01)

(58) Field of Classification Search
CPC .. C07D 311/24; C07D 405/12; C07D 407/12; A61P 33/02
See application file for complete search history.

(56) References Cited

U.S. PATENT DOCUMENTS 5,171,865 A 12/1992 Kurono et al.

FOREIGN PATENT DOCUMENTS

| DE | 964055 C | 5/1957 |
|----|----------|--------|
| DE | 970224 C | 8/1958 |
| GB | 2078719 A | 1/1982 |
| JP | S63152992 A | 6/1988 |
| JP | 2004501146 A | 1/2004 |
| JP | 2006/069906 A | 3/2006 |
| JP | 2006069906 A * | 3/2006 |
| JP | 5714575 B2 | 5/2015 |
| WO | WO-0198290 A2 | 12/2001 |
| WO | WO-2006/094601 A1 | 9/2006 |
| WO | WO-2013/153357 A1 | 10/2013 |
| WO | WO-2013160670 A1 | 10/2013 |

OTHER PUBLICATIONS

Registry (STN) [Online], Nov. 29, 2013, [Date of search: Apr. 23, 2021], CAS registration No. 1483600-36-7.
Ellis et al., "Benzopyrones. 14. Synthesis and Antialergic Properties of Some N-Tetrazolycarboxamides and related Compounds," Journal of Medicinal Chemistry, American Chemical Society, vol. 21, No. 11, pp. 1120-1126, Jan. 1978.
Davidson et al., "Chromone studies. Part 4. Structural analysis of chromone-derived 2-amino-3-(2-hydroxybenzoyl) acrylamides," Journal of the Chemical Society, Perkin Transactions 2: Physical Organic Chemistry, No. 8, pp. 1181, Jan. 1991.
Davidson et al., "Chromone studies. Part 5. Kinetics and mechanism of the reaction of 4-oxo-4H-chromene-2-carboxamides with dimethylamine," Journal of the Chemical Society, Perkin Transactions 2: Physical Organic Chemistry, No. 10, pp. 1509, Jan. 1991.
Raposo et al., "Malonic acid receptors with decarboxylative activity," Tetrahedron, Elsevier Science Publishers, Amsterdam, NL, vol. 52, No. 37, pp. 12323-12332, Jan. 1996.
Gamo et al."Thousand of chemical starting points for antimalarial lead identification" vol. 465, No. 7296, pp. 305-310, XP002698188, May 20, 2010.
Bousejra-Elgarah et al., "Synthesis and evaluation of chromone-2-carboxamide derivatives as cytotoxic agents and 5-lipoxygenase inhibitors," Medical Chemistry Research, Birkhaeuser, Boston, US, vol. 25, No. 11, pp. 2547-2556, Aug. 2016.
International Search Report Application No. PCT/GB2017/051809, dated Sep. 19, 2017.
Examination Report of European Patent Office on application No. 17734411.6 dated Nov. 11, 2019.

* cited by examiner

*Primary Examiner* — Timothy R Rozof
(74) *Attorney, Agent, or Firm* — Moser Taboada

(57) ABSTRACT

The present invention relates to a novel class of chromene-2-carboxamide compounds inhibitors of general formula I wherein $R^1$, $R^2$, $R^3$, $R^4$, $R^5$, $R^6$, $R^7$, $R^8$ and X are as defined herein, to their use in medicine, and their use as anti-infective agents in particular, to compositions containing them, to processes for their preparation and to intermediates used in such processes.

11 Claims, No Drawings

Specification includes a Sequence Listing.

ANTI-INFECTIVE AGENTS

SEQUENCE LISTING STATEMENT

Filed herewith is a Sequence Listing (name: Sequence-Listing.txt; created: Dec. 20, 2018; sized: 12,801 bytes). The content of that Sequence Listing is incorporated herein by reference in its entirety. Applicant here specifically directs the entry of the Sequence Listing filed herewith into the application. Applicant confirms that content of the computer readable Sequence Listing filed herewith, and the amendment incorporating it into the Specification, introduces no new matter (i.e., all sequences therein were identified in the specification as filed), as required by 37 CFR 1.825.

FIELD OF THE INVENTION

The present invention relates to a new class of anti-infective agents, to their use in medicine, to compositions containing them, to processes for their preparation and to intermediates used in such processes. In particular the present invention provides chromone-2-carboxamide compounds for use in the treatment or prevention of infectious diseases including: Malaria; Cryptosporidiosis; tuberculosis (TB); Schistosomiasis, African sleeping sickness (HAT and/or AAT); Chagas disease; and/or Leishmaniasis, and in the treatment or prevention of bacterial infections including: bacterial infections stemming from *Streptococcus pneumonia*, and/or *Enterococcus*; or bacterial infections stemming from the ESKAPE bacterial species. (*Enterococcus faecium, Staphylococcus aureus, Klebsiella pneumoniae, Acinetobacter baumanii, Pseudomonas aeruginosa*, and/or *Enterobacter* species.

BACKGROUND

Over 350 million people are at risk from infectious diseases such as Malaria, Cryptosporidiosis, Tuberculosis, Schistosomiasis, African sleeping sickness, Chagas disease and Leishmaniasis. Existing therapies to treat such infectious diseases are increasingly ineffective due to the development of resistance by the microbes that underpin these conditions to drugs used both in disease prevention and treatment. There is also a lack of effective therapies in some manifestations of these diseases.

Malaria

Malaria is a devastating disease with over 214 million clinical cases in 2015. In 2015, there have been an estimated 438 000 deaths attributed to malaria (WHO, Malaria Report 2015) mostly amongst children under five in sub-Saharan Africa. Malaria is caused by an infection of the red blood cells by a protozoa parasite. Five species of the protozoa *Plasmodium* are known to cause infection in humans: *Plasmodium falciparum; Plasmodium vivax; Plasmodium ovale; Plasmodium malariae*; and *Plasmodium knowlesi*. The injection of protozoa of *Plasmodium falciparum, Plasmodium vivax, Plasmodium ovale*, or *Plasmodium malariae* into the blood stream, is effected by a single source, the bite of the female Anopheles mosquito. Thus there is a need for agents which are effective against *Plasmodium falciparum, Plasmodium vivax, Plasmodium ovale, Plasmodium malariae* and *Plasmodium knowlesi* infections.

The most life-threatening form of malaria is attributable to blood cells infected with the *Plasmodium falciparum* parasite, and can cause kidney or liver failure, coma and death. It is estimated that one child dies every minute from *falciparum* malarial infections therefore the need for an effective treatment could not be higher. There is a need for agents which are: effective against *Plasmodium falciparum* infections; effective against *Plasmodium falciparum* and *Plasmodium vivax* infections; effective against *Plasmodium falciparum, Plasmodium vivax, Plasmodium malariae, Plasmodium ovale* and *Plasmodium knowlesi* infections.

*Plasmodium* species require two hosts, human and mosquito for completion of its life-cycle. In humans the infection is initiated by the inoculation of sporozoites in the saliva of an infected mosquito. Once inside the body the sporozoites migrate to the liver and there infect hepatocytes where they differentiate, via the exoerythrocytic intracellular stage, into the merozoite stage which infects red blood cells to initiate cyclical replication in the asexual blood stage. The life-cycle is completed by the differentiation of a number of merozoites in the red blood cells into sexual stage gametocytes which are ingested by the mosquito, where they develop through a series of stages in the mid gut to produce sporozoites which migrate to the salivary gland.

Many countries have been experiencing resurgence in malaria cases caused by *Plasmodium falciparum* due to the spread of parasites which are increasingly resistant to both chloroquine, the drug most widely used for prevention and treatment as well as newer, alternative treatments such as artesunate. See, Wellems et al, JID 2001; 184, Noedl et al, N Engl J Med 2008; 359:2619-2620, Tun et al, The Lancet. Infectious Diseases 2015; 15:415-21 and Takala-Harrison et al, JID 2015, 211:670-9. The development of new anti-malarial treatments with novel mode of actions is of great importance particularly given the rapid spread of parasite resistance even within newer artemisinin-based combination therapies.

Thus there is a need for new and effective anti-malarial agents with novel modes of action. In particular there is a need for new anti-malarial agents which: are effective against drug-resistant parasites; are effective against drug-resistant *Plasmodium falciparum* infections such as for example chloroquine-resistant *Plasmodium falciparum* infections; which are active against liver stage; which are active against the hypnozoite form; and/or which can be used for single-dose treatment; and/or which can be used for prophylactic treatment.

Cryptosporidiosis

Cryptosporidiosis is a diarrhoeal disease caused by the parasite species *Cryptosporidium*. Currently, there are 27 recognized species of *Cryptosporidium*, including 20 species infecting humans with *C. parvum* or *C. hominis* being responsible for the majority of human infections, Int. J. For Parasitology 2015, 45, 367-373. Cryptosporidiosis was first identified as a cause of human infection in 1976, Gastroenterology, 1976, 70, 592-598. A more recent study investigating the cause and effect of diarrhoea in more than 22,000 children under the age of 5 years, recognized *Cryptosporidium* as the second most common cause of both diarrhoea and morbidity, after rotavirus, The Lancet, 2013, 382, 9888, 209-222. Cryptosporidiosis is an opportunistic infection and individuals with underdeveloped immune systems, such as children under 5 years and immunocompromised individuals with HIV co-infection are at a higher risk of infection and mortality. Malnutrition in early childhood is also associated with persistent diarrhoea and *Cryptosporidium* infection, Lancet Infect. Dis., 2015, 15, 85-94. Nitazoxanide is the only FDA-approved drug for the treatment of Cryptosporidisosis. It has been established that the efficacy of Nitazoxanide is suboptimal and is not an effective treatment for all *Cryptosporidium*-only infected patients, J. Infect. Dis., 2001, 184, 103-06 and Clin. Gastroenterol. Hepatol., 2006, 4, 320-24. Nitazoxanide was also shown to be ineffective in clinical trials for *Cryptosporidium*-HIV co-infected patients, whom were not co-treated with HIV antiretroviral therapy, Trans. R. Soc. Trop. Med. Hyg. 1998, 92, 663-66 and BMC Infect. Dis. 2009, 9, 195. Thus there is a need for new anti-infective agents which are effective against *Cryptosporidium*, and particularly for agents which are suitable for use in the treatment or prevention of; *Cryptosporidium*-only infected subjects; immunocompromised subjects infected with *Cryptosporidium* such as *Cryptosporidium*-HIV co-infected subjects.

Leishmaniasis

Leishmaniasis is caused by several *leishmania* species transmitted to hosts (humans and animals) by the bites of infected female phlebotomine sandflies.

There are three main human forms of leishmaniasis, visceral (the most serious form of the disease), cutaneous (the most common), and mucocutaneous (the most disfiguring). Most leishmaniases can be transmitted from animals to humans and the reservoir hosts include many species of mammals. Dogs are important reservoirs of *Leishmania infantum* (*L. infantum*) which is one of the species responsible for visceral leishmaniasis. Animals can also suffer from visceral, cutaneous and mucocutaneous forms of the disease.

In 2012 there were approximately 1.3 million new cases of leishmaniasis reported and 20 000 to 30 000 deaths per year, Alvar et al, PLoS ONE, 2012, 7(5): e35671). At present effective treatment of leishmaniasis is hampered by the lack of efficacy, poor safety and drug resistance of the currently available medicaments, Seifert K., Open Med. Chem. J. 2011; 5:31-39.

As such there is a real unmet medical need for new oral drugs and combination therapy for the treatment and potential elimination of leishmaniasis in certain geographical areas, and especially for the development of multiple new oral agents for such treatments. In particular there is a need for new anti-infective agents which are effective against *Leishmania*, and particularly for agents which are suitable for use in the treatment or prevention of: *Leishmania donovani*, *Leishmania infantum* and/or *L. chagasi*, which are all causes of visceral leishmaniasis; *L. mexicana, L. amazonensis, L. venezuelensis, L. tropica, L. major, L. aethiopica, Leishmania viannia braziliensis, L. v. guyanensis, L. v. panamensis, L. v. peruviana* which are associated with other forms of the disease and in particular with the causation of cutaneous leishmaniasis; *Leishmania v. braziliensis, L. v. guyanensis* and *L. v. panamensis* which can also cause muco-cutaneous leishmaniasis.

Chagas Disease

Chagas disease is due to the protozoan parasite *Trypanosoma cruzi*. The main route of transmittion to humans and other mammals is by infected faeces of a blood-sucking triatominae bug. However it can also be transmitted from mother to un-born child and through blood transfusioin with contaminated blood.

Chagas disease is endemic throughout Central America and South America where an estimated 7 to 8 million people are infected. Migration of populations from endemic countries has increased the geographic distribution of Chagas disease, with a rising number of Chagas disease cases in the USA, Canada and in many parts of Europe. Approximately there are 13000 deaths each year due to Chagas-induced heart disease caused by Chagas chronic infection.

To date, only two drugs have proven to have efficacy against Chagas disease: benznidazole and nifurtimox. Both medicines are most effective in curing the disease when given soon after infection (acute phase). However, their efficacy is reduced when dosed at later stages of the disease and also their side effects reduce patient's compliance. Thus there is an urgent need for new, safer and more efficacious treatments for Chagas disease and especially for new anti-infective agents which are are effective against *Trypanosoma cruzi*. infection.

Human African Trypanosomiasis (HAT)

Human African Trypanosomiasis (HAT) or African sleeping sickness is caused by the protozoa parasite *Trypanosoma brucei*. It is transmitted by infected tse-tse flies, also called tsetse, tzetze or tik-tik flies, from mother to child during pregnancy as well as through blood products.

Two forms of the disease exist depending on the parasite sub-species: *Trypanosoma brucei gambiense* (*T.b. gambiense*) and *Trypanosoma brucei rhodesiense* (*T.b. rhodesiense*). *Trypanosoma brucei gambiense* which is prevalent in west and central Africa, represents approximately 95% of the reported cases of sleeping sickness and causes a chronic infection. *Trypanosoma brucei rhodesiense* which is found in eastern and southern Africa and represents approximately 5% of the reported cases.

The disease has two distinct stages. Stage 1 presents with non-specific symptoms including fever, rash, and fatigue. Untreated stage 1 HAT results in stage 2 disease or neurological phase, where parasites invade the central nervous system causing severe neurological symptoms and eventually death.

Five drugs are currently in use for the treatment of African sleeping sickness. Stage 1 of the disease is treated with intravenous or intramuscular pentamidine, for *T. b. gambiense*, or intravenous suramin, for *T. b. rhodesiense*. Stage 2 of the disease is treated with intravenous melarsoprol, or intravenous melarsoprol in combination with oral nifurtimox, or intravenous eflornithine only, or eflornithine in combination with nifurtimox. All four drugs, whether used individually or in these combination therapies have serious adverse effects. As such, new, safer and more efficacious treatments for HAT are urgently needed. In particular there is a need for new, safer and more efficacious anti-infective agents which are are effective against *Trypanosoma brucei gambiense* (*T.b. gambiense*) and/or *Trypanosoma brucei rhodesiense* (*T.b. rhodesiense*) infections.

Animal Trypanosomiasis

Animal trypanosomiasis is also known as animal African trypanosomiasis (AAT), and is a disease of vertebrate non-human animals. Human African trypanosomiasis (HAT) is commonly known as sleeping sickness. Animal trypanosomiasis is caused by various parasite species and sub-species of the *Trypanosoma* genus, trypanosomes which are pathogenic to animals, including *Trypanosoma congolense, Trypanosoma vivax, Trypanosoma brucei, Trypanosoma simiae, Trypanosoma godfreyi, Trypanosoma suis*, and *Trypanosoma evansi*. It is thought that there are likely further, un-identified trypanosome species or sub-species that are pathogenic to animals and also cause animal trypanosomiasis. HAT is caused by *Trypanosoma brucei gambiense* and *Trypanosoma brucei rhodesiense*.

Trypanosomes are protozoan parasites in the family Trypanosomatidae and most trypanosomes are transmitted by tsetse flies with the trypanosomes infecting the blood of the animal. As such, an infected animal can act as a disease reservoir with resultant potential for further disease spread in areas affected by the tsetse fly. In Africa, the disease is most common in areas affected by tsetse flies and is spread by the bite of an infected tsetse or other infected flies. Many different animals can be infected by animal trypanosomiasis, including domestic livestock, such as cattle, goats, pigs, sheep and camels. Wild animals, including elephants and leopards have also been found to have trypanosomiasis. Different parasites affect different ranges of organism.

Animals are primarily at risk from this disease wherever trypanosomes and the tsetse fly vector exist, and in Africa this "tsetse belt" is between latitude 15° N and 29° S, from the southern edge of the Sahara Desert to Zimbabwe, Angola and Mozambique.

Although AAT is most commonly found in the "tsetse belt" region of Africa there is now evidence that trypanosomes can spread beyond this area, and therefore the potential for spread of the disease with the associated risks to domesticated and wild animals extends beyond Africa. This risk of disease spread beyond the tsetse belt is particularly associated with *Trypanosoma vivax* (*T. vivax*), which does not appear to require the tsetse fly for transmission. As reported by Spickler, "African Animal Trypanosomiasis" http://www.cfsph.iastate.edu/DiseaseInfo/factsheets.php, *T. vivax* is also found in South and Central America and in the Caribbean with the associated potential risk of transmission to animals via mechanical vectors in these regions.

Thus it would be desirable to provide a treatment for animal trypanosomiasis which is effective against the *Trypanosoma vivax* and/or *Trypanosoma congolense* forms of the disease in particular.

As there is also a form of the disease which infects animals, it would also be of clear value to develop efficacious anti-infective agents which are are effective against African animal trypanosomiasis.

Schistosomiasis

Schistosomiasis is a deadly neglected infectious disease caused by parasitic trematode worms of the genus *Schistosoma* (mainly *Schistosoma haematobium*, *S. mansoni* or *S. japonicum*). WHO estimates show that at least 218 million people required preventive treatetment for schistosomiasis in 2015 (WHO, http://www.who.int/schistosomiasis/en/) The number of deaths due to schistosomiasis estimated by WHO are approximately 200,000 globally each year. The economic and health effects of Schistosomiasis are considerable due to the disability caused by the disease. In children, schistosomiasis can cause anemia, stunting and reduced ability to learn. Schistosomiasis can also exacerbate the effects of malaria, tuberculosis, HIV and hepatitis, see Lancet, 2014; 383:2253-64.

There is no vaccine available and therefore the control of schistosomiasis is based on large-scale treatment of populations at risk. Praziquantel (PZQ) is the only recommended drug for schistosomiasis and the control strategy is facilitated by this single chemotherapeutic agent. If resistance to PZQ arises, the sustainable control of schistosomiasis would be at severe risk.

Whilst PZQ is effective against adult schistosomes worms it has poor activity against immature schistosome larvae, Lancet, 2014; 383: 2253-64. In areas of constant reinfection, repeated treatment 3-6 weeks apart are required to kill resistant juvenile worms and to improve drug treatment. Resistance to PZQ can be induced experimentally, Trans. R. Soc. Trop. Med. Hyg. 2002: 96, 465-69. The threat of emerging resistance to PZQ caused by mass monotherapy is a major concern. These factors create an unmet medical need.

Tuberculosis (TB)

Tuberculosis (TB) is a bacterial infection caused by *Mycobacterium tuberculosis* and is easily spread from person-to-person when an subject with an active TB infection expels droplets containing the TB bacteria from their lungs via coughing or sneezing. TB is the second leading cause of death due to an infectious agent. It has been reported that in 2013, 9 million people developed TB, which resulted in 1.5 million deaths (WHO 2014). The presently available frontline therapies for treatment of TB are antiquated and inadequate, and typically consist of six months of treatment with a cocktail of up to 4 different drug therapies, each of which was discovered over 50 years ago. The limitations of the current treatment regimen contribute to high default rates, increased transmission, drug resistance, and ultimately death. In 2013, was estimated that 500,000 people developed a multi-drug-resistant form of TB (MDR-TB). This drug-resistant form of the disease, MDR-TB, is insensitive to both isoniazid and rifampicin which are the active species in the two leading drug therapies for TB treatment. In addition, it has been reported by Günther, G., Clin. Med. (London), 2014 June; 14(3): 279-85 2014, that there are now an increasing number of people infected with a form of TB stemming from extensively resistant bacteria (XDR-TB) that are resistant to components of both the first and the second line therapies. There is an acceptance that as a consequence of these emerging resistant strains of baceria, novel drugs are urgently required for effectively tackling TB, Koul, A., et al., *Nature,* 469, 483-490 (2011) and Wong, E. B., et. al., Trends Microbiol. 2013 September; 21(9): 493-501), http://www.ncbi.nlm.nih.gov/pubmed/23764389. Thus there is a need for new medines that; reduce the duration of current treatment; are effective against TB, MDR, and/or XDR-TB; that are effective for use as a single drug therapy; are effective for use in combination with one or more existing drug therapies.

Bacterial Infections

It is well-known that increased resistance to antibiotics is now a major problem worldwide, WHO. Antimicorbial Resistance: Global Report on Surveillance, 2014. Bacteria involved in human disease include gram-negative bacteria, *Neisseria gohorrhoease, Klebsielle, Acinetobacter, Pseudomonas aeruginosa, E. coli,* and *Yersinia pestis,* and gram-positive bacteria *Streptococcus, Staphylococcus, Corynebacterium, Listeria* (a coccobacillus), *Bacilus* and *Clostridium.*

Gram-negative bacteria cause infections including pneumonia, bloodstream infections, wound or surgical site infections, and meningitis in healthcare settings. Gram-negative bacteria are resistant to multiple drugs and are increasingly resistant to most available antibiotics. Gram-positive bacteria cause infections including Anthrax, septicemia and meningitis.

Examples of bacteria that are causing a major threat to public health are methicillin resistant *Staphylococcus aureus* (MRSA), penicillin resistant *Streptococcus pneumoniae,* and vancomycin resistant *Enterocossus.* In addition there is also a threat from bacterial infections stemming from the so-called ESKAPE group of bacterial species, *Enterococcus faecium,* which also includes *Staphylococcus aureus, Klebsiella pneumoniae, Acinetobacter baumanii, Pseudomonas aeruginosa,* and *Enterobacter* species. Thus, there is an urgent, unmet medical need for new antibiotics, and in particular for new anti-infective agents for the effective treatment of bacterial infections stemming from: one or more of *Streptococcus pneumonia*; and/or *Enterococcus*; or one or more of the ESKAPE group of bacterial species, *Enterococcus faecium, Staphylococcus aureus, Klebsiella pneumoniae, Acinetobacter baumanii, Pseudomonas aeruginosa,* and/or *Enterobacter.* Specifically *Escherichia coli* is a major cause of bacterial infections. Thus it would be especially desirable for such new antibiotics to target a vital cell function of the pathogen, to be selective for the bacteria target, and to make it more difficult for the bacteria to develop resistance by mutations.

Lysyl t-RNA Synthetase (LysRS or KRS1)

Protein synthesis is a complex, multi-step process involving many enzymes. Aminoacyl-tRNA synthetases (aaRS) catalyse the attachment of amino acids to their cognate transfer RNAs playing a key role in protein translation. Inhibition of aaRS has been successfully exploited against bacterial infections with one aaRS inhibitor, mupirocin, currently in clinical use for the topical treatment of methicillin-resistant *Staphylococcus aureus* (MRSA) infections. Mupirocin is an inhibitor of isoleulcyl-tRNA synthetase (IleRS).

Recently, cladosporin was identified as an inhibitor of lysyl-tRNA syntethase (LysRS). As reported by Scott et. al., J. Antibiot. 1971 24, 747-755 cladosporin is a fungal secondary metabolite. Cladosporin is a nanomolar inhibitor of both blood and liver stages of *Plasmodium*. It has demonstrated selectivity for *Plasmodium falciparum* when compared to human cells. Cladosporin has been shown to inhibit PfLysRS ($IC_{50}$=61 nM) with more than 100-fold selectivity vs HsLysRS, Hoepfner et al., Cell Host Microbe, 2012, 11(6):654-63. Cladosporin inhibits *Schistosoma mansoni* (Sm) lysyl-tRNA synthetase (Sm LysRS $IC_{50}$=97 nM) with more than 60 fold selectivity vs HsLysRS, Sharma et al, PLoS Negl. Trop. Dis 10(11); e0005084.

However, cladosporin is poorly bioavailable which is a key requirement for any active therapeutic agent, not only for a potential anti-malarial agent.

Recently the in vivo essentiality of mycobacterial LysRS has been demonstrated by Ravishankar et al PLOSone, 2016, 11(1):e0147188).

The present invention provides a novel class of class of anti-infective agents which are chromone-2-carboxamide compounds and *Plasmodium falciparum* 3D7 inhibitors having potential as treatment of infectious diseases and especially Malaria, Cryptosporidiosis, tuberculosis (TB), Schistosomiasis, African sleeping sickness (HAT), African animal trypanosomiasis (AAT), Chagas disease and Leishmaniasis.

The novel class of chromone-2-carboxamide compounds according to the present invention have potential for the treatment of *Plasmodium falciparum, Plasmodium vivax, Plasmodium ovale, Plasmodium malariae* and *Plasmodium knowlesi* infections. In particular the novel class of anti-infective agents according to the present invention have potential for the treatment of: *Plasmodium falciparum* infections; *Plasmodium falciparum* and *Plasmodium vivax* infections; *Plasmodium falciparum, Plasmodium vivax, Plasmodium ovale, Plasmodium malariae* and *Plasmodium knowlesi* infections; drug-resistant *Plasmodium falciparum* infections, such as for example Chloroquine-resistant *Plasmodium falciparum* infections; which are active against liver stage schizont forms; activity against liver stage dormant forms of *P. vivax*, which are active against the hypnozoite form; and/or which can be used for single-dose treatment; and/or which can be used for prophylactic treatment.

The novel class of chromone-2-carboxamide compounds according to the present invention have potential for the treatment of *Cryptosporidium* infections. In particular the novel class of anti-infective agents according to the present invention have potential for the treatment of: *Cryptosporidium*-only infected subjects; immunocompromised subjects infected with *Cryptosporidium* such as *Cryptosporidium*-HIV co-infected subjects.

The novel class of chromone-2-carboxamide compounds according to the present invention have potential for the treatment of new anti-infective agents which are effective against *Leishmania* infections. In particular the novel class of anti-infective agents according to the present invention have potential for the treatment of: *Leishmania infantum* infections; subjects infected with: of: *Leishmania donovani, Leishmania infantum* and/or *L. chagasi*, which are all causes of visceral leishmaniasis; *L. mexicana, L. amazonensis, L. venezuelensis, L. tropica, L. major, L. aethiopica, Leishmania viannia braziliensis, L. v. guyanensis, L. v. panamensis, L. v. peruviana* which are associated with other forms of the disease and in particular with the causation of cutaneous leishmaniasis; and *Leishmania v. braziliensis, L. v. guyanensis* and *L. v. panamensis* which can also cause mucocutaneous leishmaniasis.

The novel class of chromone-2-carboxamide compounds according to the present invention have potential for the treatment of Chagas disease. In particular the novel class of class of anti-infective agents according to the present invention have potential for the treatment of *Trypanosoma cruzi*. infections.

The novel class of chromone-2-carboxamide compounds according to the present invention have potential for the treatment of Schistosomiasis. In particular the novel class of class of anti-infective agents according to the present invention have potential for the treatment of: *Schistosoma haematobium, Schistosoma mansoni* and *Schistosoma japonicum* infections.

The novel class of chromone-2-carboxamide compounds according to the present invention have potential for the treatment of African sleeping sickness (HAT). In particular the novel class of class of anti-infective agents according to the present invention have potential for the treatment of: *Trypanosoma brucei gambiense* (*T.b. gambiense*) and/or *Trypanosoma brucei rhodesiense* (*T.b. rhodesiense*) infections.

The novel class of chromone-2-carboxamide compounds according to the present invention have potential for the treatment of tuberculosis (TB). In particular the novel class of class of anti-infective agents according to the present invention have potential for the treatment of TB via: reducing the duration of treatment required; provision of effective treatment of *Mycobacterium tuberculosis* infections; provision of effective treatment of TB, MDR, and/or XDR-TB; that are effective for use as a single drug therapy; are effective for use in combination with one or more existing drug therapies.

The present invention provides a novel class of class of anti-infective agents which are chromone-2-carboxamide compounds having potential as new antibiotics for use in the treatment or prevention of Gram negative and/or Gram positive bacterial infections and in particular for use in the effective treatment of bacterial infections stemming from: one or more of *Streptococcus pneumonia*; and/or *Enterococcus*; or one or more of the ESKAPE group of bacterial species, *Enterococcus faecium, Staphylococcus aureus, Klebsiella pneumoniae, Acinetobacter baumanii, Pseudomonas aeruginosa*, and/or *Enterobacter*.

Desirable properties of compounds of formula (I) according to the present invention include: potency against Pf-KRS1; potency against *Plasmodium falciparum* 3D7; potency against Mtb; potency against *Cryptosporidium parvum*; potency against *Leishmani donovani; Plasmodium falciparum* 3D7; *Plasmodium falciparum* 3D7; *Plasmodium falciparum* 3D7; worms of the genus *Schistosoma*, such as *Schistosoma haematobium, Schistosoma mansoni, Schistosoma japonicum*; low toxicity in MRC-5 or HepG2 cells; both desirable *Plasmodium falciparum* (Pf) 3D7 potency and low toxicity in MRC-5 or HepG2; desirable *Plasmo-*

*dium falciparum* and *Plasmodium vivax* (Pv) activity against clinical isolates; desirable transmission blocking activity; gametocyte inhibitory potential; activity against dormant liver stage forms; good biopharmaceutical properties such as physical stability; good solubility profiles; appropriate metabolic stability; desirable ADME properties (adsorption, distribution, metabolism, excretion).

SUMMARY OF THE INVENTION

According to a first aspect the present invention provides compounds of formula (I)

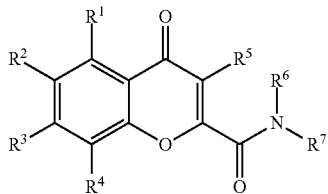

I wherein $R^1$ is H or OH;
wherein $R^2$ is H, OH, CN, halogen, a —$(C_1$-$C_3)$ alkyl group, an —O—$(C_1$-$C_3)$ alkoxy group, a —C(O) $(C_1$-$C_3)$ group, a $C(O)NR^8R^9$ group, a $C(NH)NH$ methylcyclohexyl group,
wherein said —$(C_1$-$C_3)$ alkyl ($R^2$) or —O—$(C_1$-$C_3)$ alkoxy ($R^2$) groups may be optionally substituted by one or more substituents independently selected from: OH; halogen; or CN;
wherein $R^3$ is H, OH, CN, halogen, a —$(C_1$-$C_3)$ alkyl group wherein said —$(C_1$-$C_3)$ alkyl ($R^3$) group may be optionally substituted by one or more substituents independently selected from: OH; halogen; or CN;
wherein $R^4$ is H, OH, CN, halogen, a —$(C_1$-$C_3)$ alkyl group, an —O—$(C_1$-$C_3)$ alkoxy group, a —$C(O)R^{10}$ group, —$NR^8R^9$, an —$SO_2NR^8R^9$ group, an —$N(R^{10})SO_2R^{10}$ group, or a C-linked heterocyclic group containing from one to three O or N heteroatoms
wherein said —$(C_1$-$C_3)$ alkyl ($R^4$) groups may be optionally substituted by one or more substituents independently selected from: OH; halogen; or CN,
wherein said or —O—$(C_1$-$C_3)$ alkoxy ($R^4$) groups may be optionally substituted by one or more substituents independently selected from: $NR^{11}R^{12}$; or a C-linked 6-membered heterocyclic group which may be optionally independently substituted with one or more halogens, methyl, ethyl or OH groups;
wherein $R^5$ and $R^6$ are each independently H, or a —$(C_1$-$C_3)$ alkyl group;
wherein $R^7$ represents an —X—$R^7$ group,
wherein X is a bond or a —$(C_1$-$C_3)$ alkyl group, and is represented by a —$(CH_2)_n$— group, wherein n is 0, 1, 2 or 3, or a —$[(CH_2)_m$—$CH(CH_3)]_p$— group wherein m and p are each independently 0, or 1,
wherein $R^7$ is:
(i) a C-linked saturated or unsaturated 4, 5, 6, or 7-membered cycloalkyl ring, wherein said cycloalkyl ($R^7$) ring is optionally substituted by one or more substituents independently selected from: OH; halogen; or —$(CH_2)_q$—Y wherein q is 0, 1 or 2 and wherein Y is H, $NR^{13}R^{14}$, or $CO_2R^{15}$;
(ii) a C- or N-linked 4, 5 or 6-membered saturated or unsaturated heterocyclic ring containing one or more heteroatoms selected from O, N or S, wherein said heterocyclic ($R^7$) ring is optionally substituted by one or more substituents independently selected from: a —$(C_1$-$C_3)$ alkyl group; an —$O(C_1$-$C_3)$ alkoxy group; a —$(C_3$-$C_5)$ cycloalkyl ring; a —$C(O)R^{10}$ group; an —$SO_2R^{16}$ group; and wherein said optionally substituted heterocyclic ($R^7$) ring is optionally fused to a 5- or 6-membered saturated or unsaturated ring optionally containing one or two O atoms;
(iii) an aryl or a heteroaryl group, wherein said aryl or heteroaryl groups are optionally substituted by one or more substituents independently selected from: halogen; a —$SO_2NR^{17}R^{18}$ group; a —$(CH_2)_q$—Y group wherein q is 0, 1 or 2 and wherein Y is H, $NR^{13}R^{14}$, or $CO_2R^{15}$; a —$C(O)R^{10}$ group; or a —$C(O)NR^{17}R^{18}$ group; and wherein said optionally substituted aryl or heteroaryl ($R^7$) groups are optionally fused to a 5- or 6-membered saturated or unsaturated heterocyclic ring containing one or two O and/or N atoms;
(iv) a —$(C_1$-$C_4)$ alkyl group optionally substituted by one or more substituents independently selected from: halogen;
(v) an —$SO_2R^{16}$ group;
wherein $R^8$, $R^9$, $R^{10}$, $R^{17}$ and $R^{18}$ are each independently selected from: H; or —$(C_1$-$C_3)$ alkyl;
wherein $R^{11}$ and $R^{12}$ are independently selected from: H; or a —$(C_1$-$C_3)$ alkyl group, or where together with the —N atom of the —$NR^{11}R^{12}$ amine group, the N, $R^{11}$ and/or $R^{12}$ groups form an —N-linked 4-, 5- or 6-membered saturated or unsaturated ring heterocyclic group;
wherein $R^{13}$ and $R^{14}$ are independently from one another selected from H, $CO_2R^{19}$, and $COR^{19}$ or optionally $R^{13}$, $R^{14}$ and the nitrogen of the —$NR^{13}R^{14}$ group together define a saturated or unsaturated 4, 5, 6 or 7-membered heterocyclic ring, which is optionally substituted by one or more substituents independently selected from: OH, halogen or linear or branched chain C1 to C6 alkyl;
wherein $R^{19}$ is selected from linear or branched chain $C_1$ to $C_6$ alkyl;
wherein $R^{15}$ is selected from H and linear or branched chain $C_1$ to $C_6$ alkyl;
wherein $R^{16}$ is H, a —$(C_1$-$C_3)$ alkyl group, or $NH_2$; with the proviso that when $R^1=R^2=R^3=R^4=R^5=R^6=H$, $R^7$ is not —$(CH_2)$-cyclohexyl;
or a veterinarily or pharmaceutically acceptable, salt, hydrate, solvate, isomer, prodrug or polymorph thereof.

The present invention additionally provides preferred compounds of formula I, and in particular the compounds of formulae C-I, C-II, C-III, A-I, A-II, S-I, S-II, and S-III as defined hereinafter.

Description

For the avoidance of doubt, all definitions provided herein apply equally to general formulae (I), C-I, C-II, A-I, A-II, S-I, S-II, and S-III as detailed hereinbefore. As such, reference to compounds of formula (I) includes compounds of formulae.

Scientific and technical terms used herein have the meanings with which they are commonly understood in the art unless specifically defined alternatively herein.

For the avoidance of doubt the general term chromone is used to describe the compounds of the invention, and the alternative term 4-oxo-chromene can equally be used as both terms refer to the same central scaffold of these compounds.

Where two or more moieties are described as being "each independently" selected from a list of atoms or groups, this means that the moieties may be the same or different. The identity of each moiety is therefore independent of the identities of the one or more other moieties.

In the above definitions, unless otherwise indicated, alkyl groups having two or more carbon atoms, may be unsaturated or saturated, and are preferably saturated; alkyl groups having three or more carbon atoms, may be straight chain or branched chain. For example, a $C_3$ alkyl substituent can be in the form of normal-propyl (n-propyl), or iso-propyl (i-propyl). For the avoidance of doubt where the chromone scaffold or a cyclic or heterocyclic $R^7$ group is optionally substituted by an alkyl group said alkyl substituent group(s) may not be further substituted by further (unsubstituted) alkyl groups.

The term optionally substituted as used herein indicates that the particular group or groups may have one or more non-hydrogen substituents. The total number of such substituents which may be present is equal to the number of H atoms present on the unsubstituted form of the particular group.

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

Compounds

The present invention provides compounds of formula (I):

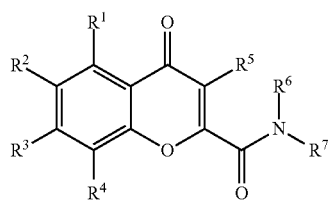

I wherein $R^1$ is H or OH;
wherein $R^2$ is H, OH, CN, halogen, a —$(C_1$-$C_3)$ alkyl group, an —O—$(C_1$-$C_3)$ alkoxy group, a —C(O)$(C_1$-$C_3)$ group, a C(O)$NR^8R^9$ group, a C(NH)NH methylcyclohexyl group,
 wherein said —$(C_1$-$C_3)$ alkyl ($R^2$) or —O—$(C_1$-$C_3)$ alkoxy ($R^2$) groups may be optionally substituted by one or more substituents independently selected from: OH; halogen; or CN;
wherein $R^3$ is H, OH, CN, halogen, a —$(C_1$-$C_3)$ alkyl group wherein said —$(C_1$-$C_3)$ alkyl ($R^3$) group may be optionally substituted by one or more substituents independently selected from: OH; halogen; or CN;
wherein $R^4$ is H, OH, CN, halogen, a —$(C_1$-$C_3)$ alkyl group, an —O—$(C_1$-$C_3)$ alkoxy group, a —C(O)$R^{10}$ group, —$NR^8R^9$, an —$SO_2NR^8R^9$ group, an —$N(R^{10})SO_2R^{10}$ group, or a C-linked heterocyclic group containing from one to three O or N heteroatoms;
 wherein said —$(C_1$-$C_3)$ alkyl ($R^4$) groups may be optionally substituted by one or more substituents independently selected from: OH; halogen; or CN,
 wherein said or —O—$(C_1$-$C_3)$ alkoxy ($R^4$) groups may be optionally substituted by one or more substituents independently selected from: $NR^{11}R^{12}$; or a C-linked 6-membered heterocyclic group which may be optionally independently substituted with one or more halogens, methyl, ethyl or OH groups;
wherein $R^5$ and $R^6$ are each independently H, or a —$(C_1$-$C_3)$ alkyl group;
wherein $R^7$ represents an —X—$R^x$ group,
 wherein X is a bond or a —$(C_1$-$C_3)$ alkyl group, and is represented by a —$(CH_2)_n$— group, wherein n is 0, 1, 2 or 3, or a —$[(CH_2)_m$—$CH(CH_3)]_p$— group wherein m and p are each independently 0, or 1,
 wherein $R^7$ is:
(i) a C-linked saturated or unsaturated 4, 5, 6, or 7-membered cycloalkyl ring, wherein said cycloalkyl ($R^x$) ring is optionally substituted by one or more substituents independently selected from: OH; halogen; or —$(CH_2)_q$—Y wherein q is 0, 1 or 2 and wherein Y is H, $NR^{13}R^{14}$, or $CO_2R^{15}$;
(ii) a C- or N-linked 4, 5 or 6-membered saturated or unsaturated heterocyclic ring containing one or more heteroatoms selected from O, N or S, wherein said heterocyclic ($R^x$) ring is optionally substituted by one or more substituents independently selected from: a —$(C_1$-$C_3)$ alkyl group; an —O$(C_1$-$C_3)$ alkoxy group; a —$(C_3$-$C_5)$ cycloalkyl ring; a —C(O)$R^{10}$ group; an —$SO_2R^{16}$ group; and wherein said optionally substituted heterocyclic ($R^x$) ring is optionally fused to a 5- or 6-membered saturated or unsaturated ring optionally containing one or two O atoms;
(iii) an aryl or a heteroaryl group, wherein said aryl or heteroaryl groups are optionally substituted by one or more substituents independently selected from: halogen; a —$SO_2NR^{17}R^{18}$ group; a —$(CH_2)_q$—Y group wherein q is 0, 1 or 2 and wherein Y is H, $NR^{13}R^{14}$, or $CO_2R^{15}$; a —C(O)$R^{10}$ group; or a —C(O)$NR^{17}R^{18}$ group; and wherein said optionally substituted aryl or heteroaryl ($R^x$) groups are optionally fused to a 5- or 6-membered saturated or unsaturated heterocyclic ring containing one or two O and/or N atoms;
(iv) a —$(C_1$-$C_4)$ alkyl group optionally substituted by one or more substituents independently selected from: halogen;
(v) an —$SO_2R^{16}$ group;
wherein $R^8$, $R^9$, $R^{10}$, $R^{17}$ and $R^{18}$ are each independently selected from: H; or —$(C_1$-$C_3)$ alkyl;
wherein $R^{11}$ and $R^{12}$ are independently selected from: H; or a —$(C_1$-$C_3)$ alkyl group, or where together with the —N atom of the —$NR^{11}R^{12}$ amine group, the N, $R^{11}$ and/or $R^{12}$ groups form an —N-linked 4-, 5- or 6-membered saturated or unsaturated ring heterocyclic group;
wherein $R^{13}$ and $R^{14}$ are independently from one another selected from H, $CO_2R^{19}$, and $COR^{19}$ or optionally $R^{13}$, $R^{14}$ and the nitrogen of the —$NR^{13}R^{14}$ group together define a saturated or unsaturated 4, 5, 6 or 7-membered heterocyclic ring, which is optionally substituted by one or more substituents independently selected from: OH, halogen or linear or branched chain C1 to C6 alkyl;

wherein $R^{19}$ is selected from H and linear or branched chain $C_1$ to $C_6$ alkyl;

wherein $R^{15}$ is selected from H and linear or branched chain $C_1$ to $C_6$ alkyl;

wherein $R^{16}$ is H, a —($C_1$-$C_3$) alkyl group, or $NH_2$; with the proviso that when $R^1=R^2=R^3=R^4=R^5=R^6=H$, $R^7$ is not —($CH_2$)-cyclohexyl;

or a veterinarily or pharmaceutically acceptable, salt, hydrate, solvate, isomer, prodrug or polymorph thereof.

There is additionally provided herein compounds of formula C-I

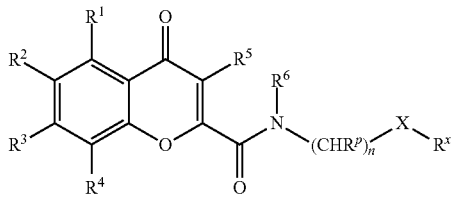

wherein the compounds of formula C-I are compounds of formula I;

wherein n is 0, 1, 2 or 3; wherein X is a bond, an —O-link, or an —S-link; wherein $R^1$ to $R^6$ and $R^x$ are as defined in accordance with formula (I) hereinbefore; wherein when $R^p$ is $CH_3$ n is 0 or 1; or a veterinarily or pharmaceutically acceptable, salt, hydrate, solvate, isomer, prodrug or polymorph thereof. When $R^1$ to $R^6$ are all H, —$(CH^p)_n$—X—$R^x$ is not —$(CH_2)$-cyclohexyl.

There is additionally provided herein compounds of formula C-II

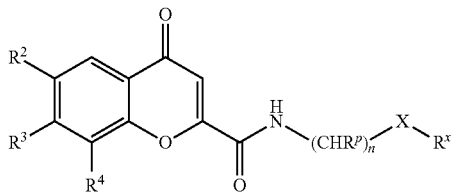

wherein the compounds of formula C-II are compounds of formula I wherein $R^1$, $R^5$ and $R^6$ are all H;

wherein n is 1; X is a bond; $R^p$ is H;

wherein $R^2$ is H, OH, F, Cl, Br, —$CH_3$, —$CH_2CH_3$, —$OCH_3$, or —CN;

wherein $R^3$ is H, F, or Cl;

wherein $R^4$ is H, F, OH, —$CH_2OH$, —C(O)OH, —$NH_2$, —$NHSO_2CH_3$, or a 1H-tetrazol-5-yl group;

wherein $R^x$ is a C-linked 6-membered saturated cycloalkyl group, which is optionally substituted with one or more groups independently selected from: OH, or F;

or a veterinarily or pharmaceutically acceptable, salt, hydrate, solvate, isomer, prodrug or polymorph thereof. When $R^2$ to $R^4$ are all H, —$(CH^p)_n$—X—$R^x$ is not —$(CH_2)$-cyclohexyl.

There is additionally provided herein compounds of formula C-III

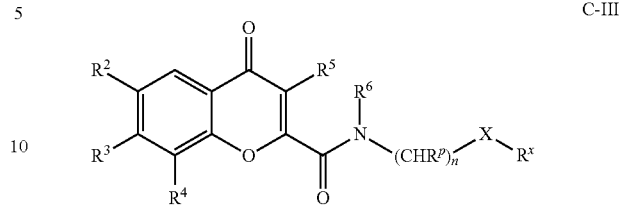

wherein the compounds of formula C-III are compounds of formula I wherein $R^1$ is H;

wherein n is 1 or 2;

wherein X is a bond;

wherein $R^x$ is a cyclohexyl, cyclopentyl, cyclobutyl, tetrahydropyranyl, or a benzoxazole group, wherein each of said $R^x$ groups may be optionally substituted by one or more groups independently selected from: OH, $CH_3$, or F;

wherein $R^p$ is H or $CH_3$ and wherein when $R^p$ is H, n is 1 or 2, and wherein when $R^p$ is $CH_3$, n is 1;

wherein $R^1$ (not shown) is H;

wherein $R^2$ is H, OH, F, Cl, Br, —$CH_3$, —$CH_2CH_3$, —$OCH_3$, or —CN;

wherein $R^3$ is H, OH, F, Cl, or —$O(CH_2)_2NH_2$;

wherein $R^4$ is H, F, Br, OH, —$OCH_3$, —$C(O)NH_2$, —$CH_2OH$, —$C(O)OH$, —$NH_2$, —$NHSO_2CH_3$, —$SO_2NH_2$, or a 1H-tetrazol-5-yl group;

wherein $R^5$ and $R^6$ are each independently selected from H or $CH_3$;

or a veterinarily or pharmaceutically acceptable, salt, hydrate, solvate, isomer, prodrug or polymorph thereof. When $R^2$ to $R^6$ are all H, —$(CH^p)_n$—X—$R^x$ is not —$(CH_2)$-cyclohexyl.

There is additionally provided herein compounds of formula A-I

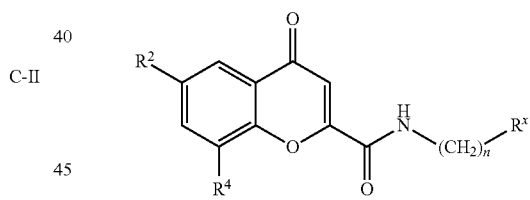

wherein the compounds of formula A-I are compounds of formula I wherein $R^1$, $R^3$, $R^5$ and $R^6$ are all H;

wherein n, $R^2$ and $R^4$ are as defined in accordance with formula I hereinbefore, and wherein $R^x$ is as defined in accordance with formula (I) hereinbefore, or a veterinarily or pharmaceutically acceptable, salt, hydrate, solvate, isomer, prodrug or polymorph thereof. When $R^2$ and $R^4$ are H and n is 1, $R^x$ is not cyclohexyl.

There is additionally provided herein compounds of formula A-II

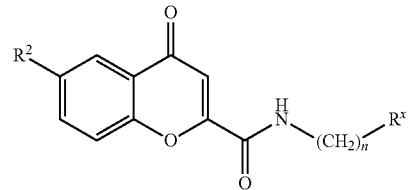

wherein the compounds of formula A-II are compounds of formula I wherein $R^1$, $R^2$, $R^3$, $R^5$ and $R^6$ are all H;

wherein n, $R^2$ and $R^4$ are as defined in accordance with formula I hereinbefore, and wherein $R^x$ is as defined in accordance with formula (I) hereinbefore, or a veterinarily or pharmaceutically acceptable, salt, hydrate, solvate, isomer, prodrug or polymorph thereof. When $R^2$ is H and n is 1, $R^x$ is not cyclohexyl.

There is additionally provided herein compounds of formula S-I

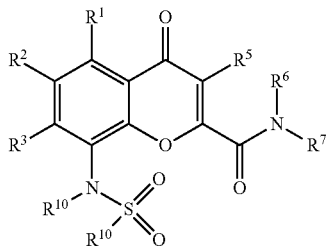

S-I wherein the compounds of formula S-I are compounds of formula I wherein $R^4$ is an —$N(R^{10})SO_2R^{10}$ group;

wherein $R^1$, $R^2$, $R^3$, $R^5$, $R^6$, $R^7$ and $R^{10}$ are as defined in accordance with formula (I) hereinbefore, or a veterinarily or pharmaceutically acceptable, salt, hydrate, solvate, isomer, prodrug or polymorph thereof.

There is additionally provided herein compounds of formula S-II

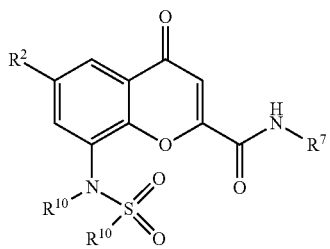

S-II wherein the compounds of formula S-II are compounds of formula I wherein $R^1$, $R^3$, $R^5$ and $R^6$ are all H and $R^4$ is an —$N(R^{10})SO_2R^{10}$ group;

wherein $R^2$, $R^7$ and $R^{10}$ are as defined in accordance with formula (I) hereinbefore, or a veterinarily or pharmaceutically acceptable, salt, hydrate, solvate, isomer, prodrug or polymorph thereof.

There is additionally provided herein compounds of formula S-III

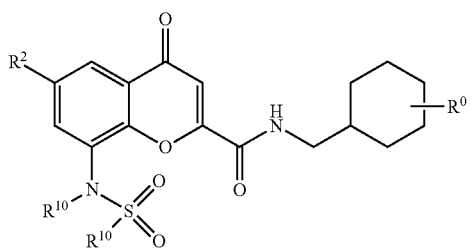

S-III wherein the compounds of formula S-III are compounds of formula I wherein $R^1$, $R^3$, $R^5$ and $R^6$ are all H, $R^4$ is an —$N(R^{10})SO_2R^{10}$ group, and $R^7$ is a cyclohexylmethyl group;

wherein said cyclohexylmethyl ($R^7$) group may be optionally substituted by one or more $R^o$ groups independently selected from: OH, $CH_3$, or F;

wherein $R^2$ and $R^{10}$ are as defined in accordance with formula (I) hereinbefore, or a veterinarily or pharmaceutically acceptable, salt, hydrate, solvate, isomer, prodrug or polymorph thereof.

Particularly preferred compounds according to the present invention are compounds of formula (I)

wherein $R^1$ is H;

wherein $R^2$ is OH, Cl, F or $CH_3$, preferably OH, Cl or F;

wherein $R^3$ is H, Cl or F, preferably H;

wherein $R^5$ is H or $CH_3$, preferably H;

wherein $R^6$ is H or $CH_3$, preferably H;

wherein n is 1 or 2;

wherein $R^P$ is H or $CH_3$, preferably H;

wherein $R^x$ is cyclohexyl optionally substituted at C-1 by OH or $CH_2OH$ OH and/or at C-4 with one or more F groups, or wherein $R^x$ is a cyclopentyl, tetrahydropyranyl, norbornanyl, spiro[3.3]heptanyl, dihydrobenzo[b][1,4]dioxinylyl, or a dihydrobenzo[b][1,3]dioxayl group wherein said groups are optionally substituted at the C-1 position by OH, or $CH_2CO_2H$ and/or at C-4 with one or more F groups;

and wherein $R^4$ is H, OH, F, $CH_2OH$, C(O)OH, $NH_2$, $NHSO_2CH_3$, tetrazolyl, or a veterinarily or pharmaceutically acceptable, salt, hydrate, solvate, isomer, prodrug or polymorph thereof.

Preferred halogen substituents for use here are F, Cl and/or Br, more preferably F and Cl, most especially F.

Preferred individual compounds of formula (I) according to the present invention, and formula C-I, are listed hereinafter as individual compounds within Group 1:

Example 6. N-(cyclohexylmethyl)-6-hydroxy-4-oxo-chromene-2-carboxamide;

Example 8. N-(cyclohexylmethyl)-8-fluoro-4-oxo-chromene-2-carboxamide;

Example 9. 7-Chloro-N-(cyclohexylmethyl)-4-oxo-chromene-2-carboxamide;

Example 10. N-(cyclohexylmethyl)-6-methoxy-4-oxo-chromene-2-carboxamide;

Example 13. 6-Hydroxy-N-[(1-hydroxycyclohexyl)methyl]-4-oxo-chromene-2-carboxamide;

Example 27. N-[(1-hydroxycyclohexyl)methyl]-4-oxo-chromene-2-carboxamide;

Example 28. N-(cyclohexylmethyl)-6-methyl-4-oxo-chromene-2-carboxamide;

Example 29. 6-Bromo-N-(cyclohexylmethyl)-4-oxo-chromene-2-carboxamide;

Example 30. 6-Chloro-N-(cyclohexylmethyl)-4-oxo-chromene-2-carboxamide;

Example 31. N-(cyclohexylmethyl)-6-fluoro-4-oxo-chromene-2-carboxamide;

Example 40. 6-Fluoro-N-[[1-(hydroxymethyl)cyclohexyl]methyl]-4-oxo-chromene-2-carboxamide;

Example 40A. 6-Fluoro-N-((1-(2-hydroxyethyl)cyclohexyl)methyl)-4-oxo-4H-chromene-2-carboxamide;

Example 41. 6-Fluoro-N-[(1-hydroxycyclohexyl)methyl]-4-oxo-chromene-2-carboxamide;

Example 42. N-(cyclohexylmethyl)-7-fluoro-4-oxo-chromene-2-carboxamide;

Example 44. 6-Cyano-N-(cyclohexylmethyl)-4-oxo-chromene-2-carboxamide;

Example 45. N-(cyclohexylmethyl)-6-ethyl-4-oxo-chromene-2-carboxamide;

Example 46. 6-ethyl-N-[(1-hydroxycyclohexyl)methyl]-4-oxo-chromene-2-carboxamide;

Example 49. 6-chloro-N-[(1-hydroxycyclohexyl)methyl]-4-oxo-chromene-2-carboxamide;

Example 54. N-[(4,4-difluoro-1-hydroxy-cyclohexyl)methyl]-6-fluoro-4-oxo-chromene-2-carboxamide;

Example 55. 6,8-difluoro-N-[(1-hydroxycyclohexyl)methyl]-4-oxo-chromene-2-carboxamide;

Example 56. N-((4,4-difluoro-1-hydroxycyclohexyl)methyl)-6,8-difluoro-4-oxo-4H-chromene-2-carboxamide;

Example 57. N-[(4,4-difluoro-1-hydroxy-cyclohexyl)methyl]-6-hydroxy-4-oxo-chromene-2-carboxamide;

Example 70. N-(cyclohexylmethyl)-6-fluoro-8-hydroxy-4-oxo-4H-chromene-2-carboxamide;

Example 73. 6-Chloro-8-hydroxy-N-((1-hydroxycyclohexyl)methyl)-4-oxo-4H-chromene-2-carboxamide;

Example 74. 6-fluoro-8-hydroxy-N-((1-hydroxycyclohexyl)methyl)-4-oxo-4H-chromene-2-carboxamide;

Example 76A. N-((4,4-difluoro-1-hydroxycyclohexyl)methyl)-6-fluoro-8-hydroxy-4-oxo-4H-chromene-2-carboxamide;

Example 77. Fluoro-8-hydroxy-N-((1-hydroxycyclohexyl)methyl)-4-oxo-4H-chromene-2-carboxamide;

Example 78. N-(cyclohexylmethyl)-7-fluoro-8-hydroxy-4-oxo-4H-chromene-2-carboxamide;

Example 82. N-(cyclohexylmethyl)-8-(hydroxymethyl)-4-oxo-chromene-2-carboxamide;

Example 84. N-(cyclohexylmethyl)-8-(methylsulfonamido)-4-oxo-4H-chromene-2-carboxamide;

Example 86. N-(cyclohexylmethyl)-4-oxo-8-(1H-tetrazol-5-yl)-4H-chromene-2-carboxamide;

Example 88. 2-((Cyclohexylmethyl)carbamoyl)-4-oxo-4H-chromene-8-carboxylic acid;

Example 21. N-[(4,4-difluorocyclohexyl)methyl]-4-oxo-chromene-2-carboxamide;

Example 23. N-(cyclopentylmethyl)-4-oxo-chromene-2-carboxamide;

Example 26. N-(2-cyclopentylethyl)-4-oxo-chromene-2-carboxamide;

Example 32. 6-fluoro-4-oxo-N-(tetrahydropyran-2-ylmethyl)chromene-2-carboxamide;

Example 36. 6-fluoro-N-(norbornan-2-ylmethyl)-4-oxo-chromene-2-carboxamide;

Example 49A. (S)—N-(1-cyclohexylethyl)-6-fluoro-4-oxo-4H-chromene-2-carboxamide;

Example 49B. (R)—N-(1-cyclohexylethyl)-6-fluoro-4-oxo-4H-chromene-2-carboxamide;

Example 50. 4-oxo-N-(tetrahydropyran-2-ylmethyl)chromene-2-carboxamide;

Example 50A. 6-fluoro-4-oxo-N-(spiro[3.3]heptan-2-ylmethyl)chromene-2-carboxamide;

Example 57C. N-((2,3-dihydrobenzo[b][1,4]dioxin-6-yl)methyl)-6-fluoro-4-oxo-4H-chromene-2-carboxamide;

Example 57D. 6-Fluoro-N-(((1S,2S)-2-hydroxycyclohexyl)methyl)-4-oxo-4H-chromene-2-carboxamide;

Example 57E. 6-Fluoro-N-(((1S,2R)-2-hydroxycyclohexyl)methyl)-4-oxo-4H-chromene-2-carboxamide;

Example 57L. 2-(1-((6-Fluoro-4-oxo-4H-chromene-2-carboxamido)methyl)cyclohexyl)acetic acid;

Example 23A. N-[(1-hydroxycyclopentyl)methyl]-4-oxo-chromene-2-carboxamide;

Example 57C-1. N-((2,3-dihydrobenzo[b][1,3]dioxa-5-yl)methyl)-4-oxo-4H-chromene-2-carboxamide;

Example 86A. N-[(1-hydroxycyclohexyl)methyl]-4-oxo-8-(1H-tetrazol-5-yl)-4H-chromene-2-carboxamide;

Example 83A. N-[(1-hydroxycyclohexyl)methyl]-8-amino-4-oxo-4H-chromene-2-carboxamide;

Example 84A. N-[(1-hydroxycyclohexyl)methyl]-8-(methylsulfonamido)-4-oxo-4H-chromene-2-carboxamide;

Example 41A. 6-fluoro-N-[(1-hydroxy-4-fluoro-cyclohex-3-enyl)methyl]-4-oxo-chromene-2-carboxamide; and and pharmaceutically and veterinarily acceptable, acid salts, hydrates, solvates, isomers, pro-drugs or polymorphs thereof.

There is provided herein any one of the individual compounds, or groups of compounds indicated in Group 1 and pharmaceutically and veterinarily acceptable acid salts, hydrates, solvates, isomers, pro-drugs or polymorphs thereof.

Highly preferred individual compounds of formula (I), and formula A-I, according to the present invention are listed hereinafter as individual compounds within Group 2:

Example 21. N-[(4,4-difluorocyclohexyl)methyl]-4-oxo-chromene-2-carboxamide;

Example 23. N-(cyclopentylmethyl)-4-oxo-chromene-2-carboxamide;

Example 26. N-(2-cyclopentylethyl)-4-oxo-chromene-2-carboxamide;

Example 32. 6-fluoro-4-oxo-N-(tetrahydropyran-2-ylmethyl)chromene-2-carboxamide;

Example 36. 6-fluoro-N-(norbornan-2-ylmethyl)-4-oxo-chromene-2-carboxamide;

Example 49A. (S)—N-(1-cyclohexylethyl)-6-fluoro-4-oxo-4H-chromene-2-carboxamide;

Example 49B. (R)—N-(1-cyclohexylethyl)-6-fluoro-4-oxo-4H-chromene-2-carboxamide;

Example 50. 4-oxo-N-(tetrahydropyran-2-ylmethyl)chromene-2-carboxamide;

Example 50A. 6-fluoro-4-oxo-N-(spiro[3.3]heptan-2-ylmethyl)chromene-2-carboxamide;

Example 57C. N-((2,3-dihydrobenzo[b][1,4]dioxin-6-yl)methyl)-6-fluoro-4-oxo-4H-chromene-2-carboxamide;

Example 57D. 6-Fluoro-N-(((1S,2S)-2-hydroxycyclohexyl)methyl)-4-oxo-4H-chromene-2-carboxamide;

Example 57E. 6-Fluoro-N-(((1S,2R)-2-hydroxycyclohexyl)methyl)-4-oxo-4H-chromene-2-carboxamide;

Example 57L. 2-(1-((6-fluoro-4-oxo-4H-chromene-2-carboxamido)methyl)cyclohexyl)acetic acid;

Example 23A. N-[(1-hydroxycyclopentyl)methyl]-4-oxo-chromene-2-carboxamide;

Example 57C-1. N-((2,3-dihydrobenzo[b][1,3]dioxa-5-yl)methyl)-4-oxo-4H-chromene-2-carboxamide;

Example 41A. 6-Fluoro-N-[(1-hydroxy-4-fluoro-cyclohex-3-enyl)methyl]-4-oxo-chromene-2-carboxamide;

Example 78C. 8-fluoro-6-hydroxy-N-((1-hydroxycyclohexyl)methyl)-4-oxo-4H-chromene-2-carboxamide Example 97: 8-amino-6-fluoro-N-[(1-fluorocyclohexyl)methyl]-4-oxo-4H-chromene-2-carboxamide Example 96: 8-amino-6-fluoro-N-[(1-hydroxycyclohexyl)methyl]-4-oxo-4H-chromene-2-carboxamide Example 95: 8-amino-N-[(3,3-difluorocyclopentyl)methyl]-6-fluoro-4-oxo-4H-chromene-2-carboxamide Example 94: 8-amino-N-[(4,4-difluorocyclohexyl)methyl]-6-fluoro-4-oxo-4H-chromene-2-carboxamide Example 93: 8-amino-N-[(4,4-difluoro-1-hydroxy-cyclohexyl)methyl]-6-fluoro-4-oxo-chromene-2-carboxamide Example 81: 8-fluoro-6-hydroxy-N-((1-hydroxycyclohexyl)methyl)-4-oxo-4H-chromene-2-carboxamide Example 76H: 6-fluoro-8-hydroxy-N-(2-methylbutyl)-4-oxo-chromene-2-carboxamide Example 76G: N-(3-cyclobutylpropyl)-6-fluoro-8-hydroxy-4-oxo-4H-chromene-2-carboxamide Example 76F: 6-fluoro-8-hydroxy-N-((1-hydroxycyclopentyl)methyl)-4-oxo-4H-chromene-2-carboxamide Example 76B: N-cyclohexyl-6-fluoro-8-hydroxy-4-oxo-chromene-2-carboxamide Example 76C: N-(3,3-Difluorocyclohexyl)-6-fluoro-8-hydroxy-4-oxo-4H-chromene-2-carboxamide Example 76D: 6-fluoro-8-hydroxy-N-((2-hydroxyspiro[3.3]heptan-2-yl)methyl)-4-oxo-4H-chromene-2-carboxamide Example 76E: N-(cyclobutylmethyl)-6-fluoro-8-hydroxy-4-oxo-4H-chromene-2-carboxamide and pharmaceutically and veterinarily acceptable, acid salts, hydrates, solvates, isomers, pro-drugs or polymorphs thereof.

There is provided herein any one of the individual compounds, or groups of compounds indicated in Group 2 and pharmaceutically and veterinarily acceptable acid salts, hydrates, solvates, isomers, pro-drugs or polymorphs thereof.

Highly preferred individual compounds of formula (I), and formula S-I, according to the present invention are listed hereinafter as individual compounds within Group 3:

Example 84A. N-[(1-hydroxycyclohexyl)methyl]-8-(methylsulfonamido)-4-oxo-4H-chromene-2-carboxamide;

Example 84. N-(cyclohexylmethyl)-8-(methylsulfonamido)-4-oxo-4H-chromene-2-carboxamide;

Example 100: N-(cyclohexylmethyl)-6-fluoro-8-(methanesulfonamido)-4-oxo-chromene-2-carboxamide and pharmaceutically and veterinarily acceptable, acid salts, hydrates, solvates, isomers, pro-drugs or polymorphs thereof.

There is provided herein any one of the individual compounds, or groups of compounds indicated in Group 3 and pharmaceutically and veterinarily acceptable, acid salts, hydrates, solvates, isomers, pro-drugs or polymorphs thereof.

There is additionally provided herein the compound of Example 54, N-[(4,4-difluoro-1-hydroxy-cyclohexyl)methyl]-6-fluoro-4-oxo-chromene-2-carboxamide and pharmaceutically and veterinarily acceptable, acid salts, hydrates, solvates, isomers, pro-drugs or polymorphs thereof.

There is also provided herein the compound of Example 70, N-(cyclohexylmethyl)-6-fluoro-8-hydroxy-4-oxo-4H-chromene-2-carboxamide and pharmaceutically and veterinarily acceptable, acid salts, hydrates, solvates, isomers, pro-drugs or polymorphs thereof.

There is also provided herein the compound of Example 74, 6-fluoro-8-hydroxy-N-((1-hydroxycyclohexyl)methyl)-4-oxo-4H-chromene-2-carboxamide and pharmaceutically and veterinarily acceptable, acid salts, hydrates, solvates, isomers, pro-drugs or polymorphs thereof.

There is additionally provided herein the compound of Example 77, Fluoro-8-hydroxy-N-((1-hydroxycyclohexyl)methyl)-4-oxo-4H-chromene-2-carboxamide and pharmaceutically and veterinarily acceptable, acid salts, hydrates, solvates, isomers, pro-drugs or polymorphs thereof.

There is additionally provided herein the compound of Example 79, N-((4,4-difluorocyclohexyl)methyl)-7-fluoro-8-hydroxy-4-oxo-4H-chromene-carboxamide and pharmaceutically and veterinarily acceptable, acid salts, hydrates, solvates, isomers, pro-drugs or polymorphs thereof.

There is additionally provided herein the compound of Example 81, 8-fluoro-6-hydroxy-N-((1-hydroxycyclohexyl)methyl)-4-oxo-4H-chromene-2-carboxamide and pharmaceutically and veterinarily acceptable, acid salts, hydrates, solvates, isomers, pro-drugs or polymorphs thereof.

There is further provided herein preferred individual compounds of Example 54. N-[(4,4-difluoro-1-hydroxy-cyclohexyl)methyl]-6-fluoro-4-oxo-chromene-2-carboxamide;

Example 77, Fluoro-8-hydroxy-N-((1-hydroxycyclohexyl)methyl)-4-oxo-4H-chromene-2-carboxamide;

Example 78: N-(cyclohexylmethyl)-7-fluoro-8-hydroxy-4-oxo-4H-chromene-2-carboxamide, Example 74. 6-fluoro-8-hydroxy-N-((1-hydroxycyclohexyl)methyl)-4-oxo-4H-chromene-2-carboxamide; and pharmaceutically and veterinarily acceptable, acid salts, hydrates, solvates, isomers, pro-drugs or polymorphs thereof.

There is further provided herein preferred individual compounds of Example 100: N-(cyclohexylmethyl)-6-fluoro-8-(methanesulfonamido)-4-oxo-chromene-2-carboxamide;

Example 99: 8-amino-N-(cyclohexylmethyl)-6-fluoro-4-oxo-chromene-2-carboxamide; Example 97: 8-amino-6-fluoro-N-[(1-fluorocyclohexyl)methyl]-4-oxo-4H-chromene-2-carboxamide; Example 96: 8-amino-6-fluoro-N-[(1-hydroxycyclohexyl)methyl]-4-oxo-4H-chromene-2-carboxamide; Example 93: 8-amino-N-[(4,4-difluoro-1-hydroxy-cyclohexyl)methyl]-6-fluoro-4-oxo-chromene-2-carboxamide; Example 92: 8-Amino-N-[(4,4-difluoro-1-hydroxy-cyclohexyl)methyl]-7-fluoro-4-oxo-chromene-2-carboxamide;

Example 81: 8-fluoro-6-hydroxy-N-((1-hydroxycyclohexyl)methyl)-4-oxo-4H-chromene-2-carboxamide;

Example 73: 6-Chloro-8-hydroxy-N-((1-hydroxycyclohexyl)methyl)-4-oxo-4H-chromene-2-carboxamide; and pharmaceutically and veterinarily acceptable, acid salts, hydrates, solvates, isomers, pro-drugs or polymorphs thereof.

Pharmaceutically acceptable acid addition salts of certain compounds of the formula (I) may be readily prepared in a conventional manner by mixing together solutions of a compound of the formula (I) and the desired acid, as appropriate. For example, a solution of the free base is treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties Selection, and Use" by Stahl and Wermuth (Wiley-VCH, Weinheim, Germany, 2002). Suitable acid addition salts for use herein include: fumarate, acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, and trifluoroacetate.

The compounds of the invention may exist in a continuum of solid states ranging from fully amorphous to fully crystalline. The compounds of the invention may also exist in unsolvated and solvated forms. The term 'solvate' as used herein describes a molecular complex comprising the compound of the invention and one or more pharmaceutically acceptable solvent molecules, for example, ethanol. The term 'hydrate' is employed when said solvent is water. Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. For a general review of multi-component complexes, see J Pharm Sci, 64 (8), 1269-1288, by Haleblian (August 1975). Hereinafter all references to compounds of formula (I) include references to salts, solvates, and multi-component complexes.

The compounds of the invention include compounds of formula (I) as hereinbefore defined, and polymorphs and crystal habits thereof.

Isomers of compounds of formula (I) as used herein, and included in the present invention include optical, geometric and tautomeric isomers. Stereoisomers such as enantiomers and diastereomers, all geometric isomers and tautomeric forms of the compounds of formula (I), including compounds exhibiting more than one type of isomerism, and mixtures of one or more thereof are included in the present invention. Also included are acid addition salts wherein the counterion is optically active, for example, d-lactate or l-lysine, or racemic, for example, dl-tartrate or dl-arginine. Geometric isomers may be separated by conventional techniques well known to those skilled in the art, for example, by chromatography and fractional crystallisation. Stereoisomers may be separated by conventional techniques known to those skilled in the art—see, for example, "Stereochemistry of Organic Compounds" by E L Eliel (Wiley, New York, 1994).

As indicated, so-called 'prodrugs' of the present compounds are also within the scope of the invention. Thus certain derivatives of compounds of formula (I), which may have little or no pharmacological activity themselves, can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T Higuchi and W Stella) and *Bioreversible Carriers in Drug Design*, Pergamon Press, 1987 (Ed. E B Roche, American Pharmaceutical Association). Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H Bundgaard (Elsevier, 1985). Finally, certain compounds of formula (I) may themselves act as prodrugs of other compounds of formula (I).

Also included within the scope of the invention are metabolites of compounds of formula I, that is, compounds formed in vivo upon administration of the drug. An example of a metabolite in accordance with the invention is a phenol derivative of a compound of formula I (-Ph→-PhOH).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature. Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Compound Preparation

Compounds of general formula (I) and salts thereof, may be prepared by the methodology described hereinafter, constituting further aspects of this invention. The general procedures which can be used to synthesise the compounds of general formula (I) are summarised in reaction Schemes 1, 2, 3 and 4 are illustrated in the Examples.

SCHEME 1

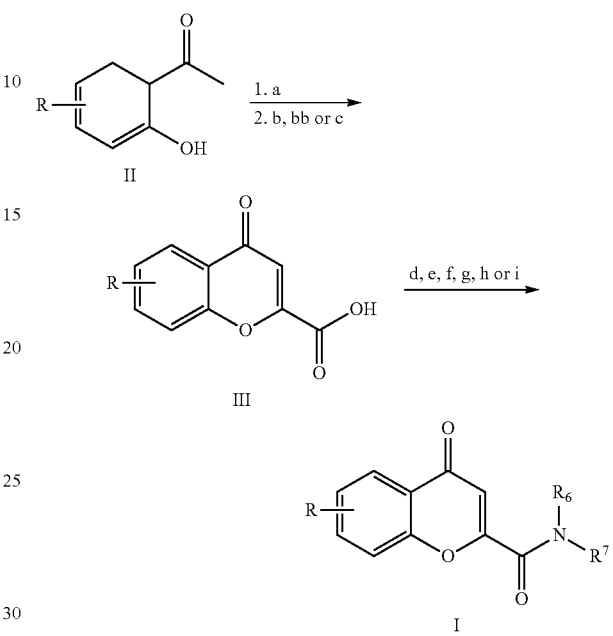

In Scheme 1, suitable reagents for effecting the chemical transformations from a 2-hydroxyacetophenone starting material of general formula (II) in steps a to c to furnish intermediate chromone acid compounds of general formula (III) are as follows: a. EtONa, diethyl oxalate, EtOH, 80° C. then HCl 37%, 90° C.; b. AcOH, HCl 37%, 90° C.; bb. AcOH, HBr, 90° C.; c. LiOH, water.

In Scheme 1, suitable reagents for effecting the chemical transformations from an intermediate chromone acid compound of general formula (III) via an amidation reaction to provide using any one of steps d, e, f, g, h or i, to furnish chromone compounds of general formula (I) having the desired "$R^7$" group in the final product, are as follows: d. PyBOP, DIPEA, DCM, $R_7NH_2$; e. C(O)Cl$_2$, DCM, a drop of DMF, $R_7NH_2$; f. COMU, DIPEA, ACN, $R_7NH_2$; g. CDMT, NMO, DCM, $R_7NH_2$; h. HBTU, Et$_3$N, DMF, $R_7NH_2$; i. EDCl, Et$_3$N, THF, $R_7NH_2$. For the avoidance of doubt the chemical names for these reagent are provided in the Abbreviations list hereinafter.

Scheme 1A illustrates the same overall process as Scheme 1, with the further illustration of the acid-catalysed cyclization of a non-isolated intermediate to provide a chromone ester intermediate.

SCHEME 1A

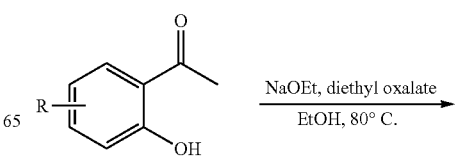

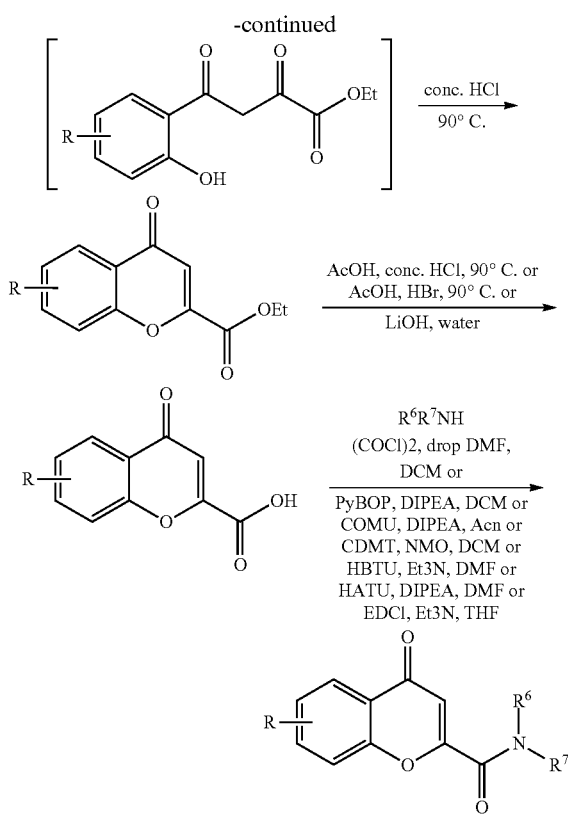

In the illustrative processes of Schemes 1 and 1A, chromone-2-carboxamides were synthesised by Claisen condensation of 2-hydroxyacetophenones with diethyl oxalate followed by acid-catalysed cyclization reaction to give chromone esters. [Lynch et al J. Med. Chem. 2006, 49: 6569]. Ester hydrolysis was undertaken in both acidic and basic conditions. Amidation via acid chloride formation or using different standard amide coupling reagents including: benzotriazol-1-yl-oxytripyrrolidinophosphonium hexafluorophosphate (PyBOP), (1-cyano-2-ethoxy-2-oxoethylidenaminooxy)dimethyl-amino-morpholino-carbenium hexafluorophosphate (COMU), 2-chloro-4,6-dimethoxy-1,3,5-triazine (CDMT), N,N,N',N'-tetramethyl-O-(1H-benzotriazol-1-yl)uronium hexafluorophosphate (HBTU), (1-[bis(dimethylamino)methylene]-1H-1,2,3-triazolo[4,5-b]pyridinium 3-oxid hexafluorophosphate) (HATU) and N-(3-Dimethylaminopropyl)-N'-ethylcarbodiimide (EDCl) provided chromone-2-carboxamide compounds of formula (I). Examples of compounds of general formula (I) prepared in accordance with the processes of Schemes 1 and 1A are provided in the Experimental section hereinafter.

The formulae illustrated in Schemes 1 and 1A have been simplified to focus on the key chemical transformations to provide chromones in accordance with the present invention. For example, the general group "R" in general formulae (II) and (III) is used to signify the presence of four substituent groups, $R^1$ to $R^4$, these groups correspond to the $R^1$ to $R^4$ groups in the compounds of formula (I). As such the definitions of each of these four substituent groups commonly referred to as "R" in the formulae in Schemes 1 and 1A is the same as the definitions for $R^1$, $R^2$, $R^3$ and $R^4$ as provided for formula (I) hereinbefore. In addition, in general formulae (II), and (I) as illustrated in Schemes 1 and 1A, $R^5$ is H. Again this simplification of the general structures has been used for illustrative purposes-only and in both general formulae (II) and (I) of Schemes 1 and 1A, $R^5$ can be any of the $R^5$ substituent groups indicated in the definition of formula (I) hereinbefore. In formula (I) of Schemes 1 and 1A, $R^6$ is H and again $R^6$ can be any of the $R^6$ substituent groups indicated in the definition of formula (I) hereinbefore.

Thus, in respect of compounds (I), (II), and (III) in Scheme 1, the definitions of $R^1$ to $R^7$ are as defined hereinbefore for compounds of formula (I) unless stated otherwise.

Thus according to a further embodiment the present invention provides a process for the preparation of chromone-2-carboxamide compounds of general formula (I) comprising amination of a chromone acid intermediate of general formula (III), and optionally wherein said process additionally provides for the preparation of the chromone acid intermediate via hydrolysis of a chromone ester intermediate of general formula (II).

In a preferred group of chromone-2-carboxamide compounds according to the present invention wherein n is 0, 1, 2 or 3; wherein X is a bond, an —O-link, or an —S-link; wherein $R^1$ to $R^6$ and $R^x$ are as defined in accordance with formula (I) hereinbefore; wherein when $R^p$ is $CH_3$ n is 0 or 1.

Thus according to a further embodiment the present invention provides a general process for the preparation of chromone-2-carboxamide compounds wherein wherein n is 0, 1, 2 or 3; wherein X is a bond, an —O-link, or an —S-link; wherein $R^1$ to $R^6$ and $R^x$ are as defined in accordance with formula (I) hereinbefore; wherein when $R^p$ is $CH_3$ n is 0 or 1 of general formula (C-I) comprising amination of a chromone acid intermediate of general formula (III), and optionally wherein said process additionally provides for the preparation of the chromone acid intermediate via hydrolysis of a chromone ester intermediate of general formula (II).

As will be appreciated by the skilled chemist the reagents and conditions employed in the transformations in the any one of the schemes herein may be utilised, modified and/or substituted for alternatives as necessary in order to furnish various alternative compounds of formula (I) via the general processes in therein.

SCHEME 2

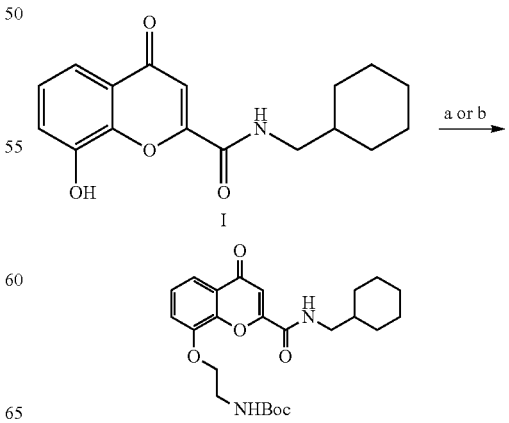

-continued

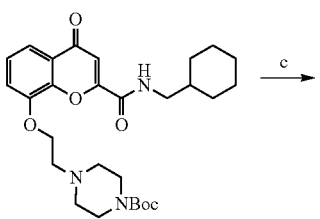

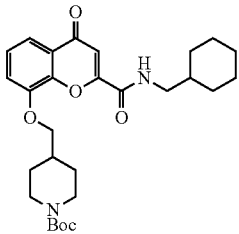

IV

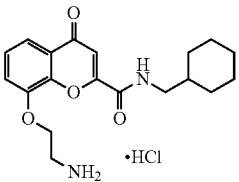

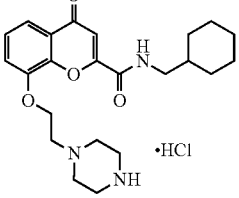

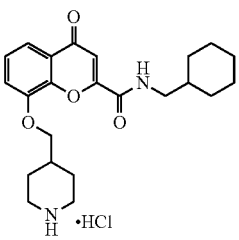

V

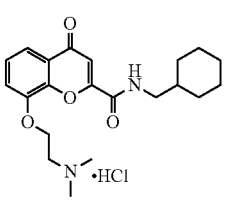

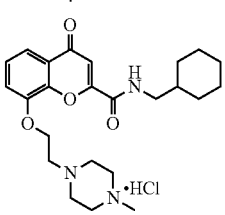

-continued

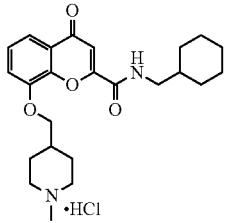

I

In Scheme 2, suitable reagents for effecting the chemical transformations for the conversion of a chromone-2-carboxamide compound of general formula (I) having $R^4$=OH into an alternative compound of general formula (I) having $R^4$=—O(CH$_2$)$_n$NR$^{11}$R$^{12}$, via an protected intermediate compound of general formula (IV) wherein $R^4$ is a protected oxyamine group, in steps a or b to furnish intermediate compounds of general formula (IV) are as follows: a. BocNHCH$_2$CH$_2$Br or tert-butyl 4-(2-chloroethyl)piperazine-1-carboxylate, K$_2$CO$_3$, DMF, 100° C., microwave (MW), 1 hour (h); b. tert-butyl 4-(bromomethyl)piperidine-1-carboxylate, K$_2$CO$_3$, DMF, 90° C., 16 h.

In Scheme 2, suitable reagents for effecting the chemical transformations for the conversion of the protected intermediate-oxyamine compounds of general formula (IV) into further secondary amine intermediate compounds of general formula (V) wherein $R^4$ is a de-protected salt form of the $R^4$ group (from the corresponding N-BOC protected compounds of general formula (IV)) is as follows: c. HCl 4M in dioxane.

In Scheme 2, suitable reagents for effecting the chemical transformations for the conversion of the amine-salt intermediate compounds of general formula (V) into compounds of general formula (I) wherein $R^4$ is an —O(CH$_2$)$_n$NR$^{11}$R$^{12}$ group, is as follows: d. formaldehyde 37%, formic acid, reflux, 1 h to 8 h.

The formulae illustrated in Scheme 2 have been simplified to focus on the key chemical transformations to provide 8-O-substituted chromones in accordance with the present invention. For example, whilst the intermediate compounds of formulae (IV) and (V), and final compounds of formula (I) as illustrated in Scheme 2 all have $R^1$ to $R^3$ and $R^5$ and $R^6$ as H-groups, it should be appreciated that this simplification of the general structures has been used for illustrative purposes-only, and the process illustrated in Scheme 2 is applicable for use starting from an intermediate compound of formulae (IV) wherein $R^1$ to $R^3$ and $R^5$ and $R^6$ are as defined hereinbefore, and particularly as defined in relation to Scheme 1. Examples of compounds of general formula (I) prepared in accordance with the processes of Scheme 2 are provided in the Experimental section hereinafter.

Thus according to a further embodiment the present invention provides a process for the preparation of compounds of general formula (I) via the process as illustrated in Scheme 2.

Scheme 3 illustrates an alternative route for the preparation of chromone-2-carboxamide compounds of general formula (I) starting from phenol or substituted phenol groups.

SCHEME 3

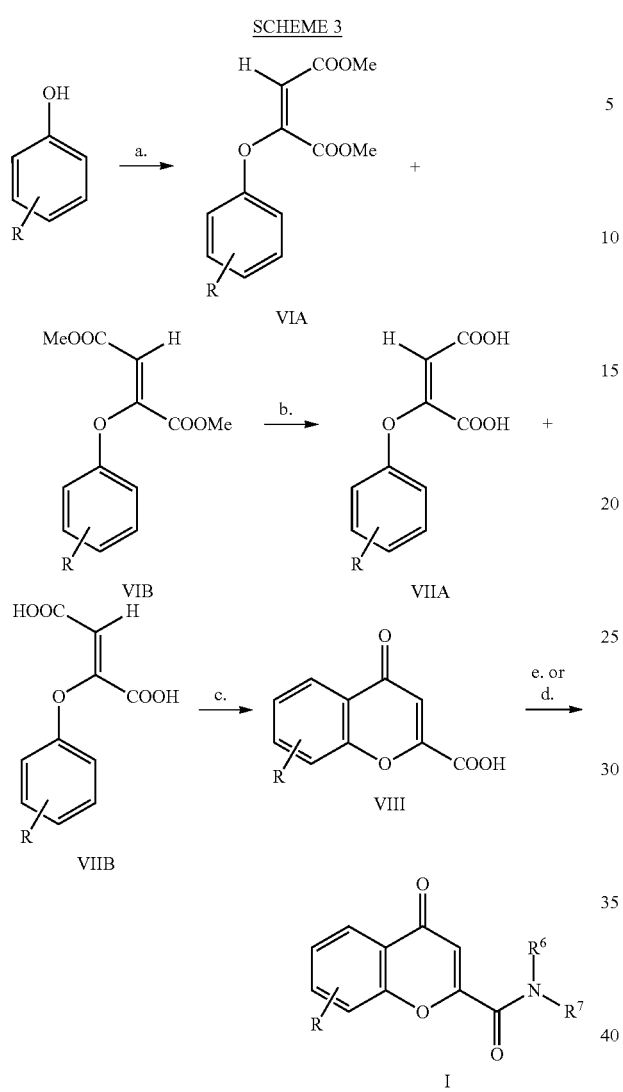

SCHEME 3A

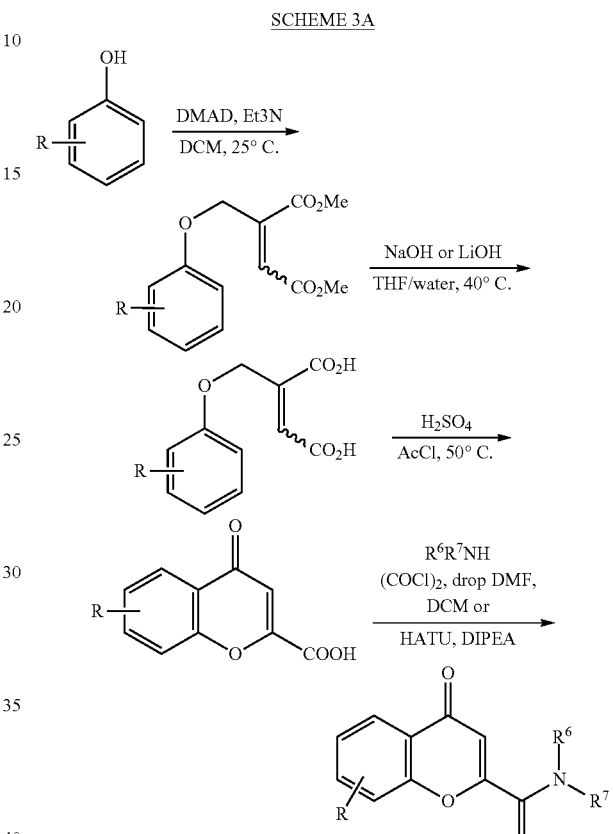

In Scheme 3, suitable reagents for effecting the chemical transformations from the starting phenolic material in steps a to to furnish a mixture of intermediate ester compounds of general formulae (VIA) and (VIB) are as follows: a. dimethyl but-2-ynedioate, $Et_3N$, DCM, 25° C., 1 h.

In Scheme 3, suitable reagents for effecting the chemical transformations from the mixture of intermediate ester compounds of general formulae (VIA) and (VIB) to provide a mixture of further intermediate olefin di-acid compounds of general formulae (VIIA) and (VIIB) are as follows: b. NaOH or LiOH, THF/$H_2O$, 40° C., 3 h.

In Scheme 3, suitable reagents for effecting the chemical transformations to convert the mixture of intermediate olefin di-acid compounds of general formulae (VIIA) and (VIIB) into chromone-2-carboxylic acid intermediate compounds of general formulae (VIII) are as follows: c. $H_2SO_4$, acetyl chloride, 50° C., 1 h.

In Scheme 3, suitable reagents for effecting the chemical transformations to convert the chromone-2-carboxylic acid intermediate compounds of general formulae (VIII) into chromone-2-carboxamide compounds of general formula (I) via reaction with a suitable amine substrate for the desired "$R^7$" group in the final product using either one of steps d, or e are as follows: d. HATU, DIPEA, $R_7NH_2$, 60° C., 15 h; e. $C(O)Cl_2$, DCM, drop of DMF, $R_7NH_2$.

Scheme 3A illustrates the same overall process as Scheme 3, where intermediates labelled A and B are consolidated into a single intermediate structure and also includes suitable reagents for each transformational step.

Using the processes illustrated in Schemes 3 and 3A, chromone-2-carboxamides were synthesised from either phenol or commercially available substituted phenols. Treatment of the corresponding phenol with dimethylacetylenedicarboxylate (DMAD, dimethyl but-2-ynedioate) followed by ester hydrolysis gave a mixture of olefin diacids. Suitable ester hydrolysis methods are provided hereinafter and are disclosed in Lynch et al. J. Med. Chem. 2006, 49: 6569. Ring closure was achieved by heating this mixture with sulfuric acid and acetyl chloride to obtain chromone-2-carboxylic acids. Amides were prepared by reaction with oxalyl chloride followed by the corresponding amine or by acid activation with HATU. Examples of compounds of general formula (I) prepared in accordance with the processes of Schemes 3 and 3A are provided in the Experimental section hereinafter.

For the avoidance of doubt, the formulae illustrated in Schemes 3 and 3A have also been simplified to focus on the key chemical transformations to provide chromones in accordance with the present invention in the same manner as previously discussed for Schemes 1, 1A and 2. As such, the general group "R" is used to signify the substituents, $R^1$ to $R^4$ and as such the definition of "R" in these formulae and in formula (I) as shown in Schemes 3 and 3A is consistent with the definitions of $R^1$ to $R^4$ as provided for formula (I)

hereinbefore. In addition whilst the Scheme illustrates compounds where $R^5$ and $R^6$ are both H, it will be appreciated that compounds where $R^5$ and/or $R^6$ are any of the alternative $R^5$ and/or $R^6$ substituent groups identified in formula (I) hereinbefore can be prepared using either an alternative reagent in the first step, or using a suitable amine $NHR^6R^7$ in the final step.

Thus according to a further embodiment the present invention provides a process for the preparation of chromone-2-carboxamide compounds of general formula (I) from phenol or a substituted phenol via the process as illustrated in Scheme 3, or Scheme 3A, wherein said substituted phenol has one, two, three or four substitutent groups, and wherein those substituent groups are $R^{1P}$, $R^{2P}$, $R^{3P}$, and $R^{4P}$ groups wherein $R^{1P}$, $R^{2P}$, $R^{3P}$, and $R^{4P}$ correspond to $R^1$, $R^2$, $R^3$ and $R^4$ as defined hereinbefore, both in respect of their functionality and their positions on the phenyl-ring relative to the final chromone-2-carboxamide compounds of formula (I).

Scheme 4 illustrates a synthetic approach for the preparation of compounds of general formula (I) having $R^2$=F or Cl, $R^3$=F or Cl, and $R^4$=OH i.e. 8-hydroxy-4-oxo-4H-chromene-2-carboxamides. In Scheme 4, the acid intermediate compounds of general formula (VIII) are firstly converted to their corresponding esters (step 1, transformation a) i.e. the intermediates of general formula (IX) having a 8-methoxy substituent, and thereafter are converted to the corresponding 8-hydroxy containing ester intermediates of general formula (X) (step 1, transformation b) prior to reaction with the desired amine having an $R^7$ group to provide the final 8-hydroxy-4-oxo-4H-chromene-2-carboxamides compounds of general formula (I) in final step, transformation c.

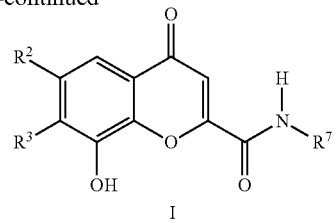

$R^2, R^3 = F, Cl$

Suitable reagents for carrying out the chemical transformations a, b and c, in steps 1 to 3 of Scheme 4 are indicated within Scheme 4 itself.

For the avoidance of doubt, the formulae illustrated in Scheme 4 have also been simplified to focus on the key chemical transformations to provide chromones in accordance with the present invention in the same manner as previously discussed for Schemes 1 to 3. As such, whilst $R^1$, $R^5$, and $R^6$ are all H in the formulae illustrated in Scheme 4 it will be appreciated that compounds of general (I) having alternative substitutents other than H, for one or more of these groups can be prepared via selection of the appropriate alternative starting materials and/or reagents as indicated hereinbefore for Scheme 3. Examples of compounds of general formula (I) prepared in accordance with the process of Scheme 4 are provided in the Experimental section hereinafter.

Thus the present invention provides a process for the preparation of 8-hydroxy-4-oxo-4H-chromene-2-carboxamide compounds of general formula (I) wherein $R^2$=F or Cl, $R^3$=F or Cl and $R^4$=OH comprising amination of the ester-intermediate of general formula (X) in accordance with the process as illustrated in Scheme 4.

Scheme 5 illustrates a synthetic approach for the preparation of 8-amino, and 8-sulfonamino chromone-2-carboxamide compounds of general formula (I) having $R^4$=an amino or a sulfamino group. In Scheme 5, 6-bromo-8-nitro intermediate compounds of general formula (XI) are firstly converted to their corresponding amines (step 1, transformation a) i.e. compounds of general formula (I) having an $R^4$/8-amino substituent, which can thereafter be converted to the corresponding $R^4$/8-sulfonamino compounds of general formula (I) (step 2, transformation b).

SCHEME 4

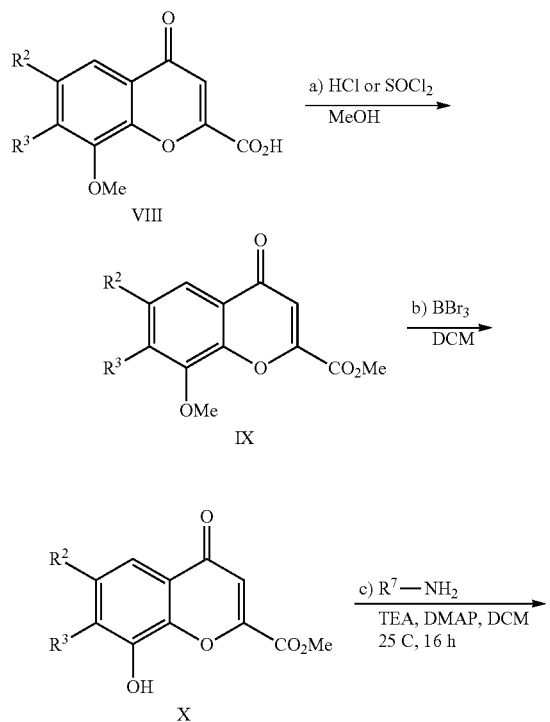

SCHEME 5

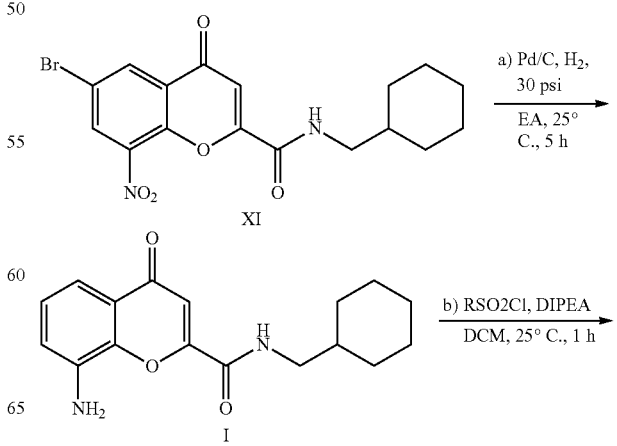

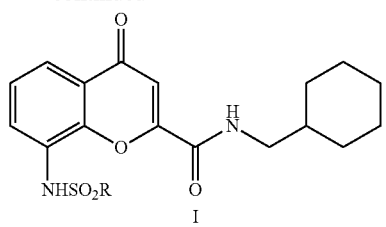

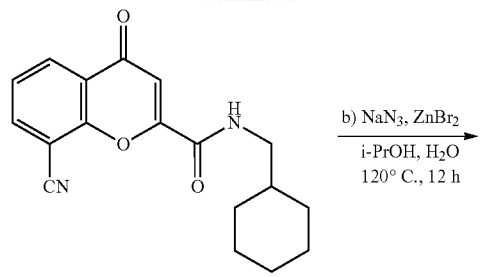

Suitable reagents for carrying out the chemical transformations a and b in steps 1 and 2 of Scheme 5 are indicated within Scheme 5 itself.

For the avoidance of doubt, the formulae illustrated in Scheme 5 have also been simplified to focus on the key chemical transformations to provide chromones in accordance with the present invention in the same manner as previously discussed for Schemes 1 to 4. As such, whilst $R^1$, $R^3$, $R^5$, and $R^6$ are all H in the formulae illustrated in Scheme 5 it will be appreciated that compounds of general (I) having alternative substitutents other than H, such as for example, where $R^5$ and/or $R^6$ are ($C_1$-$C_3$)alkyl groups, and particularly $CH_3$ can be prepared via selection of the appropriate alternative starting materials and/or reagents. Examples of compounds of general formula (I) prepared in accordance with the process of Scheme 5 are provided in the Experimental section hereinafter.

Thus the present invention provides a process for the preparation of 8-amino or 8-sulfonamino chromone-2-carboxamides compounds of general formula (I) of general formula (I) wherein $R^4$=—$NR^8R^9$, or $N(R^{10})SO_2R^{10}$ comprising reduction of the nitro-intermediate of general formula (XI), or reduction and subsequent conversion to the sulfonamino compounds of general formula (I) in accordance with the process as illustrated in Scheme 5.

Scheme 6 illustrates a synthetic approach for the preparation of 8-HET chromone-2-carboxamide compounds of general formula (I) having $R^4$=HET (tetrazole). In Scheme 6, 8-bromo-8 intermediate compounds of general formula (XII) are firstly converted to their corresponding cyano analogues (step 1, transformation a) i.e. compounds of general formula (I) having an $R^4$/8-cyano substituent, which can thereafter be converted to the corresponding $R^4$/8-HET compounds of general formula (I) (step 2, transformation b).

SCHEME 6

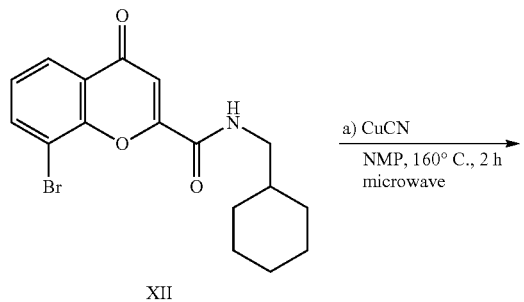

Suitable reagents for carrying out the chemical transformations a and b in steps 1 and 2 of Scheme 6 are indicated within Scheme 6 itself.

For the avoidance of doubt, the formulae illustrated in Scheme 6 have also been simplified to focus on the key chemical transformations to provide chromones in accordance with the present invention in the same manner as previously discussed for Schemes 1 to 5. As such, whilst $R^1$, $R^2$, $R^3$, $R^5$, and $R^6$ are all H in the formulae illustrated in Scheme 6, it will be appreciated that compounds of general formula (I) having alternative substitutents other than H (for one or more of these groups) can be prepared via selection of the appropriate alternative starting materials and/or reagents as discussed hereinbefore. Examples of compounds of general formula (I) prepared in accordance with the process of Scheme 6 are provided in the Experimental section hereinafter.

Thus the present invention provides a process for the preparation of 8-HET chromone-2-carboxamides compounds of general formula (I) of general formula (I) wherein $R^4$=HET (tetrazole) from the corresponding cyano compound general formula (I) in accordance with the process as illustrated in Scheme 6.

Scheme 7 illustrates a synthetic approach for the interconversion of 8-substituted chromone-2-carboxamide compounds of general formula (I) into further 8-substituted chromone-2-carboxamide compounds of general formula (I). In Scheme 7, 8-bromo-compounds of general formula (I) are firstly converted to their corresponding methylesters, (step 1, transformation a) i.e. compounds of general formula (I) having an $R^4$/8-alkyl-ester substituent, which can thereafter be converted to the corresponding $R^4$/8-carboxylates (step 2, transformation b), and then $R^4$/8-carbamoyl compounds of general formula (I) (step 3, transformation c).

SCHEME 7

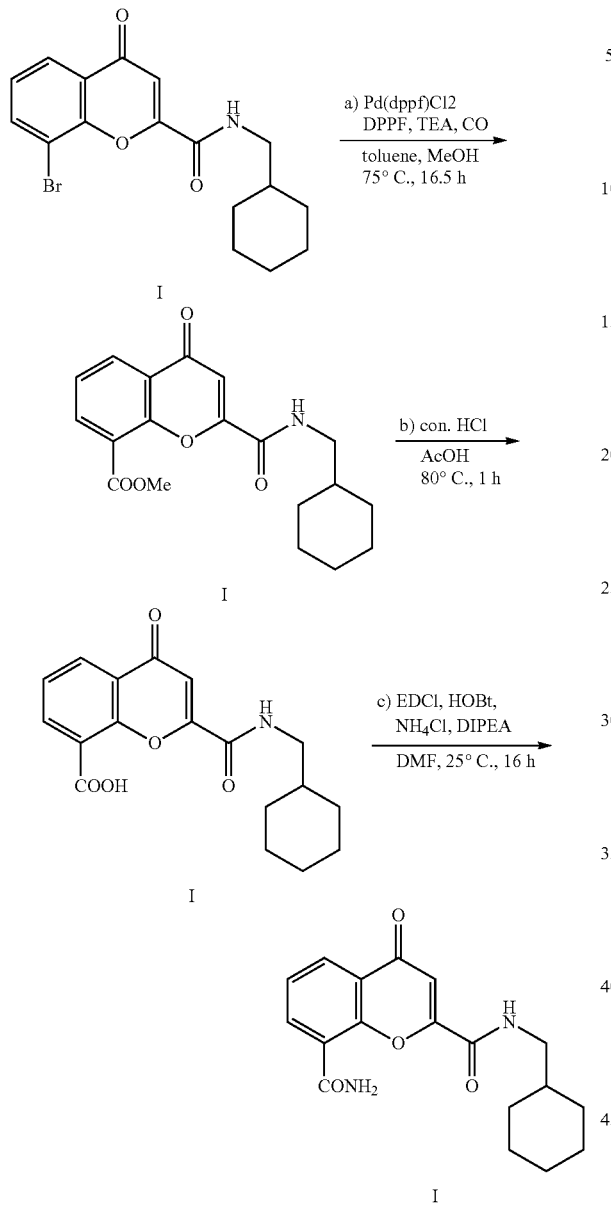

Suitable reagents for carrying out the chemical transformations a, b, and c in steps 1 2, and 3 of Scheme 7 are indicated within Scheme 7 itself.

For the avoidance of doubt, the formulae illustrated in Scheme 7 have been simplified to focus on the key chemical transformations to provide chromones in accordance as previously discussed herein, and it will be appreciated that compounds of general formula (I) having alternative $R^5$ and/or $R^6$ groups with substitutents other than H, can be prepared via selection of the appropriate alternative starting materials and/or reagents as discussed hereinbefore. Examples of compounds of general formula (I) prepared in accordance with the process of Scheme 7 are provided in the Experimental section hereinafter.

Thus the present invention provides a process for the preparation of 8-substituted chromone-2-carboxamides compounds of general formula (I) wherein $R^4$=ester, acid or carbamoyl in accordance with the process as illustrated in Scheme 7.

Scheme 8 illustrates a synthetic approach for the preparation of 3-substituted chromone-2-carboxamide compounds of general formula (I). In Scheme 8, 3-substituted compounds of general formula (I) are prepared via the reaction of a suitable acid-intermediate (which contains the desired substituent group in the 3-position relative to the final compound) of general formula (XIV) and a suitable amine-intermediate of general formula (XV). The acid intermediate can be prepared from commercially available starting materials via preparation of an ester-substituted chromone (step 1, transformation a) which is converted to the corresponding acid-substituted chromone (step 2, transformation b), and then combined with the amine-intermediate to furnish 3-substituted chromone-2-carboxamide compounds of general formula (I) (step 3, transformation c).

SCHEME 8

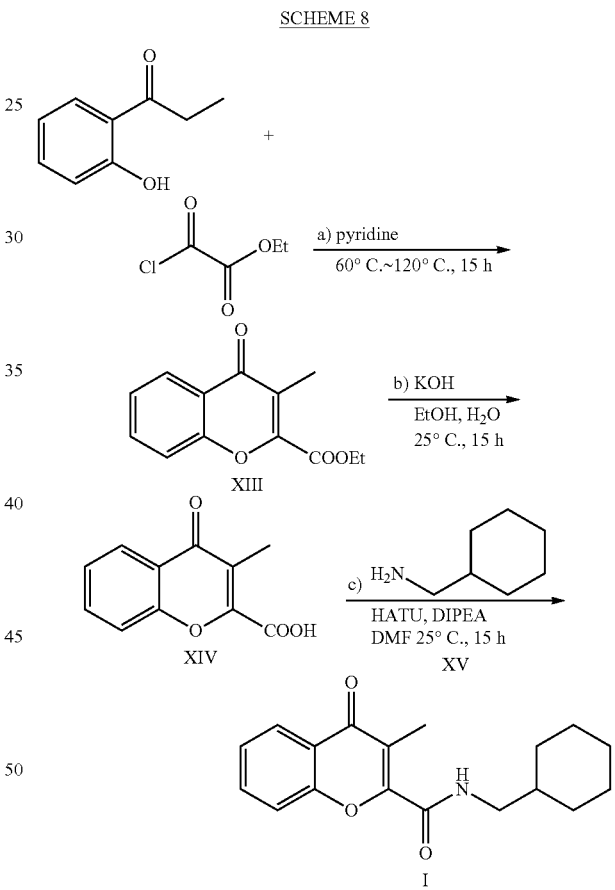

Suitable reagents for carrying out the chemical transformations a, b, and c in steps 1 2, and 3 of Scheme 8 are indicated within Scheme 8 itself.

For the avoidance of doubt, the formulae illustrated in Scheme 8 have been simplified to focus on the key chemical transformations as previously discussed herein, and it will be appreciated that compounds of general formula (I) having alternative substitutents other than H, for one or more of the $R^1$ to $R^4$ and $R^5$ groups can be prepared via selection of the appropriate alternative starting materials and/or reagents as discussed hereinbefore. Examples of compounds of general formula (I) prepared in accordance with the process of Scheme 8 are provided in the Experimental section hereinafter.

Thus the present invention provides a process for the preparation of 3-substituted chromone-2-carboxamides compounds of general formula (I) wherein $R^4$=ester, acid or carbamoyl in accordance with the process as illustrated in Scheme 8.

Scheme 9 illustrates a synthetic approach for the preparation of 3, 6-di-substituted chromone-2-carboxamide compounds of general formula (I). In Scheme 9, 3, 6-di-substituted compounds of general formula (I) are prepared via the reaction of a suitable acid-intermediate (which contains the desired substituent group in the 3-position relative to the final compound) of general formula (XVI) and a suitable amine-intermediate of general formula (XV). The acid intermediate can be prepared from commercially available starting materials in 2-steps as indicated by step 1, transformation a, and step 2, transformation b. The acid intermediate is combined with the amine-intermediate to furnish 3, 6-di-substituted chromone-2-carboxamide compounds of general formula (I) (step 3, transformation c).

be appreciated that compounds of general formula (I) having alternative substitutents other than H, for one or more of the $R^1$, $R^3$, $R^4$ and $R^6$ groups, and/or substituents other than F for the $R^2$ groups, can be prepared via selection of the appropriate alternative starting materials and/or reagents as discussed hereinbefore. Examples of compounds of general formula (I) prepared in accordance with the process of Scheme 9 are provided in the Experimental section hereinafter.

Thus the present invention provides a process for the preparation of 3, 6-di-substituted chromone-2-carboxamides compounds of general formula (I) of general formula (I) wherein $R^2$=halogen, and $R^5$=alkyl in accordance with the process as illustrated in Scheme 9.

Scheme 10 illustrates a synthetic approach for the preparation of compounds of general formula (I) with $R^2$=F or H, $R^3$=F or H and $R^4$=NH$_2$, i.e. 8-amino-4-oxo-4H-chromene-2-carboxamides. In Scheme 10, compounds of general formula (I) are prepared via the reaction of a suitable ester-intermediate of general formula (XVIII) and an amine having the desired $R^6$ and $R^7$ groups. The ester intermediate can be prepared from commercially available starting materials in 3-steps as indicated by step 1, transformation a, and step 2, transformation b and c and step 3, transformation d. The ester intermediate is combined with the amine-intermediate to furnish 8-amino-4-oxo-chromene-2-carboxamides compounds of general formula (I) (step 4, transformation e).

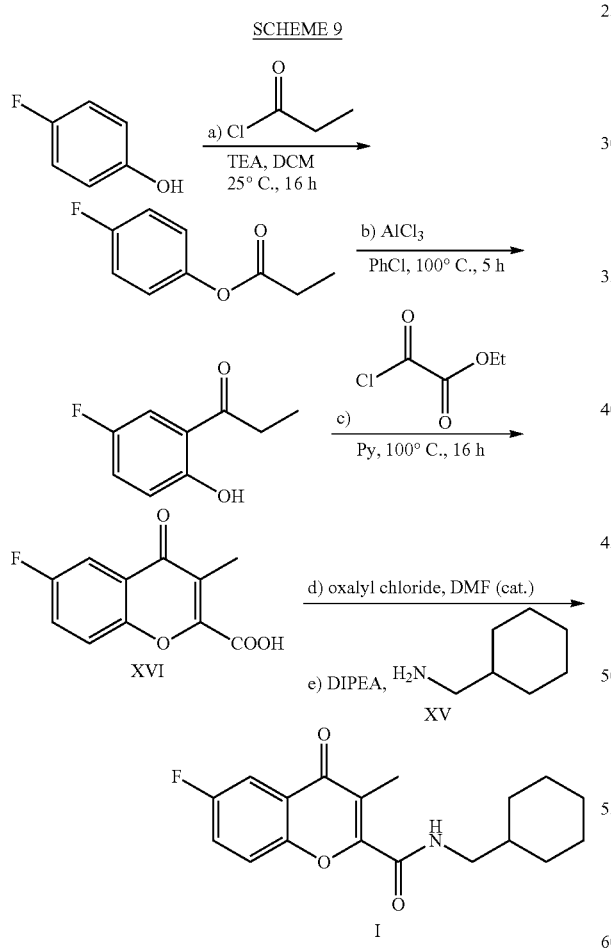

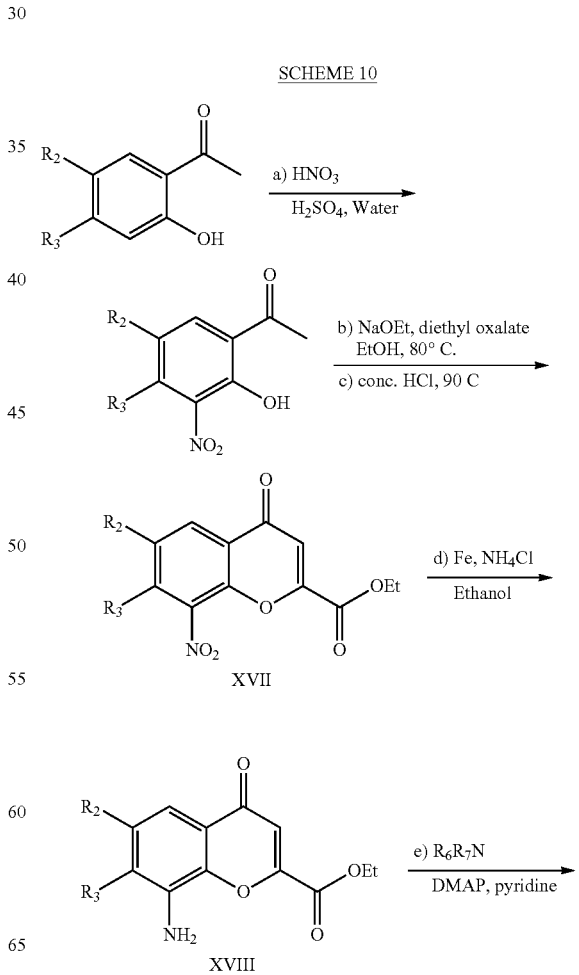

Suitable reagents for carrying out the chemical transformations a, b, and c in steps 1 2, and 3 of Scheme 9 are indicated within Scheme 9 itself.

For the avoidance of doubt, the formulae illustrated in Scheme 9 have been simplified to focus on the key chemical transformations as previously discussed herein, and it will

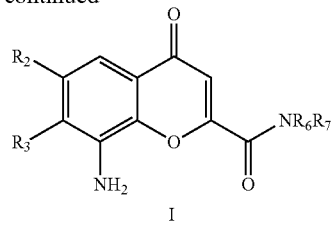

R2 = H, F
R3 = H, F

For the avoidance of doubt, the formulae illustrated in Schemes 10 have also been simplified to focus on the key chemical transformations as previously discussed herein, and it will be appreciated that compounds of general formula (I) having alternative substituents other than H, for one or more of $R^1$ and $R^5$ can be prepared via a selection of the appropriate starting materials and/or reagents as discussed hereinbefore. Examples of compounds of general formula (I) prepared in accordance with the process in Scheme 10 are provided in the Experimental section hereinafter.

Thus the present invention provides a process for the preparation of 8-amino-4-oxo-chromene-2-carboxamides compounds of general formula (I) comprising amidation of the ester-intermediate of general formula (XVIII) in accordance with the process illustrated in Scheme 10.

The general reaction mechanisms described hereinbefore for the preparation of novel starting materials used in the preceding methods are conventional and appropriate reagents and reaction conditions for their performance or preparation as well as procedures for isolating the desired products will be well-known to those skilled in the art with reference to literature precedents and the Examples and Preparations hereto.

It will also be appreciated by a person skilled in the art that the compounds of the invention could be made by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

It will also be apparent to a person skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times temperatures may typically be determined by reaction-monitoring techniques, for example thin-layer chromatography and LC-MS.

Methods of Use

It is to be appreciated that references to treatment as used herein includes prophylaxis as well as palliative treatment via the alleviation of established symptoms of a condition i.e. prevention or control. "Treating" or "treatment" of a state, disorder or condition includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i. e., causing regression of the state, disorder or condition or at least one of its clinical or subclinical symptoms.

It will be appreciated by those skilled in the art that references herein to treatment refer to the treatment of established conditions. However, the compounds of general formula (I) and pharmaceutically acceptable salts thereof may, depending on the condition, also be useful in the prevention (prophylaxis) of certain diseases.

As used herein, unless otherwise indicated, "treat", "treating" or "treatment" in reference to a disease means: (1) to ameliorate the disease or one or more of the biological manifestations of the disease (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, unless otherwise indicated, "prevent", "preventing" or "prevention" means the prophylactic administration of a drug to diminish the likelihood of the onset of or to delay the onset of a disease or biological manifestation thereof. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

Thus, in one embodiment, there is provided the treatment or prevention of a disease. In another embodiment, there is provided the treatment of a disease. In a further embodiment, there is provided the prevention of a disease.

There is thus provided as a further aspect of the invention a compound of general formula (I), or a pharmaceutically acceptable salt thereof, for use in therapy. There is further provided a compound of general formula (I), or a pharmaceutically acceptable salt thereof, for use as a medicament in therapy, which therapy is human or veterinary.

It will be appreciated that, when a compound of general formula (I) or a pharmaceutically acceptable salt thereof is used in therapy, it is used as an active therapeutic agent.

For the avoidance of doubt, general references herein to "treatment" include references to curative, palliative and prophylactic treatment.

Human and Veterinary Use

Regarding the use of the compounds of the invention in humans, there is provided:

a pharmaceutical composition comprising a compound of formula (I), or a pharmaceutically acceptable, salt, solvate, hydrate, isomer, prodrug or polymorph thereof, together with one or more pharmaceutically acceptable, carrier, diluent or excipient;

a compound of formula (I), or a pharmaceutically acceptable, salt, solvate, hydrate, isomer, prodrug or polymorph thereof, or a pharmaceutical composition containing any of the foregoing, for use as a medicament;

a compound of formula (I), or a pharmaceutically acceptable, salt, solvate, hydrate, isomer, prodrug or polymorph thereof, or a pharmaceutical composition containing any of the foregoing, for use in the prophylactic treatment of one or more infectious diseases, and particularly for use in the prophylactic treatment of one or more infectious diseases independently selected from: Malaria; Chagas Disease; human African trypanosomiasis (HAT); African animal trypanosomiasis; Leishmaniasis; Cryptosporidiosis; Schistosomiasis;

a compound of formula (I), or a pharmaceutically acceptable, salt, solvate, hydrate, isomer, prodrug or polymorph thereof, or a pharmaceutical composition containing any of the foregoing, for use in the prophylactic treatment of one or more Gram positive and/or Gram negative bacterial infections wherein the bacterial infections are independently selected from: bacterial infections stemming from: one or more of *Streptococcus pneumonia*; and/or *Enterococcus*; or one or more of the ESKAPE group of bacterial species, *Enterococcus faecium, Staphylococcus aureus, Klebsiella pneumoniae, Acinetobacter baumanii, Pseudomonas aeruginosa*, and/or *Enterobacter;* a compound of formula (I), or a pharmaceutically acceptable, salt, solvate, hydrate, isomer, prodrug or polymorph thereof, or a pharmaceutical composition containing any of the foregoing, for use in the treatment of one or more infectious diseases, and particularly for use in the prophylactic treatment of one or more infectious diseases independently selected from:

Malaria; Chagas Disease; human African trypanosomiasis (HAT); African animal trypanosomiasis (AAT); Leishmaniasis; Cryptosporidiosis;

a compound of formula (I), or a pharmaceutically acceptable, salt, solvate, hydrate, isomer, prodrug or polymorph thereof, or a pharmaceutical composition containing any of the foregoing, for use in the treatment of one or more bacterial infections, and particularly for use in the prophylactic treatment of one or more bacterial infections independently selected from: treatment of one or more Gram positive and/or Gram negative bacterial infections wherein the bacterial infections are independently selected from: bacterial infections stemming from: one or more of *Streptococcus pneumonia*; and/or *Enterococcus*; or one or more of the ESKAPE group of bacterial species, *Enterococcus faecium, Staphylococcus aureus, Klebsiella pneumoniae, Acinetobacter baumanii, Pseudomonas aeruginosa*, and/or *Enterobacter.;* use of compound of formula (I), or a pharmaceutically acceptable, salt, solvate, hydrate, isomer, prodrug or polymorph thereof for the preparation of a pharmaceutical formulation for the treatment of one or more infectious diseases, and particularly for use in the prophylactic treatment of one or more infectious diseases independently selected from:

Malaria; Chagas Disease; human African trypanosomiasis (HAT); African animal trypanosomiasis (AAT); Leishmaniasis; Cryptosporidiosis; Schistosomiasis;

use of compound of formula (I), or a pharmaceutically acceptable, salt, solvate, hydrate, isomer, prodrug or polymorph thereof for the preparation of a pharmaceutical formulation for the treatment of one or more bacterial infections, and particularly for use in the prophylactic treatment of one or more bacterial infections independently selected from: treatment of one or more Gram positive and/or Gram negative bacterial infections wherein the bacterial infections are independently selected from: bacterial infections stemming from: one or more of *Streptococcus pneumonia*; and/or *Enterococcus*; or one or more of the ESKAPE group of bacterial species, *Enterococcus faecium, Staphylococcus aureus, Klebsiella pneumoniae, Acinetobacter baumanii, Pseudomonas aeruginosa*, and/or *Enterobacter;* a compound of formula (I), or a pharmaceutically acceptable, salt, solvate, hydrate, isomer, prodrug or polymorph thereof, or a pharmaceutical composition containing any of the foregoing, for use in the treatment of one or more diseases or conditions independently selected from: drug-resistant malaria; a trypanosomal infection; visceral leishmaniasis; cutaneous leishmaniasis; Cryptosporidiosis; human African trypanosomiasis (HAT); African animal trypanosomiasis; Schistosomiasis;

a compound of formula (I), or a pharmaceutically acceptable, salt, solvate, hydrate, isomer, prodrug or polymorph thereof, or a pharmaceutical composition containing any of the foregoing, for use in the treatment of one or more bacterial infections;

Regarding the use of the compounds of the invention in animals, there is provided:

a veterinary composition comprising a compound of formula (I), or an acceptable salt, solvate, hydrate, isomer, prodrug or polymorph thereof, together with one or more acceptable carrier, diluent or excipient;

a compound of formula (I), or an acceptable salt, solvate, hydrate, isomer, prodrug or polymorph thereof, or a veterinary composition containing any of the foregoing, for use as a veterinary medicine.

For the avoidance of doubt, where use of the compounds of formula (I) is referred to herein this additional means use of the compounds of any one of the formulae independently selected from: (I), C-I, C-II, C-III, A-I, A-II, S-I, S-II, or S-III.

Treatment of Malaria

Prophylactic treatment of malaria as defined herein included includes the treatment of a subject with a prophylaxis-effective amount of compound of formula (I) wherein said prophylaxis-effective amount is an amount of compound that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites Treatment of malaria as defined herein includes: treatment of *Plasmodium falciparum, Plasmodium vivax, Plasmodium ovale, Plasmodium malariae* and/or *Plasmodium knowlesi* infections; treatment of *Plasmodium falciparum* infections; treatment of *Plasmodium falciparum* and *Plasmodium vivax* infections; treatment of *Plasmodium falciparum, Plasmodium vivax, Plasmodium ovale, Plasmodium malariae* and *Plasmodium knowlesi* infections; treatment of the latent forms of vivax malaria.

There is provided herein compounds of formula (I) having a $pEC_{50}$ for Pf 3D7 of 5 or more, preferably 5.5 or more, more preferably 6 or more, especially 6.5 or 7 or more.

There is provided herein compounds of formula (I) having a $pIC_{50}$ for Pf KRS1 of 6 or more, preferably 6.3 or more, more preferably 6.5 or more, especially 7 or more.

Treatment of Chagas Disease

A further aspect of the invention provides a method for the prophylaxis or treatment of trypanosomal infection comprising the administration of a compound of formula (I) to a subject suffering from or likely to be exposed to said *T. cruzi* infection. A related aspect of the invention provides the use of a compound of formula (I) in the treatment or prophylaxis of trypanosomal infection. A further related aspect provides the use of the compounds of formula (I) for the treatment or prophylaxis of *T. cruzi* infection.

A further aspect of the invention provides a method for the treatment of trypanosomal infection comprising the administration of a compound of formula (I) to a subject suffering from or likely to be exposed to said trypanosomal infection. A related aspect of the invention provides the use of a compound of formula I in the treatment of trypanosomal infection. A further related aspect provides the use of the compounds of formula (I) for the treatment of *T. cruzi* infection. Other related aspects provide, a compound of formula (I) for use in the treatment of trypanosomal infection, and a compound of formula (I) for use in the treatment of a *T. cruzi* infection.

In some embodiments of the invention, the trypanosomal infection is a *T. cruzi* infection. Typically the method or use of the invention relates to treatment of an ongoing infection in human subjects.

The anti-infective agents of formula (I) according to the present invention are believed to be suitable for treatment those infectious diseases in which the pathogen is present in organs such as the liver, spleen or kidney, and in particular to muscles such as heart.

In another aspect, the invention provides a kit comprising an effective amount of one or more compounds of the formulae herein in unit dosage form, together with instructions for administering the compound to a subject suffering from or susceptible to a trypanosomal infections, such as Chagas disease.

There is provided herein compounds of formula (I) having a $pEC_{50}$ for *Crytosporidium parvum* of 5 or more, preferably 5.5 or more, more preferably 6 or more, especially 6.5 or 7 or more.

Treatment of Leishmaniasis

There is also therefore provided a compound of formula (I), or a pharmaceutically acceptable salt thereof, for use in the treatment or prevention of leishmaniasis, particularly visceral leishmaniasis.

In one embodiment of the invention there is provided a compound of formula (I), or a pharmaceutically acceptable salt thereof, for use in the treatment or prevention of cutaneous leishmaniasis. There is further provided the use of a compound of formula (I), or a pharmaceutically acceptable salt thereof, for use as a medicament for the treatment or prevention of leishmaniasis, particularly visceral leishmaniasis.

There is further provided a method of treatment or prevention of leishmaniasis, particularly visceral leishmaniasis, which method comprises administering to a human subject in need thereof, a therapeutically effective amount of a compound of formula (I), or a pharmaceutically acceptable salt thereof. In another embodiment of the invention there is provided a method of treatment or prevention of cutaneous leishmaniasis, which method comprises administering to a mammal in need thereof, a therapeutically effective amount of a compound of formula (I) or a pharmaceutically acceptable salt thereof.

According to a preferred aspect the above uses, and/or methods provide compounds of formula (I), or a pharmaceutically acceptable salt thereof effective against agents which are effective against *Leishmania*, and particularly for agents which are suitable for use in the treatment or prevention of *Leishmania infantum*.

Treatment of Schistosomiasis

There is also therefore provided a compound of formula (I), or a pharmaceutically acceptable salt thereof, for use in the treatment or prevention of schistosomiasis.

There is further provided the use of a compound of formula (I), or a pharmaceutically acceptable salt thereof, for use as a medicament for the treatment or prevention of schistosomiasis.

There is further provided a method of treatment or prevention of schistosomiasis, which method comprises administering to a human subject in need thereof, a therapeutically effective amount of a compound of formula (I), or a pharmaceutically acceptable salt thereof.

According to a preferred aspect the above uses, and/or methods provide compounds of formula (I), or a pharmaceutically acceptable salt thereof effective against agents which are effective against worms of the genus *Schistosoma*, and particularly effective against *Schistosoma haematobium, Schistosoma mansoni* and/or *Schistosoma japonicum*.

Treatment of Cryptosporidiosis

There is also therefore provided a compound of formula (I), or a pharmaceutically acceptable salt thereof, for use in the treatment or prevention of Cryptosporidiosis.

There is further provided a method of treatment or prevention of Cryptosporidiosis, which method comprises administering to a human subject in need thereof, a therapeutically effective amount of a compound of formula (I), or a pharmaceutically acceptable salt thereof. In another embodiment of the invention there is provided a method of treatment or prevention of Cryptosporidiosis, which method comprises administering to a mammal in need thereof, a therapeutically effective amount of a compound of formula (I) or a pharmaceutically acceptable salt thereof.

According to a preferred aspect the above uses, and/or methods provide compounds of formula (I), or a pharmaceutically acceptable salt thereof effective against *Cryptosporidium*, and particularly compounds of formula (I) suitable for use in the treatment or prevention of; *Cryptosporidium*-only infected subjects; immunocompromised subjects infected with *Cryptosporidium* such as *Cryptosporidium*-HIV co-infected subjects.

Treatment of Human African Trypanosomiasis (HAT)

There is also provided a compound of formula (I), or a pharmaceutically acceptable salt thereof, for use in the treatment or prevention of HAT.

There is further provided a method of treatment or prevention of HAT, which method comprises administering to a human subject in need thereof, a therapeutically effective amount of a compound of formula (I), or a pharmaceutically acceptable salt thereof. In another embodiment of the invention there is provided a method of treatment or prevention of HAT, which method comprises administering to a mammal in need thereof, a therapeutically effective amount of a compound of formula (I) or a pharmaceutically acceptable salt thereof.

According to a preferred aspect the above uses, and/or methods provide compounds of formula (I), or a pharmaceutically acceptable salt thereof effective against *Trypanosoma brucei gambiense* (*T.b. gambiense*) and/or *Trypanosoma brucei rhodesiense* (*T.b. rhodesiense*) infections.

Treatment of Tuberculosis (TB)

There is also provided a compound of formula (I), or a pharmaceutically acceptable salt thereof, for use in the treatment or prevention of TB.

There is further provided a method of treatment or prevention of TB, which method comprises administering to a human subject in need thereof, a therapeutically effective amount of a compound of formula (I), or a pharmaceutically acceptable salt thereof. In another embodiment of the invention there is provided a method of treatment or prevention of TB, which method comprises administering to a mammal in need thereof, a therapeutically effective amount of a compound of formula (I) or a pharmaceutically acceptable salt thereof.

Treatment of Bacterial Infections There is also provided a compound of formula (I), or a pharmaceutically acceptable salt thereof, for use in the treatment or prevention of a bacterial infection.

There is further provided a method of treatment or prevention of bacterial infections, which method comprises administering to a human subject in need thereof, a therapeutically effective amount of a compound of formula (I), or a pharmaceutically acceptable salt thereof. In another embodiment of the invention there is provided a method of treatment or prevention of one or more bacterial infections, which method comprises administering to a mammal in need thereof, a therapeutically effective amount of a compound of formula (I) or a pharmaceutically acceptable salt thereof.

According to a preferred aspect the above uses, and/or methods provide anti-bacterial compounds of formula (I), or a pharmaceutically acceptable salt thereof suitable for use in the treatment or prevention of, or which provide effective treatment of bacterial infections stemming from: *Staphylococcus aureus; Streptococcus pneumonia; Enterococcus*; and/or *Mycobacterium tuberculosis*.

Combination Therapy

The compounds of the present invention may be delivered in combination with one or more auxiliary active agents for the treatment of malaria. Suitable auxiliary active agents for use in the combinations of the present invention include: Artemisinin and derivatives thereof such as for example Artesunate; Quinine and related agents; Chloroquine; OZ439; NITD609; ferroquine; napthoquine; piperaquine; Pyrimethamine; Proguanil; Sulphonamide based therapies; Mefloquine, including Mefloquine hydrochloride; Atovaquone; Primaquine; Halofantrine; Doxycyline; Clindamycin; Amodiaquine, marketed as Camoquin, or Flavoquine; and/or Artemether, including the further combination with lumefantrine available from Novartis as a constituent of Riamet and Coartem, or with another published compound currently under development.

The suitability of a potential combination of two, or more, antimalarial drugs can be assessed on the basis of their in vitro drug interactions wherein the interactions of the two selected antimalarial drugs are investigated in vitro using standard dose-response assays over a range of individualised concentrations. The selection of suitable conditions and concentrations for carrying out such investigations would be within the remit of the skilled practitioner.

According to a further aspect the present invention provides a pharmaceutical composition comprising: a compound of formula (I) or a pharmaceutically acceptable, salt, solvate, hydrate, isomer, prodrug, or polymorph thereof; one or more additional antimalarial agents; and one or more pharmaceutically acceptable, carriers, diluents or excipients.

Examples of suitable combinations herein include a compound of the present invention and one or more additional therapeutic agents selected from: artesunate; mefloquine; OZ439, piperaquine and mixtures thereof.

If a combination of active agents is administered, then the composition comprising a compound of formula (I) as detailed hereinbefore may be administered to an individual prior to, simultaneously, separately or sequentially with other therapeutic regiments or co-agents useful in the treatment of malaria. If a combination of active agents is administered, then the different actives may be formulated for the same or different delivery, for example one active formulated for immediate and another for sustained release. If a combined therapy is to be administered the active agents may be formulated for the same or different routes of administration, for example in a dual-therapy one active may be formulated for oral administration and another for parenteral administration.

Administration and Dose Ranges

In order to select the most appropriate dosage forms and routes of administration considered appropriate for the treatment of the desired indication, compounds of formula (I) should be assessed for their biopharmaceutical properties, such as for example, solubility, solution stability (across a range of pHs), likely dose level and permeability. Initial biopharmaceutical testing for potential as anti-malarial treatment has provided positive results.

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form. Pharmaceutically acceptable excipients include one or more of: lubricants, binding agents, diluents, surface-active agents, antioxidants, colorants, flavouring agents, preservatives, flavour enhancers, preservatives, salivary stimulating agents, cooling agents, co-solvents (including oils), emollients, bulking agents, anti-foaming agents, surfactants and taste-masking agents.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Formulations suitable for oral administration include solids, semi-solids or liquids such as tablets; soft or hard capsules; bolus; powders; lozenges (including liquid-filled); chews; multi and nano-particulates; gels; solid solutions; fast-dispersing dosage forms; fast-dissolving dosage forms; fast-disintegrating dosage forms; films; ovules; sprays; buccal/mucoadhesive patches; and liquid formulations. Liquid formulations include suspensions, solutions, elixirs and syrups. Oral administration may involve swallowing, so that the compound enters the gastrointestinal tract, and/or buccal, lingual or sublingual administration by which the compound enters the blood stream directly from the mouth. Liquid formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Formulations for oral administration may be formulated to be immediate and/or modified release. Modified release formulations include delayed-, sustained-, pulsed-, controlled-, targeted and programmed release. The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The present invention provides a pharmaceutical composition formulated for oral delivery comprising a compound of formula (I) or a pharmaceutically acceptable, salt, solvate or hydrate thereof, according to any preceding claim, together with one or more pharmaceutically acceptable excipients. The present invention further provides said pharmaceutical composition formulated for oral delivery as an immediate release, or as a modified release tablet formulation.

The compounds of the invention may also be administered parenterally, or by injection directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

The present invention provides a pharmaceutical composition formulated for parenteral delivery comprising a compound of formula (I) or a pharmaceutically acceptable, salt, solvate or hydrate thereof, according to any preceding claim, together with one or more pharmaceutically acceptable excipients. The present invention further provides said pharmaceutical composition formulated for parenteral delivery as an immediate release, or as a modified release tablet formulation suitable for intramuscular or intravenous administration.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used.

The compounds of the invention may be administered rectally or vaginally, for example, in the form of a suppository, pessary, or enema. Cocoa butter is a traditional suppository base, but various alternatives may be used as appropriate.

Pharmaceutical formulations containing compounds of the invention may be formulated to be immediate and/or modified release. Modified release formulations include delayed-, sustained-, pulsed-, controlled-, targeted and programmed release.

Dosages

Typically, a physician will determine the actual dosage which will be most suitable for an individual subject. The specific dose level and frequency of dosage for any particular individual may be varied and will depend upon a variety of factors including the condition being treated, the activity of the specific compound employed, the metabolic stability and length of action of that compound, the age, body weight, general health, sex, diet, mode and time of administration, rate of excretion, drug combination, the severity of the particular condition, and the individual undergoing therapy.

In general however a suitable dose will be in the range of from about 0.001 to about 50 mg/kg of body weight per day, in a further embodiment, of from about 0.001 to about 5 mg/kg of body weight per day; in a further embodiment of from about 0.001 to about 0.5 mg/kg of body weight per day and in yet a further embodiment of from about 0.001 to about 0.1 mg/kg of body weight per day. In further embodiments, the ranges can be of from about 0.001 to about 750 mg/kg of body weight per day, in the range of 0.5 to 60 mg/kg/day, and in the range of 1 to 20 mg/kg/day.

The desired dose may conveniently be presented in a single dose or as divided doses administered at appropriate intervals, for example as one, two, three, four or more doses per day. If the compounds are administered transdermally or in extended release form the compounds could be dosed once a day or less.

The compound is conveniently administered in unit dosage form; for example containing 0.1 to 50 mg, conveniently 0.1 to 10 mg, most conveniently 0.1 to 5 mg of active ingredient per unit dosage form. In yet a further embodiment the compound can be conveniently administered in unit dosage form; for example containing 10 to 1500 mg, 20 to 1000 mg, or 50 to 700 mg of active ingredient per unit dosage form.

These dosages are based on an average human subject having a weight of about 65 kg to 70 kg. The physician will readily be able to determine doses for subjects whose weight falls outside this range, such as infants and the elderly.

The present invention provides a pharmaceutical composition formulated as a single-dose tablet suitable for oral delivery comprising a compound of formula (I) or a pharmaceutically acceptable, salt, solvate or hydrate thereof, together with one or more pharmaceutically acceptable excipients. The present invention further provides said pharmaceutical composition formulated for oral delivery as an immediate release, or as a modified release single-dose tablet formulation.

The present invention further provides a pharmaceutical composition formulated as a single-dose tablet formulated for oral delivery as an immediate release, or as a modified release single-dose tablet formulation comprising from about 0.1 to about 3000 mg, preferably from about 0.5 to about 1500 mg, more preferably from about 1 to about 750 mg, from about 1 to about 750 mg, and especially from about 5 to about 250 mg of a compound of formula (I) or a pharmaceutically acceptable, salt, solvate or hydrate thereof, together with one or more pharmaceutically acceptable excipients.

For anti-malarial treatment a single-dose treatment is highly desirable to increase effective treatment levels; increase compliance rates; as well as to reduce treatment costs.

For anti-infective treatment, of any of the infectious conditions identified hereinbefore, and in particular for anti-malarial treatment, the present invention further provides a pharmaceutical composition formulated as a single-dose tablet formulated for oral delivery as an immediate release, or as a modified release single-dose tablet formulation comprising from 0.1 to 3000 mg, preferably from about 0.5 to about 1500 mg, more preferably from about 1 to about 750 mg and especially from about 5 to about 250 mg of a compound of formula (I) or a pharmaceutically acceptable, salt, solvate or hydrate thereof, together with one or more pharmaceutically acceptable excipients.

Where single treatment therapy via a large dose is to be administered, for example to a child, the dose could be provided by more than one tablet, such as 2×1500 mg, or 3×1000 mg, rather than a single-dose 3000 mg tablet where the tablets may be taken either one after the other, or together according to suitability.

Co-Administration

Inasmuch as it may desirable to administer a combination of active compounds, as detailed hereinbefore, for example, for the purpose of treating a particular infectious disease or biological condition, it is within the scope of the present invention that two or more pharmaceutical compositions, at least one of which contains a compound of general formula (I) as defined hereinbefore in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

Methods of Use

It will be appreciated by those skilled in the art that references herein to treatment refer to the treatment of established conditions. However, the compounds of general formula (I) and pharmaceutically acceptable salts thereof may, depending on the condition, also be useful in the prevention (prophylaxis) of certain diseases.

As used herein, unless otherwise indicated, "treat", "treating" or "treatment" in reference to a disease means: (1) to ameliorate the disease or one or more of the biological manifestations of the disease (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, unless otherwise indicated, "prevent", "preventing" or "prevention" means the prophylactic administration of a drug to diminish the likelihood of the onset of or to delay the onset of a disease or biological manifestation thereof. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

Thus, in one embodiment, there is provided the treatment or prevention of a disease. In another embodiment, there is provided the treatment of a disease. In a further embodiment, there is provided the prevention of a disease.

There is thus provided as a further aspect of the invention a compound of general formula (I), or a pharmaceutically acceptable salt thereof, for use in therapy. There is further provided a compound of general formula (I), or a pharmaceutically acceptable salt thereof, for use as a medicament in therapy, which therapy is human or veterinary.

It will be appreciated that, when a compound of general formula (I) or a pharmaceutically acceptable salt thereof is used in therapy, it is used as an active therapeutic agent.

For the avoidance of doubt, general references herein to "treatment" include references to curative, palliative and prophylactic treatment.

Malaria

Compounds of the present invention are useful in the treatment of malaria. Compounds according to the present invention have potential for the treatment of *Plasmodium falciparum*, *Plasmodium vivax*, *Plasmodium ovale*, *Plasmodium malariae* and *Plasmodium knowlesi* infections. In particular the novel class of class of quinolone-4-carboxamide compounds according to the present invention have potential for the treatment of *Plasmodium falciparum* infections; *Plasmodium falciparum* and *Plasmodium vivax* infections; *Plasmodium falciparum*, *Plasmodium vivax*, *Plasmodium malariae*, *Plasmodium ovale* and *Plasmodium knowlesi* infections.

In particular the novel class of class of chromone compounds of general formula (I) according to the present invention have potential for the treatment of malaria attributable to infection from the life-threatening form of malaria attributable to *Plasmodium falciparum*.

Malaria is caused by an infection of the red blood cells with a tiny organism or parasite called protozoa. Infection of the five species of the malaria protozoa, *Plasmodium falciparum*, *Plasmodium vivax*, *Plasmodium ovale*, *Plasmodium malariae* and *Plasmodium knowlesi* occurs through the injection of protozoa into the blood stream, is effected by a single source, the bite of the female Anopheles mosquito.

*Plasmodium* species, requires two hosts, human and mosquito for completion of its life-cycle. In humans the infection is initiated by the inoculation of sporozoites in the saliva of an infected mosquito. Once inside the body the sporozoites migrate to the liver and there infect hepatocytes where they differentiate, via the exoerythrocytic intracellular stage, into the merozoite stage which infects red blood cells to initiate cyclical replication in the asexual blood stage. The life-cycle is completed by the differentiation of a number of merozoites in the red blood cells into sexual stage gametocytes which are ingested by the mosquito, where they develop through a series of stages in the mid gut to produce sporozoites which migrate to the salivary gland. According to a further aspect the present invention provides chromone compounds of general formula (I) for use as antimalarial medicaments.

Compounds of the invention have been demonstrated to display both functional in vitro potency against a malarial *Plasmodium* strain and desirable in vivo potency in a *Plasmodium* mouse model.

Protein Expression and Purification Method: For PPT111 His-MBP-TEV-Pf-KRS

The gene encoding a truncated form of *Plasmodium falciparum* lysyl-tRNA-synthetase (Uniprot code Q8IDJ8), residues 80-583, was codon optimized and synthesized by Genscript, with additional NdeI and XhoI restriction sites added at the termini of the gene. The gene was subsequently digested out the provided pUC57 vector and ligated into a modified pET15B vector encoding an N-terminal Hexa-His tagged Maltose Binding Protein (MBP) tag with an additional Tobacco Etch Virus (TEV) cleavage site between the protein and the tag to allow increased soluble expression, ease of affinity capture and subsequent cleavage during purification. All plasmids were sent for sequencing to confirm identity at the DNA sequencing and services (Dundee University).

The plasmid translation for PfKRS, from a modified pET15B vector (Novagen) is provided hereinafter. The gene was synthesised by Genscript (USA) and cloned using FastDigest enzymes (Fermentas).

```
His Tag-
                                          (SEQ ID NO: 1)
MGSSHHHHHHGSS

Maltose Binding protein (required for KRS1
stability)-
                                          (SEQ ID NO: 2)
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNNL

TEV Clevage site-
                                          (SEQ ID NO: 3)
GENLYFQGH Pf KRS1-
                                          (SEQ ID NO: 4)
MEVDPRLYFENRSKFIQDQKDKGINPYPHKFERTISIPEFIEKYKDLGNG

EHLEDTILNITGRIMRVSASGQKLRFFDLVGDGEKIQVLANYSFHNHEKG

NFAECYDKIRRGDIVGIVGFPGKSKKGELSIFPKETILLSACLHMLPMKY

GLKDTEIRYRQRYLDLLINESSRHTFVTRTKIINFLRNFLNERGFFEVET

PMMNLIAGGANARPFITHHNDLDLDLYLRIATELPLKMLIVGGIDKVYEI

GKVFRNEGIDNTHNPEFTSCEFYWAYADYNDLIKWSEDFFSQLVYHLFGT

YKISYNKDGPENQPIEIDFTPPYPKVSIVEEIEKVTNTILEQPFDSNETI

EKMINIIKEHKIELPNPPTAAKLLDQLASHFIENKYNDKPFFIVEHPQIM

SPLAKYHRTKPGLTERLEMFICGKEVLNAYTELNDPFKQKECFKLQQKDR

EKGDTEAAQLDSAFCTSLEYGLPPTGGLGLGIDRITMELTNKNSIKDVIL

EPTMRPAN
```

The plasmid was transformed into BL21 (DE3) cells (Stratagene) using the heat shock methods prior to plating onto LB agar plates supplemented with 50 ug$^{-1}$ ml$^{-1}$ ampicillin and incubated overnight at 37° C. Cell scrapings were taken and used to inoculate Autoinduction media (Studier, 2005) supplemented with 50 ug$^{-1}$ ml$^{-1}$ ampicillin. Cultures were grown at 37° C. 200 rpm shaking for four hours prior to being grown for 18 hours overnight at 21° C. to allow expression of the protein.

Cultures were pelleted at 3,500 g, 4° C. for 30 minutes prior to being frozen at -20° C. until required. Cells were defrosted and resuspended in buffer A (25 mM TRIS, 500 mM NaCl, 20 mM imidazole, pH 8.5) supplemented with 10 ug$^{-1}$ ml$^{-1}$ DNAse (Sigma) and protease inhibitor tablets (Roche) prior to being lysed at 30 KPSI on a Constant Cell Disruption System (Constant Systems, UK). Cell debris was removed by centrifugation at 37,500 g 4° C. for 30 minutes prior to the supernatant being filtered to 0.25 um. Supernatant was loaded onto a pre-charged HisTrap HP 5 ml column (GE healthcare) equilibrated in buffer A. Initial purification was carried out over 20 column volumes against buffer B (25 mM TRIS, 500 mM NaCl, 500 mM imidazole, pH 8.5) and peaks containing His-MBP-TEV-PfKRS analysed by SDS-PAGE. The protein was then either subjected to dialysis overnight with buffer C (25 mM TRIS, 150 mM NaCl, pH 7.5) on its own for assays or in the presence of TEV to remove the His-MBP tag for crystallography. Samples for crystallography were then subject to a further round of IMAC purification to remove the His-MBP tag and any uncleaved protein. Both samples were then subjected to gel filtration using a calibrated Superdex 200 26/60 column (GE healthcare) equilibrated with buffer C. Cleaved Pf KRS eluted as a dimer, whilst the tagged version eluted as a trimer. Samples were subjected to ESI-TOF analysis by the University of Dundee Proteomics Facility to further confirm their identity. Typically the final samples were in excess of 95% pure by SDS-PAGE analysis.

*Plasmodium falciparum* Lysine tRNA Synthetase (KRS1) Biochemical Assay Methodology.

Lysine tRNA Synthetase (KRS1) is an enzyme which catalyses the esterification of L-Lysine to the appropriate transfer ribonucleic acid (tRNA), to form an aminoacyl-tRNA. Once the tRNA is charged, a ribosome transfers the amino acid from the tRNA onto a growing peptide, according to the genetic code.

The substrates of this reaction are L-lysine, and adenosine triphosphate (ATP), the overall reaction is: amino acid+tRNA+ATP→aminoacyl-tRNA+AMP+PP$_i$ In this overall reaction AMP is adenosine monophosphate and PP; is inorganic pyrophosphate. The reaction progression in a biochemical assay can be tracked by the depletion of one of the substrates, in the case of this invention, ATP. This was done using the proprietary assay kit, Kinase Glo® Assay which is a luminescent kinase assay platform suitable for monitoring kinase activities using up to 10 μm ATP which is commercially available from the Promega Corporation of Madison, Wis., USA. The Kinase-Glo® Assay was performed in a single well of a multiwell plate by adding a volume of Kinase-Glo® Reagent equal to the volume of a completed kinase reaction and measuring luminescence. The resulting luminescent signal is correlated with the amount of ATP present and is inversely correlated with the amount of kinase activity. As such by use of this assay methodology a reduction of the luminescent signal is relative to the reduction in ATP as the reaction progresses. A compound which inhibits the action of KRS will show no drop in the luminescent signal from assay controls.

Assays were performed using both *Plasmodium falciparum* and human KRS to assess any selectivity of various test compounds.

Test compounds were solubilized in DMSO at a top concentration of 10 mM and serially diluted 1 in 3 to achieve a range of final assay concentrations of 50 μM to 2.5 nM in 10 μl reaction volume.

KRS was diluted to a working concentration of 75 nM in assay buffer (25 mM HEPES, 25 mM KOH, 10 mM MgCl$_2$.6H$_2$O, 50 mM KCl), and the following 'Master Mix' prepared in assay buffer: 0.1 mg/ml BSA, 250 µM DTT, 200 µM Spermine, 0.05% NP-40, ATP 3 µM for Pf KRS1 (4 µM for Hs KRS1), 0.4 mg/ml tRNA from Yeast, 60 µM L-Lysine, 0.5 U/ml Pyrophosphatase.

Plates were incubated at room temperature for 5 h for Pf KRS (2.5 hrs for HsKRS), then the assay stopped by the addition of 10 µl of The Kinase-Glo® Reagent Assay was performed in a single well of a multiwell plate by adding a volume of Kinase-Glo® Reagent which is commercially available from the Promega Corporation of Madison, Wis., USA. The plates were incubated in the dark for a further 15 mins before being read for luminescence on a BMG PHER-Astar® FSX plate reader which is a multi-mode reader for use in high-throughput screening available from BMG Labtech if Cary, N.C., USA. Data were analysed by calculating the percentage inhibition compared to the maximum and minimum assay controls. Concentration effect curves were fitted using nonlinear regression within ActivityBase and IC50 values were determined using standard protocols.

Plasmodium falciparum In Vitro Screening

Compounds of general formula (I) according to the present invention have been shown to have desirable inhibitory activity, expressed as an EC$_{50}$, against Plasmodium falciparum strain 3D7, Pf (3D7). The experimental methods and some results are provided hereinafter.

Parasite Cultures and Cytotoxicity Assay Methodology for Plasmodium falciparum.

Cultures of the widely-used malaria reference strain of chloroquinone-sensitive Plasmodium falciparum strain 3D7 were maintained in a 5% suspension of human red blood cells cultured in RPMI 1640 medium supplemented with 0.5% Albumax II (available from Gibco Life Technologies, San Diego, Calif., cat. no. 11021-037), 12 mM sodium bicarbonate, 0.2 mM hypoxanthine, (pH 7.3), and 20 mg/litre gentamicin at 37° C., in a humified atmosphere of 1% O$_2$, 3% CO$_2$ with a gas balance of nitrogen.

Growth inhibition of the Plasmodium falciparum cultures was quantified in a 10-point dose response curve with a 1 in 3 dilution series from a top assay concentration of 50 µM. This 384 well plate based fluorescence assay utilises the binding of SYBRgreen I (Thermo Fisher Scientific/Invitrogen cat. no. S7585) to double stranded DNA, which greatly increases the fluorescent signal at 528 nm after excitation at 485 nm. Mefloquine was used as a drug control to monitor the quality of the assay (Z'=0.6 to 0.8, where Z' is a measure of the discrimination between the positive and negative controls on a screen plate). Dose-response curves were determined from a minimum of 3 independent experiments. Compound bioactivity was expressed as EC$_{50}$, the effective concentration of compound causing 50% parasite death. EC$_{50}$ values were determined from a minimum of 3 independent experiments.

Measurement of Anti-Malarial In Vivo Efficacy

The in vivo measurement of the potential efficacy of compounds of formula (I) in a malarial model has been carried out. These in vivo experiments were run in accordance with the method published in Jimenez-Diaz, M. B. et al., Antimicrob. Agents Chemother. 53, 4533-4536, (2009). Results from these experiments are provided in the Experimental Results hereinafter.

Cytotoxicity Studies

In-vitro cytotoxicity studies can be carried out using Hep G2 (Human Caucasian hepatocyte carcinoma, HPACC cat. no. 85011430) used as indicators for general mammalian cell toxicity. Hep G2 in-vitro cytotoxicity can be assessed using the assay procedure as described in "Use of a human-derived liver cell line for the detection of cytoprotective, antigenotoxic and cogenotoxic agents", Volker Mersch-Sundermann, Siegfried Knasmüller, Xin-jiang Wu, Firouz Darroudi, Fekadu Kassie. J. Tox 198 (2004) 329-340) the contents of which are incorporated herein by reference.

Compounds of formula (I) have demonstrated cellular selectivity in a Hep G2 model using the methodology provided hereinafter.

Protein Expression and Purification Method: For PPT210 His-TEV-MtbKRS

The gene encoding a truncated form of Mycobacterium tuberculosis lysyl-tRNA-synthetase (Uniprot code I6YCJO) was codon optimized and synthesized by Genscript, with additional NdeI and XhoI restriction sites added at the termini of the gene. The gene was subsequently digested out the provided pUC57 vector and ligated into a modified pET15B vector encoding an N-terminal Hexa-His tag with an additional Tobacco Etch Virus (TEV) cleavage site between the protein and the tag to allow increased soluble expression, ease of affinity capture and subsequent cleavage during purification if required. All plasmids were sent for sequencing to confirm identity at the DNA sequencing and services (Dundee University).

The plasmid translation for MtbKRS 1, from a modified pET15B vector (Novagen) is provided hereinafter. The gene was synthesised by Genscript (USA) and cloned using FastDigest enzymes (Fermentas).

```
His Tag-
                                        (SEQ ID NO: 1)
MGSSHHHHHHGSS

TEV Clevage site-
                                        (SEQ ID NO: 3)
GENLYFQGH MtbKRS1-
                                        (SEQ ID NO: 5)
MSAADTAEDLPEQFRIRRDKRARLLAQGRDPYPVAVPRTHTLAEVRAAHP

DLPIDTATEDIVGVAGRVIFARNSGKLCFATLQDGDGTQLQVMISLDKVG

QAALDAWKADVDLGDIVYVHGAVISSRRGELSVLADCWRIAAKSLRPLPV

AHKEMSEESRVRQRYVDLIVRPEARAVARLRIAVVRAIRTALQRRGFLEV

ETPVLQTLAGGAAARPFATHSNALDIDLYLRIAPELFLKRCIVGGFDKVF

ELNRVFRNEGADSTHSPEFSMLETYQTYGTYDDSAVVTRELIQEVADEAI

GTRQLPLPDGSVYDIDGEWATIQMYPSLSVALGEEITPQTTVDRLRGIAD

SLGLEKDPAIHDNRGFGHGKLIEELWERTVGKSLSAPTFVKDFPVQTTPL

TRQHRSIPGVTEKWDLYLRGIELATGYSELSDPVVQRERFADQARAAAAG

DDEAMVLDEDFLAALEYGMPPCTGTGMGIDRLLMSLTGLSIRETVLFPIV

RPHSN*
```

The plasmid was transformed into BL21 (DE3) cells (Stratagene) using the heat shock methods prior to plating onto LB agar plates supplemented with 50 ug$^{-1}$ ml$^{-1}$ ampicillin and incubated overnight at 37° C. Cell scrapings were taken and used to inoculate Autoinduction media (Studier, 2005) supplemented with 50 ug$^{-1}$ ml$^{-1}$ ampicillin. Cultures were grown at 20° C. 200 rpm shaking for forty eight hours to allow expression of the protein.

Cultures were pelleted at 3,500 g, 4° C. for 30 minutes prior to being frozen at −20° C. until required. Cells were defrosted and resuspended in buffer A (100 mM HEPES, 150 mM NaCl, 20 mM imidazole, pH 7.5) supplemented with 10 ug$^{-1}$ ml$^{-1}$ DNAse (Sigma) and protease inhibitor tablets (Pierce) prior to being lysed at 30 KPSI on a Constant Cell Disruption System (Constant Systems, UK). Cell debris was removed by centrifugation at 40,000 g 4° C. for 30 minutes prior to the supernatant being filtered to GFA prefilter. Supernatant was incubated with 5 ml Ni Sepharose HP (GE healthcare) equilibrated in buffer A for 1.5 hrs. An Initial wash step was carried out to remove His Rich proteins over 4 column volumes against 5% buffer B (100 mM HEPES, 150 mM NaCl, 500 mM imidazole, 5% Glycerol pH 7.5). The protein was then eluted in 2×2 CV Buffer B. Fractions containing His-TEV-MtbKRS1 analyzed by SDS-PAGE. The protein was subjected to dialysis overnight with buffer C (100 mM HEPES, 150 mM NaCl, 5% Glycerol, pH 7.5). The samples were then subjected to gel filtration using a calibrated Superdex 200 50/60 column (GE healthcare) equilibrated with buffer C. Mtb KRS1 eluted as a dimer. Samples were subjected to ESI-TOF analysis by the University of Dundee Proteomics Facility to further confirm their identity. Typically the final samples were in excess of 80% pure by SDS-PAGE analysis.

*Mycobacterium tuberculosis* Lysine tRNA Synthetase (KRS1) Biochemical Assay Methodology.

*Mycobacterium tuberculosis* lysyl-tRNA synthetase (or lysyl-tRNA ligase), briefly MtKRS, is a dimeric multistep enzyme catalysing the reaction of L-lysine and ATP in the first step and in the second step the transfer of lysine onto the respective tRNA. In the first step it releases pyrophosphate and in the second step AMP as by-products. The main product is lysyl-tRNA which is an essential building block for protein synthesis.

MtKRS Catalysed Reaction:
Step 1: Lysine+ATP→Lysyl-AMP+PP$_i$
Step 2: Lysyl-AMP+tRNA→Lysyl-tRNA+AMP
Detection Principle:
PP$_i$–[pyrophosphatase]→P$_i$+P$_i$ (simultaneous reaction with MtKRS).
P$_i$+BioMol Green→P$_i$-molybdate-Malachite Green complex (final addition, stops assay).
Read absorption at 650 nm.

MtKRS enzyme activity is tested in a BioMol Green based endpoint assay. A pyrophosphatase enzyme is continuously driving the first step of the reaction by hydrolysing the released inorganic pyrophosphate (PP$_i$) creating free phosphate (P$_i$). This class of enzyme is a natural driver of pyrophosphate releasing enzymes in cells. In this assay free inorganic phosphate (P$_i$) is finally detected via a chemical reaction using Biomol Green (ENZO®).

BioMol Green consists of the dye Malachite Green, ammonium molybdate and a strong acid (HCl). Free phosphate builds a complex with molybdate and Malachite Green and approximately 13 protons, which are also incorporated and removed from solution. The reaction mix changes colour from orange to green—this is detected by a change in absorbance at 650 nm.

This assay detects the first step of the MtKRS reaction. And it is not necessary to supply the reaction mixture with tRNA which reduces costs substantially.

The final assay mixture contained 250 nM MtKRS, 30 mM Tris-HCl pH8, 40 mM MgCl$_2$, 140 mM NaCl, 30 mM KCl, 0.01% Brij-35, 1 mM DTT, 3 µM ATP, 12 µM L-lysine, 0.5 U/mL yeast pyrophosphatase (Sigma). The assay mixture was plated on 384-well plates (Greiner 781101) with a reaction volume of 50 uL per well. After 4 hours of incubation at room temperature the reaction was stopped by addition of an equal amount of 50 uL BioMol Green (ENZO®). The stopped reaction mix was incubated for 20 minutes and absorbance read at 650 nm on BMG PHERAstar® FSX plate reader which is a multi-mode reader for use in high-throughput screening available from BMG Labtech if Cary, N.C., USA.

Test compounds were solubilized in DMSO at a top concentration of 10 mM and serially diluted 1 in 3 to achieve a range of final assay concentrations of 50 µM to 2.5 nM in 10 µl reaction volume.

Onto each plate rows of 100% and 0% inhibition controls were included. Instead of compound DMSO was added. 100% inhibition controls were lacking L-lysine and 0% inhibition controls were normal assay mixture.

Data were analysed by calculating the percentage inhibition compared to the maximum (100%) and minimum (0%) assay controls. Concentration effect curves were fitted using nonlinear regression within ActivityBase and IC50 values were determined using standard protocols.

Assays were performed using both mycobacterial and human KRS to assess any selectivity of various test compounds.

Assay Method for Measurement of In Vitro Inhibition of *M. tuberculosis* H37Rv (Mtb. H37Rv)

The in vitro measurement of the minimum inhibitory concentration (MIC) versus Mtb exhibited by compounds of formula (I) has been carried out. These experiments were run in accordance with the method published in Ballel et al. ChemMedChem, 2013, 8:313. Details of the assay method are provided hereinafter and results from these experiments are provided in the Experimental Results.

The measurement of the minimum inhibitory concentration (MIC) versus *M. tuberculosis* (Mtb) H37Rv exhibited by compounds of formula (I) has been carried out. In these experiments, the MIC for test compounds, versus *M. tuberculosis* H37Rv, was performed in 96-well flat-bottom polystyrene microtiter plates. Ten two-fold dilutions of each test compound (drug dilutions), in neat DMSO starting at 50 mM were performed. These drug solutions (5 µL) were added to 95 µL Middlebrook 7H9 medium (lines A-H, rows 1-10 of the plate layout). Isoniazid (Isonicotinyl hydrazine, INHA) was used as a positive control; eight twofold dilutions of isoniazid starting at 160 µg mL$^{-1}$ were prepared, and this control curve (5 µL) was added to 95 µL Middlebrook 7H9 medium (row 11, lines A-H). Neat DMSO (5 µL) was added to row 12 (growth and blank controls). The inoculum was standardized to ~1×10$^7$ CFU mL$^{-1}$ and diluted 1:100 in Middlebrook 7H9 broth (Middlebrook ADC enrichment, a dehydrated culture medium which supports growth of mycobacterial species, available from Becton-Dickinson, cat. #211887), to produce the final inoculum of H37Rv strain (ATTC25618) http://www.uniprot.org/proteomes/UP000001584. This inoculum (100 µL) was added to the entire plate except G-12 and H-12 wells (blank controls). All plates were placed in a sealed box to prevent drying out of the peripheral wells and were incubated at 37° C. without shaking for six days. A dye-solution containing resazurin (diazoresorcinol) was prepared by dissolving one tablet of resazurin (VWR International Ltd., *Resazurin Tablets for Milk Testing*, cat. #330884Y') in 30 mL sterile phosphate-buffered saline (PBS). Of this solution, 25 µL were added to each well. Fluorescence was measured (Spectramax M5, Molecular Devices; λ$_{ex}$ 530 nm, λ$_{em}$ 590 nm) after 48 h to determine the MIC value.

Assay Method for Measurement of In Vitro Inhibition of *Crytosporidium*.

The in vitro measurement of EC$_{50}$, the effective concentration of compound causing 50% parasite death versus *Crytosporidium* exhibited by compounds of formula (I) has been carried out. These experiments were run in accordance with the method of Besssoff et. al. Antimicrob. Agents Chemother. 2013, 57:1804-1814. Results from these experiments are provided in the Experimental Results hereinafter.

Measurement of Anti-*Cryptosporidium* In Vivo Efficacy

The in vivo measurement of the potential efficacy of compounds of formula (I) in two *cryptosporidium* models has been carried out.

The cryptosporidiosis IFN-γ-knockout mouse in vivo experiments were run in accordance with the method published in Vinayak et. al. Nature 2015, 523:477-482.

The cryptosporidiosis NOD SCID gamma mouse model were run as follows: Male NOD SCID gamma mice (NOD.Cg-Prkdc$^{scid}$ Il2rg$^{tm1Wjl}$/SzJ, Jackson Labs) were infected approximately 2 weeks post weaning with 10^5 *C. parvum* Iowa strain oocysts by oral gavage. Four mice were used per experimental group. This establishes a chronic, asymptomatic infection of the small intestine, cecum, and biliary tree. Fecal parasite shedding is monitored by quantitative PCR to amplify *C. parvum* DNA. One week after infection (which is the timing with which shedding becomes uniformly detected), compounds are dosed by oral gavage based. Treatment continued for four days total. Fecal oocyst shedding is reported on day 1 (7 days after initial infection with sample taken just prior to the first dose of compound) and day 5 (1 day after completion of the last dose).

Results from these experiments are provided in the Experimental Results hereinafter.

Assay Method for Measurement of In Vitro Inhibition of *Leishmania donovani*.

The in vitro measurement of $EC_{50}$, the effective concentration of compound causing 50% parasite death, versus *Leishmania donovani* exhibited by compounds of formula (I) has been carried out. These experiments were run in accordance with the method as detailed herein and results from these experiments are provided in the Experimental Results hereinafter.

The intramacrophage *Leishmania* assay was performed as described in de Rycker et al (Antimicrob Agents Chemother, 2013 July; 57(7):2913-22. doi: 10.1128/AAC.02398-12). Briefly, 1 μl of compound was pre-dispensed into 384 well sterile intermediary plates. For single point screening, amphotericin B was added to all wells of column 24 as a positive control (final concentration 2 μM) and DMSO to column 23. For potency determinations, ten-point, one in three dilution curves were created with the highest concentration being 50 μM and on each plate a control curve of amphotericin B was included. Controls were as follows: columns 11 and 12: DMSO, columns 23 and 24: amphotericin B (final concentration 2 μM). To the intermediary plates, 100 μl of THP-1 media was added and plates were shaken for >5 min to ensure complete mixing. THP-1 cells (8,000 per well, 50 μl) were plated into black clear-bottom 384 well plates (Corning) in presence of 10 nM PMA. After 20 min at room temperature, the plates were incubated at 37° C. under 5% CO2 in a humidified incubator for 75 h. The cells were then washed with 450 μl sterile phosphate buffered saline (PBS) supplemented with 1 mM CaCl$_2$, 0.5 mM MgCl$_2$, 0.1% (w/v) bovine serum albumin (PBS-A) and amastigotes were added to all wells at a multiplicity of infection of 5 (40,000 amastigotes per well). After 40 min at room temperature, plates were returned to the incubator. Amastigotes were incubated in the presence of macrophages for 16 h. Any remaining extracellular amastigotes were subsequently removed with an overflow wash of 1 ml PBS-A per well (wash buffer is being aspirated from the top of the well as it is being dispensed) followed by addition of 25 μl of the compound pre-dilutions using a Matrix Hydra DT pipetting station. The final dilution of each compound was 200-fold. Plates were incubated for 72 h and then washed (250 μl PBS-A) and fixed (4% (v/v) formaldehyde-PBS, 30 min, room temperature). After fixation, the wells were washed with 250 μl PBS, stained (10 μg/ml DAPI, 0.4 μg ml-1 HCS Cellmask Deep Red in PBS+0.1% (v/v) Triton X-100, 30 min, room temperature) and washed with 250 μl PBS. Finally, PBS+0.05% (v/v) thimerosal was added to the wells, the plates were sealed and imaged on a high-content microscope (GE IN Cell 1000 or GE IN Cell 2000) using a 10× objective. Image analysis was carried out with GE IN Cell Analyzer 1000 Workstation using the "Multi Target Analysis" module. Settings for segmentation were as follows: nuclei: minimum area: 142.384 μm$^2$, sensitivity: 81, method: top-hat; cells: characteristic area: 2500 μm$^2$, sensitivity: 60, method: multiscale top-hat; organelles (amastigotes): granule size 1-3, 3 scales, sensitivity: 90, detection in entire cell. For each well, THP-1 cell count and average number of amastigotes per cell were reported.

Assay Method for Measurement of In Vitro Inhibition of *Trypanosoma cruzi*.

The in vitro measurement of $EC_{50}$, the effective concentration of compound causing 50% parasite death versus *Trypanosoma cruzi* exhibited by compounds of formula (I) has been carried out. These experiments were run in accordance with the method of Pena et. al., *Scientific Reports* 5, Article number: 8771 (2015). Results from these experiments are provided in the Experimental Results hereinafter.

Biological Data and Experimental Results

For the avoidance of doubt, where activity data is presented as an pIC50 value this is not the same as an IC50 value. Both $pIC_{50}$ and $IC_{50}$ are terms of the art and it will be readily appreciated by the skilled person that compounds which have an $IC_{50}$ value of less than about 10 μM will have a corresponding $pIC_{50}$ value of greater than about 5.

Generally speaking, an $IC_{50}$ value of 1 μM is equivalent to a $pIC_{50}$ value of 6, and an $IC_{50}$ value of 100 nM is equivalent to a $pIC_{50}$ value of 7.

1. In Vitro Data

1-A. Pf-KRS1 Inhibition Data

Compounds of formula (I) have demonstrated Pf-KRS inhibitory activity. The Pf-KRS-$pIC_{50}$ data for some of the Exemplary compounds herein from these *Plasmodium falciparum* lysyl t-RNA synthetase (Pf-KRS1) inhibition assay tests are provided in Table 1.

TABLE 1

| EXAMPLE | Pf-KRS $pIC_{50}$ |
|---|---|
| 4 | 6.0 |
| 54 | 6.6 |
| 23 | 6.4 |
| 9 | 6.7 |
| 32 | 6.1 |
| 42 | 6.7 |
| 26 | 6.3 |
| 66 | 6.3 |
| 43 | 6.4 |
| 71 | 6.4 |
| 32 | 6.4 |
| 41 | 7.0 |
| 91 | 6.2 |
| 49A | 6.9 |
| 36 | 6.9 |
| 40 | 6.6 |
| 48 | 6.9 |
| 70 | 7.3 |
| 54 | 6.9 |

TABLE 1-continued

| EXAMPLE | Pf-KRS pIC$_{50}$ |
|---|---|
| 61 | 6.2 |
| 55 | 6.7 |
| 56 | 6.5 |
| 84 | 6.9 |
| 57K | 6.5 |
| 13 | 7.1 |
| 74 | 7.3 |
| 75 | 7.1 |
| 76A | 7.3 |
| 54 | 6.9 |
| 6 | 7.2 |
| 31 | 7.1 |
| 27 | 6.9 |
| 67 | 7.2 |
| 57 | 6.9 |
| 78 | 7.1 |
| 77 | 7.0 |
| 73 | 7.3 |
| 93 | 7.3 |
| 40A | 6.7 |
| 82 | 6.6 |
| 90 | 5.9 |
| 91 | 6.2 |
| 76B | 6.4 |
| 76C | 6.5 |
| 76D | 6.9 |
| 76E | 6.6 |
| 76F | 7.1 |
| 76G | 6.9 |
| 76H | 6.6 |
| 79 | 6.7 |
| 80 | 6.5 |
| 81 | 6.7 |
| 83 | 7.3 |
| 89 | 6.3 |
| 93 | 7.2 |
| 99 | 7.3 |
| 100 | 6.8 |

1-B. Pf 3D7 Inhibition Data

Compounds of formula (I) have demonstrated *Plasmodium falciparum* Pf 3D7 inhibitory activity. The Pf 3D7 pEC$_{50}$ data for some of the Exemplary compounds herein from these in vitro *Plasmodium falciparum* inhibition assay tests are provided in Table 2.

TABLE 2

| EXAMPLE | pEC$_{50}$ for Pf 3D7 |
|---|---|
| 4 | 5.9 |
| 54 | 6.1 |
| 23 | 5.8 |
| 9 | 5.8 |
| 32 | 5.8 |
| 42 | 6.1 |
| 26 | 5.2 |
| 66 | 5.6 |
| 43 | 5.5 |
| 71 | 5.5 |
| 32 | 5.8 |
| 41 | 6.7 |
| 91 | 5.3 |
| 49A | 6.4 |
| 36 | 6.1 |
| 40 | 6.1 |
| 48 | 6.4 |
| 70 | 7.0 |
| 54 | 6.5 |
| 61 | 5.8 |
| 55 | 6.4 |
| 56 | 5.8 |
| 84 | 6.5 |
| 57L | 6.1 |
| 13 | 7.3 |

TABLE 2-continued

| EXAMPLE | pEC$_{50}$ for Pf 3D7 |
|---|---|
| 74 | 7.2 |
| 75 | 6.7 |
| 76A | 7.1 |
| 54 | 6.6 |
| 6 | 6.8 |
| 31 | 6.5 |
| 27 | 6.6 |
| 67 | 7.2 |
| 57 | 6.8 |
| 78 | 7.0 |
| 77 | 6.9 |
| 93 | 8.1 |
| 40A | 6.7 |
| 82 | 6.7 |
| 90 | 5.3 |
| 91 | 5.2 |
| 76B | 5.8 |
| 76C | 6.0 |
| 76D | 6.4 |
| 76E | 6.1 |
| 76F | 6.3 |
| 76H | 6.6 |
| 76G | 5.8 |
| 83 | 7.7 |
| 87 | 6.9 |
| 92 | 7.1 |
| 93 | 7.6 |
| 94 | 7.3 |
| 95 | 7.3 |
| 96 | 7.9 |
| 97 | 7.4 |
| 98 | 6.2 |
| 99 | 8.0 |
| 100 | 6.7 |

1-C. Mtb KRS1 Inhibition Data

Compounds of formula (I) have demonstrated Mtb KRS inhibitory activity. The Mtb KRS pIC$_{50}$ data for some of the Exemplary compounds herein from these *Mycobacterium tuberculosis* lysyl t-RNA synthetase (Mtb KRS) inhibition assay tests are provided in Table 3.

TABLE 3

| EXAMPLE | Mtb KRS pIC$_{50}$ |
|---|---|
| 76B | 5.1 |
| 76C | 4.8 |
| 76E | 4.5 |
| 76H | 4.3 |

1-D. Mtb Inhibition Data

Compounds of formula (I) have demonstrated Mtb inhibitory activity. The Mtb MIC data for some of the Exemplary compounds herein from these *Mycobacterium tuberculosis* in vitro inhibition assay tests are provided in Table 4.

TABLE 4

| EXAMPLE | Mtb MIC (μM) |
|---|---|
| 70 | 30 |
| 74 | 25 |

1-E. *Crytosporidium* Inhibition Data

Compounds of formula (I) have demonstrated *Crytosporidium* inhibitory activity. The *Cryptosporidium parvum* pEC$_{50}$ data for some of the Exemplary compounds herein from these in vitro *Crytosporidium* inhibition assay tests are provided in Table 5.

TABLE 5

| EXAMPLE | *Cryptosporidium parvum* pEC$_{50}$ |
|---|---|
| 4 | 5.8 |
| 21 | 5.1 |
| 23 | 5.7 |
| 9 | 5.45 |
| 32 | 5.4 |
| 42 | 5.9 |
| 26 | 5 |
| 43 | 5.3 |
| 71 | 5.4 |
| 32 | 5.8 |
| 41 | 6.3 |
| 91 | 5.6 |
| 49A | 6.8 |
| 36 | 5.9 |
| 40 | 5.8 |
| 48 | 7.2 |
| 70 | 7.4 |
| 54 | 5.9 |
| 61 | 5 |
| 55 | 6.3 |
| 56 | 5.1 |
| 84 | 6.2 |
| 57L | 5.3 |
| 13 | 6.92 |
| 74 | 7.4 |
| 75 | 6.1 |
| 76A | 5.5 |
| 54 | 5.8 |
| 6 | 6.9 |
| 31 | 6.2 |
| 27 | 6.5 |
| 67 | 6.5 |
| 57 | 5.3 |
| 78 | 9 |
| 77 | 6.9 |
| 73 | 7.4 |
| 79 | 6.1 |
| 81 | 6.9 |
| 93 | 6.3 |
| 88 | 5.1 |
| 76G | 5.9 |
| 76C | 5.7 |
| 76D | 5.4 |
| 99 | 7.8 |

1-F. *Leishmania donovani* Inhibition Data

Compounds of formula (I) have demonstrated *Leishmania donovani* inhibitory activity. The data for some of the Exemplary compounds herein from these in vitro *Leishmania donovani* intramacrophage inhibition assay tests are provided in Table 6.

TABLE 6

| EXAMPLE | Ld-INMAC pEC$_{50}$ | THP1 pEC$_{50}$ | Ld-cAxAm-TP-pMIC pEC$_{50}$ |
|---|---|---|---|
| 48 | 5.1 | <4.3 | 5.0 |
| 70 | 4.8 | 4.3 | 6.1 |
| 54 | 4.5 | 4.3 | 4.9 |
| 81 | 4.7 | <4.3 | 5.2 |

1-G. *Trypanosoma cruzi* Inhibition Data

Compounds of formula (I) have demonstrated *Trypanosoma cruzi* inhibitory activity. The data for some of the Exemplary compounds herein from these in vitro *Trypanosoma cruzi* intracellular imaging assay tests are provided in Table 7.

TABLE 7

| EXAMPLE | *Trypanosoma cruzi* pEC$_{50}$ |
|---|---|
| 6 | 7.7 |
| 31 | 6.9 |
| 12 | 6.5 |
| 83 | 6.8 |
| 13 | 6.6 |
| 99 | 7.6 |
| 94 | 7.3 |
| 95 | 7.2 |

1-H. Cytotoxicity

Compounds of formula (I) have demonstrated cellular selectivity. The Hep G2 pEC50 data for some Exemplary compounds herein from these Hep G2 In-vitro cytotoxicity assays are provided in Table 8.

TABLE 8

| EXAMPLE | Hs HEPG2 pEC$_{50}$ |
|---|---|
| 4 | 4.3 |
| 6 | 4.8 |
| 21 | 4.3 |
| 31 | 4.3 |
| 8 | 4.3 |
| 27 | 4.3 |
| 12 | 4.6 |
| 41 | 4.6 |
| 62 | 4.3 |
| 40 | 4.3 |
| 45 | 4.3 |
| 48 | 4.5 |
| 70 | 4.5 |
| 54 | 4.3 |
| 89 | 4.3 |
| 87 | 4.6 |
| 55 | 4.3 |
| 84 | 4.3 |
| 57L | 4.3 |
| 83 | 5.1 |
| 13 | 4.7 |
| 84A | 4.3 |
| 40A | 4.3 |
| 74 | 4.5 |
| 75 | 4.3 |
| 76A | 4.3 |
| 73 | 4.7 |
| 82 | 4.3 |
| 57E | 4.3 |
| 78 | 4.7 |
| 77 | 4.4 |
| 81 | 4.8 |
| 93 | 4.9 |
| 79 | 4.3 |
| 80 | 4.3 |
| 83 | 5.1 |
| 89 | 4.3 |
| 76C | 4.3 |
| 76D | 4.3 |
| 76G | 4.5 |
| 97 | 4.7 |
| 98 | 4.3 |
| 99 | 5.3 |
| 100 | 4.3 |

2. In Vivo Data

Compounds of formula (I) have demonstrated efficacy in an in vivo anti-malarial and anti-cryptosporisiosis mouse models. Results of these in vivo tests for anti-malarial and anti-cryptosporisiosis efficacy are provided and discussed hereinafter. Tables 8, 9 and 10 illustrate the relative bioactivity of compounds of formula (I) against *Plasmodium falciparum* SCID mouse model, *Cryptosporidium parvum* INF-g-knockout model and the *Cryptosporidium parvum* NOD SCID gamma mouse model respectively.

TABLE 8

| EXAMPLE | Dose mg/kg 4 days x | % Reduction in parasitaemia |
|---|---|---|
| 54 | 20 mg/kg | 99.2 % |

TABLE 9

| EXAMPLE | Dose mg/kg 7 days x | % Reduction in parasitaemia |
|---|---|---|
| 54 | 20 mg/kg | Below level of detection |

TABLE 10

| EXAMPLE | Dose mg/kg 4 days x | % Reduction in parasitaemia |
|---|---|---|
| 77 | 50 mg/kg, twice a day (bid) | 99.6% |
| 78 | 50 mg/kg, twice a day (bid) | 99.4% |
| 74 | 50 mg/kg, twice a day (bid) | 92.5% |

The invention is illustrated by the following non-limiting examples in which the following abbreviations and definitions are used:

Abbreviations
δ chemical shift
d doublet
dd double doublet
ACN acetonitrile
DCM dichloromethane
COMU (1-cyano-2-ethoxy-2-oxoethylidenaminooxy)dimethylamino-morpholino-carbenium hexafluorophosphate
DMF dimethylformamide
CDMT 2-chloro-4,6-dimethoxy-1,3,5-triazine
DIPEA di-isopropyl ethyl amine (Hünig's base)
DMAP N,N-dimethyl-4-aminopyridine
DMAD Dimethylbut-2-ynedioate
ES low resolution electro spray mass spectroscopy
EDCl 3-(ethyliminomethyleneamino)-N,N-dimethylpropan-1-amine
EtOAc ethyl acetate
Eq(s) equivalent(s)
HBTU N,N,N',N'-tetramethyl-O-(1H-benzotriazol-1-yl) uronium hexafluorophosphate
HPLC high performance liquid chromatography
HRMS high resolution mass spectrum
LCMS liquid chromatography mass spectrometry
m multiplet
min minutes
m/z mass spectrum peak
NMO N-methyl morpholine
NMR nuclear magnetic resonance
PyBOP benzotriazol-1-yl-oxytripyrrolidinophosphonium hexafluorophosphate
q quartet
rt room temperature
S singlet
T triplet
TEA triethylamine
THF tetrahydrofuran
TLC thin layer chromatography
Equipment Reactions using microwave irradiation were carried out in a Biotage Initiator microwave. Normal phase TLCs were carried out on pre-coated silica plates (Kieselgel 60 $F_{254}$, BDH) with visualisation via U.V. light (UV254/365 nm) and/or ninhydrin solution. Flash chromatography was performed using Combiflash Companion Rf (commercially available from Teledyne ISCO) and prepacked silica gel columns purchased from Teledyne ISCO. Mass-directed preparative HPLC separations were performed using a Waters HPLC (2545 binary gradient pumps, 515 HPLC make up pump, 2767 sample manager) connected to a Waters 2998 photodiode array and a Waters 3100 mass detector. Preparative HPLC separations were performed with a Gilson HPLC (321 pumps, 819 injection module, 215 liquid handler/injector) connected to a Gilson 155 UV/vis detector. On both instruments, HPLC chromatographic separations were conducted using Waters XBridge C18 columns, 19×100 mm, 5 um particle size; using 0.1% ammonia in water (solvent A) and acetonitrile (solvent B) as mobile phase. $^1$H NMR spectra were recorded on a Bruker Avance DPX 500 spectrometer ($^1$H at 500.1 MHz, $^{13}$C at 125 MHz $^{19}$F at 470.5 MHz), or a Bruker Avance DPX 300 ($^1$H at 300 MHz). Chemical shifts (δ) are expressed in ppm recorded using the residual solvent as the internal reference in all cases. Signal splitting patterns are described as singlet (s), doublet (d), triplet (t), quartet (q), multiplet (m), broad (br), or a combination thereof. Coupling constants (J) are quoted to the nearest 0.5 Hz. Low resolution electrospray (ES) mass spectra were recorded on a Bruker MicroTof mass spectrometer, run in positive mode. LC-MS analysis and chromatographic separation were conducted with a Brucker MicrOTOf mass spectrometer or an Agilent Technologies 1200 series HPLC connected to an Agilent Technologies 6130 quadrupole LC/MS, where both instruments were connected to an Agilent diode array detector. The column used was a Waters XBridge column (50 mm×2.1 mm, 3.5 μm particle size,) and the compounds were eluted with a gradient of 5 to 95% acetonitrile/water+0.1% Ammonia.

Unless otherwise stated herein reactions have not been optimised. Solvents and reagents were purchased from commercial suppliers and used without further purification. Dry solvents were purchased in sure sealed bottles stored over molecular sieves.

The preparations and compounds have been named using the ChemDraw Ultra 12.0 naming application which is commercially available from the CambridgeSoft Corporation.

Preparative Compounds and Exemplary Compounds for the Process Illustrated in Scheme 1.

General Procedure for Schemes 1 and 1A—STEP 1 transformation a:

A solution of 2-hydroxyphenyl-ethanone, or the corresponding substituted 2-hydroxyphenyl-ethanone, (7.07 mmol) in diethyl oxalate (3.8 mL, 4 eq., 28.3 mmol) was added to sodium ethoxide 21% in ethanol (15.6 mL, 6 eq., 42.5 mmol). The mixture was stirred at 80° C. for from 1 h to 12 h. The mixture was cooled at room temperature and hydrochloric acid (HCl) 37% (5 mL) was added and the reaction mixture was stirred at 90° C. for 1 h. The solvent was then evaporated and the residue taken up with EtOAc and washed with water. LC-MS (ESI), analysis was consistent with the desired intermediate product and the washed residue was taken directly onto STEP 1, transformation b, bb or c as desired.

The following preparative (prep.) compounds were prepared according to procedure a as illustrated in Schemes 1 and 1A:

Prep. 1: ethyl 8-fluoro-4-oxo-4H-chromene-2-carboxylate

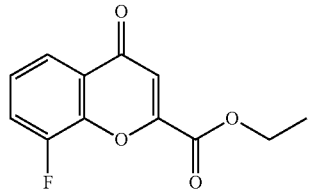 [SMILES: CCOC(=O)c1cc(=O)c2cccc(F)c2o1]

LC-MS (ESI), m/z 237 [M+H]$^+$.

Prep. 2: ethyl 6-methoxy-4-oxo-chromene-2-carboxylate

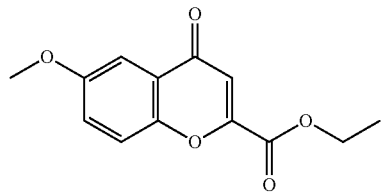 [SMILES: CCOC(=O)c1cc(=O)c2cc(OC)ccc2o1]

LC-MS (ESI), m/z 249 [M+H]$^+$.

Prep. 3: ethyl 6-cyano-4-oxo-chromene-2-carboxylate

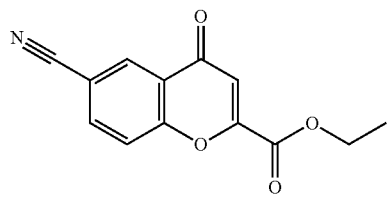 [SMILES: CCOC(=O)c1cc(=O)c2cc(C#N)ccc2o1]

LC-MS (ESI), m/z 244 [M+H]$^+$.

Prep. 4: ethyl 6-ethoxy-4-oxo-chromene-2-carboxylate

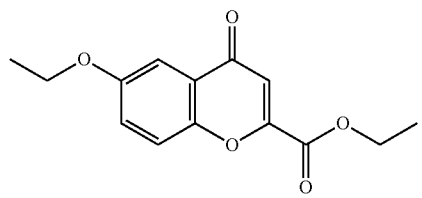 [SMILES: CCOC(=O)c1cc(=O)c2cc(OCC)ccc2o1]

LC-MS (ESI), m/z 263 [M+H]$^+$.

Prep. 5: ethyl 6-hydroxy-4-oxo-chromene-2-carboxylate

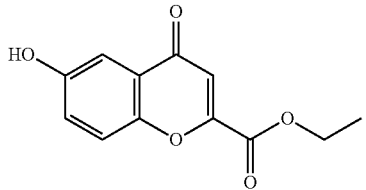 [SMILES: CCOC(=O)c1cc(=O)c2cc(O)ccc2o1]

LC-MS (ESI), m/z 235 [M+H]$^+$.

Prep. 6: ethyl 5-methoxy-4-oxo-chromene-2-carboxylate

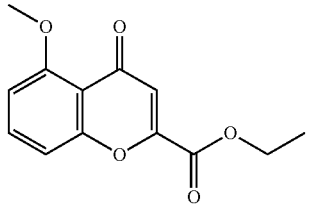 [SMILES: CCOC(=O)c1cc(=O)c2c(OC)cccc2o1]

LC-MS (ESI), m/z 249 [M+H]$^+$.

Prep. 7: ethyl 7-hydroxy-4-oxo-chromene-2-carboxylate

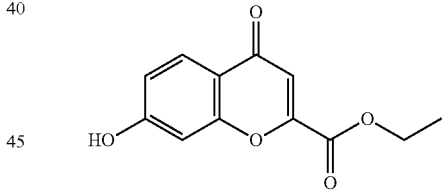

The compound of preparation 7 is also commercially available from Apollo, Scientific, Cheshire, UK and has CAS number 23866-72-0.

Prep. 8: ethyl 6,8-difluoro-4-oxo-4H-chromene-2-carboxylate

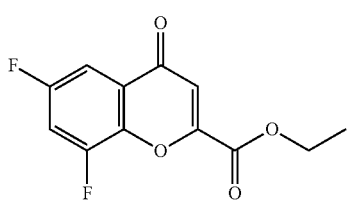 [SMILES: CCOC(=O)c1cc(=O)c2cc(F)cc(F)c2o1]

Prep. 8A. Ethyl 6-bromo-8-nitro-4-oxo-4H-chromene-2-carboxylate

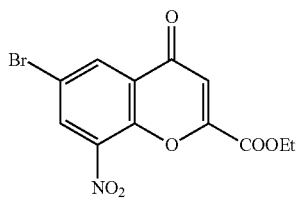

To a solution of 1-(5-bromo-2-hydroxyphenyl)ethan-1-one (1 g, 4.65 mmol) in CCl$_4$ (6 mL) was added HNO$_3$ (0.52 mL). The mixture was stirred at 70° C. for 1 h and then cooled to 25° C. and the precipitate was collected. The precipitate was washed with water (20 mL) and then petroleum ether (10 mL) to obtain a yellow solid.

Prep. 8B ethyl 8-bromo-4-oxo-4H-chromene-2-carboxylate

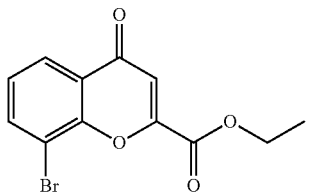 [SMILES: CCOC(=O)c1cc(=O)c2cccc(Br)c2o1]

General Procedure a was followed to obtain ethyl 6-bromo-8-nitro-4-oxo-4H-chromene-2-carboxylate.
LC-MS (ESI), m/z 342, 344 [M+H]$^+$. $^1$H NMR (400 MHz, CDCl$_3$) δ 8.61-8.60 (d, J=2.4 Hz, 1H), 8.51-8.50 (d, J=2.4 Hz, 1H), 7.24 (s, 1H), 4.54-4.49 (q, J=3.2 Hz, 2H), 1.49-1.46 (t, J=3.2 Hz, 2H).

General Procedure for Schemes 1 and 1A—STEP 2, Transformation b

A solution of 4-oxo-chromene-2-carboxylate, or a corresponding substituted 4-oxo-chromene-2-carboxylate, (7.1 mmol) in acetic acid (15 mL) and hydrochloric acid (HCl) 37% (10 mL) was stirred at 90° C. for 6 h. After that time LC-MS (ESI), analysis showed almost complete hydrolysis of the starting carboxylate material. The reaction mixture was then allowed to cool to room temperature and poured onto cold water. The resulting precipitated material was filtered-off to furnish the desired acid as a brown solid in a 46-91% yield over the two steps. LC-MS (ESI) analysis confirmed the material was consistent with the desired product. The reaction product was taken onto the next step without further purification.

The following preparative (prep.) compounds were prepared according to the general procedure for Schemes 1 and 1A—STEP 2, transformation b:

Prep. 9: 8-fluoro-4-oxo-chromene-2-carboxylic acid

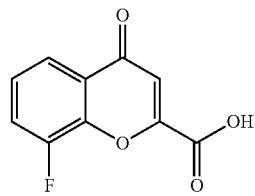

LC-MS (ESI), m/z 209 [M+H]$^+$.

Prep. 10: 7-hydroxy-4-oxo-chromene-2-carboxylic acid

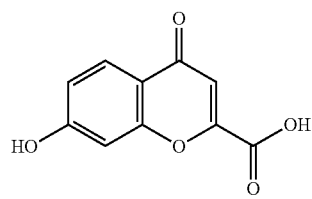 [SMILES: O=C(O)c1cc(=O)c2ccc(O)cc2o1]

LC-MS (ESI), m/z 207 [M+H]$^+$.

Prep. 11: 6-methoxy-4-oxo-chromene-2-carboxylic acid

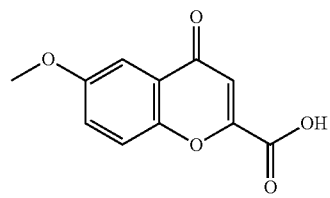 [SMILES: COc1ccc2oc(C(=O)O)cc(=O)c2c1]

LC-MS (ESI), m/z 221 [M+H]$^+$.

Prep. 12: 6-ethoxy-4-oxo-chromene-2-carboxylic acid

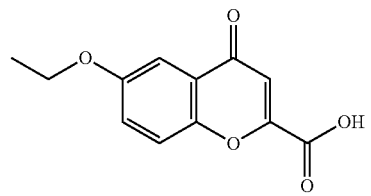 [SMILES: CCOc1ccc2oc(C(=O)O)cc(=O)c2c1]

LC-MS (ESI), m/z 235 [M+H]$^+$.

Prep. 13: 6-hydroxy-4-oxo-chromene-2-carboxylic acid

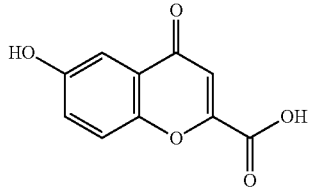 [SMILES: O=C(O)c1cc(=O)c2cc(O)ccc2o1]

LC-MS (ESI), m/z 207 [M+H]⁺.

Prep. 14: 6,8-difluoro-4-oxo-chromene-2-carboxylic acid

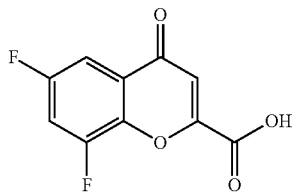 [SMILES: O=C(O)c1cc(=O)c2cc(F)cc(F)c2o1]

LC-MS (ESI), m/z 227 (M+H)⁺

Prep. 15: 6-chloro-4-oxo-4H-chromene-2-carboxylic acid. The compound of preparation 15 is also commercially available from Fluorochem Limited, Hatfield, UK and has CAS number 5006-45-1).

Prep. 16: 6-ethyl-4-oxo-4H-chromene-2-carboxylic acid. The compound of preparation 16 is also commercially available from Fluorochem Limited, Hatfield, UK and has CAS number 5527-91-3).

Prep. 17: 4-oxochromene-2-carboxylic acid. The compound of preparation 17 is also commercially available from Fluorochem Limited, Hatfield, UK and has CAS number 4940-39-0.

Prep. 18: 6-carbamoyl-4-oxo-chromene-2-carboxylic acid

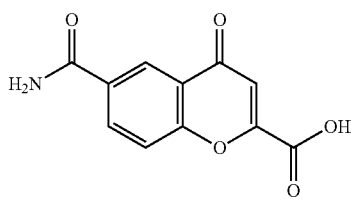 [SMILES: NC(=O)c1ccc2oc(C(=O)O)cc(=O)c2c1]

A solution of ethyl 6-cyano-4-oxo-chromene-2-carboxylate (783 mg, 3.22 mmol) in acetic acid (193 mg, 3.22 mmol) and hydrochloric acid 37% (117 mg, 3.22 mmol) was stirred at 50° C. for 6 h. After that time LC-MS (ESI), analysis showed almost complete hydrolysis of the starting carboxylate material. The reaction mixture was allowed to cool to room temperature and poured onto cold water. The precipitate was filtered off to give the desired 6-carbamoyl-4-oxo-chromene-2-carboxylic acid (500 mg, 2 mmol), in a 63% yield over the two steps. LC-MS (ESI), m/z 234 [M+H]⁺.

General Procedure for Schemes 1 and 1A—STEP 2, transformation bb.

Procedure bb for the Preparation of 5-hydroxy-4-oxo-chromene-2-carboxylic acid—Prep. 20

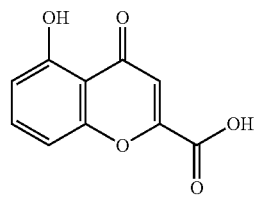 [SMILES: O=C(O)c1cc(=O)c2c(O)cccc2o1]

A mixture of ethyl 5-methoxy-4-oxo-chromene-2-carboxylate (200 mg, 0.81 mmol) in acetic acid (2.6 mL) and hydrobromic acid (HBr) 48% (1.4 mL) was stirred at 95° C. for 4 h. After allowing the mixture to cool to rt the aqueous phase was extracted with DCM, the organic phases were dried and concentrated to give the desired 5-hydroxy-4-oxo-chromene-2-carboxylic acid (113 mg, 0.55 mmol), in a 68% yield. This crude acid product was taken onto next step. LC-MS (ESI) analysis was consistent with the desired acid product. LC-MS (ESI), m/z 207 [M+H]⁺.

General Procedure for Schemes 1 and 1A—STEP 2, Transformation c.

Procedure c for the preparation of 6-cyano-4-oxo-chromene-2-carboxylic acid—Prep 21

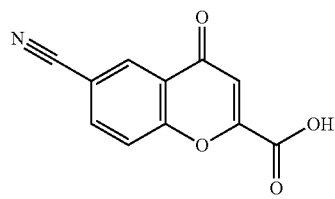 [SMILES: N#Cc1ccc2oc(C(=O)O)cc(=O)c2c1]

To a solution of ethyl 6-cyano-4-oxo-chromene-2-carboxylate (243 mg, 1 mmol) in THF (7 mL), a solution of lithium hydroxide (LiOH) (168 mg, 4 mmol) in water (4 mL) was added, and the reaction stirred at room temperature for 5 min. LC-MS (ESI) analysis, showed complete conversion of the starting carboxylate to the desired acid. The solvent (THF) was evaporated and the resulting aqueous solution was acidified with HCl 2N. The precipitate was filtered-off to provide 6-cyano-4-oxo-chromene-2-carboxylic acid (64 mg, 0.3 mmol) in a 27% yield. No further purification of the acid was required, and LC-MS (ESI) analysis was consistent with the desired product. LC-MS (ESI), m/z 216 [M+H]⁺.

Procedure c for the preparation of
6-bromo-8-nitro-4-oxo-4H-chromene-2-carboxylic
acid—Prep. 21A

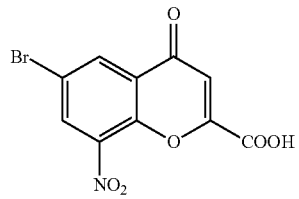 [SMILES: O=C(O)c1cc(=O)c2cc(Br)cc([N+](=O)[O-])c2o1]

To a solution of ethyl 6-bromo-8-nitro-4-oxo-4H-chromene-2-carboxylate (800 mg, 2.34 mmol) in MeOH (8 mL) and water (2 mL) was added NaOH (140 mg, 3.51 mmol). The mixture was stirred at 25° C. for 1 h. The solvent was removed and the residue was acidified by 2N HCl (10 mL). Then the mixture was extracted with ethyl acetate (20 mL). The organic layer was separated and evaporated under reduced pressure to afford (650 mg, 88% yield) as yellow solid. LC-MS (ESI), m/z 314, 316 [M+H]$^+$. $^1$H NMR (400 MHz, DMSO) δ 8.78-8.77 (d, J=2.4 Hz, 1H), 8.43-8.42 (d, J=2.4 Hz, 1H), 7.07 (s, 1H).

General Procedure for Schemes 1 and 1A, STEP 3, Amination d to Provide Exemplary Compounds of General Formula (I) from Intermediate Compounds of General Formula (III).

Exemplary Method 1:

4-oxo-chromene-2-carboxylic acid, or alternatively a corresponding substituted 4-oxo-chromene-2-carboxylic acid, (2.7 mmol) was dissolved in DMF (4 mL) and di-isopropyl ethyl amine (DIPEA) (346 mg, 2.7 mmol) were added. The reaction mixture was then cooled to 0° C. with an ice water bath and thereafter a solution of PyBOP (1.4 g, 2.7 mmol) in dry DCM (4 mL) was added. The resulting mixture was stirred at 0° C. for 20 minutes and then the appropriate amine was added to provide the desired product (2.7 mmol) was added and the reaction was stirred at room temperature for between 4 and 12 h. After solvent evaporation the crude material was purified by flash column chromatography (using Redisep® Normal-phase disposable silica flash column commercially available from Teledyne ISCO, Lincoln, Nebr., US), eluting with EtOAc in heptane. The desired fractions were concentrated to dryness to furnish the desired product. The compound was further purified by re-precipitation from MeOH.

For the avoidance of doubt, in the Examples hereinafter where flash column chromatography is used and (Redisep®) is used to describe the equipment this means that a Redisep® Normal-phase disposable silica flash column, as commercially available from Teledyne ISCO, Lincoln, Nebr., USA was used.

The following further exemplary compounds were prepared according to the general procedure for Schemes 1 and 1A, Step 3, transformation d:

Example 3

23 N-[(4-chlorophenyl)methyl]-4-oxo-chromene-2-carboxamide

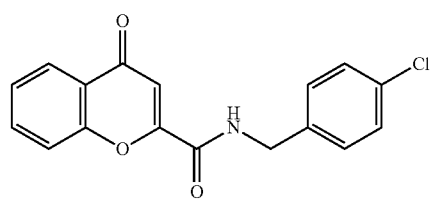 [SMILES: O=C(NCc1ccc(Cl)cc1)c1cc(=O)c2ccccc2o1]

The compound was purified by flash column chromatography eluting with 40% EtOAc in heptane, 63% yield. LC-MS (ESI), m/z 314 [M+H]$^+$. $^1$H NMR (400 MHz, DMSO) δ 9.73 (t, J=6.0 Hz, 1H), 8.07 (dd, J=1.5, 8.0 Hz, 1H), 7.93-7.88 (m, 1H), 7.73 (d, J=8.3 Hz, 1H), 7.55 (dd, J=7.6, 7.6 Hz, 1H), 7.42-7.39 (m, 4H), 6.87 (s, 1H), 4.52 (d, J=6.1 Hz, 2H).

Example 4

N-(cyclohexylmethyl)-7-hydroxy-4-oxo-chromene-2-carboxamide

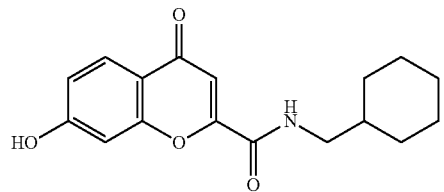 [SMILES: O=C(NCC1CCCCC1)c1cc(=O)c2ccc(O)cc2o1]

The compound was purified by flash column chromatography eluting with 40% EtOAc in heptane, 56% yield. LC-MS (ESI), m/z 302 [M+H]$^+$. $^1$H NMR (400 MHz, DMSO) δ 9.04 (t, J=6.0 Hz, 1H), 7.89 (d, J=8.8 Hz, 1H), 7.02-6.94 (m, 2H), 6.70 (s, 1H), 3.18-3.12 (m, 2H), 1.73-1.68 (m, 4H), 1.57 (d, J=7.9 Hz, 2H), 1.18 (s, 4H), 0.95 (s, 2H).

Example 5

N-(cyclohexylmethyl)-5-hydroxy-4-oxo-chromene-2-carboxamide

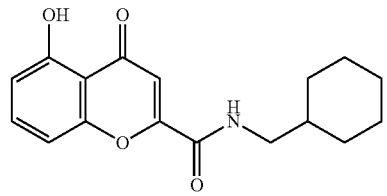 [SMILES: O=C(NCC1CCCCC1)c1cc(=O)c2c(O)cccc2o1]

The compound was purified by flash column chromatography eluting with 30% EtOAc in heptane, 81% yield. LC-MS (ESI), m/z 302 [M+H]$^+$. $^1$H NMR (400 MHz, DMSO) δ 12.29 (s, 1H), 9.15 (t, J=5.8 Hz, 1H), 7.76 (dd, J=8.4, 8.4 Hz, 1H), 7.18 (d, J=8.3 Hz, 1H), 6.89-6.85 (m, 2H), 3.15 (dd, J=6.5, 6.5 Hz, 2H), 1.73-1.68 (m, 4H), 1.58 (dd, J=3.7, 7.3 Hz, 2H), 1.18-1.16 (m, 3H), 0.97 (d, J=11.7 Hz, 2H).

Example 6

N-(cyclohexylmethyl)-6-hydroxy-4-oxo-chromene-2-carboxamide

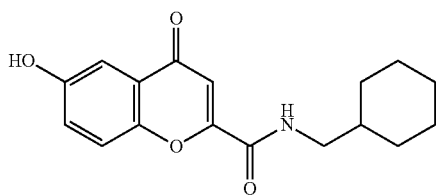 [SMILES: O=C(NCC1CCCCC1)c1cc(=O)c2cc(O)ccc2o1]

The compound was purified by flash column chromatography eluting with 55% EtOAc in heptane. The compound was further purified by re-precipitation from MeOH to furnish the desired chromene-2-carboxamide in a 31% yield. LC-MS (ESI), m/z 302 [M+H]$^+$. $^1$H NMR (500 MHz, DMSO) δ 10.13 (s, 1H), 9.04 (t, J=5.9 Hz, 1H), 7.63-7.61 (m, 1H), 7.34-7.30 (m, 2H), 6.74 (s, 1H), 3.15 (dd, J=6.5, 6.5 Hz, 2H), 1.75-1.68 (m, 4H), 1.65-1.55 (m, 2H), 1.22-1.14 (m, 3H), 0.98-0.90 (m, 2H).

Example 7

N-benzyl-4-oxo-chromene-2-carboxamide

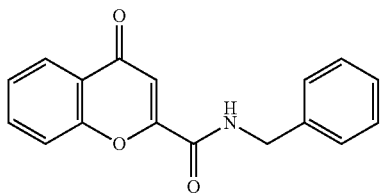 [SMILES: O=C(NCc1ccccc1)c1cc(=O)c2ccccc2o1]

The compound was purified by flash column chromatography eluting with 40% EtOAc in heptane, 15% yield. LC-MS (ESI), m/z 280 [M+H]$^+$. $^1$H NMR (400 MHz, DMSO) δ 9.71 (t, J=5.9 Hz, 1H), 8.07 (dd, J=1.6, 7.9 Hz, 1H), 7.93-7.88 (m, 1H), 7.74 (d, J=8.3 Hz, 1H), 7.55 (dd, J=7.7, 7.7 Hz, 1H), 7.37-7.36 (m, 5H), 6.87 (s, 1H), 4.53 (d, J=6.1 Hz, 2H).

Example 8

N-(cyclohexylmethyl)-8-fluoro-4-oxo-chromene-2-carboxamide

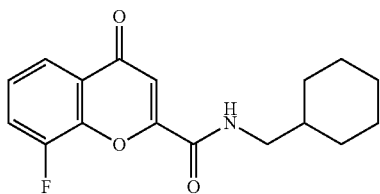 [SMILES: O=C(NCC1CCCCC1)c1cc(=O)c2cccc(F)c2o1]

The compound was purified by flash column chromatography eluting with 30% EtOAc in heptane, 27% yield. LC-MS (ESI), m/z 304 [M+H]$^+$. $^1$H NMR (400 MHz, DMSO) δ 8.92 (s, 1H), 7.88-7.83 (m, 2H), 7.55-7.50 (m, 1H), 6.90 (s, 1H), 3.15 (dd, J=6.5, 6.5 Hz, 2H), 1.69 (s, 4H), 1.21 (d, J=16.9 Hz, 4H), 0.95 (s, 3H).

Example 9

7-chloro-N-(cyclohexylmethyl)-4-oxo-chromene-2-carboxamide

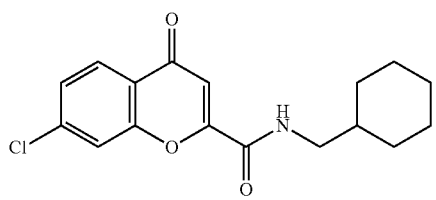 [SMILES: O=C(NCC1CCCCC1)c1cc(=O)c2ccc(Cl)cc2o1]

The compound was purified by flash column chromatography eluting with 25% EtOAc in heptane, 56% yield. LC-MS (ESI), m/z 320 [M+H]$^+$. $^1$H NMR (400 MHz, DMSO) δ 9.04 (s, 1H), 8.05 (d, J=8.6 Hz, 1H), 7.87 (d, J=1.8 Hz, 1H), 7.60 (dd, J=1.9, 8.6 Hz, 1H), 6.83 (s, 1H), 3.16 (dd, J=6.5, 6.5 Hz, 2H), 2.51 (s, 5H), 1.71 (s, 6H).

Example 10

N-(cyclohexylmethyl)-6-methoxy-4-oxo-chromene-2-carboxamide

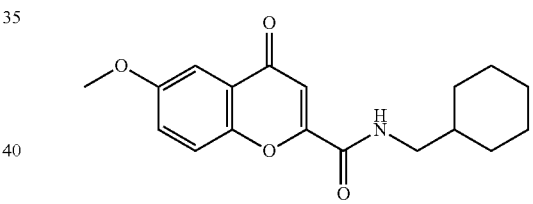

The compound was purified by flash column chromatography eluting with 25% EtOAc in heptane, 23% yield. LC-MS (ESI), m/z 316 [M+H]$^+$. $^1$H NMR (400 MHz, DMSO) δ 9.08 (t, J=6.0 Hz, 1H), 7.71 (d, J=9.2 Hz, 1H), 7.50 (dd, J=3.1, 9.2 Hz, 1H), 7.42 (d, J=3.1 Hz, 1H), 6.80 (s, 1H), 3.88 (s, 3H), 3.15 (dd, J=6.6, 6.6 Hz, 2H), 1.70-1.68 (m, 4H), 1.59 (t, J=3.6 Hz, 2H), 1.19-1.16 (m, 3H), 0.94 (d, J=10.5 Hz, 2H).

Example 11

8-bromo-N-(cyclohexylmethyl)-4-oxo-chromene-2-carboxamide

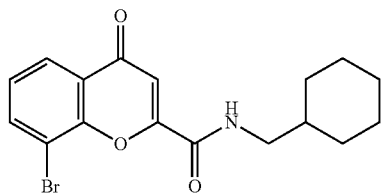 [SMILES: O=C(NCC1CCCCC1)c1cc(=O)c2cccc(Br)c2o1]

The compound was purified by flash column chromatography eluting with 25% EtOAc in heptane, 55% yield. LC-MS (ESI), m/z 365 [M+H]⁺. ¹H NMR (400 MHz, DMSO) δ 8.55 (t, J=5.7 Hz, 1H), 8.19 (d, J=7.7 Hz, 1H), 8.04 (d, J=7.9 Hz, 1H), 7.47 (dd, J=7.8, 7.8 Hz, 1H), 6.89 (s, 1H), 3.17 (dd, J=6.4, 6.4 Hz, 2H), 1.75-1.69 (m, 4H), 1.62-1.55 (m, 2H), 1.26-1.13 (m, 3H), 1.01-0.92 (m, 2H).

Example 12

N-(cyclohexylmethyl)-8-hydroxy-4-oxo-chromene-2-carboxamide

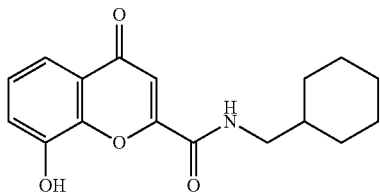 [SMILES: O=C(NCC1CCCCC1)c1cc(=O)c2cccc(O)c2o1]

The compound was purified by flash column chromatography eluting with 45% EtOAc in heptane, 11% yield. LC-MS (ESI), m/z 302 [M+H]⁺. ¹H NMR (500 MHz, DMSO) δ 10.32-10.29 (m, 1H), 9.15 (s, 1H), 7.48 (dd, J=1.7, 7.6 Hz, 1H), 7.38-7.30 (m, 2H), 6.83 (s, 1H), 3.20 (dd, J=6.6, 6.6 Hz, 2H), 1.77-1.68 (m, 3H), 1.64-1.57 (m, 2H), 1.25-1.15 (m, 4H), 1.00-0.93 (m, 2H).

Example 13

6-hydroxy-N-[(1-hydroxycyclohexyl)methyl]-4-oxo-chromene-2-carboxamide

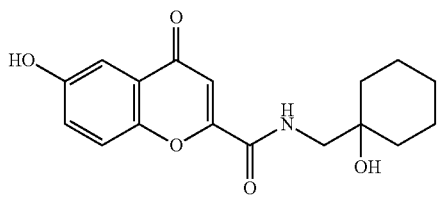 [SMILES: O=C(NCC1(O)CCCCC1)c1cc(=O)c2cc(O)ccc2o1]

The compound was purified by flash column chromatography eluting with 65% to 80% EtOAc in heptane and then further purified by prep HPLC, acidic method, 5-95% ACN in water, 24% yield. LC-MS (ESI), m/z 318 [M+H]⁺. ¹H NMR (400 MHz, DMSO) δ 10.14 (s, 1H), 8.67 (t, J=6.1 Hz, 1H), 7.67-7.63 (m, 1H), 7.34-7.30 (m, 2H), 6.78 (s, 1H), 4.41 (s, 1H), 3.29 (d, J=6.2 Hz, 2H), 1.58-1.44 (m, 6H), 1.42-1.35 (m, 4H).

Example 14

N-[(4-chlorophenyl)methyl]-7-hydroxy-4-oxo-chromene-2-carboxamide

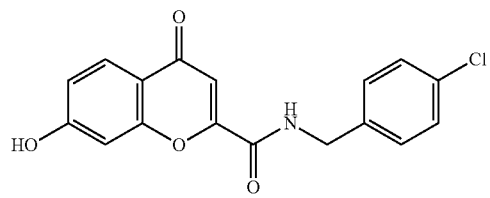 [SMILES: O=C(NCc1ccc(Cl)cc1)c1cc(=O)c2ccc(O)cc2o1]

The compound was purified by flash column chromatography eluting with 40% EtOAc in heptane, 56% yield. LC-MS (ESI), m/z 330 [M+H]⁺. ¹H NMR (400 MHz, DMSO) δ 9.66 (t, J=5.9 Hz, 1H), 7.89 (d, J=8.6 Hz, 1H), 7.43-7.36 (m, 4H), 7.00-6.94 (m, 2H), 6.74 (s, 1H), 4.50 (d, J=6.1 Hz, 2H).

Example 15

N-[(4-chlorophenyl)methyl]-5-hydroxy-4-oxo-chromene-2-carboxamide

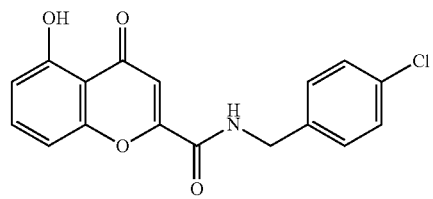 [SMILES: O=C(NCc1ccc(Cl)cc1)c1cc(=O)c2c(O)cccc2o1]

The compound was purified by flash column chromatography eluting with 40% EtOAc in heptane, 53% yield. LC-MS (ESI), m/z 330 [M+H]⁺. ¹H NMR (400 MHz, DMSO) δ 12.27 (s, 1H), 9.75 (d, J=5.9 Hz, 1H), 7.76 (dd, J=8.3, 8.3 Hz, 1H), 7.44-7.37 (m, 4H), 7.16 (d, J=8.3 Hz, 1H), 6.90-6.87 (m, 2H), 4.51 (d, J=6.1 Hz, 2H).

Example 16

7-hydroxy-N-isobutyl-4-oxo-chromene-2-carboxamide

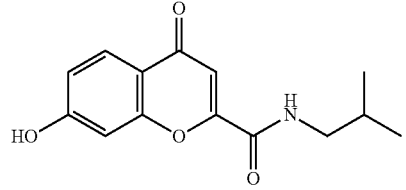 [SMILES: CC(C)CNC(=O)c1cc(=O)c2ccc(O)cc2o1]

The compound was purified by flash column chromatography eluting with 65% EtOAc in heptane and then further purified by prep HPLC, acidic method, 5-95% ACN in water, to furnish the desired product in a 17% yield. LC-MS (ESI), m/z 262 [M+H]⁺. ¹H NMR (400 MHz, DMSO) δ 11.05-11.05 (m, 1H), 9.06 (t, J=5.8 Hz, 1H), 7.88 (d, J=8.7

Hz, 1H), 7.01-6.93 (m, 2H), 6.70 (s, 1H), 3.12 (dd, J=6.6, 6.6 Hz, 2H), 1.92-1.85 (m, 1H), 0.91 (d, J=6.7 Hz, 6H).

Example 17

N-isobutyl-4-oxo-chromene-2-carboxamide

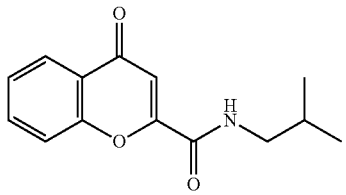 [SMILES: CC(C)CNC(=O)c1cc(=O)c2ccccc2o1]

The compound was purified by flash column chromatography eluting with 40% EtOAc in heptane, 23% yield. LC-MS (ESI), m/z 246 [M+H]$^+$. $^1$H NMR (400 MHz, DMSO) δ 9.14-9.11 (m, 1H), 8.06 (dd, J=1.7, 8.0 Hz, 1H), 7.93-7.88 (m, 1H), 7.76 (d, J=8.5 Hz, 1H), 7.55 (dd, J=7.6, 7.6 Hz, 1H), 6.83 (s, 1H), 3.14 (dd, J=6.6, 6.6 Hz, 2H), 1.93-1.86 (m, 1H), 0.92 (d, J=6.7 Hz, 6H).

Example 18

N-[(3-carbamoylphenyl)methyl]-4-oxo-chromene-2-carboxamide

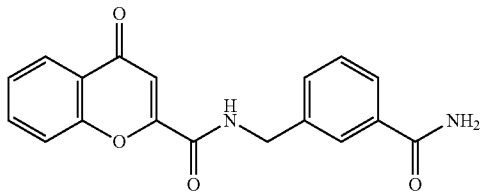 [SMILES: NC(=O)c1cccc(CNC(=O)c2cc(=O)c3ccccc3o2)c1]

The compound was purified by flash column chromatography eluting with 2% MeOH in DCM and then further purified by re-precipitation from DCM, 14% yield. LC-MS (ESI), m/z 323 [M+H]$^+$. $^1$H NMR (400 MHz, DMSO) δ 9.74 (s, 1H), 8.07 (dd, J=1.5, 7.9 Hz, 1H), 7.93-7.86 (m, 3H), 7.80-7.73 (m, 2H), 7.57-7.50 (m, 2H), 7.46-7.41 (m, 2H), 6.88 (s, 1H), 4.57 (d, J=6.1 Hz, 2H).

Example 19

N-cyclohexyl-4-oxo-chromene-2-carboxamide

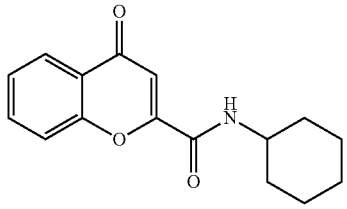 [SMILES: O=C(NC1CCCCC1)c1cc(=O)c2ccccc2o1]

Product was purified by preparative HPLC (Gilson) using a 5-50% method and 0.1% NH$_3$ in water and acetonitrile as eluents, 44% yield. $^1$H NMR (500 MHz, CDCl$_3$) δ 8.24 (dd, J=1.4, 8.0 Hz, 1H), 7.78-7.74 (m, 1H), 7.56 (d, J=7.9 Hz, 1H), 7.50-7.46 (m, 1H), 7.19 (s, 1H), 6.75 (d, J=7.6 Hz, 1H), 4.05-3.96 (m, 1H), 2.10-2.03 (m, 1H), 1.86-1.79 (m, 2H), 1.73-1.66 (m, 2H), 1.51-1.23 (m, 5H). LC-MS (ESI), m/z 272 (M+H)$^+$.

Example 20

4-oxo-N-(tetrahydropyran-4-ylmethyl)chromene-2-carboxamide

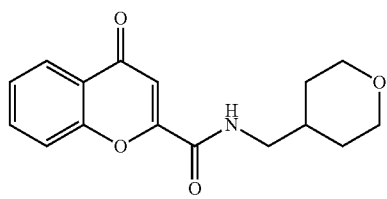 [SMILES: O=C(NCC1CCOCC1)c1cc(=O)c2ccccc2o1]

Product was purified by preparative HPLC (Gilson) using a 5-50% method and 0.1% HCO$_2$H in water and acetonitrile as eluents. The product was then further purified using a mass directed autopreparative (MDA, Waters) using a 5-40% method and 0.1% HCO$_2$H in water and acetonitrile as eluents. Purified product obtained in a 3% yield. $^1$H NMR (500 MHz, CDCl$_3$) δ 8.26 (dd, J=1.7, 7.9 Hz, 1H), 7.80-7.75 (m, 1H), 7.56-7.48 (m, 2H), 7.21 (s, 1H), 7.00 (s, 1H), 4.04 (dd, J=3.6, 10.9 Hz, 2H), 3.46-3.40 (m, 4H), 2.01-1.93 (m, 1H), 1.72 (dd, J=1.8, 13.0 Hz, 2H), 1.49-1.39 (m, 2H). LC-MS (ESI), m/z 288 (M+H)$^+$.

Example 21

N-[(4,4-difluorocyclohexyl)methyl]-4-oxo-chromene-2-carboxamide

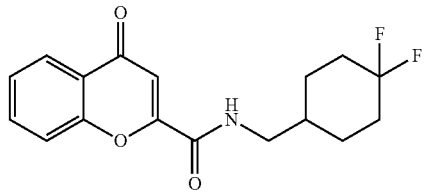 [SMILES: O=C(NCC1CCC(F)(F)CC1)c1cc(=O)c2ccccc2o1]

Product was purified by preparative HPLC (Gilson) using a 5-50% method and 0.1% NH$_3$ in water and acetonitrile as eluents. Purified product obtained in a 17% yield. $^1$H NMR (500 MHz, CDCl$_3$) δ 8.25 (dd, J=1.4, 7.9 Hz, 1H), 7.79-7.76 (m, 1H), 7.56-7.48 (m, 2H), 7.20 (s, 1H), 7.04 (d, J=10.7 Hz, 1H), 3.45 (dd, J=6.6, 6.6 Hz, 2H), 2.20-1.69 (m, 7H), 1.47-1.37 (m, 2H). LC-MS (ESI), m/z 322 (M+H)$^+$.

Example 22

N-[(4-methylcyclohexyl)methyl]-4-oxo-chromene-2-carboxamide

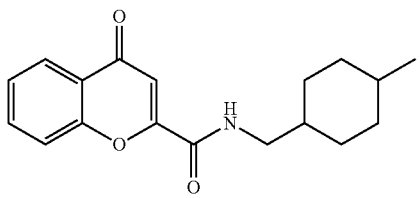 [SMILES: CC1CCC(CNC(=O)c2cc(=O)c3ccccc3o2)CC1]

Product was purified by preparative HPLC (Gilson) using a 5-50% method and 0.1% $NH_3$ in water and acetonitrile as eluents. Purified product obtained in a 45% yield. $^1$H NMR (500 MHz, DMSO) δ 9.10 (dd, J=5.7, 5.7 Hz, 1H), 8.06 (dd, J=1.7, 7.9 Hz, 1H), 7.92-7.88 (m, 1H), 7.75 (d, J=7.8 Hz, 1H), 7.56-7.53 (m, 1H), 6.83 (d, J=1.7 Hz, 1H), 3.16 (dd, J=6.5, 6.5 Hz, 2H), 1.82-1.65 (m, 3H), 1.55-1.40 (m, 3H), 1.33-1.24 (m, 1H), 1.03-0.89 (m, 3H), 0.86 (d, J=6.7 Hz, 3H). LC-MS (ESI), m/z 300 (M+H)$^+$.

Example 23

N-(cyclopentylmethyl)-4-oxo-chromene-2-carboxamide

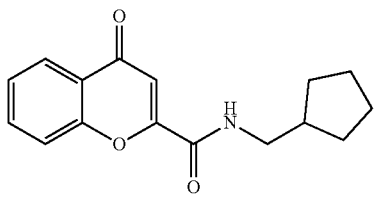 [SMILES: O=C(NCC1CCCC1)c1cc(=O)c2ccccc2o1]

Product was purified by preparative HPLC (Gilson) using a 5-50% method and 0.1% $NH_3$ in water and acetonitrile as eluents. Purified product obtained in a 34% yield. $^1$H NMR (500 MHz, DMSO) δ 9.14 (t, J=5.7 Hz, 1H), 8.06 (dd, J=1.4, 8.0 Hz, 1H), 7.92-7.88 (m, 1H), 7.76 (d, J=7.8 Hz, 1H), 7.57-7.53 (m, 1H), 6.83 (s, 1H), 3.24 (dd, J=6.0, 7.3 Hz, 2H), 2.24-2.14 (m, 1H), 1.74-1.48 (m, 6H), 1.32-1.23 (m, 2H). LC-MS (ESI), m/z 272 (M+H)$^+$.

The 1-hydroxy analogue, N-[(1-hydroxycyclopentyl) methyl]-4-oxo-chromene-2-carboxamide, Example 23A, was prepared from the appropriate starting materials using analagous chemistry.

Example 24

4-oxo-N-(tetrahydrofuran-2-ylmethyl)chromene-2-carboxamide

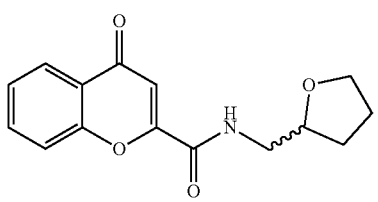 [SMILES: O=C(NCC1CCCO1)c1cc(=O)c2ccccc2o1]

Product was purified by preparative HPLC (Gilson) using a 5-50% method and 0.1% $NH_3$ in water and acetonitrile as eluents. Purified product obtained in a 7% yield. $^1$H NMR (500 MHz, CDCl$_3$) δ 8.24 (dd, J=1.4, 7.9 Hz, 1H), 7.78-7.74 (m, 1H), 7.56 (d, J=7.9 Hz, 1H), 7.50-7.46 (m, 1H), 7.29 (s, 1H), 7.19 (s, 1H), 4.12 (ddd, J=3.1, 7.3, 14.6 Hz, 1H), 3.98-3.93 (m, 1H), 3.87-3.82 (m, 2H), 3.41-3.35 (m, 1H), 2.13-2.06 (m, 1H), 2.01-1.96 (m, 2H), 1.64 (ddd, J=7.6, 12.3, 15.8 Hz, 1H). LC-MS (ESI), m/z 274 (M+H)$^+$.

Example 25

N-cycloheptyl-4-oxo-chromene-2-carboxamide

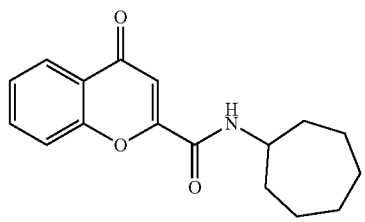 [SMILES: O=C(NC1CCCCCC1)c1cc(=O)c2ccccc2o1]

Product was purified by preparative HPLC (Gilson) using a 5-50% method and 0.1% $NH_3$ in water and acetonitrile as eluents. Purified product obtained in a 9% yield. $^1$H NMR (400 MHz, CDCl$_3$) δ 8.25 (dd, J=1.5, 8.0 Hz, 1H), 7.79-7.74 (m, 1H), 7.57-7.46 (m, 2H), 7.19 (s, 1H), 6.78 (d, J=7.1 Hz, 1H), 4.22-4.14 (m, 1H), 2.12-2.06 (m, 2H), 1.75-1.58 (m, 10H). LC-MS (ESI), m/z 286 (M+H)$^+$.

Example 26

N-(2-cyclopentylethyl)-4-oxo-chromene-2-carboxamide

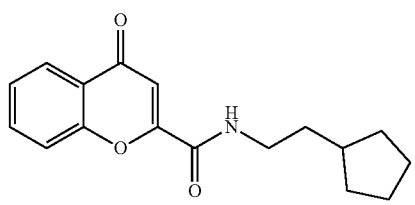 [SMILES: O=C(NCCC1CCCC1)c1cc(=O)c2ccccc2o1]

Product was purified by preparative HPLC (Gilson) using a 5-95% method and 0.1% $NH_3$ in water and acetonitrile as eluents. Purified product obtained in a 13% yield. $^1$H NMR (400 MHz, CDCl$_3$) δ 8.25 (dd, J=1.5, 8.0 Hz, 1H), 7.78-7.74 (m, 1H), 7.55-7.46 (m, 2H), 7.28 (s, 1H), 7.19 (s, 1H), 6.90-6.90 (m, 1H), 3.57-3.51 (m, 2H), 1.92-1.84 (m, 4H), 1.75-1.55 (m, 5H), 1.25-1.15 (m, 2H). LC-MS (ESI), m/z 286 (M+H)$^+$.

Example 27

N-[(1-hydroxycyclohexyl)methyl]-4-oxo-chromene-2-carboxamide

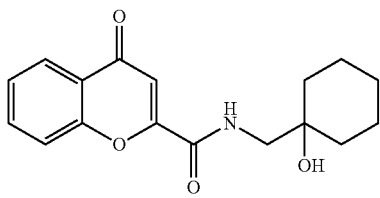 [SMILES: O=C(NCC1(O)CCCCC1)c1cc(=O)c2ccccc2o1]

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 45% yield. $^1$H NMR (500 MHz, CDCl$_3$) δ 8.18 (dd, J=1.7, 7.9 Hz, 1H), 7.73-7.69 (m, 1H), 7.52 (d, J=7.9 Hz, 1H), 7.45-7.41 (m, 2H), 3.54 (d, J=6.1 Hz, 2H), 2.37 (s, 1H), 1.67-1.52 (m, 9H), 1.42-1.34 (m, 1H). LC-MS (ESI), m/z 302 (M+H)$^+$.

Example 28

N-(cyclohexylmethyl)-6-methyl-4-oxo-chromene-2-carboxamide

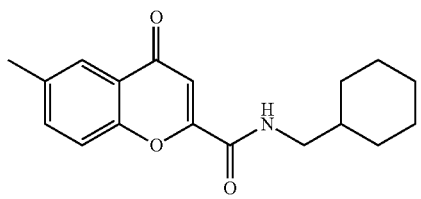 [SMILES: Cc1ccc2oc(C(=O)NCC3CCCCC3)cc(=O)c2c1]

Product was purified by column chromatography using a 12 g silica cartridge (Redisep®) and heptane (A) and ethyl acetate (B) as solvents. The following purification gradient was used: 3 min hold A, 18 min ramp to 70% B, 3 min hold 70% B. Purified product obtained in a 32% yield. $^1$H NMR (400 MHz, CDCl$_3$) δ 7.89 (d, J=1.2 Hz, 1H), 7.45 (dd, J=1.9, 8.6 Hz, 1H), 7.35 (d, J=8.5 Hz, 1H), 7.15-7.10 (m, 1H), 7.06 (s, 1H), 3.28-3.23 (m, 2H), 2.37 (s, 3H), 1.73-1.53 (m, 5H), 1.23-1.06 (m, 4H), 0.99-0.78 (m, 2H). LC-MS (ESI), m/z 300 (M+H)$^+$.

Example 29

6-bromo-N-(cyclohexylmethyl)-4-oxo-chromene-2-carboxamide

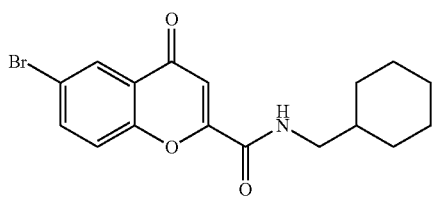

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 29% yield. $^1$H NMR (500 MHz, CDCl$_3$) δ 8.37 (d, J=2.4 Hz, 1H), 7.84 (dd, J=2.4, 9.0 Hz, 1H), 7.46 (d, J=8.9 Hz, 1H), 7.20 (s, 1H), 6.90 (s, 1H), 3.37 (dd, J=6.6, 6.6 Hz, 2H), 1.83-1.64 (m, 6H), 1.32-1.20 (m, 3H), 1.10-1.00 (m, 2H). LC-MS (ESI), m/z 363 and 366 (M+H)$^+$.

Example 30

6-Chloro-N-(cyclohexylmethyl)-4-oxo-chromene-2-carboxamide

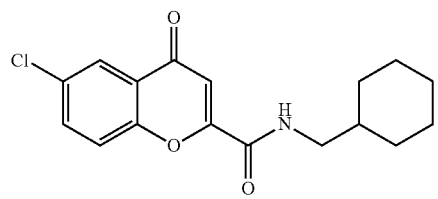 [SMILES: O=C(NCC1CCCCC1)c1cc(=O)c2cc(Cl)ccc2o1]

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 31% yield. $^1$H NMR (500 MHz, CDCl$_3$) δ 8.22 (d, J=2.4 Hz, 1H), 7.71 (dd, J=2.7, 8.9 Hz, 1H), 7.53 (d, J=9.0 Hz, 1H), 7.20 (s, 1H), 6.89 (s, 1H), 3.37 (dd, J=6.6, 6.6 Hz, 2H), 1.84-1.64 (m, 6H), 1.33-1.20 (m, 3H), 1.10-1.01 (m, 2H).

Example 31

N-(cyclohexylmethyl)-6-fluoro-4-oxo-chromene-2-carboxamide

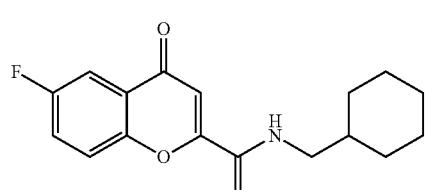

Product was purified by column chromatography using a 12 g silica cartridge (Redisep®) and heptane (A) and ethyl acetate (B) as solvents. The product was precipitated from a mixture of methanol and DMSO. Purified product obtained in a 10% yield. $^1$H NMR (500 MHz, CDCl$_3$) δ 7.87 (dd, J=3.1, 8.1 Hz, 1H), 7.56 (dd, J=4.1, 9.2 Hz, 1H), 7.47 (ddd, J=3.1, 7.4, 9.2 Hz, 1H), 7.17 (s, 1H), 6.88 (s, 1H), 3.36 (dd, J=6.6, 6.6 Hz, 2H), 1.84-1.75 (m, 3H), 1.74-1.62 (m, 2H), 1.56 (s, 1H), 1.33-1.18 (m, 3H), 1.08-0.99 (m, 2H). LC-MS (ESI), m/z 304 (M+H)$^+$.

Example 32

6-fluoro-4-oxo-N-(tetrahydropyran-2-ylmethyl)chromene-2-carboxamide

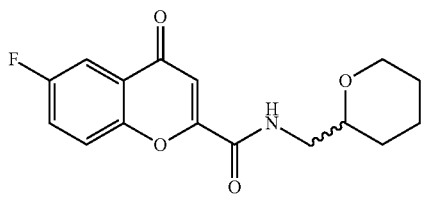 [SMILES: O=C(NCC1CCCCO1)c1cc(=O)c2cc(F)ccc2o1]

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 21% yield. $^1$H NMR (500 MHz, CDCl$_3$) δ 7.81 (dd, J=3.1, 8.1 Hz, 1H), 7.56-7.52 (m, 1H), 7.43 (ddd, J=3.1, 7.5, 9.2 Hz, 1H), 7.28 (s, 1H), 7.12 (s, 1H), 4.02-3.97 (m, 1H), 3.75 (ddd, J=3.1, 7.2, 13.9 Hz, 1H), 3.52-3.42 (m, 2H), 3.22 (ddd, J=4.4, 8.4, 13.9 Hz, 1H), 1.88-1.82 (m, 1H), 1.64-1.48 (m, 4H), 1.36-1.20 (m, 1H). LC-MS (ESI), m/z 306 (M+H)$^+$.

Example 33

6-fluoro-4-oxo-N-(tetrahydropyran-3-ylmethyl)chromene-2-carboxamide

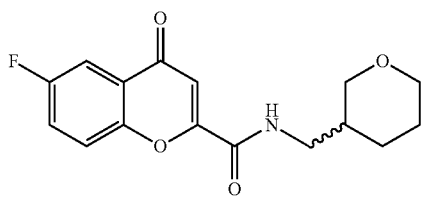 [SMILES: O=C(NCC1CCCOC1)c1cc(=O)c2cc(F)ccc2o1]

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 70% yield. $^1$H NMR (500 MHz, DMSO) δ 9.15 (dd, J=5.8, 5.8 Hz, 1H), 7.84-7.73 (m, 3H), 6.84 (s, 1H), 3.81-3.69 (m, 2H), 3.36 (dd, J=2.7, 10.6 Hz, 1H), 3.23-3.13 (m, 3H), 1.88-1.76 (m, 2H), 1.61 (ddd, J=3.9, 7.5, 17.2 Hz, 1H), 1.51-1.42 (m, 1H), 1.32-1.17 (m, 1H). LC-MS (ESI), m/z 306 (M+H)$^+$.

Example 34

6-fluoro-4-oxo-N-[(2-oxo-3-piperidyl)methyl]chromene-2-carboxamide

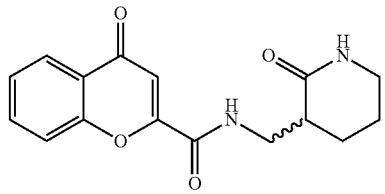 [SMILES: O=C(NCC1CCCNC1=O)c1cc(=O)c2ccccc2o1]

Product was purified by preparative HPLC (Gilson) using a 5-40% method and 0.1% NH$_3$ in water and acetonitrile as eluents. Purified product obtained in a 39% yield. $^1$H NMR (500 MHz, DMSO) δ 9.19-9.16 (m, 1H), 7.83-7.80 (m, 2H), 7.79-7.74 (m, 1H), 7.56 (s, 1H), 6.85 (s, 1H), 3.71-3.66 (m, 1H), 3.44 (ddd, J=7.2, 9.0, 13.2 Hz, 1H), 3.16-3.11 (m, 2H), 2.50-2.45 (m, 1H), 1.92-1.86 (m, 1H), 1.82-1.76 (m, 1H), 1.64-1.58 (m, 1H), 1.54-1.46 (m, 1H). LC-MS (ESI), m/z 319 (M+H)$^+$.

Example 35

6-fluoro-4-oxo-N-(4,4,4-trifluorobutyl)chromene-2-carboxamide

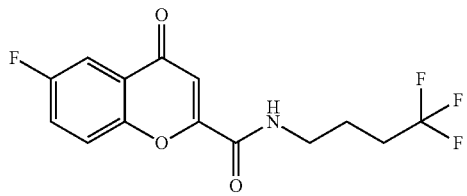 [SMILES: O=C(NCCCC(F)(F)F)c1cc(=O)c2cc(F)ccc2o1]

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 33% yield. $^1$H NMR (500 MHz, DMSO) δ9.21 (t, J=5.7 Hz, 1H), 7.83-7.80 (m, 2H), 7.76-7.73 (m, 1H), 6.85 (s, 1H), 3.43-3.31 (m, 2H), 2.41-2.30 (m, 2H), 1.83-1.76 (m, 2H). LC-MS (ESI), m/z 318 (M+H)$^+$.

Example 36

6-fluoro-N-(norbornan-2-ylmethyl)-4-oxo-chromene-2-carboxamide

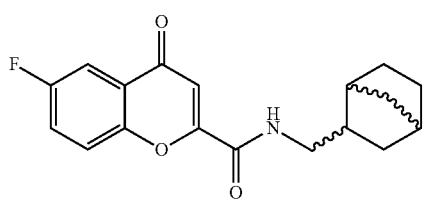

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 54% yield. $^1$H NMR (500 MHz, DMSO) δ 9.18 (dd, J=5.8, 5.8 Hz, 1H), 7.86-7.73 (m, 3H), 6.84 (s, 1H), 3.19-3.03 (m, 2H), 2.23-2.17 (m, 2H), 2.11 (d, J=3.2 Hz, 1H), 1.79-1.59 (m, 1H), 1.53-1.45 (m, 2H), 1.39-1.26 (m, 2H), 1.15-1.08 (m, 3H). LC-MS (ESI), m/z 316 (M+H)$^+$.

Example 37 tert-butyl N-[1-[[(6-fluoro-4-oxo-chromene-2-carbonyl)amino]-methyl]cyclohexyl]carbamate

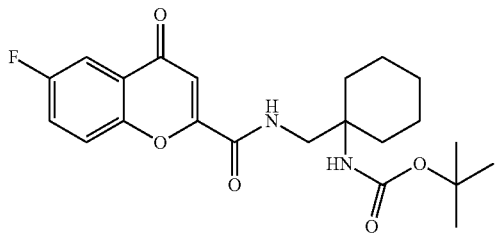 [SMILES: CC(C)(C)OC(=O)NC1(CNC(=O)c2cc(=O)c3cc(F)ccc3o2)CCCCC1]

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 71% yield. $^1$H NMR (500 MHz, DMSO) δ 8.96-8.92 (m, 1H), 7.84-7.81 (m, 2H), 7.77-7.74 (m, 1H), 6.87 (s, 1H), 6.49-6.46 (m, 1H), 3.47 (d, J=6.1 Hz, 2H), 2.10 (d, J=12.2 Hz, 2H), 1.41 (s, 13H), 1.32-1.18 (m, 4H). LC-MS (ESI), m/z 319 (M+H−t-BuCO)$^+$.

Example 38

N-[(1-aminocyclohexyl)methyl]-6-fluoro-4-oxo-chromene-2-carboxamide hydrochloride

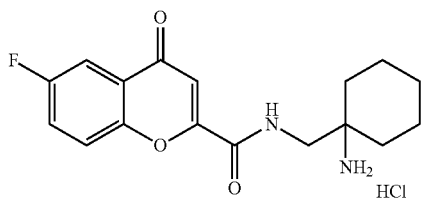 [SMILES: NC1(CNC(=O)c2cc(=O)c3cc(F)ccc3o2)CCCCC1 ; Cl]

tert-butyl N-[1-[[(6-fluoro-4-oxo-chromene-2-carbonyl)amino]methyl]cyclohexyl] carbamate (277 mg, 0.63 mmol) was dissolved in a 4 M solution of hydrogen chloride in Dioxane (3.14 mL, 12.58 mmol) at room temperature to give a clear solution. The reaction mixture was stirred at room temperature for 4 h and a white precipitate was formed. Solvents were removed under reduced pressured. The resulting residue was suspended in acetonitrile (20 mL) and the solvent was removed under reduced pressure to obtain N-[(1-aminocyclohexyl)methyl]-6-fluoro-4-oxo-chromene-2-carboxamide hydro-chloride (230 mg, 98% yield) as an off-white solid. $^1$H NMR (500 MHz, DMSO) δ 9.53 (dd, J=6.2, 6.2 Hz, 1H), 8.14 (s, 3H), 8.00 (dd, J=4.3, 9.2 Hz, 1H), 7.86-7.80 (m, 1H), 7.76 (dd, J=3.2, 8.2 Hz, 1H), 6.94 (s, 1H), 3.63-3.57 (m, 2H), 1.73 (dd, J=5.3, 11.4 Hz, 2H), 1.66-1.56 (m, 4H), 1.53-1.48 (m, 3H), 1.35-1.28 (m, 1H). LC-MS (ESI), m/z 319 (M+H)$^+$.

Example 39

N-[(1-aminocyclohexyl)methyl]-6-fluoro-4-oxo-chromene-2-carboxamide hydrochloride

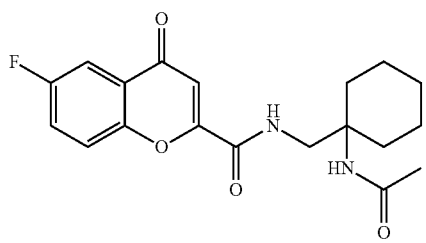 [SMILES: CC(=O)NC1(CNC(=O)c2cc(=O)c3cc(F)ccc3o2)CCCCC1]

To a solution of N-[(1-aminocyclohexyl)methyl]-6-fluoro-4-oxo-chromene-2-carboxamide hydrochloride (72 mg, 0.19 mmol) and diisopropylethylamine (50 mg, 0.39 mmol) in DCM (5 mL), acetyl chloride (0.03 mL, 0.42 mmol) was added. The reaction was stirred at room temperature overnight. Reaction was quenched with an aqueous saturated solution of NaHCO$_3$ and extracted with DCM. The organic phase was separated and dried over MgSO$_4$. The solvent was removed under reduced pressure. Product was purified by preparative HPLC (Gilson) using 5-50% method and 0.1% NH$_3$ in water and acetonitrile as eluents. Fractions containing product were evaporated (Genevac) and pooled together to obtain the desired N-[(1-acetamidocyclohexyl)methyl]-6-fluoro-4-oxo-chromene-2-carboxamide (25 mg, 34% yield) as a white solid. $^1$H NMR (500 MHz, DMSO) δ 9.27-9.24 (m, 1H), 7.86-7.74 (m, 3H), 7.35 (s, 1H), 6.87 (s, 1H), 3.56 (d, J=6.0 Hz, 2H), 2.09 (d, J=13.4 Hz, 2H), 1.89 (s, 3H), 1.53-1.28 (m, 7H), 1.23-1.19 (m, 1H). LC-MS (ESI), m/z 361 (M+H)$^+$.

Example 40

6-fluoro-N-[[1-(hydroxymethyl)cyclohexyl]methyl]-4-oxo-chromene-2-carboxamide

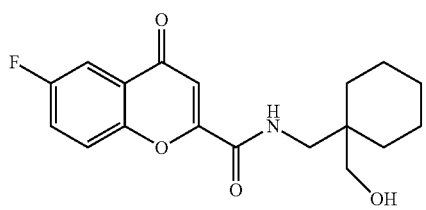 [SMILES: O=C(NCC1(CO)CCCCC1)c1cc(=O)c2cc(F)ccc2o1]

Product was purified by column chromatography using a 12 g silica cartridge (Redisep®) and heptane (A) and ethyl acetate (B) as solvents. The following purification gradient was used: 3 min hold A, 18 min ramp to 100% B, 3 min hold 100% B. Purified product obtained in a 56% yield. $^1$H NMR (500 MHz, DMSO) δ 8.86 (t, J=6.1 Hz, 1H), 7.83-7.80 (m, 2H), 7.79-7.74 (m, 1H), 6.85 (s, 1H), 4.70 (t, J=5.7 Hz, 1H), 3.34-3.32 (m, 2H), 1.48-1.28 (m, 12H). LC-MS (ESI), m/z 334 (M+H)+.

Example 40A

6-Fluoro-N-((1-(2-hydroxyethyl)cyclohexyl)methyl)-4-oxo-4H-chromene-2-carboxamide

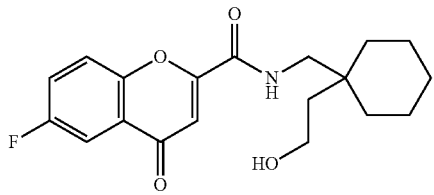 [SMILES: O=C(NCC1(CCO)CCCCC1)c1cc(=O)c2cc(F)ccc2o1]

The product was purified by preparative HPLC (column: YMC-Actus ODS-AQ 150*30 5u; mobile phase: [water (0.1% TFA)-ACN]; B %:35%-65%, 11 min), 50% yield. ¹H NMR (400 MHz, DMSO) δ 9.14 (s, 1H), 7.84-7.73 (m, 3H), 6.84 (s, 1H), 4.99 (s, 1H), 3.58-3.58 (m, 2H), 3.31-3.29 (m, 2H), 1.53-1.31 (m, 12H). LC-MS (ESI), m/z 348 (M+H)+

Example 41

6-fluoro-N-[(1-hydroxycyclohexyl)methyl]-4-oxo-chromene-2-carboxamide

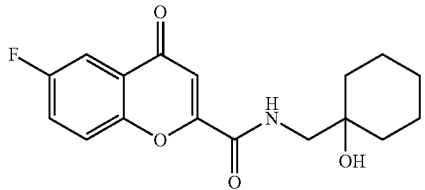 [SMILES: O=C(NCC1(O)CCCCC1)c1cc(=O)c2cc(F)ccc2o1]

Product was purified by column chromatography using a 12 g silica cartridge (Redisep® Normal-phase disposable silica flash column commercially available from Teledyne ISCO, Lincoln, Nebr., USA) using heptane (solvent A) and ethyl acetate (solvent B) as solvents. The following purification gradient was used: 3 min hold A, 11 min ramp to 50% B, 10 min hold 50% B. Samples containing product were pooled together to obtain crude product as a yellow solid (260 mg). The product was further purified by preparative HPLC (Gilson) using a 5-50% method and using 0.1% formic acid in water and acetonitrile as eluents. 21% yield. ¹H NMR (500 MHz, CDCl₃) δ 7.83 (dd, J=3.1, 7.9 Hz, 1H), 7.60-7.56 (m, 1H), 7.46 (ddd, J=3.1, 7.5, 9.2 Hz, 1H), 7.37 (t, J=5.5 Hz, 1H), 7.16 (s, 1H), 3.54 (d, J=6.1 Hz, 2H), 2.22-2.15 (m, 1H), 1.66-1.53 (m, 9H), 1.41-1.34 (m, 1H). LC-MS (ESI), 320 (M+H)+.

The corresponding 4-fluoro-cyclohex-3-enyl analogue, 1-hydroxy analogue, 6-fluoro-N-[(1-hydroxy-4-fluoro-cyclohex-3-enyl)methyl]-4-oxo-chromene-2-carboxamide, Example 41A, was prepared from the appropriate starting materials using analagous chemistry.

Example 42

N-(cyclohexylmethyl)-7-fluoro-4-oxo-chromene-2-carboxamide

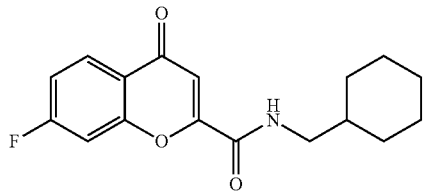 [SMILES: O=C(NCC1CCCCC1)c1cc(=O)c2ccc(F)cc2o1]

Product was purified by preparative HPLC (Gilson) using the 5-50% method with 0.1% NH₃ in water and acetonitrile as eluents. The purified product was obtained in a 42% yield. ¹H NMR (500 MHz, CDCl₃) δ 8.27 (dd, J=6.3, 8.9 Hz, 1H), 7.29-7.19 (m, 2H), 7.18 (s, 1H), 6.91 (s, 1H), 3.37 (dd, J=6.6, 6.6 Hz, 2H), 1.85-1.63 (m, 6H), 1.34-1.20 (m, 3H), 1.10-1.00 (m, 2H). LC-MS (ESI), m/z 304 (M+H)+.

Example 43

N2-(cyclohexylmethyl)-4-oxo-chromene-2,6-dicarboxamide

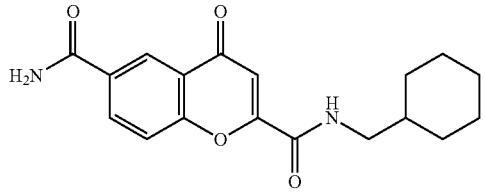 [SMILES: NC(=O)c1ccc2oc(C(=O)NCC3CCCCC3)cc(=O)c2c1]

6-Carbamoyl-4-oxo-chromene-2-carboxylic acid (208 mg, 0.8920 mmol) was suspended in MeCN (2 mL) and di-isopropylethyl amine (115 mg, 0.9 mmol) was added. The reaction mixture was then cooled to 0° C. with an ice water bath and a solution of PyBOP (464 mg, 0.9 mmol) in DCM (2 mL) was added. The mixture was stirred at 0° C. for 30 minutes then cyclohexylmethanamine (101 mg, 0.9 mmol) was added and the reaction was stirred at room temperature for 4 h. After solvent evaporation the crude material was taken up in methanol and the white precipitate filtered to give the desired product, N2-(cyclohexylmethyl)-4-oxo-chromene-2,6-dicarboxamide (140 mg, 0.4 mmol), in a 45% yield. LC-MS (ESI), m/z 329 [M+H]+. ¹H NMR (400 MHz, DMSO) δ 9.13 (dd, J=5.8, 5.8 Hz, 1H), 8.58 (s, 1H), 8.35-8.30 (m, 2H), 7.80 (d, J=8.8 Hz, 1H), 7.56 (s, 1H), 6.86 (s, 1H), 3.17 (dd, J=6.5, 6.5 Hz, 2H), 1.74-1.64 (m, 6H), 1.22-1.14 (m, 3H), 0.96 (dd, J=11.6, 11.6 Hz, 2H).

General Procedure for Schemes 1 and 1A, STEP 3, Amination e to Provide Exemplary Compounds of General Formula (I) from Intermediate Compounds of General Formula (III).

4-oxo-chromene-2-carboxylic acid, or alternatively a corresponding substituted 4-oxo-chromene-2-carboxylic acid (0.62 mmol) was suspended in dry DCM (2 mL) and oxalyl chloride in DCM (99 mg, 1.2 eq., 0.78 mmol) and a drop of DMF were added. After 10 min. a solution of the selected amine having the desired —R⁷ functionality (1.1 eq., 0.68 mmol) and Et₃N (94 mg, 1.5 eq., 0.93 mmol) in DCM (1 mL) were added to the reaction mixture and the reaction stirred under N$_2$ at rt for 2 h. After that time the reaction mixture was diluted with water and extracted with DCM to give a crude material that was purified by flash column chromatography using EtOAc in heptane as eluent, using Redisep® column with the appropriate solvent conditions specified for each example. The desired fractions were concentrated to dryness to give the desired product.

The following exemplary compounds of formula (I) were prepared according to the above general procedure e:

Example 43A 6-cyano-N-(cyclohexylmethyl)-4-oxo-chromene-2-carboxamide

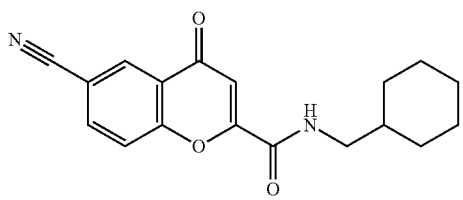 [SMILES: N#Cc1ccc2oc(C(=O)NCC3CCCCC3)cc(=O)c2c1]

The compound was purified by flash column chromatography eluting with 45% EtOAc in heptane, to provide the desired chromene-2-carboxamide in a 24% yield. LC-MS (ESI), m/z 311 [M+H]$^+$. $^1$H NMR (500 MHz, DMSO) δ 9.14 (t, J=5.9 Hz, 1H), 8.47 (d, J=1.8 Hz, 1H), 8.29 (dd, J=2.1, 8.7 Hz, 1H), 7.91 (d, J=8.9 Hz, 1H), 6.90 (s, 1H), 3.17 (dd, J=6.6, 6.6 Hz, 2H), 1.74-1.67 (m, 4H), 1.64-1.56 (m, 2H), 1.25-1.14 (m, 3H), 0.99-0.91 (m, 2H).

Example 44

N-(cyclohexylmethyl)-6-ethyl-4-oxo-chromene-2-carboxamide

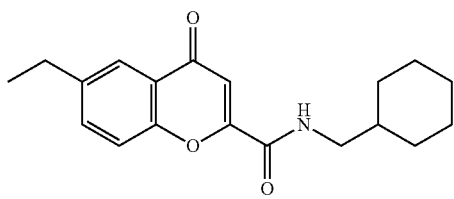 [SMILES: CCc1ccc2oc(C(=O)NCC3CCCCC3)cc(=O)c2c1]

The compound was purified by flash column chromatography eluting with 30% EtOAc in heptane, to provide the desired chromene-2-carboxamide in a 57% yield. LC-MS (ESI), m/z 314 [M+H]$^+$. $^1$H NMR (500 MHz, DMSO) δ 9.08 (t, J=5.7 Hz, 1H), 7.86 (d, J=2.1 Hz, 1H), 7.77 (dd, J=2.1, 8.7 Hz, 1H), 7.68 (d, J=8.7 Hz, 1H), 6.80 (s, 1H), 3.16 (dd, J=6.5, 6.5 Hz, 2H), 2.76 (q, J=7.6 Hz, 2H), 1.74-1.68 (m, 3H), 1.64-1.56 (m, 2H), 1.26-1.22 (m, 7H), 0.98-0.90 (m, 2H).

Example 45

6-ethyl-N-[(1-hydroxycyclohexyl)methyl]-4-oxo-chromene-2-carboxamide

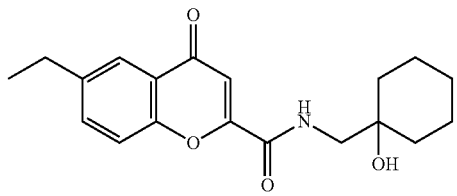 [SMILES: CCc1ccc2oc(C(=O)NCC3(O)CCCCC3)cc(=O)c2c1]

The compound was purified by flash column chromatography eluting with 50% EtOAc in heptane, to provide the desired chromene-2-carboxamide in a 44% yield. LC-MS (ESI), m/z 330 [M+H]$^+$. $^1$H NMR (500 MHz, DMSO) δ 8.70 (t, J=5.6 Hz, 1H), 7.87 (s, 1H), 7.79-7.70 (m, 2H), 6.85 (s, 1H), 4.41 (s, 1H), 3.33-3.29 (m, 2H), 2.77 (q, J=7.6 Hz, 2H), 1.57 (dd, J=11.2, 11.2 Hz, 2H), 1.49-1.34 (m, 8H), 1.24 (t, J=7.6 Hz, 3H).

Example 46

N-(cyclohexylmethyl)-6-ethoxy-4-oxo-chromene-2-carboxamide

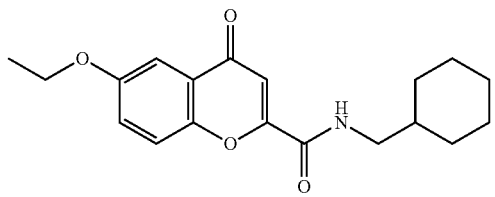 [SMILES: CCOc1ccc2oc(C(=O)NCC3CCCCC3)cc(=O)c2c1]

The compound was purified by flash column chromatography eluting with 35% EtOAc in heptane, to provide the desired chromene-2-carboxamide in a 54% yield. LC-MS (ESI), m/z 330 [M+H]$^+$. $^1$H NMR (500 MHz, DMSO) δ 9.07 (t, J=5.6 Hz, 1H), 7.70 (d, J=9.2 Hz, 1H), 7.49 (dd, J=3.1, 9.2 Hz, 1H), 7.40 (d, J=3.1 Hz, 1H), 6.80 (s, 1H), 4.15 (q, J=6.9 Hz, 2H), 3.16 (dd, J=6.5, 6.5 Hz, 2H), 1.75-1.68 (m, 4H), 1.64-1.56 (m, 2H), 1.38 (t, J=6.9 Hz, 3H), 1.25-1.14 (m, 3H), 0.98-0.91 (m, 2H).

Example 47

6-ethoxy-N-[(1-hydroxycyclohexyl)methyl]-4-oxo-chromene-2-carboxamide

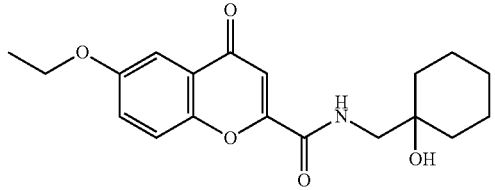 [SMILES: CCOc1ccc2oc(C(=O)NCC3(O)CCCCC3)cc(=O)c2c1]

The compound was purified by flash column chromatography eluting with 50% EtOAc in heptane, to provide the desired chromene-2-carboxamide in a 41% yield. LC-MS (ESI), m/z 346 [M+H]+. 1H NMR (500 MHz, DMSO) δ 8.70 (t, J=5.7 Hz, 1H), 7.74 (d, J=9.2 Hz, 1H), 7.48 (dd, J=3.1, 9.2 Hz, 1H), 7.40 (d, J=3.1 Hz, 1H), 6.83 (s, 1H), 4.40 (s, 1H), 4.15 (q, J=7.0 Hz, 2H), 3.30 (d, J=6.4 Hz, 2H), 1.60-1.53 (m, 2H), 1.48-1.42 (m, 5H), 1.40-1.35 (m, 5H), 1.23-1.20 (m, 1H).

Example 48

6-chloro-N-[(1-hydroxycyclohexyl)methyl]-4-oxo-chromene-2-carboxamide

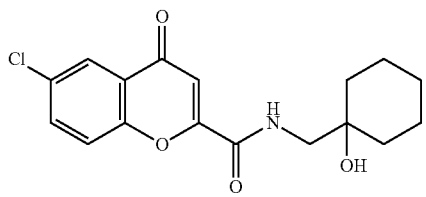 [SMILES: O=C(NCC1(O)CCCCC1)c1cc(=O)c2cc(Cl)ccc2o1]

The compound was purified by flash column chromatography eluting with 50% EtOAc in heptane, to provide the desired chromene-2-carboxamide in a 35% yield. LC-MS (ESI), m/z 336 [M+H]+. 1H NMR (500 MHz, DMSO) δ 8.78-8.75 (m, 1H), 8.01-7.93 (m, 2H), 7.85 (d, J=9.0 Hz, 1H), 6.89 (s, 1H), 4.40 (s, 1H), 3.30 (s, 2H), 1.60-1.53 (m, 2H), 1.50-1.34 (m, 7H), 1.25-1.20 (m, 1H).

Example 49

N-(cyclohexylmethyl)-4-oxo-6-(trifluoromethoxy)chromene-2-carboxamide

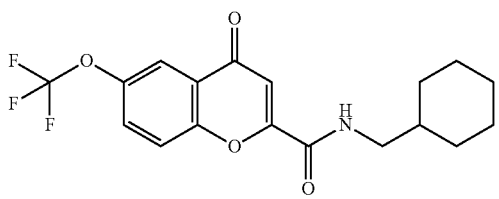 [SMILES: O=C(NCC1CCCCC1)c1cc(=O)c2cc(OC(F)(F)F)ccc2o1]

The compound was purified by flash column chromatography eluting with 30% EtOAc in heptane, to provide the desired chromene-2-carboxamide in a 53% yield. LC-MS (ESI), m/z 370 [M+H]+. 1H NMR (500 MHz, DMSO) δ 9.14 (t, J=5.1 Hz, 1H), 7.94-7.89 (m, 3H), 6.87 (s, 1H), 3.17 (dd, J=6.5, 6.5 Hz, 2H), 1.72 (t, J=13.4 Hz, 4H), 1.64 (s, 2H), 1.25-1.18 (m, 3H), 0.99-0.92 (m, 2H).

Example 49A (S)—N-(1-cyclohexylethyl)-6-fluoro-4-oxo-4H-chromene-2-carboxamide

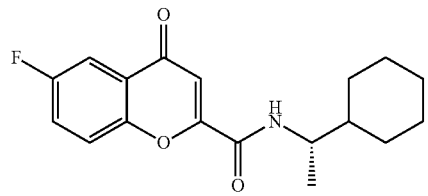 [SMILES: C[C@H](NC(=O)c1cc(=O)c2cc(F)ccc2o1)C1CCCCC1]

The product was purified firstly by preparative TLC (DCM/MeOH 10/1), and then by flash column chromatography (0.1% formic acid/H2O/ACN), 20% yield. LC-MS (ESI), m/z 318 [M+H]+. 1H NMR (500 MHz, CDCl3) δ 7.85-7.83 (d, J=5.2 Hz, 1H), 7.59-7.47 (m, 2H), 7.15 (s, 1H), 6.74-6.72 (d, J=7.2 Hz, 1H), 4.08-4.06 (d, J=7.2 Hz, 1H), 1.79-1.70 (m, 5H), 1.67 (m, 1H), 1.25-1.24 (m, 1H), 1.17-1.06 (m, 7H).

Example 49B (R)—N-(1-cyclohexylethyl)-6-fluoro-4-oxo-4H-chromene-2-carboxamide

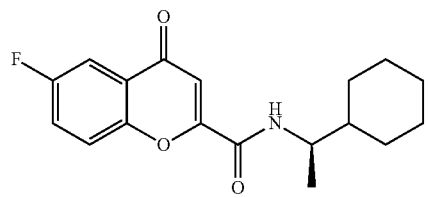 [SMILES: C[C@@H](NC(=O)c1cc(=O)c2cc(F)ccc2o1)C1CCCCC1]

The product was purified firstly by preparative TLC (DCM/MeOH 10/1), and then by flash column chromatography (0.1% formic acid/H2O/ACN), 20% yield. LC-MS (ESI), m/z 318 [M+H]+. 1H NMR (500 MHz, CDCl3) δ 7.87-7.84 (m, 1H), 7.58-7.55 (d, t=4.6 Hz, 1H), 7.47-7.46 (d, J=3.2 Hz, 1H), 7.16 (s, 1H), 6.63-6.60 (d, J=9.2 Hz, 1H), 4.10-4.04 (m, 1H), 1.77 (m, 4H), 1.57 (m, 1H), 1.27-1.26 (m, 1H), 1.17-1.05 (m, 8H).

Procedure for Schemes 1 and 1A, STEP 3, Amination f to Provide Exemplary Compounds of General Formula (I).

Example 50

4-oxo-N-(tetrahydropyran-2-ylmethyl)chromene-2-carboxamide

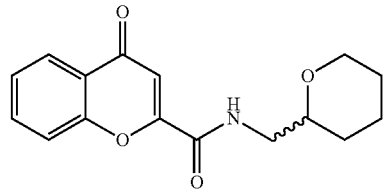 [SMILES: O=C(NCC1CCCCO1)c1cc(=O)c2ccccc2o1]

To a solution of 4-oxo-chromene-2-carboxylic acid (120 mg, 0.6 mmol) in acetonitrile (5 mL) tetrahydropyran-2-ylmethanamine (80 mg, 0.7 mmol) and COMU (324 mg, 0.8 mmol) were added. After stirring for 15 mins at rt, di-isopropylethylamine (0.22 mL, 1.3 mmol) was added dropwise and the reaction was stirred at room temperature for 5 hrs. The reaction was then partitioned between DCM and water and passed through a phase separator. The product was purified by preparative HPLC (Gilson) using the 5-50% method with 0.1% $NH_3$ in water and acetonitrile as eluents. Fractions containing product were pooled together to obtain 4-oxo-N-(tetrahydropyran-2-ylmethyl)chromene-2-carboxamide (20 mg, 10% yield) as an off-white solid. $^1$H NMR (500 MHz, $CDCl_3$) δ 8.25 (dd, J=1.7, 7.9 Hz, 1H), 7.79-7.74 (m, 1H), 7.57 (d, J=8.1 Hz, 1H), 7.48 (dd, J=7.6, 7.6 Hz, 1H), 7.35 (s, 1H), 7.20 (s, 1H), 4.08-4.04 (m, 1H), 3.82 (ddd, J=2.9, 7.3, 13.9 Hz, 1H), 3.57-3.48 (m, 2H), 3.30-3.24 (m, 1H), 1.94-1.88 (m, 1H), 1.71-1.53 (m, 4H), 1.43-1.33 (m, 1H). LC-MS (ESI), m/z 288 $(M+H)^+$.

General Procedure for Schemes 1 and 1A, STEP 3, Amination g to Provide Exemplary Compounds of General Formula (I) from Intermediate Compounds of General Formula (III).

To a solution of 4-oxo-chromene-2-carboxylic acid or the corresponding substituted 4-oxo-chromene-2-carboxylic acid (0.48 mmol) in DCM (10 mL) was added 2-chloro-4,6-dimethoxy-1,3,5-triazine (CDMT) (101 mg, 0.58 mmol) followed by N-methylmorpholine (NMO), (0.211 mL, 1.92 mmol) and the resultant mixture was stirred for 30 mins. The desired amine, to provide the desired final compound of formula (I), (1.2 eq., 0.58 mmol) was then added in one portion and the mixture stirred at room temperature overnight. The mixture was then washed with a saturated aqueous solution of $NaHCO_3$ (5 mL). The organic phase was separated, dried over $MgSO_4$ and then evaporated to dryness under reduced pressure. The residue was applied to a SPE column containing Isolute® SCX cation exchange sorbent, available from Biotage AB, Uppsala, Sweden, (2 g) and the crude product was eluted with MeOH. The methanol filtrate was concentrated under reduced pressure and the product was purified by preparative HPLC (Gilson).

The following further exemplary compounds were prepared according to the general procedure for transformation q:

Example 50A 6-fluoro-4-oxo-N-(spiro[3.3]heptan-2-ylmethyl)chromene-2-carboxamide

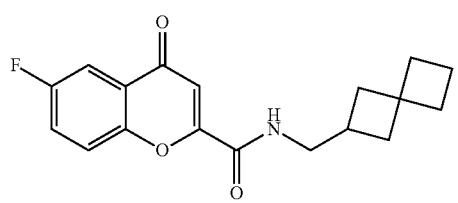 [SMILES: O=C(NCC1CC2(CCC2)C1)c1cc(=O)c2cc(F)ccc2o1]

Product was purified by preparative HPLC (Gilson) with a 5-95% method using 0.1% $HCO_2H$ in water and acetonitrile as eluents. The desired purified product was furnished in a 41% yield. $^1$H NMR (500 MHz, DMSO) δ 9.11 (dd, J=5.6, 5.6 Hz, 1H), 7.83-7.72 (m, 3H), 6.83 (s, 1H), 3.30 (d, J=6.9 Hz, 2H), 2.44-2.34 (m, 1H), 2.09-2.03 (m, 2H), 1.98-1.89 (m, 4H), 1.79-1.70 (m, 4H). LC-MS (ESI), m/z 316 $(M+H)^+$.

Example 51

N-[(3,3-difluorocyclobutyl)methyl]-6-fluoro-4-oxo-chromene-2-carboxamide

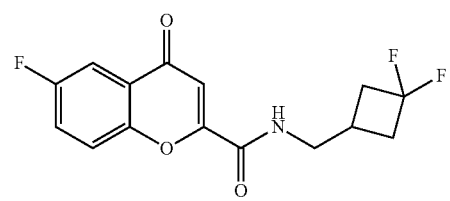 [SMILES: O=C(NCC1CC(F)(F)C1)c1cc(=O)c2cc(F)ccc2o1]

Product was purified by preparative HPLC (Gilson) with a 5-50% method using 0.1% $NH_3$ in water and acetonitrile as eluents. The desired purified product was furnished in a 30% yield. $^1$H NMR (500 MHz, DMSO) δ 9.28 (t, J=5.8 Hz, 1H), 7.83-7.80 (m, 2H), 7.74 (d, J=7.8 Hz, 1H), 6.85 (s, 1H), 3.45 (dd, J=6.2, 6.2 Hz, 2H), 2.72-2.62 (m, 2H), 2.51-2.39 (m, 3H). LC-MS (ESI), m/z 312 $(M+H)^+$.

Example 52

6-fluoro-N-[(3-fluorocyclobutyl)methyl]-4-oxo-chromene-2-carboxamide

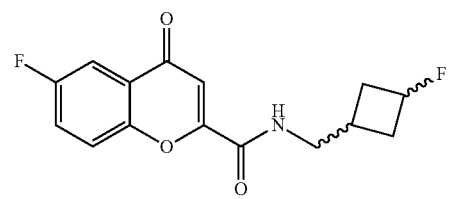 [SMILES: O=C(NCC1CC(F)C1)c1cc(=O)c2cc(F)ccc2o1]

Product was purified by preparative HPLC (Gilson) with a 5-95% method using 0.1% $NH_3$ in water and acetonitrile as eluents. The desired purified product was furnished in a 31% yield. $^1$H NMR (500 MHz, DMSO) δ 9.20 (t, J=5.6 Hz, 1H), 7.83-7.71 (m, 3H), 6.84 (s, 1H), 5.27-5.10 (m, 1H), 3.37-3.31 (m, 3H), 2.28-2.19 (m, 4H). LC-MS (ESI), m/z 294 $(M+H)^+$.

Example 53

6-fluoro-N-[(1-methoxycyclohexyl)methyl]-4-oxo-chromene-2-carboxamide

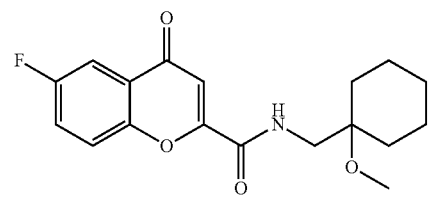 [SMILES: COC1(CNC(=O)c2cc(=O)c3cc(F)ccc3o2)CCCCC1]

Product was purified by preparative HPLC (Gilson) with a 5-60% method using 0.1% $NH_3$ in water and acetonitrile as eluents. The desired purified product was furnished in a 48% yield. $^1$H NMR (500 MHz, DMSO) δ 8.70 (t, J=6.0 Hz, 1H), 7.89 (dd, J=4.3, 9.2 Hz, 1H), 7.82-7.71 (m, 2H), 6.85 (s, 1H), 3.40-3.34 (m, 2H), 3.17 (s, 3H), 1.70 (d, J=13.1 Hz, 2H), 1.54-1.41 (m, 4H), 1.35-1.18 (m, 4H). LC-MS (ESI), 334 $(M+H)^+$.

Example 54

N-[(4,4-difluoro-1-hydroxy-cyclohexyl)methyl]-6-fluoro-4-oxo-chromene-2-carboxamide

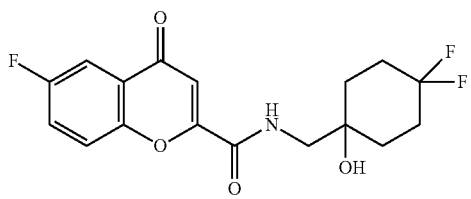 [SMILES: O=C(NCC1(O)CCC(F)(F)CC1)c1cc(=O)c2cc(F)ccc2o1]

Product was purified by preparative HPLC with a 5-50% method. The desired purified product was furnished in a 37% yield. $^1$H NMR (500 MHz, DMSO) δ 8.99 (t, J=6.2 Hz, 1H), 7.89-7.73 (m, 3H), 6.88 (s, 1H), 4.80 (s, 1H), 3.37 (d, J=6.4 Hz, 2H), 2.10-1.86 (m, 4H), 1.68-1.53 (m, 4H). LC-MS (ESI), m/z 356 $(M+H)^+$.

Example 55

6,8-difluoro-N-[(1-hydroxycyclohexyl)methyl]-4-oxo-chromene-2-carboxamide

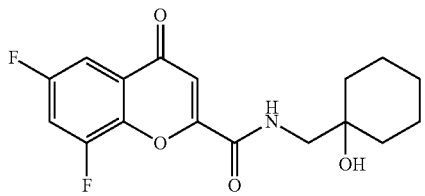

Product was purified by preparative HPLC with a 5-50% method and 0.1% $HCO_2H$ in water and acetonitrile as eluents. The desired purified product was furnished in a 25% yield. $^1$H NMR (500 MHz, CDCl$_3$) δ 8.43 (dd, J=5.9, 5.9 Hz, 1H), 8.04-7.98 (m, 1H), 7.59 (d, J=7.9 Hz, 1H), 6.94 (s, 1H), 4.45 (s, 1H), 3.30 (d, J=6.3 Hz, 2H), 1.61-1.51 (m, 2H), 1.47-1.32 (m, 8H), 1.27-1.17 (m, 1H). LC-MS (ESI), m/z 338 $(M+H)^+$.

Example 56

N-((4,4-difluoro-1-hydroxycyclohexyl)methyl)-6,8-difluoro-4-oxo-4H-chromene-2-carboxamide

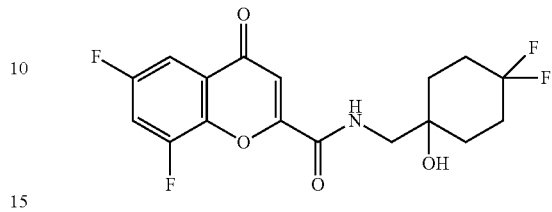

Product was purified by preparative HPLC with a 5-50% method and 0.1% $HCO_2H$ in water and acetonitrile as eluents. 23% yield. $^1$H NMR (500 MHz, DMSO) δ 8.70 (t, J=6.0 Hz, 1H), 8.04-7.98 (m, 1H), 7.60-7.57 (m, 1H), 6.95 (s, 1H), 4.81 (s, 1H), 3.37-3.32 (m, 2H), 2.10-1.85 (m, 4H), 1.68-1.51 (m, 4H). LC-MS (ESI), m/z 374 $(M+H)^+$.

Procedure for Schemes 1 and 1A, STEP 3, Amination h to Provide Exemplary Compounds of General Formula (I).

Example 57

N-[(4,4-difluoro-1-hydroxy-cyclohexyl)methyl]-6-hydroxy-4-oxo-chromene-2-carboxamide

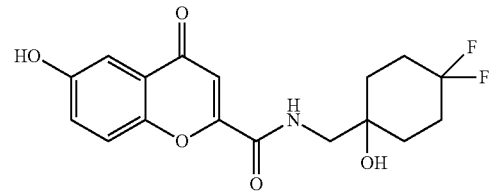 [SMILES: O=C(NCC1(O)CCC(F)(F)CC1)c1cc(=O)c2cc(O)ccc2o1]

To a solution of 6-hydroxy-4-oxo-chromene-2-carboxylic acid (100 mg, 0.5 mmol) in DMF (5 mL) was added HBTU (202 mg, 0.5 mmol) at room temperature. The resulting reaction mixture was stirred at room temperature for 1 h to provide an activated acid solution. To a separated solution of 1-(aminomethyl)-4,4-difluoro-cyclohexanol hydrochloride, purchased from ChemBridge Corporation, San Diego, USA, (117 mg, 0.6 mmol) in DMF (1 mL) was added $Et_3N$ (0.081 mL, 0.6 mmol) and mixed at room temperature. This amine solution was added to the activated acid solution at room temperature and the reaction mixture was stirred overnight. The solvent was evaporated under reduced pressured. The resulting residue was taken up into DCM (20 mL) and then washed with an aqueous saturated solution of $NaHCO_3$ (5 mL). The organic phase was separated, dried over $MgSO_4$ and evaporated to dryness under reduced pressure. The crude product was purified by preparative HPLC (Gilson) eluting with 0.1% $NH_3$ in water and acetonitrile and a 5-50% method. The fractions containing product were pooled together. The product was further purified by preparative HPLC (Gilson) eluting with 0.1% $HCO_2H$ in water and acetonitrile and a 5-50% method. The fractions containing product were pooled together to obtain N-[(4,4-difluoro-1-hydroxy-cyclohexyl)methyl]-6-hydroxy-4-oxo-chromene-2-carboxamide (27 mg, 15% yield) as a white solid. $^1$H NMR (500 MHz, DMSO) δ 10.17 (s, 1H), 8.92 (t, J=6.3 Hz, 1H), 7.65 (d, J=9.3 Hz, 1H), 7.34-7.31 (m, 2H), 6.79 (s, 1H), 4.80 (s, 1H), 3.37-3.34 (m, 2H), 2.10-1.88 (m, 4H), 1.67-1.52 (m, 4H). LC-MS (ESI), m/z 354 (M+H)+.

Procedure for Schemes 1 and 1A, STEP 3, Amination i

To a solution of chromene-4-oxo-chromene-2-carboxylic acid or the corresponding substituted 4-oxo-chromene-2-carboxylic acid (1 eq) in DMF (5 mL), was added cyclohexylmethanamine or the corresponding amine (1.2 eq), HATU (1.5 eq) and DIPEA (3 eq). The reaction mixture was stirred for 16 h at room temperature and then diluted with water (20 mL) and extracted ethyl acetate (2×20 mL). The combined organic layers were dried over $Na_2SO_4$, filtered and concentrated under reduced pressure. The products were purified by column chromatography.

The Following Compounds were Prepared According to STEP 3, Transformation i:

Example 57A

6-Bromo-N-(cyclohexylmethyl)-8-nitro-4-oxo-4H-chromene-2-carboxamide

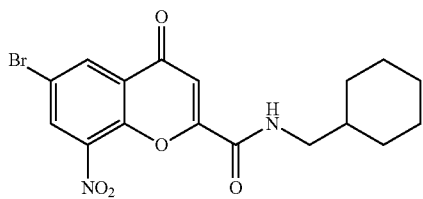

The product was purified by column chromatography (petroleum ether/ethyl acetate 5/1 to 3/1). 50% yield. 1H NMR (400 MHz, CDCl3) δ 8.68-8.66 (m, 2H), 7.28 (s, 1H), 7.24 (m, 1H), 3.4-3.37 (m, 2H), 1.85-1.71 (m, 6H), 1.33-1.04 (m, 5H). LC-MS (ESI), m/z 408, 410 (M+H)+.

Example 57B 6-fluoro-4-oxo-N-((2-oxopiperidin-4-yl)methyl)-4H-chromene-2-carboxamide

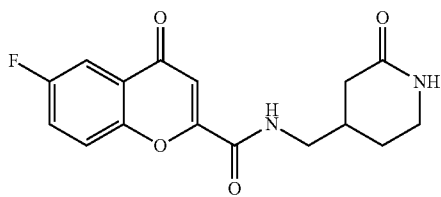 [SMILES: O=C1CC(CNC(=O)c2cc(=O)c3cc(F)ccc3o2)CCN1]

The product was purified by column chromatography by preparative HPLC (TFA) and then by preparative HPLC (Base), 5% yield. 1H NMR (300 MHz, d6-MeOD) δ 7.84-7.79 (m, 2H), 7.72-7.68 (t, J=7.4 Hz, 1H), 7.01 (s, 1H), 3.45-3.36 (m, 3H), 3.32-3.24 (m, 1H), 2.46-2.45 (m, 1H), 2.15-2.12 (m, 1H), 2.10-1.97 (m, 1H), 1.57-1.55 (m, 1H), 1.51 (m, 1H). LC-MS (ESI), m/z 319 (M+H)+.

Example 57C

N-((2,3-dihydrobenzo[b][1,4]dioxin-6-yl)methyl)-6-fluoro-4-oxo-4H-chromene-2-carboxamide

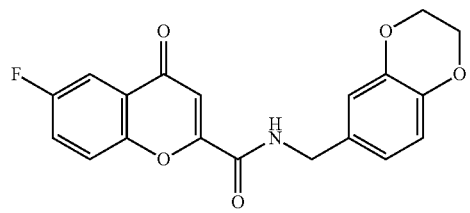 [SMILES: O=C(NCc1ccc2c(c1)OCCO2)c1cc(=O)c2cc(F)ccc2o1]

The reaction mixture was poured into water (50 mL) and filtered, 29.29% yield. 1H NMR (400 MHz, DMSO) δ 8.20 (s, 1H), 7.69-7.76 (m, 2H), 7.58-7.68 (d, 1H), 6.91 (s, 1H), 6.86 (s, 1H), 6.80-6.82 (m, 2H), 4.44-4.46 (d, 2H), 4.22 (s, 4H). LC-MS (ESI), m/z 356 (M+H)+.

The compound of Example 57C-1, N-((2,3-dihydrobenzo[b][1,3]dioxa-5-yl)methyl)-4-oxo-4H-chromene-2-carboxamide was prepared from the appropriate starting materials using analagous chemistry.

Example 57D

6-Fluoro-N-(((1S,2S)-2-hydroxycyclohexyl)methyl)-4-oxo-4H-chromene-2-carboxamide

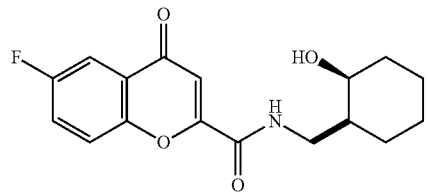

The product was purified by preparative HPLC [Instrument: GX-E; Column: Phenomenex Synergi C18 250×21.2 mm, particle size: 4 μm; Mobile phase: 25-55% acetonitrile in $H_2O$ (add 0.1% $NH_3.H_2O$, v/v) to afford 6-fluoro-N-(((1S,2S)-2-hydroxycyclohexyl)methyl)-4-oxo-4H-chromene-2-carboxamide (80 mg, 27% yield) as a yellow solid. 1H NMR (400 MHz, MeOD) δ 7.82-7.79 (m, 2H), 7.68-7.65 (m, 1H), 7.01 (s, 1H), 3.95 (d, J=3.6 Hz, 1H), 3.56-3.51 (m, 1H), 3.38-3.33 (m, 1H), 1.84-1.82 (m, 2H), 1.73-1.68 (m, 2H), 1.53-1.49 (m, 4H), 1.47-1.35 (m, 1H). LC-MS (ESI), m/z 320 (M+H)+.

Example 57E

6-Fluoro-N-(((1S,2R)-2-hydroxycyclohexyl)methyl)-4-oxo-4H-chromene-2-carboxamide

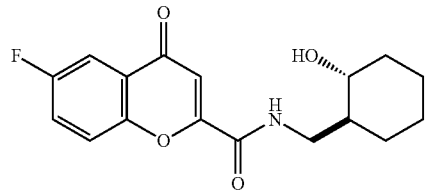

The product was purified by Prep-HPLC (TFA) [Instrument: GX-E; Column: Phenomenex Synergi C18 250×21.2 mm, particle size: 4 μm; Mobile phase: 25-55% acetonitrile in H$_2$O (add 0.05% TFA, v/v)] to afford 6-fluoro-N-(((1S,2R)-2-hydroxycyclohexyl)methyl)-4-oxo-4H-chromene-2-carboxamide (70 mg, 24% yield) as a white solid. $^1$H NMR (400 MHz, DMSO) δ 9.07 (s, 1H), 7.82 (d, J=5.2 Hz, 2H), 7.76-7.74 (m, 1H), 6.84 (s, 1H), 4.80 (d, J=4.8 Hz, 1H), 3.59-3.54 (m, 1H), 3.28-3.26 (m, 2H), 2.68 (s, 2H), 2.34 (s, 2H), 1.86-1.57 (m, 2H), 1.25-0.95 (m, 3H). LC-MS (ESI), m/z 320 (M+H)$^+$.

Example 57F (S)—N-(1-cyclohexyl-2-hydroxyethyl)-6-fluoro-4-oxo-4H-chromene-2-carboxamide

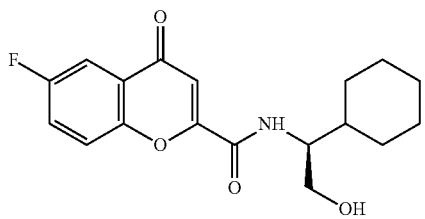 [SMILES: O=C(N[C@H](CO)C1CCCCC1)c1cc(=O)c2cc(F)ccc2o1]

The product was purified by preparative HPLC (Method: TFA), 25% yield. $^1$H NMR (400 MHz, CDCl$_3$) δ 7.88-7.86 (dd, J$_1$=2.8 Hz, J$_2$=8.0 Hz, 1H), 7.61-7.59 (t, J=4.6 Hz, 1H), 7.58-7.48 (m, 1H), 7.48 (s, 1H), 7.18 (s, 1H), 4.03-4.01 (m, 1H), 3.94-3.83 (m, 2H), 1.84-1.79 (m, 6H), 1.29-1.12 (m, 5H). LC-MS (ESI), m/z 334 (M+H)$^+$.

Example 57G (R)—N-(1-cyclohexyl-2-hydroxyethyl)-6-fluoro-4-oxo-4H-chromene-2-carboxamide

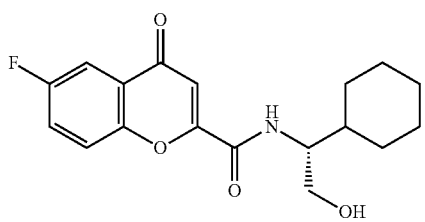 [SMILES: O=C(N[C@@H](CO)C1CCCCC1)c1cc(=O)c2cc(F)ccc2o1]

The product was purified by preparative HPLC (Method: TFA), 19% yield. $^1$H NMR (400 MHz, CDCl$_3$) δ 7.88-7.86 (dd, J$_1$=2.8 Hz, J$_2$=7.6 Hz, 1H), 7.60-7.58 (t, J=4.2 Hz, 1H), 7.49 (m, 1H), 7.48 (s, 1H), 7.18 (s, 1H), 4.02-4.00 (m, 1H), 3.94-3.83 (m, 2H), 1.84-1.81 (m, 6H), 1.29-1.12 (m, 5H). LC-MS (ESI), m/z 334 (M+H)$^+$.

Example 57H

N-(cyclohexylmethyl)-6-fluoro-N-methyl-4-oxo-4H-chromene-2-carboxamide

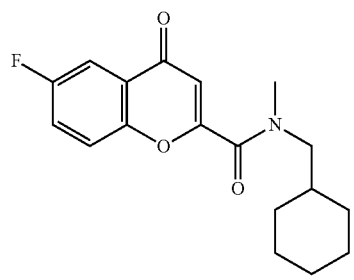 [SMILES: CN(CC1CCCCC1)C(=O)c1cc(=O)c2cc(F)ccc2o1]

The product was purified by preparative HPLC (Method: TFA), 25% yield. $^1$H NMR (400 MHz, CDCl$_3$) δ 7.88-7.86 (t, J=4.2 Hz, 1H), 7.54-7.45 (m, 2H), 6.52-6.48 (d, J=13.6 Hz, 1H), 3.42-3.40 (d, J=7.6 Hz, 1H), 3.22-3.20 (d, J=7.2 Hz, 1H), 3.10-3.09 (d, J=2 Hz, 3H), 1.81-1.72 (m, 6H), 1.27-1.22 (m, 4H), 0.81-0.79 (m, 1H). LC-MS (ESI), m/z 318 (M+H)$^+$.

Example 57I

N-(2-ethylbutyl)-6-fluoro-4-oxo-4H-chromene-2-carboxamide

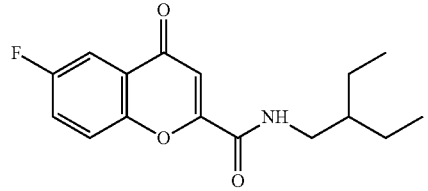 [SMILES: CCC(CC)CNC(=O)c1cc(=O)c2cc(F)ccc2o1]

The product was purified by preparative HPLC (Method: TFA), 49% yield. $^1$H NMR (400 MHz, CDCl$_3$) δ 7.80-7.79 (d, J=4.8 Hz, 1H), 7.48-7.42 (m, 1H), 7.39-7.38 (m, 1H), 7.09 (s, 1H), 6.73 (s, 1H), 3.39-3.36 (t, J=6.2 Hz, 2H), 1.35-1.34 (m, 1H), 1.33-1.32 (m, 4H), 0.90-0.87 (m, 6H). LC-MS (ESI), m/z 292 (M+H)$^+$.

Example 57J

6-Fluoro-N-(2-methylbutyl)-4-oxo-4H-chromene-2-carboxamide

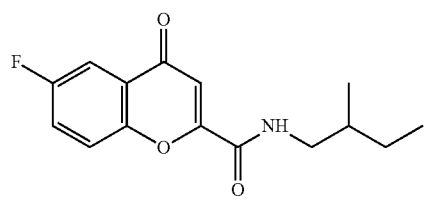 [SMILES: CCC(C)CNC(=O)c1cc(=O)c2cc(F)ccc2o1]

The product was purified by preparative HPLC (Method: TFA), 49% yield. $^1$H NMR (400 MHz, CDCl$_3$) δ 7.90-7.87

(dd, J$_1$=3.2 Hz, J$_2$=8.0 Hz, 1H), 7.56-7.55 (d, J=4 Hz, 1H), 7.51-7.48 (m, 1H), 7.18 (s, 1H), 6.89 (s, 1H), 3.48-3.43 (m, 1H), 3.37-3.32 (m, 1H), 1.76-1.74 (m, 1H), 1.50-1.48 (m, 1H), 1.31-1.27 (m, 1H), 1.02-0.96 (m, 6H). LC-MS (ESI), m/z 278 (M+H)$^+$.

Example 57K

Ethyl 2-(1-((6-fluoro-4-oxo-4H-chromene-2-carboxamido)methyl)cyclohexyl)acetate

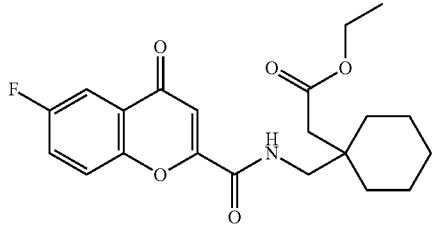 [SMILES: CCOC(=O)CC1(CNC(=O)c2cc(=O)c3cc(F)ccc3o2)CCCCC1]

To a solution of 2-(1-(aminomethyl)cyclohexyl)acetic acid (200 mg, 1.17 mmol) in EtOH (4 mL) was added SOCl$_2$ (278 mg, 2.34 mmol, 0.169 mL) dropwise at 25° C., the reaction mixture was stirred at 80° C. for 3 h. The solvent was removed under reduced pressure and the resulting amine was used without further purification on the amidation step following general procedure i. The product was purified by silica gel column chromatography (DCM/MeOH 50:1 to 20:1), 69% yield. LC-MS (ESI), m/z 390 (M+H)$^+$.

Example 57L 2-(1-((6-fluoro-4-oxo-4H-chromene-2-carboxamido)methyl)cyclohexyl)acetic acid

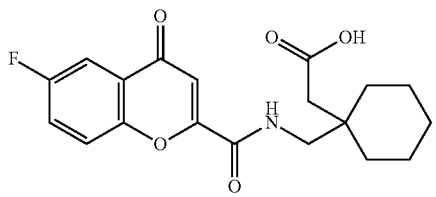 [SMILES: O=C(O)CC1(CNC(=O)c2cc(=O)c3cc(F)ccc3o2)CCCCC1]

Ethyl 2-(1-((6-fluoro-4-oxo-4H-chromene-2-carboxamido)methyl)cyclohexyl)acetate (120 mg, 0.38 mmol), concentrated, HCl (0.377 mL) and AcOH (0.53 mL) was stirred at 80° C. for 30 min. The reaction mixture was concentrated under reduced pressure. The product was purified by preparative HPLC (acidic method) to obtain 2-(1-((6-fluoro-4-oxo-4H-chromene-2-carboxamido)methyl)cyclohexyl)acetic acid (50 mg, 0.135 mmol, 44% yield) as a white solid was obtained. $^1$H NMR (400 MHz, DMSO) δ 12.20 (s, 1H), 8.88 (s, 1H), 7.86-7.80 (m, 2H), 7.76-7.74 (t, J=4.2 Hz, 1H), 6.85 (s, 1H), 3.45-3.44 (d, J=6.4 Hz, 2H), 2.33 (s, 2H), 1.49-1.36 (m, 10H). LC-MS (ESI), m/z 362 (M+H)$^+$.

Preparative Compounds and Exemplary Compounds for the Process Illustrated in Scheme 2.

General Procedure for Scheme 2—STEP 1 Transformation a to Provide Exemplary Intermediate Compounds of General Formula (IV):

Example 58

Intermediate Compound

To a suspension of N-(cyclohexylmethyl)-8-hydroxy-4-oxo-chromene-2-carboxamide (48 mg, 0.16 mmol) in DMF (2 mL), potassium carbonate (51 mg, 0.37 mmol) was added and after 20 minutes tert-butyl N-(2-bromoethyl)carbamate or alternatively tert-butyl 4-(bromomethyl)piperidine-1-carboxylate (1.2 eq.) was added and the reaction was stirred under N$_2$, at 90° C. overnight. After that time LC-MS (ESI) analysis confirmed the presence of some residual starting material in the reaction mixture. 10 mg of potassium carbonate and a further equivalent of tert-butyl N-(2-bromoethyl)carbamate, or tert-butyl 4-(bromomethyl)piperidine-1-carboxylate (as appropriate) was added and the mixture stirred for a further 4 h at 90° C. The reaction mixture was then filtered and evaporated to furnish crude intermediate material that was purified by flash column chromatography eluting with an appropriate amount of EtOAc in heptane for each example (as detailed in previous general procedures) to give the desired intermediate compound.

The Following Further Exemplary Intermediate Compounds of General Formula (IV) were Prepared According to the General Procedure for Transformation a in STEP 1 of Scheme 2:

Example 59

Intermediate Compound, tert-butyl (2-((2-((cyclohexylmethyl)carbamoyl)-4-oxo-4H-chromen-8-yl)oxy)ethyl)carbamate

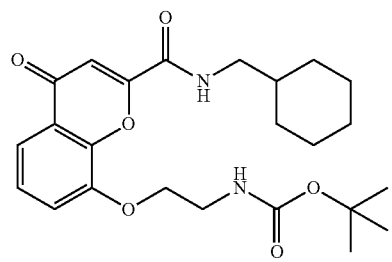 [SMILES: CC(C)(C)OC(=O)NCCOc1cccc2c(=O)cc(C(=O)NCC3CCCCC3)oc12]

The compound was purified by flash column chromatography eluting with 45% EtOAc in heptane, to furnish the t-BOC protected intermediate in a 56% yield, as a yellowish solid. LC-MS (ESI) basic condition, m/z 445 [M+H]$^+$.

Example 59

Intermediate Compound, tert-butyl 4-[[2-(cyclohexylmethylcarbamoyl)-4-oxo-chromen-8-yl]oxymethyl]piperidine-1-carboxylate

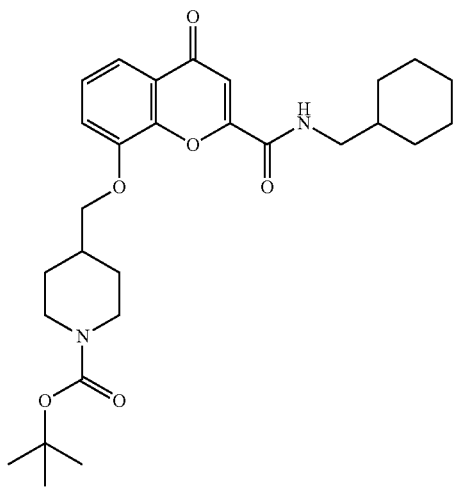 [SMILES: CC(C)(C)OC(=O)N1CCC(COc2cccc3c(=O)cc(C(=O)NCC4CCCCC4)oc23)CC1]

The compound was purified by flash column chromatography eluting with 45% EtOAc in heptane, to provide the t-BOC protected compound in an 82% yield, as a white solid. LC-MS (ESI) basic condition, m/z 499 [M+H]$^+$.

General Procedure for Scheme 2—STEP 1 Transformation b to Provide Exemplary Intermediate Compounds of General Formula (IV):

Example 60

Intermediate Compound, tert-butyl 4-[2-[2-(cyclohexylmethylcarbamoyl)-4-oxo-chromen-8-yl]oxyethyl]piperazine-1-carboxylate

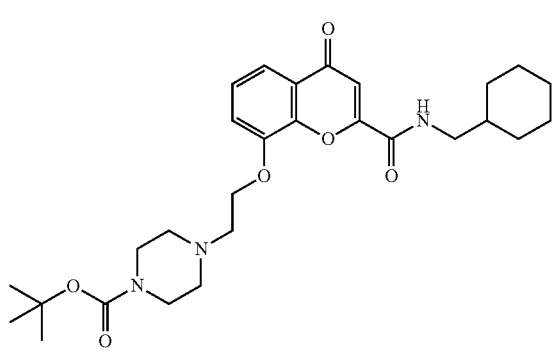 [SMILES: CC(C)(C)OC(=O)N1CCN(CCOc2cccc3c(=O)cc(C(=O)NCC4CCCCC4)oc23)CC1]

To a solution of N-(cyclohexylmethyl)-8-hydroxy-4-oxo-chromene-2-carboxamide (45 mg, 0.15 mmol) in DMF (2 mL), potassium carbonate (48 mg, 0.34 mmol) was added and after 20 minutes tert-butyl 4-(2-chloroethyl)piperazine-1-carboxylate (58 mg, 0.22 mmol) was also added and the reaction was stirred in a microwave reactor at 100° C. for 1 h. After that time LC-MS (ESI) analysis confirmed complete conversion of the starting material into desired intermediate product. The reaction mixture was then filtered and evaporated to give the crude intermediate material which was then purified further using flash column chromatography eluting with 0-10% MeOH in DCM to give tert-butyl 4-[2-[2-(cyclohexylmethylcarbamoyl)-4-oxo-chromen-8-yl]oxyethyl]piperazine-1-carboxylate (23 mg, 0.04 mmol), in a 28% yield and as a white solid. LC-MS (ESI) analysis of the so-purified product was consistent with the desired product and the material was then taken directly into the next step, conversion to intermediate compound of general formula (V) without further analysis. LC-MS (ESI) m/z 514 [M+H]$^+$.

General Procedure for Scheme 2—STEP 2 Transformation c to Provide Exemplary Intermediate Compounds of General Formula (V):

A solution of the desired Boc protected-8-substituted starting material, for example, N-(cyclohexylmethyl)-4-oxo-chromene-2-carboxamide (0.0810 mmol) in 4M HCl in dioxane (0.5 mL) was stirred under N$_2$ for 1 h. After that time a precipitate was formed and LC-MS (ESI), showed one peak which corresponded to the desired de-protected derivative. Solvent was evaporated to dryness to give the intermediate de-protected product as a white solid.

The Following Further Exemplary Intermediate Compounds were Prepared According to the General Procedure for Scheme 2, Step 2, Transformation c:

Example 61

Intermediate Compound, 8-(2-aminoethoxy)-N-(cyclohexylmethyl)-4-oxo-chromene-2-carboxamide hydrochloride

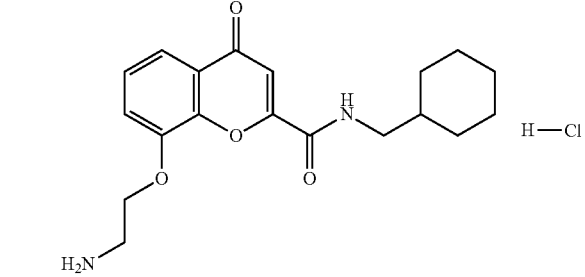

The intermediate was obtained in 95% yield. LC-MS (ESI) m/z 345 [M+H]$^+$. $^1$H NMR (500 MHz, DMSO) δ 8.76-8.75 (m, 1H), 8.19-8.16 (m, 3H), 7.66 (d, J=7.9 Hz, 1H), 7.60 (d, J=8.1 Hz, 1H), 7.48 (dd, J=8.0, 8.0 Hz, 1H), 6.88 (s, 1H), 4.40 (t, J=5.0 Hz, 2H), 3.19 (dd, J=6.5, 6.5 Hz, 2H), 2.52-2.50 (m, 2H), 1.73-1.70 (m, 4H), 1.63 (d, J=13.6 Hz, 2H), 1.23-1.17 (m, 3H), 0.99-0.94 (m, 2H).

Example 61

Intermediate Compound, N-(cyclohexylmethyl)-4-oxo-8-(4-piperidylmethoxy)chromene-2-carboxamide hydrochloride

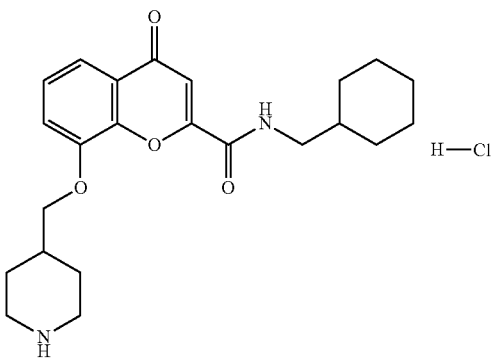

The intermediate was obtained in 83% yield. LC-MS (ESI) m/z 399 [M+H]⁺. $^1$H NMR (500 MHz, DMSO) δ 8.57 (m, 2H), 7.61-7.54 (m, 2H), 7.45 (dd, J=8.0, 8.0 Hz, 1H), 6.84 (s, 1H), 4.10 (d, J=6.7 Hz, 2H), 3.58 (s, 1H), 3.16 (m, 2H), 2.93 (m, 2H), 2.23-2.17 (m, 1H), 2.05-2.01 (m, 2H), 1.73-1.68 (m, 4H), 1.65-1.63 (m, 1H), 1.58-1.48 (m, 3H), 1.23-1.14 (m, 3H), 0.99-0.91 (m, 2H).

Example 62

Intermediate Compound, N-(cyclohexylmethyl)-4-oxo-8-(2-piperazin-1-ylethoxy)chromene-2-carboxamide dihydrochloride

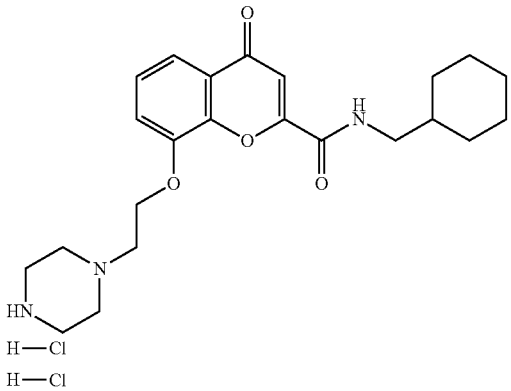

The intermediate was obtained in 83% yield. LC-MS (ESI) m/z 414 [M+H]⁺. $^1$H NMR (500 MHz, DMSO) δ 7.64 (d, J=7.8 Hz, 1H), 7.58 (d, J=7.5 Hz, 1H), 7.48 (dd, J=8.0, 8.0 Hz, 1H), 6.93 (s, 1H), 4.58-4.58 (m, 2H), 3.65 (s, 6H), 3.57 (s, 3H), 3.17 (dd, J=6.5, 6.5 Hz, 2H), 1.73-1.69 (m, 4H), 1.64-1.59 (m, 2H), 1.24-1.14 (m, 4H), 0.98-0.93 (m, 2H).

General Procedure for Scheme 2—STEP 3 Transformation d to Provide Exemplary 8-O Substituted Compounds of General Formula (I):

To a solution of containing an intermediate compound of general formula (V) as indicated from General Procedure C hereinbefore, (0.07 mmol) in formic acid (0.1 mL), was added an excess of formaldehyde 37% in water (0.03 mL) and the reaction mixture was stirred at reflux for from 1 h to 8 h. After solvent evaporation the crude material was purified by preparative HPLC (acidic method, 5-95% ACN in water) to provide the desired product as a solid.

The Following Further Exemplary Compounds were Prepared According to the General Procedure for Scheme 2, Step 2, Transformation d:

Example 63

N-(cyclohexylmethyl)-8-[2-(dimethylamino)ethoxy]-4-oxo-chromene-2-carboxamide

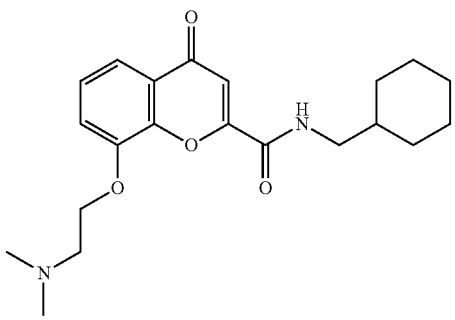 [SMILES: CN(C)CCOc1cccc2c(=O)cc(C(=O)NCC3CCCCC3)oc12]

The compound was obtained in 35% yield. δ 8.45 (t, J=5.6 Hz, 1H), 7.60-7.52 (m, 2H), 7.44 (dd, J=8.0, 8.0 Hz, 1H), 6.80 (s, 1H), 4.27 (t, J=5.6 Hz, 2H), 3.16 (t, J=6.4 Hz, 2H), 2.75 (dd, J=5.7, 5.7 Hz, 2H), 2.27 (s, 6H), 1.75-1.65 (m, 5H), 1.58-1.52 (m, 1H), 1.23-1.15 (m, 3H), 1.00-0.92 (m, 2H). LC-MS (ESI) m/z 373 [M+H]⁺. $^1$H NMR (500 MHz, DMSO).

Example 64

N-(cyclohexylmethyl)-8-[(1-methyl-4-piperidyl)methoxy]-4-oxo-chromene-2-carboxamide hydrochloride

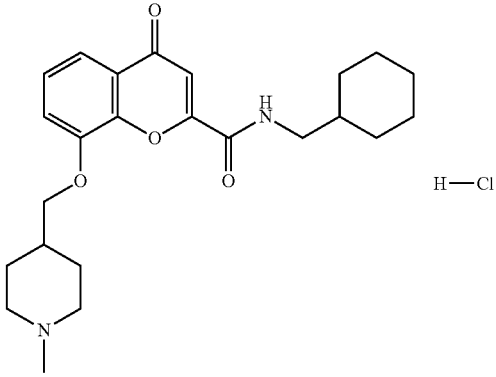 [SMILES: CN1CCC(COc2cccc3c(=O)cc(C(=O)NCC4CCCCC4)oc23)CC1 ; Cl]

The product was obtained in 46% yield. LC-MS (ESI) m/z 413 [M+H]⁺. $^1$H NMR (500 MHz, DMSO) δ 8.46 (t, J=5.0 Hz, 1H), 7.59-7.51 (m, 2H), 7.44 (dd, J=7.9, 7.9 Hz, 1H), 6.81 (s, 1H), 4.06 (d, J=6.1 Hz, 2H), 3.16 (dd, J=6.4, 6.4 Hz, 2H), 2.99-2.99 (m, 2H), 2.52-2.50 (m, 3H), 2.38-2.35 (m, 2H), 1.93-1.86 (m, 3H), 1.76-1.63 (m, 5H), 1.57-1.53 (m, 1H), 1.45-1.42 (m, 2H), 1.24-1.14 (m, 3H), 1.00-0.92 (m, 2H).

Example 65

N-(cyclohexylmethyl)-8-[2-(4-methylpiperazin-1-yl)ethoxy]-4-oxo-chromene-2-carboxamide dihydrochloride

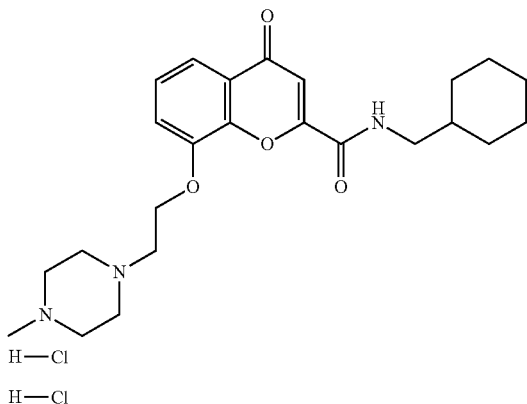

The product was obtained in 87% yield. LC-MS (ESI) m/z 428 [M+H]$^+$. $^1$H NMR (500 MHz, DMSO) δ 7.64 (d, J=7.8 Hz, 1H), 7.58 (d, J=7.2 Hz, 1H), 7.48 (dd, J=7.9, 7.9 Hz, 1H), 6.92 (s, 1H), 5.77 (s, 1H), 4.68 (s, 2H), 3.51-3.49 (m, 6H), 3.24-3.17 (m, 2H), 2.82 (s, 3H), 2.74 (dd, J=5.4, 5.4 Hz, 1H), 1.73-1.69 (m, 4H), 1.63 (s, 4H), 1.24-1.15 (m, 5H), 0.99-0.94 (m, 2H).

Preparative Compounds and Exemplary Compounds for the Process Illustrated in Schemes 3 and 3A.

General Procedure for the Synthesis of Olefin Diesters

To a mixture of phenol (1 eq) and Et$_3$N (2 eq) in DCM, was added DMAD (1.1 eq). The reaction mixture was stirred at 25° C. for 2 h. The mixture was diluted with water (200 mL) and extracted with DCM (2×200 mL), the organic layers were separated and dried over Na$_2$SO$_4$ and filtered. The solvent was concentrated under reduced pressured. Product was purified by column chromatography.

General Procedure for Ester Hydrolysis of Olefin Diesters

To a mixture of the corresponding maleate and fumarate 1/1 (1 eq) was dissolved in THF/Water 1/1 and NaOH (6 eq) was added. The reaction mixture was stirred at room temperature overnight. The reaction mixture was acidified with concentrated HCl and filtered. The solid was collected and dried to give the desired products.

General Procedure for the Preparation of 2-Chromone Carboxylic Acids

A mixture of corresponding maleic acid and fumaric acid (1 eq) in H$_2$SO$_4$ (4 eq) and acetyl chloride (10 mL) was stirred at 25° C. overnight. The reaction mixture was poured into ice-water (50 mL). The precipitate was filtered and dried under reduced pressure. The residue was purified by column chromatography.

Prep. 19 Dimethyl 2-(2-methoxyphenoxy)maleate and Dimethyl 2-(2-methoxyphenoxy)fumarate

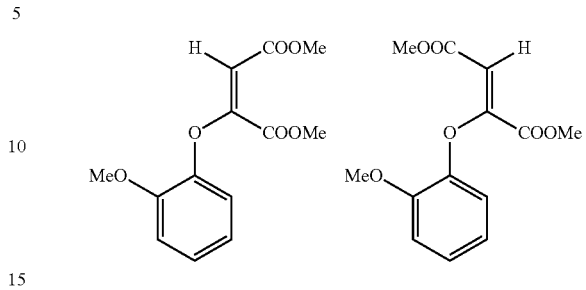

Prepared following general procedure for the synthesis of olefin diesters. The product was purified by silica gel column chromatography (Petroleum ether/acetate 10/1 to 2/1). $^1$H NMR (400 MHz, CDCl$_3$) δ 7.32-7.20 (m, 1H), 7.15-6.83 (m, 12H), 6.48 (s, 2H), 5.03 (s, 1H), 3.95 (s, 3H), 3.87 (m, 8H), 3.75 (s, 5H), 3.71-3.67 (m, 8H). To a mixture of 2-methoxyphenol (20 g, 161 mmol) and Et$_3$N (24 g, 242 mmol) in DCM (200 mL), was added dimethyl but-2-ynedioate (25 g, 177 mmol). The reaction mixture was stirred at 25° C. for 30 minutes. The mixture was diluted with water (200 mL) and extracted with DCM (2×200 mL), the organic layers were separated and dried over Na$_2$SO$_4$ and filtered. The solvent was concentrated under reduced pressured and the residue was purified by silica gel column chromatography (Petroleum ether/acetate 10/1 to 2/1) to obtain a mixture of dimethyl 2-(2-methoxyphenoxy)maleate and dimethyl 2-(2-methoxyphenoxy)fumarate (24 g) as a colourless oil. $^1$H NMR (400 MHz, CDCl$_3$) δ 7.32-7.20 (m, 1H), 7.15-6.83 (m, 12H), 6.48 (s, 2H), 5.03 (s, 1H), 3.95 (s, 3H), 3.87 (m, 8H), 3.75 (s, 5H), 3.71-3.67 (m, 8H).

Prep. 20 2-(2-Methoxyphenoxy)maleic acid and 2-(2-methoxyphenoxy)fumaric acid

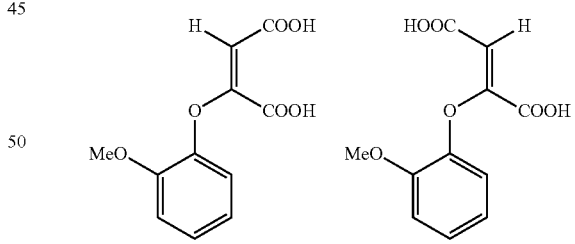

Prepared following general procedure for the synthesis of olefin diacids. A mixture of dimethyl 2-(2-methoxyphenoxy)maleate and dimethyl 2-(2-methoxyphenoxy)fumarate (24 g) and NaOH (18 g, 450 mmol) in H$_2$O (150 mL) and THF (100 mL) was stirred at 100° C. for 3 h. The reaction mixture was acidified with concentrated. HCl (50 mL) and filtered. The solid was collected and dried to give a mixture of 2-(2-methoxyphenoxy)maleic acid and 2-(2-methoxyphenoxy)fumaric acid (10 g, 52% yield) as a white solid.

Prep. 21
8-Methoxy-4-oxo-4H-chromene-2-carboxylic acid

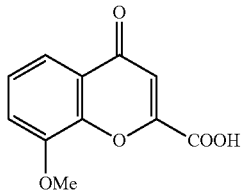 [SMILES: COc1cccc2c(=O)cc(C(=O)O)oc12]

Prepared following general procedure for the synthesis of 2-chromone carboxylic acids. A mixture of 2-(2-methoxyphenoxy)maleic acid and 2-(2-methoxyphenoxy)fumaric acid (10 g, 42 mmol) in $H_2SO_4$ (20 mL) and acetyl chloride (200 mL) was stirred at 25° C. for 16 h. The reaction mixture was concentrated under reduced pressured. The residue was purified by column chromatography [TFA/$H_2O$ 1/1000, 60% ($H_2O$:MeCN)] to obtain 8-methoxy-4-oxo-4H-chromene-2-carboxylic acid (1.00 g, 10% yield) as a pink solid. $^1H$ NMR (400 MHz, Methanol-d4) δ 7.58-7.55 (m, 1H), 7.51-7.44 (m, 2H), 6.90 (s, 1H), 3.97 (s, 3H). LCMS (ESI) m/z 221 (M+H)$^+$.

Example 66
N-(cyclohexylmethyl)-8-methoxy-4-oxo-4H-chromene-2-carboxamide

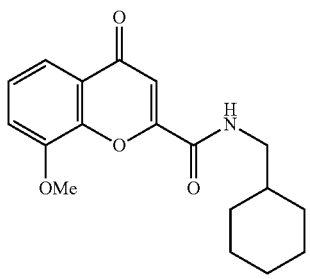

Prepared following to general procedure e for the synthesis of 2-chromone carboxamides. A mixture of 8-methoxy-4-oxo-4H-chromene-2-carboxylic acid (500 mg, 2.27 mmol) and oxalyl dichloride (865 mg, 6.81 mmol) in DCM (1 mL) was stirred at 0° C. for 2 h. The mixture was added into a solution of cyclohexylmethanamine (308 mg, 2.72 mmol) and $Et_3N$ (345 mg, 3.41 mmol) in DCM (5 mL) at 0° C. and the resulting reaction mixture was stirred at 15° C. for 2 h. The reaction mixture was diluted with water (5 mL) and extracted with DCM (3×5 mL). The combined organic layers were dried over $Na_2SO_4$, filtered and concentrated. The residue was purified by silica gel column chromatography (petroleum ether/ethyl acetate 10/1 to 1/1) to obtain N-(cyclohexylmethyl)-8-methoxy-4-oxo-4H-chromene-2-carboxamide (268 mg, 35% yield) as a light yellow solid. $^1H$ NMR (400 MHz, Methanol-d4) δ 7.70-7.64 (m, 1H), 7.49-7.43 (m, 2H), 6.97 (s, 1H), 4.06 (s, 3H), 3.29-3.27 (d, J=7.0 Hz, 2H), 1.82-1.62 (m, 6H), 1.36-1.21 (m, 3H), 1.07-0.96 (m, 2H). LCMS (ESI) m/z 317 (M+H)$^+$.

Example 67
N-(cyclohexylmethyl)-8-hydroxy-4-oxo-4H-chromene-2-carboxamide

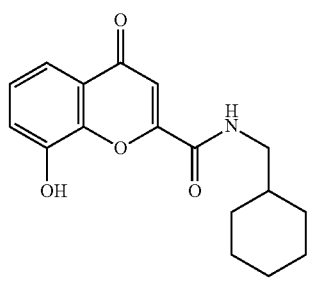

To a solution of N-(cyclohexylmethyl)-8-methoxy-4-oxo-4H-chromene-2-carboxamide (200 mg, 0.63 mmol) in DCM (1 mL) was added borontribromide ($BBr_3$) (636 mg, 2.54 mmol) at −78° C. The reaction mixture was stirred at −78° C. for 2 h. The reaction mixture was quenched with MeOH (1 mL) and concentrated under reduced pressure. The residue was diluted with MeOH (1 mL) and stirred for 10 min, then the mixture was filtered and the solid was collected and dried to give N-(cyclohexylmethyl)-8-hydroxy-4-oxo-4H-chromene-2-carboxamide (79 mg, 40% yield) as an off-white solid. $^1H$ NMR (400 MHz, DMSO) δ 10.28 (s, 1H), 9.15-9.12 (t, J=5.6 Hz, 1H), 7.48-7.36 (m, 1H), 7.35-7.30 (m, 2H), 6.81 (s, 1H), 3.20-3.17 (m, 2H), 1.75-1.60 (m, 6H), 1.22-1.13 (m, 2H), 0.97-0.94 (m, 3H). LCMS (ESI) m/z 302 (M+H)$^+$.

Prep. 24 Dimethyl 2-(2-(trifluoromethyl)phenoxy) fumarate and dimethyl 2-(2-(trifluoromethyl)phenoxy)maleate (1:1)

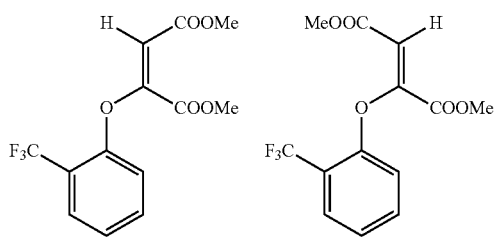 [SMILES: COC(=O)/C=C(/Oc1ccccc1C(F)(F)F)C(=O)OC ; COC(=O)/C=C(\Oc1ccccc1C(F)(F)F)C(=O)OC]

Prepared following general procedure for the synthesis of olefin diesters. To a solution of 2-(trifluoromethyl)phenol (5 g, 31 mmol) and $Et_3N$ (4.7 g, 46 mmol) in DCM (50 mL) was added dimethyl but-2-ynedioate (4.4 g, 31 mmol). The mixture was stirred at 25° C. for 1 h. The solvent was concentrated under reduced pressured and the residue was purified by silica gel column chromatography (petroleum ether/acetate 7/1) to obtain a 1/1 mixture of dimethyl 2-(2-(trifluoromethyl)phenoxy)fumarate and dimethyl 2-(2-(trifluoromethyl)phenoxy)maleate (7 g) as a light yellow oil.

Prep. 25 2-(2-(trifluoromethyl)phenoxy)fumaric acid and 2-(2-(trifluoromethyl)phenoxy)maleic acid (1:1)

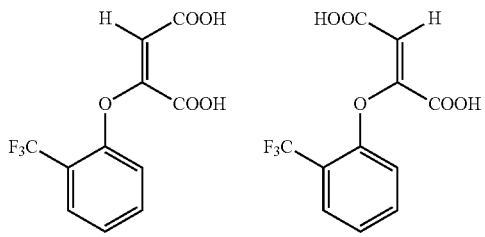 [SMILES: O=C(O)/C=C(/Oc1ccccc1C(F)(F)F)C(=O)O ; O=C(O)/C=C(\Oc1ccccc1C(F)(F)F)C(=O)O]

Prepared following general procedure for the synthesis of 2-chromone carboxylic acids. To a solution of a 1/1 mixture of dimethyl 2-(2-(trifluoromethyl)phenoxy)fumarate and dimethyl 2-(2-(trifluoromethyl)phenoxy)maleate (7 g) in THF (35 mL) and H$_2$O (35 mL) was added LiOH (3.86 g, 92.00 mmol). The reaction mixture was stirred at 25° C. for 3 h. The reaction was concentrated under reduced pressure then the residue was acidified with 4N HCl to pH ~2-3. The precipitate was filtered and dried under vacuum to obtain 2-(2-(trifluoromethyl)phenoxy)fumaric acid and 2-(2-(trifluoromethyl) phenoxy)maleic acid (1:1) (6.2 g, 98% yield) as white solid.

Prep. 26 4-oxo-8-(trifluoromethyl)-4H-chromene-2-carboxylic acid

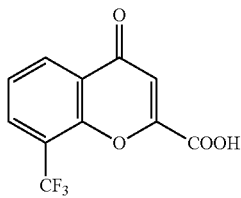

Prepared following general procedure for the synthesis of 2-chromone carboxylic acids. To a solution of 2-(2-(trifluoromethyl)phenoxy)fumaric acid and 2-(2-(trifluoromethyl)phenoxy)maleic acid (1:1) (6.2 g) in acetyl chloride (120 mL) was added H$_2$SO$_4$ (7.2 g, 73 mmol). The mixture was stirred at 50° C. for 1 h. The solvent was removed under reduced pressure and the residue was poured into ice-water (50 mL). The precipitate was filtered and dried under reduced pressure. The solid was purified by preparative HPLC under acidic conditions to afford 4-oxo-8-(trifluoromethyl)-4H-chromene-2-carboxylic acid (1.3 g, 45% yield) as white solid. $^1$H NMR (400 MHz, DMSO) δ 8.34-8.32 (m, 1H), 8.27-8.25 (m, 1H), 7.71-7.67 (m, 1H), 7.01 (s, 1H). LCMS (ESI) m/z 259 (M+H)$^+$.

Example 68

N-(cyclohexylmethyl)-4-oxo-8-(trifluoromethyl)-4H-chromene-2-carboxamide

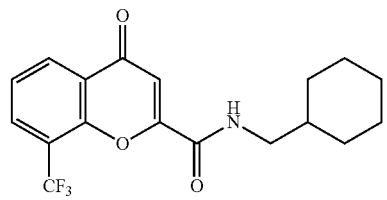 [SMILES: O=C(NCC1CCCCC1)c1cc(=O)c2cccc(C(F)(F)F)c2o1]

Prepared following to general procedure e for the synthesis of 2-chromone carboxamides. To a solution of 4-oxo-8-(trifluoromethyl)chromene-2-carboxylic acid (100 mg, 0.39 mmol) in DCM (1 mL) was added dropwise C(O)Cl$_2$ (98 mg, 0.77 mmol) at 0° C. The reaction mixture was stirred at 20° C. for 30 minutes. The reaction was concentrated under reduced pressure and the residue diluted with DCM (1 mL). The solution was added to a solution of cyclohexylmethanamine (57 mg, 0.50 mmol) and Et$_3$N (78 mg, 0.77 mmol) in DCM (1 mL). The reaction mixture was stirred at 20° C. for another 2.5 h. The mixture was then diluted with water (10 mL), and subsequently extracted with DCM (3×5 mL). The organic layers were combined and concentrated under reduced pressure. The residue was purified by preparative TLC (DCM/MeOH 5/1) to obtain N-(cyclohexylmethyl)-4-oxo-8-(trifluoromethyl)chromene-2-carboxamide (71 mg, 50.% yield) as a white solid. $^1$H NMR (400 MHz, DMSO) δ 8.53-8.52 (m, 1H), 8.34-8.32 (m, 1H), 8.27-8.25 (m, 1H) 7.71-7.68 (m, 1H), 7.00 (s, 1H), 3.17-3.14 (m, 2H), 1.73-1.56 (m, 6H), 1.22-1.15 (m, 3H), 0.96-0.93 (m, 2H). LCMS (ESI) m/z 354 (M+H)$^+$.

Prep. 28 Dimethyl 2-(4-fluoro-2-methoxyphenoxy) fumarate and dimethyl 2-(4-fluoro-2-methoxyphenoxy)maleate (1:1)

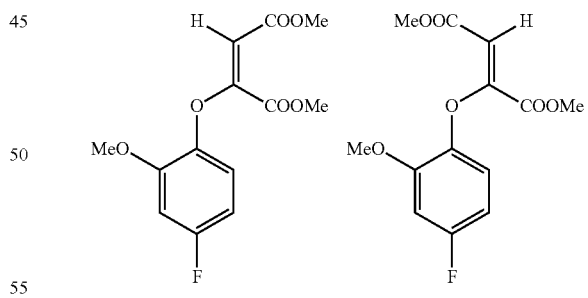

Prepared following general procedure for the synthesis of olefin diesters.

To the solution of 4-fluoro-2-methoxyphenol (5 g, 35 mmol, 4 mL) and dimethyl but-2-ynedioate (5 g, 35 mmol) in DCM (50 mL) was added Et$_3$N (3.56 g, 35 mmol, 4.88 mL). The reaction mixture was stirred at 25° C. for 2 h and then was concentrated under reduced pressure to obtain a 1/1 mixture of dimethyl 2-(4-fluoro-2-methoxyphenoxy)fumarate and dimethyl 2-(4-fluoro-2-methoxyphenoxy) maleate (5.5 g, 55% yield) as a red oil. The crude products were used for the next step without further purification.

Prep. 29 2-(4-Fluoro-2-methoxyphenoxy)fumaric acid and 2-(4-fluoro-2-methoxyphenoxy)maleic acid (1:1)

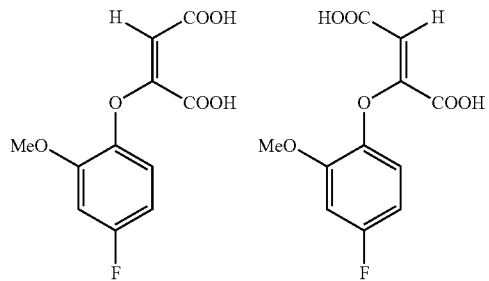 [SMILES: COc1cc(F)ccc1O/C(=C/C(=O)O)C(=O)O ; COc1cc(F)ccc1O/C(=C\C(=O)O)C(=O)O]

Prepared following general procedure for the synthesis of 2-chromone carboxylic acids. To the solution of dimethyl 2-(4-fluoro-2-methoxyphenoxy)fumarate and dimethyl 2-(4-fluoro-2-methoxyphenoxy)maleate (5.5 g, 19 mmol) in MeOH (90 mL), was added a solution of NaOH (3.1 g, 77 mmol) in $H_2O$ (30 mL). The reaction mixture was stirred at 25° C. for 5 h. The reaction mixture was concentrated under reduced pressure to remove MeOH and then washed with ethyl acetate (2×200 mL). The aqueous layer was acidified with 4N HCl to pH ~2-3 and then extracted with ethyl acetate (2×100 mL). The combined organic layers were washed with brine (50 mL) and dried with $Na_2SO_4$. The solvent was removed under reduced pressure to obtain a mixture of 2-(4-fluoro-2-methoxyphenoxy)fumaric acid and 2-(4-fluoro-2-methoxyphenoxy)maleic acid (1:1) (1.50 g, 30% yield) as light yellow solid.

Prep. 30 6-Fluoro-8-methoxy-4-oxo-4H-chromene-2-carboxylic acid

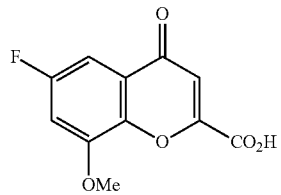 [SMILES: COc1cc(F)cc2c(=O)cc(C(=O)O)oc12]

To a solution of 2-(4-fluoro-2-methoxyphenoxy)fumaric acid and 2-(4-fluoro-2-methoxyphenoxy)maleic acid (1:1) (2 g, 7.8 mmol) in acetyl chloride (50 mL) was added $H_2SO_4$ (4.6 g, 47 mmol, 2.5 mL) drop-wise. The reaction mixture was stirred at 50° C. for 2 h and then was poured slowly into water (100 mL). The precipitate was filtered and dried under reduced pressure to afford 6-fluoro-8-methoxy-4-oxo-4H-chromene-2-carboxylic acid (800 mg, 43% yield) as an off-white solid. $^1$H NMR (400 MHz, Methanol-d4) δ 7.35-7.29 (m, 2H), 7.07 (s, 1H), 4.06 (s, 3H). LCMS (ESI) m/z 352 (M+H)$^+$.

Example 69

N-(cyclohexylmethyl)-6-fluoro-8-methoxy-4-oxo-4H-chromene-2-carboxamide

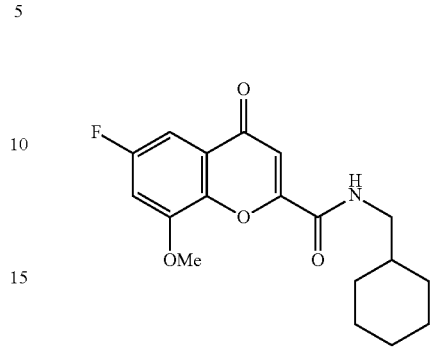

Prepared following General Procedure i.

To a solution of 6-fluoro-8-methoxy-4-oxo-4H-chromene-2-carboxylic acid (400 mg, 1.68 mmol) in DMF (5 mL) were added. cyclohexylmethanamine (285 mg, 2.52 mmol, 327 μL), HATU (1.28 g, 3.36 mmol) and DIPEA (868 mg, 6.72 mmol, 1.17 mL). The reaction mixture was stirred at 60° C. for 15 h and then diluted with $H_2O$ (20 mL) and extracted ethyl acetate (2×20 mL). The combined organic layers were dried over $Na_2SO_4$, filtered and concentrated under reduced pressure. The product was purified by column chromatography ($SiO_2$, petroleum ether/EtOAc 20/1 to 3:1) to obtain N-(cyclohexylmethyl)-6-fluoro-8-methoxy-4-oxo-4H-chromene-2-carboxamide (140 mg, 25% yield) as a yellow oil. LCMS (ESI) m/z 334 (M+H)$^+$.

Example 70

N-(cyclohexylmethyl)-6-fluoro-8-hydroxy-4-oxo-4H-chromene-2-carboxamide

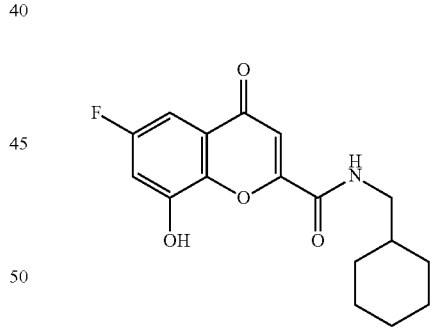

To a solution of N-(cyclohexylmethyl)-6-fluoro-8-methoxy-4-oxo-4H-chromene-2-carboxamide (100 mg, 0.3 mmol) in DCM (3 mL) was added $BBr_3$ (225 mg, 0.9 mmol, 87 μL) at −78° C. and stirred for 2 h. The mixture was allow to warm to 25° C. and stirred for 13 h. The reaction mixture was quenched by addition of EtOH (10 mL) at 25° C., and then was concentrated under reduced pressure. The residue was purified by preparative HPLC under acidic conditions to afford N-(cyclohexylmethyl)-6-fluoro-8-hydroxy-4-oxo-4H-chromene-2-carboxamide (32 mg, 33% yield) as a yellow solid. $^1$H NMR (400 MHz, DMSO) δ 10.93-10.92 (m, 1H), 9.15-9.12 (m, 1H), 7.24-7.20 (m, 1H), 7.17-7.14 (m, 1H), 6.84 (s, 1H), 3.21-3.18 (m, 2H), 1.75-1.61 (m, 6H), 1.24-0.94 (m, 5H). LCMS (ESI) m/z 320 (M+H)$^+$.

Prep. 33. Dimethyl 2-(4-chloro-2-methoxyphenoxy) fumarate and dimethyl 2-(4-chloro-2-methoxyphenoxy)maleate (1:1)

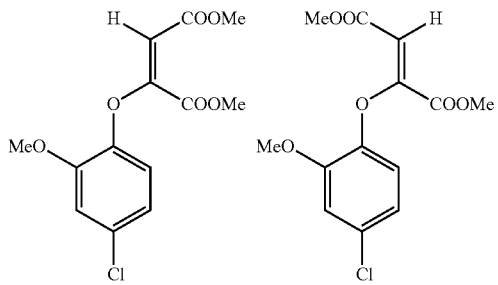 [SMILES: COC(=O)/C=C(/Oc1ccc(Cl)cc1OC)C(=O)OC ; COC(=O)/C=C(\Oc1ccc(Cl)cc1OC)C(=O)OC]

Prepared following general procedure for the synthesis of olefin diesters.

A solution of 4-chloro-2-methoxyphenol (1 g, 6.3 mmol, 770 µL) and Et$_3$N (640 mg, 6.31 mmol, 875 µL) was dissolved in DCM (20 mL), then dimethyl but-2-ynedioate (900 mg, 6.31 mmol) was added. The mixture was stirred at 20° C. for 2 hours and then poured into water (200 mL). The aqueous phase was extracted with DCM (3×100 mL). The combined organic phase was washed with brine (2×200 mL), dried with anhydrous Na$_2$SO$_4$, filtered and concentrated in vacuum to obtain dimethyl 2-(4-chloro-2-methoxyphenoxy)fumarate and dimethyl 2-(4-chloro-2-methoxyphenoxy)maleate (1:1) (2 g) as a yellow oil. LCMS (ESI) m/z 301 (M+H)$^+$.

Prep. 34. 2-(4-chloro-2-methoxyphenoxy)fumaric acid compound with 2-(4-chloro-2-methoxyphenoxy)maleic acid (1:1)

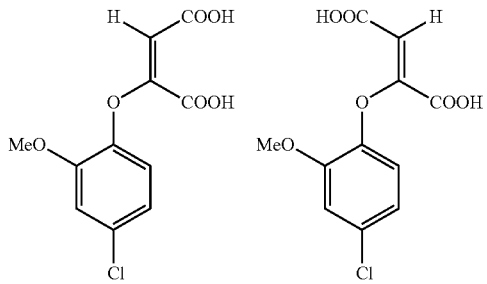 [SMILES: COc1cc(Cl)ccc1O/C(=C/C(=O)O)C(=O)O ; COc1cc(Cl)ccc1O/C(=C\C(=O)O)C(=O)O]

Prepared following general procedure for the synthesis of 2-chromone carboxylic acids.

A mixture of dimethyl 2-(4-chloro-2-methoxyphenoxy) fumarate and dimethyl 2-(4-chloro-2-methoxyphenoxy) maleate (1:1) (2.00 g) was dissolved in MeOH (15 mL) and H$_2$O (5 mL), then NaOH (533 mg, 13 mmol) was added. The mixture was stirred at 20° C. for 12 hours and then the mixture was poured into water (300 mL). The aqueous phase was extracted with ethyl acetate (3×300 mL). The aqueous layer was acidified with 4N HCl to pH ~2-3 and then extracted with ethyl acetate (2×100 mL). The combined organic phase was washed with brine (NaCl) (2×500 mL), dried with anhydrous Na$_2$SO$_4$, filtered and concentrated in vacuum to obtain a mixture of 2-(4-chloro-2-methoxyphenoxy)fumaric acid compound with 2-(4-chloro-2-methoxyphenoxy)maleic acid (1:1) (2 g) as a white solid.

Prep. 35. 6-chloro-8-methoxy-4-oxo-4H-chromene-2-carboxylic acid

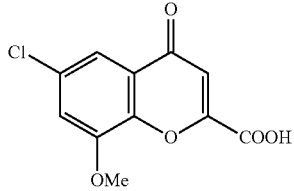 [SMILES: COc1cc(Cl)cc2c(=O)cc(C(=O)O)oc12]

Prepared following general procedure for the synthesis of 2-chromone carboxylic acids. A mixture of 2-(4-chloro-2-methoxyphenoxy)fumaric acid compound with 2-(4-chloro-2-methoxyphenoxy)maleic acid (1:1) (2 g, crude) was dissolved in acetyl chloride (20 mL), H$_2$SO$_4$ (1.44 g, 15 mmol, 0.78 mL) was added. The mixture was stirred at 50° C. for 2 h and then poured into ice-water (200 mL). The precipitate was filtered to afford 6-chloro-8-methoxy-4-oxo-4H-chromene-2-carboxylic acid (0.5 g, 31% yield) as a white solid. $^1$H NMR (400 MHz, CDCl$_3$) δ 7.61 (d, J=2.4 Hz 1H), 7.45 (d, J=2.0 Hz 1H), 7.07 (s, 1H), 4.05 (s, 3H). LCMS (ESI) m/z 255 (M+H)$^+$.

Prep. 35A. Dimethyl 2-(3-fluoro-4-methoxy phenoxy)fumarate and dimethyl 2-(3-fluoro-4-methoxyphenoxy)maleate (1:1)

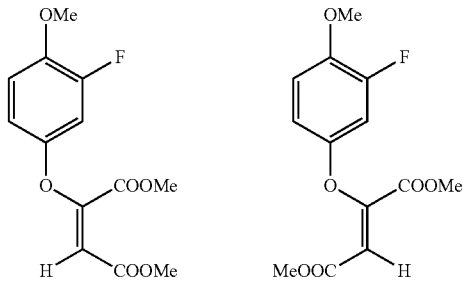 [SMILES: COC(=O)/C=C(/Oc1ccc(OC)c(F)c1)C(=O)OC ; COC(=O)/C=C(\Oc1ccc(OC)c(F)c1)C(=O)OC]

Prepared following general procedure for the synthesis of olefin diesters. The products were purified by column chromatography (petroleum ether/ethyl acetate 7/1), 29% yield.

Prep. 35B. 2-(3-Fluoro-4-methoxyphenoxy)fumaric acid and 2-(3-fluoro-4-methoxyphenoxy)maleic acid (1:1)

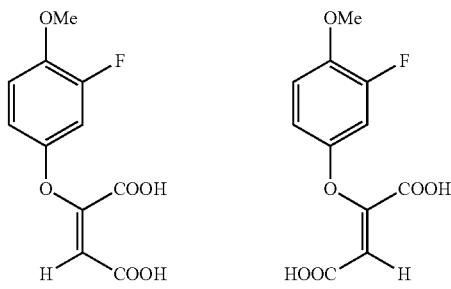 [SMILES: COc1ccc(O/C(=C/C(=O)O)C(=O)O)cc1F ; COc1ccc(O/C(=C\C(=O)O)C(=O)O)cc1F]

Prepared following general procedure for the synthesis of 2-chromone carboxylic acids, 81% yield.

Prep. 35C.
7-Fluoro-6-methoxy-4-oxo-4H-chromene-2-carboxylic acid

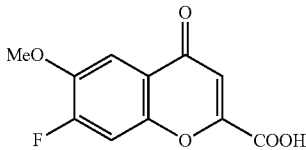 [SMILES: COc1cc2c(=O)cc(C(=O)O)oc2cc1F]

Prepared following general procedure for the synthesis of 2-chromone carboxylic acids, 98% yield. $^1$H NMR (400 MHz, DMSO) δ 7.86-7.83 (d, J=11.2 Hz, 1H), 7.60-7.57 (d, J=9.2 Hz, 1H), 6.91 (s, 1H), 3.96 (s, 3H).

Example 71

N-(cyclohexylmethyl)-7-fluoro-6-methoxy-4-oxo-4H-chromene-2-carboxamide

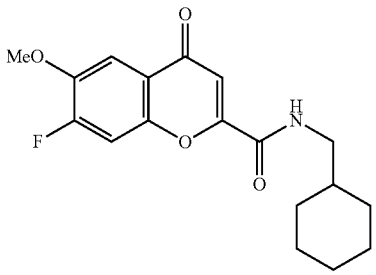 [SMILES: COc1cc2c(=O)cc(C(=O)NCC3CCCCC3)oc2cc1F]

Prepared following general procedure i for the synthesis of 2-chromone carboxamides. The product was purified by preparative HPLC, 9% yield. $^1$H NMR (400 MHz, DMSO) δ 9.04-9.01 (m, 1H), 7.67-7.65 (d, J=11.2 Hz, 1H), 7.60-7.57 (d, J=9.6 Hz, 1H), 6.80 (s, 1H), 3.96 (s, 3H), 3.16-3.12 (t, J=6.8 Hz, 2H), 1.73-1.57 (m, 6H), 1.21-1.16 (m, 3H), 0.98-0.92 (m, 2H). LCMS (ESI) m/z 334 (M+H)$^+$.

Example 72

N-(cyclohexylmethyl)-7-fluoro-6-hydroxy-4-oxo-4H-chromene-2-carboxamide

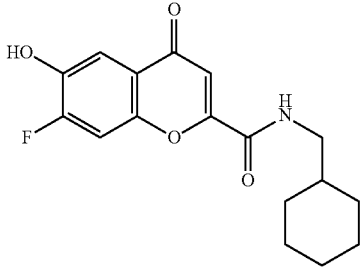 [SMILES: O=C(NCC1CCCCC1)c1cc(=O)c2cc(O)c(F)cc2o1]

To a solution of N-(cyclohexylmethyl)-7-fluoro-6-methoxy-4-oxo-4H-chromene-2-carboxamide (200 mg, 0.6 mmol) in DCM (2 mL) was added BBr$_3$ (751 mg, 3. mmol) at −78° C. Then the mixture was stirred at 25° C. for 30 min. The mixture was quenched with MeOH and concentrated under reduced pressure. The product was purified by preparative HPLC to give N-(cyclohexylmethyl)-7-fluoro-6-hydroxy-4-oxo-4H-chromene-2-carboxamide (44 mg, 23% yield) as a white solid. $^1$H NMR (400 MHz, DMSO) δ 9.01-8.98 (t, J=6.0 Hz, 1H), 7.59-7.57 (d, J=11.2 Hz, 1H), 7.51-7.49 (d, J=9.6 Hz, 1H), 6.74 (s, 1H), 3.16-3.12 (t, J=6.4 Hz, 2H), 1.72-1.68 (m, 6H), 1.21-1.18 (m, 3H), 0.95-0.92 (m, 2H). LCMS (ESI) m/z 320 (M+H)$^+$ Preparative Compounds and Exemplary Compounds for the Process Illustrated in Scheme 4.

Prep. 36 Methyl
6-chloro-8-methoxy-4-oxo-4H-chromene-2-carboxylate

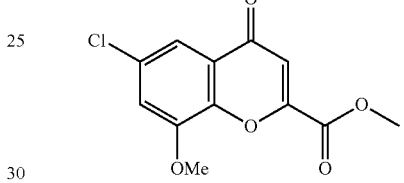

6-Chloro-8-methoxy-4-oxo-4H-chromene-2-carboxylic acid (0.5 g, 2 mmol) was dissolved in MeOH (10 mL) and SOCl$_2$ (0.47 g, 4.0 mmol, 0.285 mL) was added at 0° C. The reaction mixture was stirred at 65° C. for 1 hour and then filtered to afford methyl 6-chloro-8-methoxy-4-oxo-4H-chromene-2-carboxylate (300 mg) as a dark brown solid. $^1$H NMR (400 MHz, DMSO) δ 7.67 (d, J=2.4 Hz 1H), 7.58 (d, J=2.4 Hz 1H), 7.05 (s, 1H), 4.08 (s, 3H), 4.00 (s, 3H).

Prep. 37 Methyl
6-chloro-8-hydroxy-4-oxo-4H-chromene-2-carboxylate

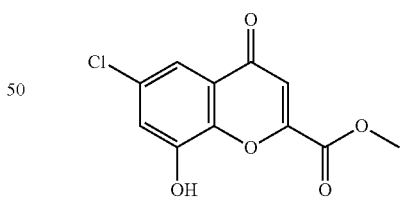

Methyl 6-chloro-8-methoxy-4-oxo-4H-chromene-2-carboxylate (300 mg, 1.12 mmol) was dissolved in DCM (10 mL) and BBr$_3$ (1.68 g, 6.70 mmol, 0.65 mL) was added at −78° C. under nitrogen. The reaction mixture was stirred at 25° C. for 12 hours and then poured into ice-water (50 mL). The aqueous phase was extracted with DCM (3×50 mL). The combined organic phase was washed with brine (2×100 mL), dried with anhydrous Na$_2$SO$_4$, filtered and concentrated in vacuum to afford methyl 6-chloro-8-hydroxy-4-oxo-4H-chromene-2-carboxylate (200.00 mg, crude) as a yellow solid. LCMS (ESI) m/z 255 (M+H)$^+$.

Example 73

6-Chloro-8-hydroxy-N-((1-hydroxycyclohexyl)methyl)-4-oxo-4H-chromene-2-carboxamide

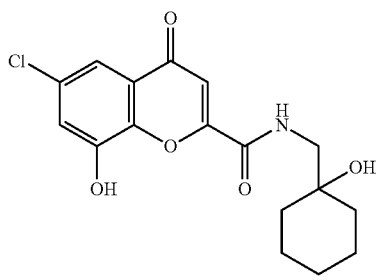 [SMILES: O=C(NCC1(O)CCCCC1)c1cc(=O)c2cc(Cl)cc(O)c2o1]

Methyl 6-chloro-8-hydroxy-4-oxo-4H-chromene-2-carboxylate (100 mg, 0.39 mmol) and 1-(aminomethyl)cyclohexanol (76 mg, 0.59 mmol) were dissolved in THF (2 mL), 4-dimethylaminopyridine (DMAP) (5 mg, 0.04 mmol) and Et$_3$N (120 mg, 1.18 mmol, 0.16 mL) were added. The mixture was stirred at 20° C. for 30 minutes. The mixture was poured into water (50 mL) and the aqueous phase was extracted with ethyl acetate (3×30 mL). The combined organic phase was washed with brine (2×100 mL), dried with anhydrous Na$_2$SO$_4$, filtered and concentrated in vacuum. The product was purified by preparative HPLC (acidic conditions) [Instrument: GX-E; Column: Phenomenex Synergi C18 250×21.2 mm, particle size: 4 μm; Mobile phase: 25-55% acetonitrile in H$_2$O (add 0.05% TFA, v/v)] to afford 6-chloro-8-hydroxy-N-((1-hydroxycyclohexyl)methyl)-4-oxo-4H-chromene-2-carboxamide (60 mg, 43% yield) as a white solid. $^1$H NMR (400 MHz, DMSO) δ11.19 (s, 1H), 8.96 (t, J=6.0 Hz, 1H), 7.41 (d, J=2.4 Hz, 1H), 7.35 (d, J=2.4 Hz, 1H), 6.88 (s, 1H), 4.47 (s, 1H), 3.34 (s, 2H), 1.68-1.20 (m, 10H). LCMS (ESI) m/z 352 (M+H)$^+$.

Prep. 39 Methyl 6-fluoro-8-methoxy-4-oxo-4H-chromene-2-carboxylate

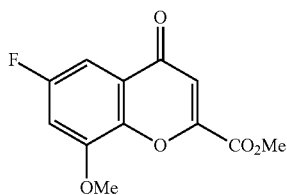 [SMILES: COC(=O)c1cc(=O)c2cc(F)cc(OC)c2o1]

A solution of 6-fluoro-8-methoxy-4-oxo-4H-chromene-2-carboxylic acid (600 mg, 2.52 mmol) in HCl/MeOH (6 mL) was stirred at 75° C. for 5 h. The reaction mixture was concentrated to obtain methyl 6-fluoro-8-methoxy-4-oxo-4H-chromene-2-carboxylate (350 mg, 55% yield) as an off-white solid.

Prep. 40A Methyl 6-fluoro-8-hydroxy-4-oxo-4H-chromene-2-carboxylate

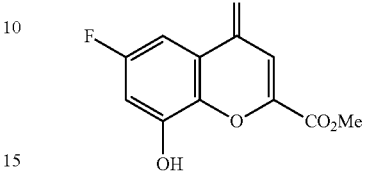

To a solution of compound 6-fluoro-8-methoxy-4-oxo-4H-chromene-2-carboxylate (180 mg, 0.71 mmol) in DCM (5 mL) was added BBr$_3$ (1.07 g, 4.28 mmol, 412 μL) dropwise at −78° C. The reaction mixture was then allowed to warm to 25° C. and stirred for 2 h. The reaction was diluted with DCM (20 mL) and quenched with an aqueous saturated solution of NaHCO$_3$ (20 mL) at 5° C. The organic layer was separated, washed with brine (10 mL) and dried over Na$_2$SO$_4$. The solvents was removed under reduced pressure and the residue was purified by preparative TLC (petroleum ether/ethyl acetate 1/2) to afford methyl 6-fluoro-8-hydroxy-4-oxo-4H-chromene-2-carboxylate (100 mg, 59% yield) as a yellow solid.

Prep. 40B 6-fluoro-8-hydroxy-4-oxo-4H-chromene-2-carboxylic acid

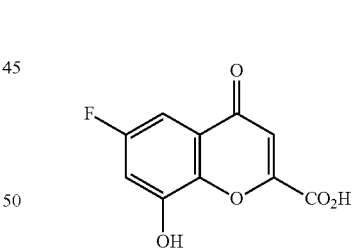

To a mixture of 6-fluoro-8-hydroxy-4-oxo-4H-chromene-2-carboxylate (1.5 g, 6.30 mmol, 1 eq) in MeOH (20 mL) was added K$_2$CO$_3$ (1.74 g, 12.60 mmol, 2 eq) at 20° C. and was stirred at 20° C. for 15 h. The mixture was filtered off, the filtrate was adjusted pH=2 with 4N HCl (10 mL), then filtered off to collected the filter cake. The filter cake was triturated with MeOH, then filtered off to give 6-fluoro-8-hydroxy-4-oxo-4H-chromene-2-carboxylic acid (1 g, 4.5 mmol, 71% yield) as a light yellow solid. $^1$H NMR (400 MHz, DMSO) δ 7.11-7.04 (m, 2H), 6.67 (s, 1H).

Example 74

6-fluoro-8-hydroxy-N-((1-hydroxycyclohexyl)methyl)-4-oxo-4H-chromene-2-carboxamide

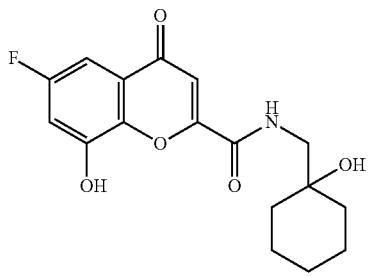 [SMILES: O=C(NCC1(O)CCCCC1)c1cc(=O)c2cc(F)cc(O)c2o1]

To a solution of methyl 6-fluoro-8-hydroxy-4-oxo-4H-chromene-2-carboxylate (15 mg, 0.63 mmol), DMAP (1.5 mg, 0.01 mmol) and Et$_3$N (25 mg, 0.25 mmol, 35 µL) in THF (0.5 mL) was added 1-(aminomethyl)cyclohexanol (24 mg, 0.19 mmol). The mixture was stirred at 25° C. for 1 h and then solvents were removed under reduced pressure. The residue was purified by preparative HPLC (column: Phenomenex Synergi C18 150*25*10 um; mobile phase: [water (0.225% FA)-ACN]; B %: 25%-55%, 10 min) to obtain 6-fluoro-8-hydroxy-N-((1-hydroxycyclohexyl)methyl)-4-oxo-4H-chromene-2-carboxamide (10 mg, 47% yield) as a white solid. $^1$H NMR (400 MHz, DMSO) δ 9.13-9.12 (m, 1H), 7.17-7.08 (m, 2H), 6.85 (s, 1H), 4.49 (s, 1H), 3.32-3.30 (m, 2H), 1.56-1.15 (m, 10H). LCMS (ESI) m/z 336 (M+H)$^+$.

Example 75

N-((4,4-difluorocyclohexyl)methyl)-6-fluoro-8-hydroxy-4-oxo-4H-chromene-2-carboxamide

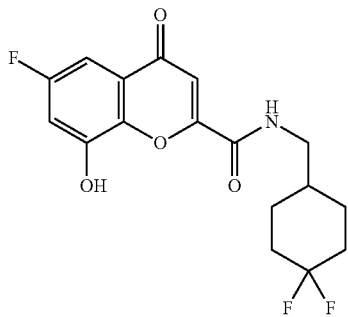 [SMILES: O=C(NCC1CCC(F)(F)CC1)c1cc(=O)c2cc(F)cc(O)c2o1]

To a solution of 6-fluoro-8-hydroxy-4-oxo-4H-chromene-2-carboxylate (60 mg, 0.25 mmol), DMAP (6 mg, 0.05 mol) and Et$_3$N (102 mg, 1.01 mmol, 139.68 µL) in THF (0.5 mL) was added (4,4-difluorocyclohexyl)methanamine (94 mg, 0.62 mmol). The mixture was stirred at 25° C. for 1 h and then solvents were removed under reduced pressure. The residue was purified by preparative HPLC (column: Phenomenex Synergi C18 150*25*10 um; mobile phase: [water (0.225% FA)-ACN]; B %: 35%-65%, 10 min) to obtain N-((4,4-difluorocyclohexyl)methyl)-6-fluoro-8-hydroxy-4-oxo-4H-chromene-2-carboxamide (18 mg, 19% yield) as a white solid. $^1$H NMR (400 MHz, DMSO) δ 9.42-9.41 (m, 1H), 7.14-7.05 (m, 2H), 6.82 (m, 1H), 3.25-3.23 (m, 2H), 2.10-2.08 (m, 2H), 1.79-1.71 (m, 5H), 1.22-1.15 (m, 2H). LCMS (ESI) m/z 356 (M+H)$^+$.

Example 76A

N-((4,4-difluoro-1-hydroxycyclohexyl)methyl)-6-fluoro-8-hydroxy-4-oxo-4H-chromene-2-carboxamide

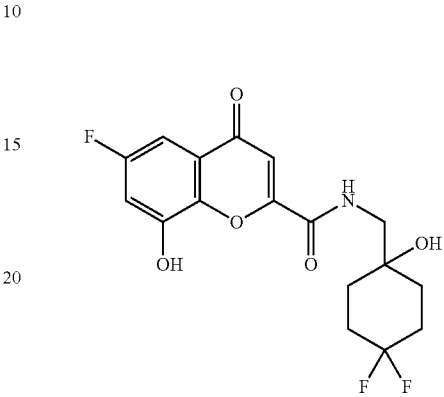

To a solution of 6-fluoro-8-hydroxy-4-oxo-4H-chromene-2-carboxylate (80 mg, 0.35 mmol), DMAP (8 mg, 0.07 mmol) and Et$_3$N (136 mg, 1.34 mmol, 186 µL) in THF (0.5 mL) was added 1-(aminomethyl)-4,4-difluoro-cyclohexanol (139 mg, 0.84 mmol). The mixture was stirred at 25° C. for 16 h and then solvents were removed under reduced pressure. The residue was purified by preparative HPLC (column: Welch Ultimate AQ-C18 150*30 mm*5 um; mobile phase: [water (0.1% TFA)-ACN]; B %: 30%-60%, 13 min) to obtain N-((4,4-difluoro-1-hydroxycyclohexyl)methyl)-6-fluoro-8-hydroxy-4-oxo-4H-chromene-2-carboxamide (13 mg, 10% yield) as a white solid. $^1$H NMR (400 MHz, DMSO) δ 9.14-9.11 (m, 1H), 7.24-7.21 (m, 1H), 7.18-7.15 (m, 1H), 6.88 (s, 1H), 4.86 (s, 1H), 3.40-3.38 (d, J=6.4 Hz, 2H), 2.15-1.83 (m, 4H), 1.66-1.58 (m, 4H). LCMS (ESI) m/z 372 (M+H)$^+$.

Example 76B

N-cyclohexyl-6-fluoro-8-hydroxy-4-oxo-chromene-2-carboxamide

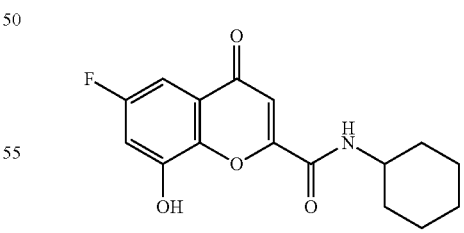

To a suspension of 6-fluoro-8-hydroxy-4-oxo-chromene-2-carboxylic acid (50 mg, 0.22 mmol) in anhydrous THF (0.5 mL) was added EDCl (51.3 mg, 0.27 mmol) and stirred for at room temperature for 1 hour. Cyclohexanamine (33.2 mg, 0.33 mmol) and trimethylamine (27 mg, 0.27 mmol) were then added and the reaction left at room temperature for 36 h. The reaction was diluted with a 6:3:1 solution of DMSO: MeOH: WATER and purified by preparative HPLC (Waters) using 5-95% method and 0.1% formic acid in water and acetonitrile as eluents. Fractions containing product were evaporated (Genevac) and pooled together to obtain the desired N-cyclohexyl-6-fluoro-8-hydroxy-4-oxo-chromene-2-carboxamide (10 mg, 13%) as a white solid. $^1$H NMR (400 MHz, DMSO) δ 11.03 (brs, 1H), 8.87 (d, J=8 Hz, 1H), 7.21 (dd, J=3, 9.9 Hz, 1H), 7.15 (dd, J=3, 8.3 Hz, 1H), 6.84 (s, 1H), 3.8 (m, 1H), 1.84 (m, 4H), 1.65 (m, 1H), 1.35 (m, 4H), 1.16 (m, 1H). LC-MS (ESI), m/z 306 [M+H]$^+$.

Example 76C

N-(3,3-Difluorocyclohexyl)-6-fluoro-8-hydroxy-4-oxo-4H-chromene-2-carboxamide

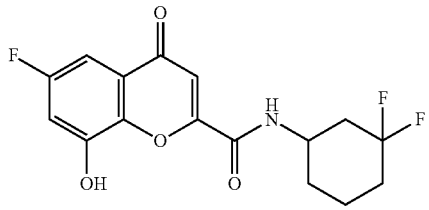 [SMILES: O=C(NC1CCCC(F)(F)C1)c1cc(=O)c2cc(F)cc(O)c2o1]

Following procedure for the preparation of example 76C. The compound was purified by preparative HPLC (acidic conditions), 21% yield. $^1$H NMR (400 MHz, MeOD) d 7.25 (dd, J=3.0, 8.2 Hz, 1H), 7.11 (dd, J=3.0, 9.6 Hz, 1H), 7.03 (s, 1H), 4.23-4.16 (m, 1H), 2.48-2.38 (m, 1H), 2.15-2.02 (m, 2H), 1.97-1.90 (m, 2H), 1.89-1.77 (m, 1H), 1.75-1.60 (m, 2H), 1.57-1.46 (m, 1H). LC-MS (ESI), m/z 342 [M+H]$^+$.

Prep 40C 2-trimethylsilyloxyspiro[3.3]heptane-2-carbonitrile

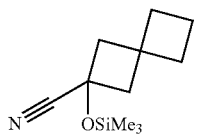

To a solution of diiodozinc (3 mg, 0.01 mmol) in anhydrous DCM (1.8 mL) that was cooled in an ice bath, were added spiro[3.3]heptan-2-one (100 mg, 0.90 mmol) and trimethylsilylformonitrile (90 mg, 0.91 mmol). The reaction mixture was stirred for 1 h at room temperature. The reaction was quenched with a 10% aq. solution of sodium carbonate and product was extracted with DCM and passed through a hydrophobic frit and the volatiles removed in vacuo. 2-trimethylsilyloxyspiro[3.3]heptane-2-carbonitrile was obtained (180 mg, 90%) as an orange oil. $^1$H NMR (400 MHz, CDCl$_3$) 2.51 (m, 2H), 2.07 (m, 2H), 1.99 (m, 2H), 1.78 (m, 2H), 1.65 (m, 2H).

Prep 40D 2-(aminomethyl)spiro[3.3]heptan-2-ol hydrochloride

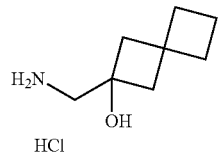

LiAlH$_4$ (1M in THF) (49 mg, 1.29 mmol) was diluted with anhydrous ether (6.15 mL) and cooled in an ice bath before the dropwise addition of 2-trimethylsilyloxyspiro [3.3]heptane-2-carbonitrile (180 mg, 0.86 mmol) in ether (6.15 mL). After complete addition, the reaction was allowed to warm to room temperature for 2 h. The reaction was then cooled in an ice bath and ice added until no effervescence was observed. Approx. 2 ml of 1M NaOH was added and the mixture stirred at room temperature for approximately 10 mins before being filtered through a celite cartridge. 1.5 ml of 4M HCl in dioxane was added and the volatiles removed in vacuo. The residue was triturated with ether to give 2-(aminomethyl)spiro[3.3]heptan-2-ol hydrochloride (72 mg, 45%) as an off white solid. $^1$H NMR (500 MHz, DMSO) 7.08 (br s, 3H), 5.60 (br s, 1H), 2.74 (m, 2H), 2.4 (m, 1H), 1.97 (m, 6H), 1.77 (m, 2H).

Example 76D 6-fluoro-8-hydroxy-N-((2-hydroxyspiro[3.3]heptan-2-yl)methyl)-4-oxo-4H-chromene-2-carboxamide

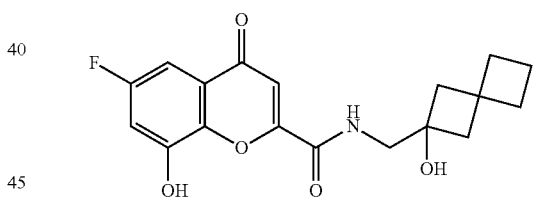

To a suspension of 6-fluoro-8-hydroxy-4-oxo-chromene-2-carboxylic acid (80 mg, 0.36 mmol) in anhydrous THF (5 mL) was added EDCl (82 mg, 0.43 mmol) and stirred at room temperature for 1 hour. 2-(aminomethyl)spiro[3.3] heptan-2-ol hydrochloride (73 mg, 0.41 mmol) was added followed by triethylamine (74 mg, 0.74 mmol) and the reaction left at room temperature for 16 h. DCM and saturated NaHCO$_3$ were added and the organics isolated using a hydrophobic frit. The volatiles were removed and the residue purified by preparative HPLC using 5-95% method and 0.1% formic acid in water and acetonitrile as eluents. Fractions containing product were evaporated and pooled together to obtain the desired 6-fluoro-8-hydroxy-N-((2-hydroxyspiro[3.3]heptan-2-yl)methyl)-4-oxo-4H-chromene-2-carboxamide (12.8 mg, 10% yield) as a white solid. $^1$H NMR (400 MHz, DMSO) 11.19 (s, 1H), 9.10 (t, J=6 Hz, 1H), 7.21 (dd, J=3, 9.9 Hz, 1H), 7.16 (dd, J=3, 8.4 Hz, 1H), 6.89 (s, 1H), 5.26 (s, 1H), 3.40 (d, J=6.2 Hz, 2H), 2.19 (m, 2H), 2.07 (m, 2H), 1.94 (m, 4H), 1.77 (m, 2H). LC-MS (ESI), m/z 348 [M+H]$^+$.

Example 76E

N-(cyclobutylmethyl)-6-fluoro-8-hydroxy-4-oxo-4H-chromene-2-carboxamide

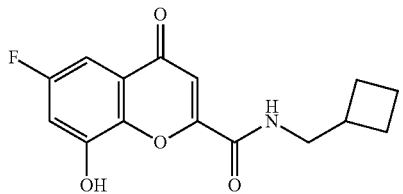

To a suspension of 6-fluoro-8-hydroxy-4-oxo-chromene-2-carboxylic acid (100 mg, 0.45 mmol) in anhydrous THF (5 mL) was added EDCl (103 mg, 0.54 mmol). After 1 hour, cyclobutylmethaneamine (38 mg, 0.45 mmol) and Et$_3$N (54 mg, 0.54 mmol) were added and the reaction left overnight at room temperature. Product was partitioned between DCM (10 mL) and NaHCO$_3$ (5 mL) and organic phase was concentrated under reduced pressure. The product was purified by preparative HPLC. Fractions containing product were evaporated and pooled together to obtain the desired N-(cyclobutylmethyl)-6-fluoro-8-hydroxy-4-oxo-4H-chromene-2-carboxamide (16 mg, 12% yield) as a white solid. $^1$H NMR (500 MHz, DMSO) δ 10.96-10.96 (m, 1H), 9.13 (dd, J=5.8, 5.8 Hz, 1H), 7.22-7.12 (m, 2H), 6.84 (s, 1H), 3.41-3.38 (m, 2H), 2.60-2.59 (m, 1H), 2.07-1.99 (m, 2H), 1.87-1.82 (m, 2H), 1.78-1.71 (m, 2H). LC-MS (ESI), m/z 292 [M+H]$^+$.

Example 76F 6-fluoro-8-hydroxy-N-((1-hydroxycyclopentyl)methyl)-4-oxo-4H-chromene-2-carboxamide

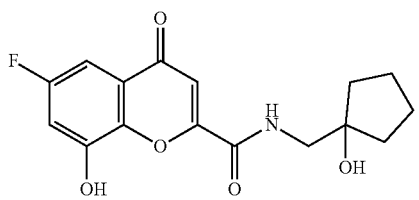 [SMILES: O=C(NCC1(O)CCCC1)c1cc(=O)c2cc(F)cc(O)c2o1]

To a suspension of 6-fluoro-8-hydroxy-4-oxo-chromene-2-carboxylic acid (100 mg, 0.45 mmol) in anhydrous THF (5 mL) was added EDCl (103 mg, 0.54 mmol). After 1 hour, 1-(aminomethyl)cyclopentanol (52 mg, 0.45 mmol) and Et$_3$N (54 mg, 0.54 mmol) were added and the reaction left overnight at room temperature. Product was partitioned between DCM (10 mL) and NaHCO$_3$ (5 mL) and organic phase was concentrated under reduced pressure. The product was purified by preparative HPLC. Fractions containing product were evaporated and pooled together to obtain the desired 6-fluoro-8-hydroxy-N-((1-hydroxycyclopentyl)methyl)-4-oxo-4H-chromene-2-carboxamide (20 mg, 13% yield) as a white solid. $^1$H NMR (500 MHz, DMSO) δ 9.09 (t, J=6.3 Hz, 1H), 7.22-7.12 (m, 2H), 6.87 (s, 1H), 4.63 (s, 1H), 3.44 (d, J=6.3 Hz, 2H), 1.74-1.69 (m, 2H), 1.61-1.53 (m, 6H). LC-MS (ESI), m/z 322 [M+H]$^+$.

Example 76G

N-(3-cyclobutylpropyl)-6-fluoro-8-hydroxy-4-oxo-4H-chromene-2-carboxamide

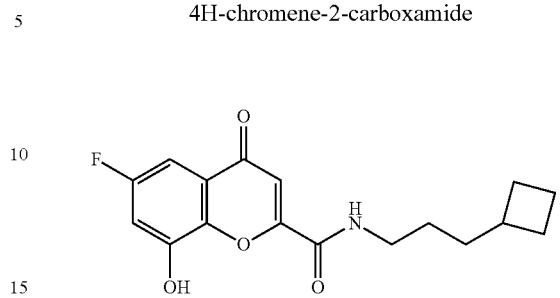

To a suspension of 6-fluoro-8-hydroxy-4-oxo-chromene-2-carboxylic acid (100 mg, 0.5 mmol) in anhydrous THF (3 mL) was added EDCl (103 mg, 0.5 mmol). The reaction mixture was stirred at rt to give a clear solution. After 1 hour, 3-cyclobutylpropan-1-amine hydrochloride (134 mg, 0.9 mmol) in DCM and Et$_3$N (59 mg, 0.6 mmol) was added. The reaction mixture was stirred for 18 h. The solvent was removed in vacuo and the residue purified by preparative HPLC. Fractions containing product were evaporated and pooled together to obtain the desired N-(3-cyclobutylpropyl)-6-fluoro-8-hydroxy-4-oxo-4H-chromene-2-carboxamide (19 mg, 12% yield) as a white solid. $^1$H NMR (500 MHz, DMSO) δ 9.13 (t, J=5.5 Hz, 1H), 7.23-7.13 (m, 2H), 6.83 (s, 1H), 3.29 (d, J=6.9 Hz, 1H), 2.52-2.50 (m, 2H), 2.34-2.24 (m, 1H), 2.06-1.97 (m, 2H), 1.86-1.74 (m, 2H), 1.62-1.74 (m, 2H). LC-MS (ESI), m/z 320 [M+H]$^+$.

Example 76H 6-fluoro-8-hydroxy-N-(2-methylbutyl)-4-oxo-chromene-2-carboxamide

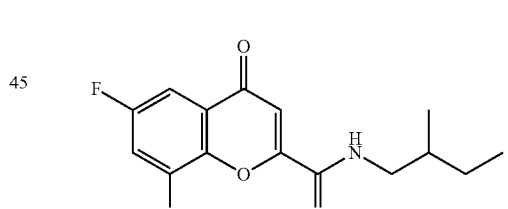

To a suspension of 6-fluoro-8-hydroxy-4-oxo-chromene-2-carboxylic acid (100 mg, 0.45 mmol) in anhydrous THF (1.1 mL) was added EDCl (103 mg, 0.5 mmol) and stirred at room temperature. After 1 hour, 2-methylbutan-1-amine (39 mg, 0.45 mmol) and Et$_3$N (54 mg, 0.5 mmol) were added and left overnight at room temperature. The product was purified by preparative HPLC. Fractions containing product were evaporated and pooled together to obtain the desired 6-fluoro-8-hydroxy-N-(2-methylbutyl)-4-oxo-chromene-2-carboxamide (23 mg, 16% yield) as light yellow solid. $^1$H NMR (400 MHz, DMSO) δ 10.90 (s, 1H), 9.12 (dd, J=5.9, 5.9 Hz, 1H), 7.24-7.14 (m, 2H), 6.84 (s, 1H), 3.27 (dd, J=6.5, 13.1 Hz, 1H), 3.20-3.12 (m, 1H), 1.68 (dd, J=6.7, 12.6 Hz, 1H), 1.47-1.39 (m, 1H), 1.21-1.10 (m, 1H), 0.93-0.88 (m, 6H). LC-MS (ESI), m/z 294 [M+H]$^+$.

Prep. 40A. Dimethyl 2-(3-fluoro-2-methoxyphenoxy)fumarate and dimethyl 2-(3-fluoro-2-methoxyphenoxy)maleate (1:1)

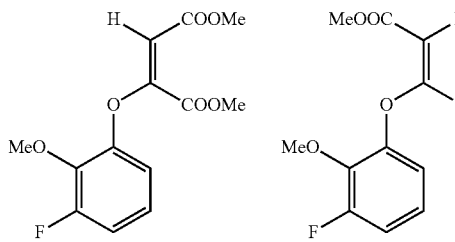

Starting from 3-fluoro-2-methoxyphenol (Combi-Blocks, OT-0938) prepared following general procedure for the synthesis of olefin diesters. The product was purified by column chromatography (petroleum ether/ethyl acetate 7/1), 69% yield. LCMS (ESI) m/z 285 (M+H)$^+$.

Prep. 40B. 2-(3-Fluoro-2-methoxyphenoxy)fumaric acid and 2-(3-fluoro-2-methoxyphenoxy)maleic acid (1:1)

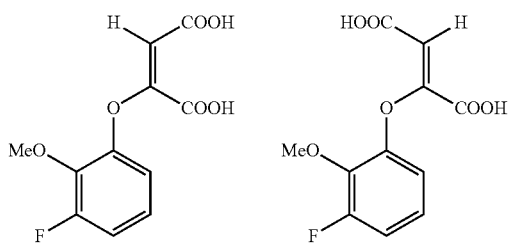 [SMILES: COc1c(F)cccc1O/C(=C/C(=O)O)C(=O)O ; COc1c(F)cccc1O/C(=C\C(=O)O)C(=O)O]

Prepared following general procedure for the synthesis of 2-chromone carboxylic acids. The reaction crude was poured into 1 N HCl (50 mL). The aqueous phase was extracted with ethyl acetate (3×50 mL). The combined organic phase was washed with brine (2×100 mL), dried with anhydrous Na$_2$SO$_4$, filtered and concentrated in vacuum.

Prep. 40C. 7-fluoro-8-methoxy-4-oxo-4H-chromene-2-carboxylic acid

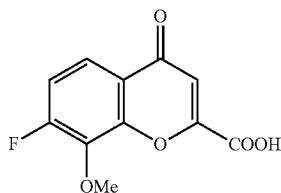 [SMILES: COc1c(F)ccc2c(=O)cc(C(=O)O)oc12]

Prepared following general procedure for the synthesis of 2-chromone carboxylic acids, 67% yield. $^1$H NMR (400 MHz, DMSO) δ 7.81-7.75 (m, 1H), 7.48 (t, J=9.8 Hz, 1H), 6.92 (s, 1H), 4.08 (s, 3H). LCMS (ESI) m/z 239 (M+H)$^+$

Prep. 40D. Methyl 7-fluoro-8-methoxy-4-oxo-4H-chromene-2-carboxylate

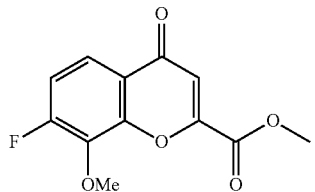 [SMILES: COC(=O)c1cc(=O)c2ccc(F)c(OC)c2o1]

7-Fluoro-8-methoxy-4-oxo-4H-chromene-2-carboxylic acid (500 mg, 2.1 mmol) was dissolved in MeOH (5 mL), SOCl$_2$ (499 mg, 4.20 mmol, 0.304 mL) was added. The mixture was stirred at 65° C. for 2 hours. The mixture was filtered to afford methyl 7-fluoro-8-methoxy-4-oxo-4H-chromene-2-carboxylate (400 mg, 75% yield) as an off-white solid. LCMS (ESI) m/z 253 (M+H)$^+$.

Prep. 40B. Methyl 7-fluoro-8-hydroxy-4-oxo-4H-chromene-2-carboxylate

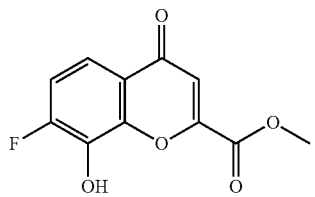 [SMILES: COC(=O)c1cc(=O)c2ccc(F)c(O)c2o1]

Methyl 7-fluoro-8-methoxy-4-oxo-4H-chromene-2-carboxylate (500 mg, 2 mmol) was dissolved in DCM (5 mL), BBr$_3$ (1.5 g, 6.0 mmol, 0.57 mL) was added at −78° C. The mixture was stirred at 25° C. for 16 hours. The mixture was poured into water (50 mL). The aqueous phase was extracted with DCM (2×50 mL). The combined organic phase was washed with brine (3×200 mL), dried with anhydrous Na$_2$SO$_4$, filtered and concentrated in vacuum to afford methyl 7-fluoro-8-hydroxy-4-oxo-4H-chromene-2-carboxylate (200 mg, 42% yield) as yellow solid. LCMS (ESI) m/z 239 (M+H)$^+$.

Example 77

Fluoro-8-hydroxy-N-((1-hydroxycyclohexyl)methyl)-4-oxo-4H-chromene-2-carboxamide

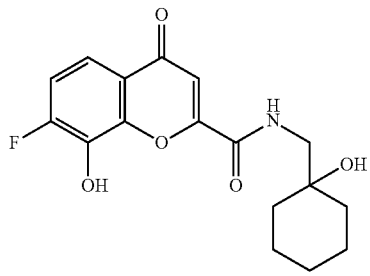 [SMILES: O=C(NCC1(O)CCCCC1)c1cc(=O)c2ccc(F)c(O)c2o1]

Methyl 7-fluoro-8-hydroxy-4-oxo-4H-chromene-2-carboxylate (100 mg, 0.42 mmol) and 1-(aminomethyl)cyclohexanol (55 mg, 0.42 mmol) were dissolved in THF (2 mL), Et₃N (127 mg, 1.26 mmol, 0.174 mL) and DMAP (5 mg, 0.042 mmol) were added. The mixture was stirred at 25° C. for 1 hour. The mixture was poured into water (30 mL). The aqueous phase was extracted with ethyl acetate (3×30 mL). The combined organic phase was washed with brine (2×50 mL), dried with anhydrous Na₂SO₄, filtered and concentrated in vacuum. The crude product was purified by preparative HPLC (TFA) [Instrument: GX-E; Column: Phenomenex Synergi C18 250×21.2 mm, particle size: 4 μm; Mobile phase: 25-55% acetonitrile in 0.05% TFA in water] to afford 7-fluoro-8-hydroxy-N-((1-hydroxycyclohexyl)methyl)-4-oxo-4H-chromene-2-carboxamide (7 mg, 5% yield) as a white solid. ¹H NMR (400 MHz, MeOD) δ 7.68-7.64 (m, 1H), 7.32 (t, J=9.8 Hz, 1H), 7.03 (s, 1H), 3.49 (s, 2H), 1.71-1.53 (m, 10H). LCMS (ESI) m/z 336 (M+H)⁺.

Example 78

N-(cyclohexylmethyl)-7-fluoro-8-hydroxy-4-oxo-4H-chromene-2-carboxamide

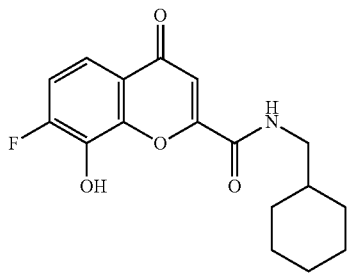 [SMILES: O=C(NCC1CCCCC1)c1cc(=O)c2ccc(F)c(O)c2o1]

Methyl 7-fluoro-8-hydroxy-4-oxo-4H-chromene-2-carboxylate (100 mg, 0.42 mmol) and cyclohexylmethanamine (48 mg, 0.42 mmol, 0.055 mL) were dissolved in THF (2 mL), Et₃N (127 mg, 1.26 mmol, 0.174 mL) and DMAP (5 mg, 0.042 mmol) were added. The mixture was stirred at 25° C. for 1 hour. The mixture was poured into water (30 mL). The aqueous phase was extracted with ethyl acetate (3×30 mL). The combined organic phase was washed with brine (2×50 mL), dried with anhydrous Na₂SO₄, filtered and concentrated in vacuum. The crude product was purified by preparative HPLC (TFA) [Instrument: GX-E; Column: Phenomenex Synergi C18 250×21.2 mm, particle size: 4 μm; Mobile phase: 25-55% acetonitrile in 0.05% TFA in water] to afford N-(cyclohexylmethyl)-7-fluoro-8-hydroxy-4-oxo-4H-chromene-2-carboxamide (42 mg, 31% yield) as a white solid. ¹H NMR (400 MHz, MeOD) δ 7.67-7.64 (m, 1H), 7.32 (t, J=9.6 Hz, 1H), 7.01 (s, 1H), 3.33 (s, 2H), 1.85-1.70 (m, 6H), 1.34-1.26 (m, 3H), 1.06-1.01 (m, 2H). LCMS (ESI) m/z 320 (M+H)⁺.

Example 79

N-((4,4-difluorocyclohexyl)methyl)-7-fluoro-8-hydroxy-4-oxo-4H-chromene-2-carboxamide

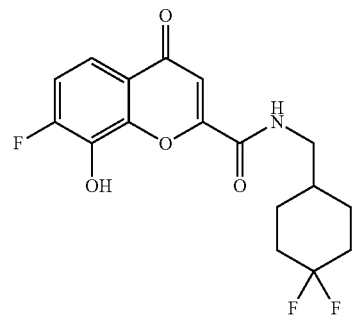 [SMILES: O=C(NCC1CCC(F)(F)CC1)c1cc(=O)c2ccc(F)c(O)c2o1]

Methyl 7-fluoro-8-hydroxy-4-oxo-4H-chromene-2-carboxylate (300 mg, 1.26 mmol, 1 eq) and (4,4-difluorocyclohexyl)methanamine (280 mg, 1.50 mmol, 1.2 eq, HCl) were dissolved in THF (2 mL), TEA (510 mg, 5 mmol, 700 uL, 4 eq) and DMAP (16 mg, 126 umol, 0.1 eq) was added. The mixture was stirred at 25° C. for 1 hour. The mixture was poured into water (100 mL). The aqueous phase was extracted with ethyl acetate (100 mL×3). The combined organic phase was washed with 1N HCl (100 mL) and brine (100 mL×2), dried with anhydrous Na₂SO₄, filtered and concentrated in vacuum. The products washed with MeCN (20 mL) to afford N-((4,4-difluorocyclohexyl)methyl)-7-fluoro-8-hydroxy-4-oxo-4H-chromene-2-carboxamide (78 mg, 219 umol, 17% yield, 99% purity) as white solid. ¹H NMR (400 MHz, DMSO-d6) δ 9.31-9.28 (t, J=6.0 Hz, 1H), 7.59-7.55 (m, 1H), 7.48-7.44 (m, 1H), 6.88 (s, 1H), 3.35-3.32 (m, 2H), 2.10-2.05 (m, 2H), 1.90-1.79 (m, 5H), 1.32-1.24 (m, 2H). LCMS (ESI) m/z 356.0 (M+H)⁺.

Example 80

N-((4,4-difluoro-1-hydroxycyclohexyl)methyl)-7-fluoro-8-hydroxy-4-oxo-4H-chromene-2-carboxamide

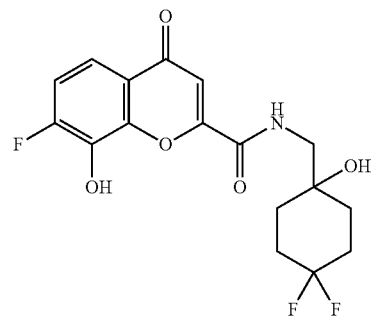 [SMILES: O=C(NCC1(O)CCC(F)(F)CC1)c1cc(=O)c2ccc(F)c(O)c2o1]

Methyl 7-fluoro-8-hydroxy-4-oxo-4H-chromene-2-carboxylate (300 mg, 1.26 mmol, 1 eq) and (4,4-difluoro-1-hydroxycyclohexyl)methanamine (254 mg, 1.26 mmol, 1 eq, HCl) was dissolved in THF (5 mL), TEA (383 mg, 3.8 mmol, 525 uL, 3 eq) and DMAP (16 mg, 126 umol, 0.1 eq) was added. The mixture was stirred at 25° C. for 1 hour. The mixture was poured into water (30 mL). The aqueous phase was extracted with ethyl acetate (30 mL×3). The combined organic phase was washed with brine (50 mL×2), dried with anhydrous Na$_2$SO$_4$, filtered and concentrated in vacuum. The products was washed with MeCN (50 mL) to afford N-((4,4-difluoro-1-hydroxycyclohexyl)methyl)-7-fluoro-8-hydroxy-4-oxo-4H-chromene-2-carboxamide (59 mg, 159 umol, 13% yield, 99% purity) as white solid. $^1$H NMR (400 MHz, DMSO-d6) δ 11.06 (s, 1H), 9.26-9.23 (t, J=6.0 Hz, 1H), 7.59-7.55 (m, 1H), 7.49-7.44 (m, 1H), 6.91 (s, 1H), 4.92 (s, 1H), 3.46 (d, J=6.4 Hz, 2H), 2.13-1.96 (m, 4H), 1.75-1.64 (m, 4H). LCMS (ESI) m/z 372.1 (M+H)$^+$.

Prep. 41A. dimethyl 2-(2-fluoro-4-methoxyphenoxy)maleate and dimethyl 2-(2-fluoro-4-methoxyphenoxy)fumarate (1:1)

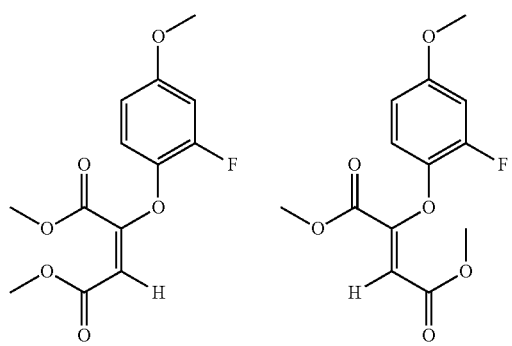 [SMILES: COC(=O)/C=C(/Oc1ccc(OC)cc1F)C(=O)OC ; COC(=O)/C=C(\Oc1ccc(OC)cc1F)C(=O)OC]

Prepared following general procedure for the synthesis of olefin diesters. The products were purified were used in the next step without further purification.

Prep. 41B. 2-(2-fluoro-4-methoxyphenoxy)maleic acid and 2-(2-fluoro-4-methoxyphenoxy)fumaric acid (1:1)

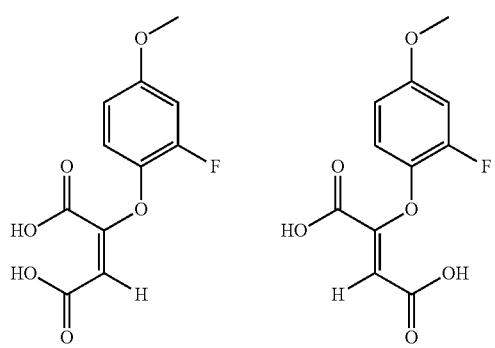 [SMILES: COc1ccc(O/C(=C/C(=O)O)C(=O)O)c(F)c1 ; COc1ccc(O/C(=C\C(=O)O)C(=O)O)c(F)c1]

Prepared following general procedure for the synthesis of 2-chromone carboxylic acids, 78% yield.

Prep. 41C. 8-fluoro-6-methoxy-4-oxo-4H-chromene-2-carboxylic acid

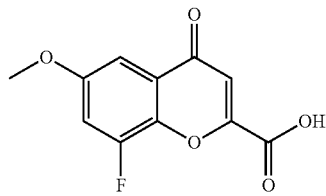 [SMILES: COc1cc(F)c2oc(C(=O)O)cc(=O)c2c1]

Prepared following general procedure for the synthesis of 2-chromone carboxylic acids, 79% yield. $^1$H NMR (400 MHz, DMSO) δ 7.44 (s, 1H), 6.93 (s, 1H), 6.90-6.90 (m, 2H), 6.88-6.83 (m, 2H), 6.26 (s, 1H), 4.94 (s, 1H), 3.79-3.78 (m, 3H). LCMS (ESI) m/z 239.0 (M+1)+.

Prep. 42A. methyl 8-fluoro-6-methoxy-4-oxo-4H-chromene-2-carboxylate

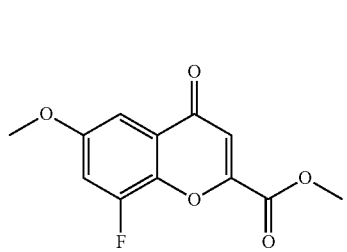

To a solution of 8-fluoro-6-methoxy-4-oxo-4H-chromene-2-carboxylic acid (2.20 g, 9.24 mmol, 1.00 eq) in MeOH (170.00 mL) was added SOCl2 (3.08 g, 25.86 mmol, 1.88 mL, 2.80 eq) dropwise. The mixture was stirred at 65° C. for 1 h. TLC (PE:EA=3:1; Rf=0.51) showed there was a major new spot appeared. The mixture was filtered and the filter cake was collected giving methyl 8-fluoro-6-methoxy-4-oxo-4H-chromene-2-carboxylate (2.00 g, 6.39 mmol, 69.16% yield, 80.58% purity) as a white solid. $^1$H NMR (400 MHz, DMSO) δ 7.61-7.57 (dd, J1=2.8 Hz, J2=6.0 Hz, 1H), 7.26 (s, 1H), 6.97 (s, 1H), 3.95 (s, 3H), 3.88 (s, 3H). LCMS (ESI) m/z 253.1 (M+1)+.

Prep. 42B. methyl 8-fluoro-6-hydroxy-4-oxo-4H-chromene-2-carboxylate

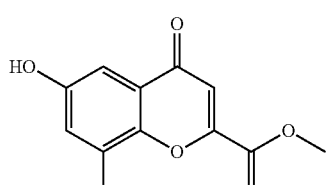

To a solution of methyl 8-fluoro-6-methoxy-4-oxo-4H-chromene-2-carboxylate (2.00 g, 7.93 mmol, 1.00 eq) in DCM (10.00 mL) was added BBr3 (5.96 g, 23.79 mmol, 2.29 mL, 3.00 eq) dropwise at −78° C., the mixture was stirred at 25° C. for 16 h. TLC (PE:EA=2:1; Rf=0.24) showed there was a major spot appeared. The mixture was poured into water (50 mL). The aqueous phase was extracted with DCM (50 mL*2). The combined organic phase was washed with brine (200 mL*3), dried with anhydrous Na2SO4, filtered and concentrated in vacuum. methyl 8-fluoro-6-hydroxy-4-oxo-4H-chromene-2-carboxylate (1.20 g, 4.96 mmol, 62.60% yield, 98.53% purity) as a yellow solid was obtained. LCMS (ESI) m/z 238.9 (M+1)+.

Prep. 42C
8-fluoro-6-hydroxy-4-oxo-4H-chromene-2-carboxylic acid

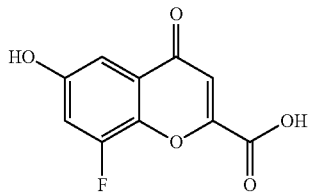 [SMILES: O=C(O)c1cc(=O)c2cc(O)cc(F)c2o1]

Prepared following general procedure for the synthesis of 2-chromone carboxylic acids, 67% yield. ¹H NMR (400 MHz, DMSO) δ 7.81-7.75 (m, 1H), 7.48 (t, J=9.8 Hz, 1H), 6.92 (s, 1H), 4.08 (s, 3H). LCMS (ESI) m/z 239 (M+H)⁺

Example 81

8-fluoro-6-hydroxy-N-((1-hydroxycyclohexyl) methyl)-4-oxo-4H-chromene-2-carboxamide

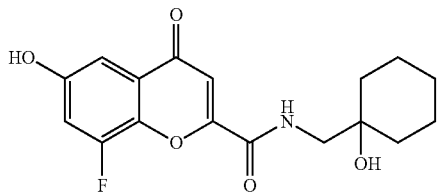 [SMILES: O=C(NCC1(O)CCCCC1)c1cc(=O)c2cc(O)cc(F)c2o1]

methyl 8-fluoro-6-hydroxy-4-oxo-4H-chromene-2-carboxylate (200.00 mg, 839.74 umol, 1.00 eq) and 1-(aminomethyl)cyclohexanol (108 mg, 839 umol, 1.00 eq) were dissolved in THF (2.00 mL), TEA (254 mg, 2.52 mmol, 349 uL, 3.00 eq) and DMAP (10 mg, 83 umol, 0.10 eq) was added. The mixture was stirred at 25° C. for 12 hour. LCMS showed there was desired MS found. The mixture was neutralized by HCl (2M, 3 mL) to pH=5~6 and extracted with EA (3 mL*3). The organic layer was concentrated. The residue was purified by prep-HPLC (column: Agela ASB 150*25 mm*5 um; mobile phase: [water (0.1% TFA)-ACN]; B %: 18%-48%, 11 min). 8-fluoro-6-hydroxy-N-((1-hydroxycyclohexyl)methyl)-4-oxo-4H-chromene-2-carboxamide (41.00 mg, 122 umol, 15% yield) as a yellow solid was obtained. ¹H NMR (400 MHz, DMSO) δ 10.53 (s, 1H), 8.39-8.36 (t, J1=5.6 Hz, J2=6.0 Hz, 1H), 7.30-7.27 (m, 1H), 7.14 (s, 1H), 6.84 (s, 1H), 4.46 (s, 1H), 3.30-3.28 (m, 2H), 1.55-1.32 (m, 10H). LCMS (ESI) m/z 336.1 (M+1)+.

Prep. 43. Ethyl
8-methyl-4-oxo-4-chromene-2-carboxylate

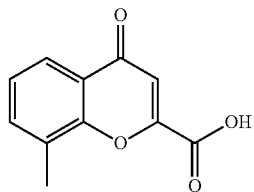

A mixture of hydroxylithium hydrate (3151 mg, 75.09 mmol) in DCM (50 mL) was prepared at rt and dimethyl but-2-ynedioate (2.31 mL, 2668 mg, 18.77 mmol) was added followed by o-cresol (2-methylphenol) (2.0 mL, 2030 mg, 18.77 mmol) and the mixture stirred at rt for 2 h. The mixture was then washed with water (2×20 mL), filtered through a phase separator and the crude filtrate concentrated under reduced pressure to afford a green oil. The oil was dissolved in THF (25 mL) and hydroxylithium hydrate (3151 mg, 75.09 mmol) in water (25 mL) added and the mixture stirred at rt for 18 h. The mixture was then concentrated under reduced pressure then dissolved in water (20 mL) and 6M aqueous HCl was added and the solution adjusted to pH 1-2 and then the mixture was stirred at rt for 1 h. Resulting precipitate was filtered, washed with water (2×50 mL) and dried under vacuum. The crude precipitate was then suspended in concentrated sulphuric acid (30 mL) and heated to 80° C. for 18 h and cooled to rt. Mixture was cooled to 0° C. and water (40 mL) added to mixture (light brown precipitate formed) and stirred for 30 mins then allowed to warm to rt and stirred for a further 30 mins. Precipitate then filtered through a fritted column and crude solid re-suspended in water (60 mL) and stirred for 2 hours then filtered, filter cake washed with water (2×20 mL) and precipitate dried under vacuum. Solid suspended in acetonitrile and concentrated under reduced pressure to afford 8-methyl-4-oxo-chromene-2-carboxylic acid (1318 mg, 32%) as a tan coloured solid. ¹H NMR (500 MHz, DMSO) δ 7.90 (d, J=7.8 Hz, 1H), 7.75 (d, J=7.0 Hz, 1H), 7.44 (t, J=7.6 Hz, 1H), 6.92 (s, 1H), 2.52-2.50 (m, 3H) (OH proton not observed); LCMS m/z 202 (M–H)⁻.

Prep. 44. Ethyl
8-methyl-4-oxo-4H-chromene-2-carboxylate

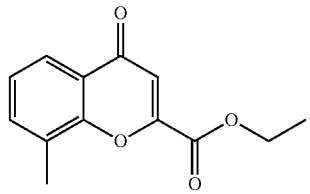 [SMILES: CCOC(=O)c1cc(=O)c2cccc(C)c2o1]

A mixture of 8-methyl-4-oxo-chromene-2-carboxylic acid (1087 mg, 5.32 mmol) and sulphuric acid (1 mL, 1840 mg, 18.76 mmol) was prepared at rt and heated to 80° C. for 30 mins. Mixture then cooled to room temperature and ethanol (15 mL, 11835 mg, 256.89 mmol) added and the mixture heated to 80° C. for 16 h. Mixture then concentrated under reduced pressure to remove ethanol then diluted with DCM (30 mL), washed with water (10 mL) filtered through a phase separator and organics purified by using a strong anion exchange resin (SAX) in a suitable column for acid capture. Briefly, organics were diluted with DCM (10 mL), filtered through strong anion exchange SAX column (Isolute) and washed with DCM (50 mL). Filtrate concentrated under reduced pressure to afford the desired product ethyl 8-methyl-4-oxo-chromene-2-carboxylate (1136 mg, 87% yield) as an off-white solid. $^1$H NMR (500 MHz, DMSO) δ 7.89 (d, J=7.6 Hz, 1H), 7.75 (d, J=7.2 Hz, 1H), 7.44 (t, J=7.6, Hz, 1H), 6.94 (s, 1H), 4.41 (q, J=7.1 Hz, 2H), 2.50-2.49 (m, 3H), 1.36 (t, J=7.1 Hz, 3H); LCMS m/z 233 (M+H)$^+$.

Prep. 45. Ethyl 8-(bromomethyl)-4-oxo-4-chromene-2-carboxylate

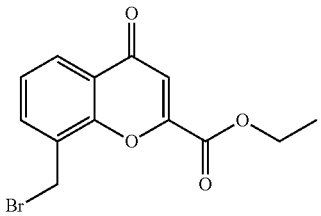 [SMILES: CCOC(=O)c1cc(=O)c2cccc(CBr)c2o1]

A mixture of 1-bromopyrrolidine-2,5-dione (1711 mg, 9.62 mmol) and chlorobenzene (60 mL) was prepared at room temperature and benzoyl benzenecarboperoxoate (21 mg, 0.09 mmol) and ethyl 8-methyl-4-oxo-chromene-2-carboxylate (2030 mg, 8.74 mmol) were added and the mixture heated to from 140 to 145° C. for 20 h. The mixture was cooled to rt, filtered through a celite pad, and the pad subsequently washed with 1:1 ethyl acetate/heptane mixture and the filtrate concentrated under reduced pressure. Crude mixture suspended in ethyl acetate, loaded onto column directly and purified by column chromatography to afford the desired product ethyl 8-(bromomethyl)-4-oxo-chromene-2-carboxylate (1582 mg, 55% yield) as a colourless solid. $^1$H NMR (400 MHz, CDCl$_3$) δ 8.17 (dd, J=1.7, 8.0 Hz, 1H), 7.80 (dd, J=1.7, 7.4 Hz, 1H), 7.43 (t, J=7.7 Hz, 1H), 7.14 (s, 1H), 4.79 (s, 2H), 4.48 (q, J=7.2 Hz, 2H), 1.45 (t, J=7.2 Hz, 3H); LCMS m/z 312 (M+H)$^+$.

Prep. 46. Ethyl 8-(hydroxymethyl)-4-oxo-4-chromene-2-carboxylate

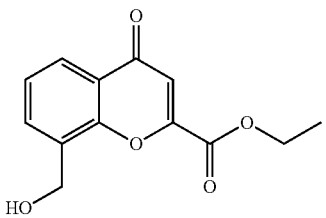 [SMILES: CCOC(=O)c1cc(=O)c2cccc(CO)c2o1]

A mixture of ethyl 8-(bromomethyl)-4-oxo-chromene-2-carboxylate (325 mg, 1.05 mmol) in acetone (2 mL) was prepared at rt and water (8 mL) was added and the mixture heated to 100° C. for 0.5 h in a capped glass tube. LCMS analysis confirmed the presence of both the desired product and starting material. The mixture was cooled to rt and diluted with DCM (10 mL) and filtered through a phase separator. On further inspection of LCMS and TLC, significant levels of starting material still remained. The mixture was then re-dissolved in a further amount of acetone (3 mL) and water (12 mL) was subsequently added and the mixture was heated in a round-bottomed flask (RBF) to 100° C. Note: Complete dissolution occurred following increased dilution of original concentration, in the ratio of 20% acetone/80% water. After 45 mins, the relative amount of product to starting material had increased from 1:1 to >2:1. The mixture heated for a further 75 minutes and analysis of the reaction confirmed presence of desired product only and no starting material. The mixture was cooled to rt and diluted with DCM (10 mL) and filtered through a phase separator. The organic phase was separated and concentrated under reduced pressure and purified by column chromatography (solubilised in DCM and loaded directly onto the column, eluent: 10-50% ethyl acetate/heptane) to afford ethyl 8-(hydroxymethyl)-4-oxo-chromene-2-carboxylate (216 mg, 79%) as a colourless solid. $^1$H NMR (500 MHz, CDCl$_3$) δ 8.14 (dd, J=1.7, 7.9 Hz, 1H), 7.84-7.82 (m, 1H), 7.45 (t, J=7.6, 1H), 7.13 (s, 1H), 5.05 (d, J=6.4 Hz, 2H), 4.47 (q, J=7.1 Hz, 2H), 2.32 (t, J=6.4 Hz, 1H), 1.44 (t, J=7.1 Hz, 3H); LCMS m/z 249 (M+H)$^+$.

Example 82

N-(cyclohexylmethyl)-8-(hydroxymethyl)-4-oxo-chromene-2-carboxamide

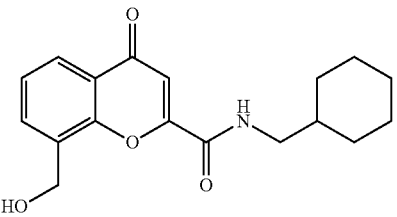 [SMILES: O=C(NCC1CCCCC1)c1cc(=O)c2cccc(CO)c2o1]

A mixture of ethyl 8-(hydroxymethyl)-4-oxo-chromene-2-carboxylate (215 mg, 0.87 mmol) was dissolved in THF (5 mL) and hydroxylithium hydrate (91 mg, 2.2 mmol) in water (3 mL) was added drop-wise over 1 minute and the mixture stirred at rt for 3 h. The mixture showed the presence of the starting carboxylate by LCMS and the mixture was concentrated under reduced pressure to dryness. The mixture was then acidified with 6M HCl aqueous solution to pH 1 then diluted with DCM, and subsequently concentrated under reduced pressure to dryness. Mixture then suspended in DMF (8 mL) and HBTU (361 mg, 0.95 mmol) was added and the resultant mixture was stirred for 1 h at room temperature. Cyclohexylmethanamine (0.169 mL, 147 mg, 1.30 mmol), was then added and the mixture stirred for a further 3 h at room temperature and progress of the reaction was monitored by LCMS. The reaction mixture was then diluted with ethyl acetate (30 mL), the organics were then separated out and washed with 5% LiCl aq. (3×10 mL), brine (NaCl) (10 mL), and then dried over magnesium sulphate and concentrated under reduced pressure. The crude product was then purified by SCX column (to remove excess cyclohexylmethanamine), then further purified by column chromatography (10-50% ethyl acetate/heptane) to afford the desired product N-(cyclohexylmethyl)-8-(hydroxymethyl)-4-oxo-chromene-2-carboxamide (106 mg, 0.32 mmol), 37% yield as a colourless solid. $^1$H NMR (500

MHz, CDCl₃) δ 8.17 (dd, J=1.7, 7.9 Hz, 1H), 7.74 (dd, J=1.6, 7.2 Hz, 1H), 7.43 (t, J=7.6 Hz, 1H), 7.13 (s, 1H), 7.06 (brs, 1H), 5.02 (d, J=6.1 Hz, 2H), 3.35 (t, J=6.5 Hz, 2H), 1.94 (t, J=6.1 Hz, 1H), 1.83-1.74 (m, 4H), 1.73-1.57 (m, 2H), 1.32-1.16 (m, 3H), 1.09-0.99 (m, 2H); LCMS m/z 316 (M+H)⁺.

Preparative Compounds and Exemplary Compounds for the Process Illustrated in Scheme 5.

Example 83

8-Amino-N-(cyclohexylmethyl)-4-oxo-4H-chromene-2-carboxamide

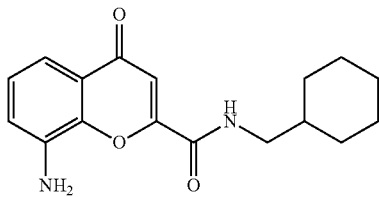 [SMILES: Nc1cccc2c(=O)cc(C(=O)NCC3CCCCC3)oc12]

To a solution of 6-bromo-N-(cyclohexylmethyl)-8-nitro-4-oxo-4H-chromene-2-carboxamide (100 mg, 0.24 mmol) and DIPEA (63 mg, 0.49 mmol, 85 μL) in ethyl acetate (2 mL), was added Pd/C (20 mg). Then the reaction was stirred at 25° C. for 5 h under hydrogen. The mixture was filtered and the filtrate was washed with water (2 mL). Then the organic layer was dried over anhydrous Na₂SO₄, filtered and evaporated under reduced pressured to afford the desired compound, 8-amino-N-(cyclohexylmethyl)-4-oxo-4H-chromene-2-carboxamide (80 mg) as yellow solid. LCMS (ESI) m/z 301 (M+H)⁺.

The 1-hydroxy analogue, N-[(1-hydroxycyclohexyl)methyl]-8-amino-4-oxo-4H-chromene-2-carboxamide, Example 83A, was prepared from the appropriate starting materials using analagous chemistry.

Example 84

N-(cyclohexylmethyl)-8-(methylsulfonamido)-4-oxo-4H-chromene-2-carboxamide

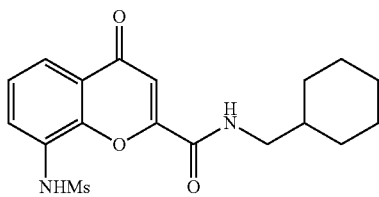

To a solution of 8-amino-N-(cyclohexylmethyl)-4-oxo-4H-chromene-2-carboxamide (80 mg, 0.26 mmol) and DIPEA (69 mg, 0.53 mmol, 0.93 mL) in DCM (1 mL) was added methanesulfonyl chloride (46 mg, 0.40 mmol, 0.03 mL). The reaction mixture was stirred at 25° C. for 1 h and then washed with water (2 mL). The organic layer was evaporated under reduced pressured and the residue was purified by preparative HPLC (acid conditions) to afford N-(cyclohexylmethyl)-8-(methylsulfonamido)-4-oxo-4H-chromene-2-carboxamide (10 mg, 9% yield) as yellow solid.

¹H NMR (400 MHz, CDCl₃) δ 8.07-8.05 (m, 1H), 7.74-7.72 (m, 1H), 7.62 (brs, 1H), 7.42-7.38 (m, 1H), 7.08 (s, 1H), 3.27-3.24 (m, 2H), 1.73-1.55 (m, 6H), 1.16-1.14 (m, 3H), 0.96-0.93 (m, 2H). LCMS (ESI) m/z 379 (M+H)⁺.

The 1-hydroxy analogue, N-[(1-hydroxycyclohexyl)methyl]-8-(methylsulfonamido)-4-oxo-4H-chromene-2-carboxamide, Example 84A, was prepared from the appropriate starting materials using analagous chemistry.

Preparative Compounds and Exemplary Compounds for the Process Illustrated in Scheme 6.

Example 85

8-Cyano-N-(cyclohexylmethyl)-4-oxo-4H-chromene-2-carboxamide

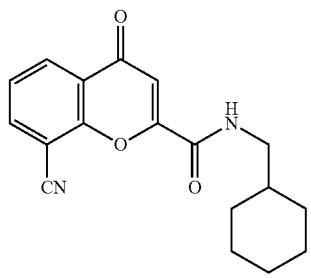 [SMILES: N#Cc1cccc2c(=O)cc(C(=O)NCC3CCCCC3)oc12]

To a solution 8-bromo-N-(cyclohexylmethyl)-4-oxo-4H-chromene-2-carboxamide of (80 mg, 0.22 mmol) in NMP (0.5 mL) was added CuCN (59 mg, 0.65 mmol). The reaction mixture was stirred at 160° C. for 2 h under microwave irradiation. The reaction was filtered and the filtrate was evaporated under reduced pressure. The residue was purified by preparative HPLC (acid conditions) to afford 8-cyano-N-(cyclohexylmethyl)-4-oxo-4H-chromene-2-carboxamide (5 mg, 7% yield) as white solid. ¹H NMR (400 MHz, CDCl₃) δ 8.49-8.46 (m, 1H), 8.08-8.06 (m, 1H), 7.62-7.58 (m, 1H), 7.28 (s, 1H), 7.05 (s, 1H), 3.41-3.38 (m, 2H), 1.85-1.73 (m, 6H), 1.32-1.06 (m, 5H). LCMS (ESI) m/z 311 (M+H)⁺.

Example 86

N-(cyclohexylmethyl)-4-oxo-8-(1H-tetrazol-5-yl)-4H-chromene-2-carboxamide

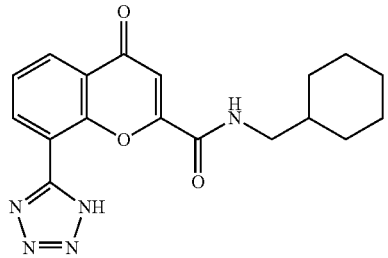 [SMILES: O=C(NCC1CCCCC1)c1cc(=O)c2cccc(-c3nnn[nH]3)c2o1]

A mixture of 8-cyano-N-(cyclohexylmethyl)-4-oxo-4H-chromene-2-carboxamide (45 mg, 0.14 mmol), ZnBr₂ (33 mg, 0.14 mmol, 0.007 mL) and NaN₃ (28 mg, 0.434 mmol, 0.015 mL,) in i-PrOH (0.8 mL) and H₂O (0.4 mL) was stirred at 120° C. for 12 hr. The reaction mixture was diluted with H₂O (200 mL) and filtered. The solid was washed with H₂O (10 mL), ethyl acetate (20 mL) and MeOH (30 mL). The product was purified by preparative HPLC (TFA condition) to obtain N-(cyclohexylmethyl)-4-oxo-8-(1H-tetrazol-5-yl)-4H-chromene-2-carboxamide (23 mg, 43% yield) as a yellow solid. ¹H NMR (400 MHz, DMSO) δ 8.78-8.75 (m, 1H), 8.48-8.46 (m, 1H), 8.24-8.22 (d, 1H), 7.75-7.71 (m, 1H), 6.87 (s, 1H), 3.24-3.22 (m, 2H), 1.81-1.65 (m, 6H), 1.26-1.17 (m, 3H), 1.03-1.01 (m, 2H). LCMS (ESI) m/z 354 (M+H)⁺.

The 1-hydroxy analogue, N-[(1-hydroxycyclohexyl)methyl]-4-oxo-8-(1H-tetrazol-5-yl)-4H-chromene-2-carboxamide, Example 86A, was prepared from the appropriate starting materials using analagous chemistry.

Preparative Compounds and Exemplary Compounds for the Process Illustrated in Scheme 7.

Example 87

Methyl 2-((cyclohexylmethyl)carbamoyl)-4-oxo-4H-chromene-8-carboxylate

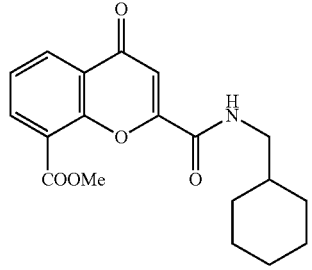 [SMILES: COC(=O)c1cccc2c(=O)cc(C(=O)NCC3CCCCC3)oc12]

To a solution of Pd(dppf)Cl₂ (52 mg, 0.71 mmol) and 1,1'-ferrocenediyl-bis(diphenylphosphine) (DPPF) (79 mg, 0.14 mmol) in toluene (2 mL) were added 8-bromo-N-(cyclohexylmethyl)-4-oxo-4H-chromene-2-carboxamide (520 mg, 1.43 mmol), Et₃N (144 mg, 1.43 mmol, 0.197 mL) and MeOH (7 mL). The reaction mixture was stirred at 75° C. under carbon monoxide (CO) gas (45 Psi/310264 Pa) for 16 hrs.

Then the mixture was concentrated and extracted with ethyl acetate (2×20 mL). The combined organic layers were washed with brine (2×20 mL) and dried with Na₂SO₄. The solvent was concentrated to give methyl 2-((cyclohexylmethyl)carbamoyl)-4-oxo-4H-chromene-8-carboxylate (300 mg, 54% yield) as an off-white solid. ¹H NMR (400 MHz, DMSO) δ 8.34-8.31 (m, 3H), 7.66-7.62 (m, 1H), 6.86 (s, 1H), 3.94 (s, 3H), 3.24-3.20 (m, 2H), 1.78-1.57 (m, 6H), 1.25-0.99 (m, 5H). LCMS (ESI) m/z 334 (M+H)⁺.

Example 88

2-((Cyclohexylmethyl)carbamoyl)-4-oxo-4H-chromene-8-carboxylic acid

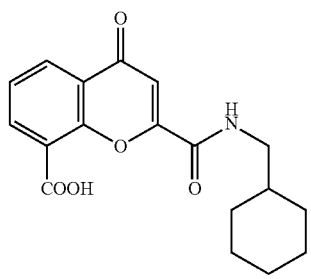 [SMILES: O=C(NCC1CCCCC1)c1cc(=O)c2cccc(C(=O)O)c2o1]

A mixture of methyl 2-((cyclohexylmethyl)carbamoyl)-4-oxo-4H-chromene-8-carboxylate (280 mg, 0.81 mmol) and HCl (12 M, 1.40 mL) in AcOH (50 NL) was stirred at 80° C. for 1 hr. The reaction mixture was quenched with acetonitrile (20 mL) and concentrated to give crude product (90 mg, 33% yield) as an off-white solid. Further purification by preparative HPLC (acidic condition) of 30 mg of crude product gave 11 mg of purified 2-((cyclohexylmethyl)carbamoyl)-4-oxo-4H-chromene-8-carboxylic acid. ¹H NMR (400 MHz, CDCl₃) δ 8.37-8.35 (m, 1H), 8.28-8.26 (m, 1H), 8.11-8.09 (m, 1H), 7.64-7.60 (m, 1H), 6.84 (m, 1H), 1.78-1.62 (m, 6H), 1.24-0.98 (m, 4H). LCMS (ESI) m/z 330 (M+H)⁺.

Example 89

N2-(cyclohexylmethyl)-4-oxo-4H-chromene-2,8-dicarboxamide

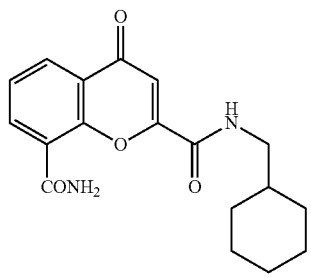 [SMILES: NC(=O)c1cccc2c(=O)cc(C(=O)NCC3CCCCC3)oc12]

A mixture of 2-(cyclohexylmethylcarbamoyl)-4-oxo-chromene-8-carboxylic acid (60 mg, 0.18 mmol), 1-(3-dimethylaminopropyl)-3-ethylcarbodiimide hydrochloride (EDCl) (Sigma-Aldrich) (52 mg, 0.27 mmol), HOBt (37 mg, 0.27 mmol), DIPEA (118 mg, 0.91 mmol, 0.15 mL), NH₄Cl (97 mg, 1.82 mmol, 0.063 mL) in DMF (1 mL) was stirred at 25° C. for 16 h. The reaction mixture was filtrated and the filtrate was collected. The solvent was removed under reduced pressure and the residue was purified with preparative HPLC (acidic conditions) to afford N2-(cyclohexylmethyl)-4-oxo-4H-chromene-2,8-dicarboxamide (12 mg, 19% yield) as a white solid. ¹H NMR (400 MHz, CDCl₃) δ 8.17-8.11 (m, 2H), 7.61-7.57 (m, 1H), 6.89 (s, 1H), 3.17-3.15 (m, 2H), 1.73-1.54 (m, 6H), 1.21-0.93 (m, 5H). LCMS (ESI) m/z 329 (M+H)⁺.

Preparative Compounds and Exemplary Compounds for the Process Illustrated in Scheme 8.

Prep. 47 Ethyl 3-methyl-4-oxo-4H-chromene-2-carboxylate

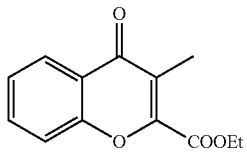 [SMILES: CCOC(=O)c1oc2ccccc2c(=O)c1C]

A mixture of 1-(2-hydroxyphenyl)propan-1-one (1 g, 6.7 mmol) and ethyl 2-chloro-2-oxoacetate (1.1 g, 8.0 mmol) in pyridine (10 mL) was stirred at 60° C. for 2 hr, then heated at 120° C. for 13 hr. The reaction mixture was diluted with water (30 mL) and extracted with ethyl acetate (2×25 mL). The combined organic layers were dried over Na$_2$SO$_4$, filtered and concentrated under reduced pressure. The product was purified by column chromatography (SiO$_2$, petroleum ether/ethyl acetate 50/1 to 15/1) to obtain ethyl 3-methyl-4-oxo-4H-chromene-2-carboxylate (600 mg, 39% yield) as a white solid.

Prep. 48 3-Methyl-4-oxo-4H-chromene-2-carboxylic acid

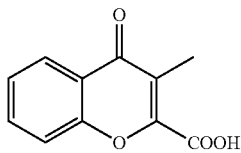

To a solution of ethyl 3-methyl-4-oxo-4H-chromene-2-carboxylate (300 mg, 1.3 mmol) in EtOH (5 mL) and H$_2$O (5 mL) was added KOH (145 mg, 2.6 mmol). The mixture was stirred at 25° C. for 15 hour. The reaction mixture was concentrated under reduced pressure and pH was adjusted to pH=2-3 with HCl (2N), the precipitate was filtered to obtain 3-methyl-4-oxo-4H-chromene-2-carboxylic acid (100 mg, 38% yield) was obtained as a white solid.

Example 90

N-(cyclohexylmethyl)-3-methyl-4-oxo-4H-chromene-2-carboxamide

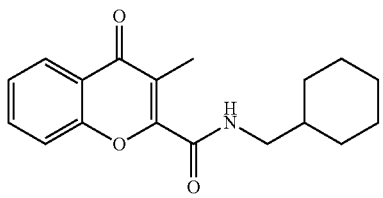 [SMILES: Cc1c(C(=O)NCC2CCCCC2)oc2ccccc2c1=O]

To a solution of 3-methyl-4-oxo-4H-chromene-2-carboxylic acid (50 mg, 0.24 mmol) in DMF (1 mL) was added HATU (140 mg, 0.37 mmol) and cyclohexylmethanamine (42 mg, 0.367 mmol, 0.047 mL), DIPEA (63 mg, 0.489 mmol, 0.085 mL). The mixture was stirred at 25° C. for 15 hour. The reaction mixture was diluted with H$_2$O (10 mL) and extracted with ethyl acetate (2×5 mL). The combined organic layers were dried over Na$_2$SO$_4$, filtered and concentrated under reduced pressure. The product was purified by preparative HPLC (acid conditions) to obtain N-(cyclohexylmethyl)-3-methyl-4-oxo-4H-chromene-2-carboxamide (23 mg, 32% yield) as a yellow solid. $^1$H NMR (400 MHz, MeOD) δ 8.18-8.15 (m, 1H), 7.83-7.81 (m, 1H), 7.67-7.66 (m, 1H), 7.53-7.51 (m, 1H), 3.28-3.26 (m, 2H), 2.26 (s, 3H), 1.86-1.74 (m, 6H), 1.35-1.04 (m, 5H). LCMS (ESI) m/z 300 (M+H)$^+$.

Preparative Compounds and Exemplary Compounds for the Process Illustrated in Scheme 9.

Prep. 49 4-Fluorophenyl propionate

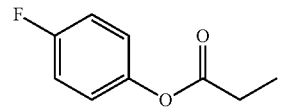

To a solution of 4-fluorophenol (2 g, 18 mmol) and Et$_3$N (2.2 g, 21.41 mmol) in DCM (20 mL) was added propanoyl chloride (1.82 g, 19.62 mmol) at 0° C. The reaction mixture was stirred at 25° C. for 16 h. The mixture was washed with water (50 mL). The organic layer was separated and evaporated under reduced pressure. The product was purified by column chromatography (petroleum ether/ethyl acetate 30/1 to 10/1) to afford 4-fluorophenyl propionate (2 g, 67% yield) as a colourless oil. $^1$H NMR (400 MHz, CDCl$_3$) δ7.08-7.06 (m, 3H), 2.64-2.58 (q, J=7.6 Hz, 2H), 1.31-1.27 (d, J=7.6 Hz, 3H).

Prep. 50 1-(5-Fluoro-2-hydroxyphenyl)propan-1-one

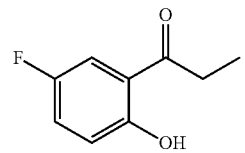

To a solution of 4-fluorophenyl propionate (499 mg, 2.97 mmol) in chlorobenzene (5 mL) was added AlCl$_3$ (594 mg, 4.46 mmol) and stirred at 100° C. for 5 h. The reaction mixture was cooled to 25° C. and then poured into water (20 mL). The mixture was extracted with methyl tert-butyl ether (2×10 mL). The organic layer was separated and solvents were evaporated under reduced pressured. The product was purified by column chromatography (petroleum ether/ethyl acetate 30/1) to afford 1-(5-fluoro-2-hydroxyphenyl)propan-1-one (400 mg, 80% yield) as a yellow solid. $^1$H NMR (400 MHz, CDCl$_3$) δ 7.46-7.43 (m, 1H), 7.23-7.20 (m, 1H), 6.99-6.96 (m, 1H), 3.05-3.00 (q, J=7.2 Hz, 2H), 1.29-1.25 (d, J=7.2 Hz, 3H).

Prep. 51
6-Fluoro-3-methyl-4-oxo-4H-chromene-2-carboxylic acid

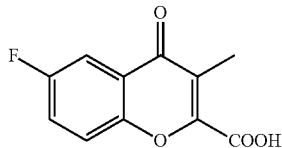 [SMILES: Cc1c(C(=O)O)oc2ccc(F)cc2c1=O]

To a solution of 1-(5-fluoro-2-hydroxyphenyl)propan-1-one (400 mg, 2.38 mmol) in pyridine (4 mL) was added ethyl 2-chloro-2-oxo-acetate (357 mg, 2.62 mmol) and the reaction mixture was stirred at 100° C. for 16 h. Solvents were removed under reduced pressure and the residue was purified by preparative HPLC (HCl condition) to afford 6-fluoro-3-methyl-4-oxo-4H-chromene-2-carboxylic acid (70 mg, 13% yield) as a white solid. $^1$H NMR (400 MHz, DMSO) δ 7.78-7.24 (m, 3H), 2.23 (s, 3H).

Example 91
N-(cyclohexylmethyl)-6-fluoro-3-methyl-4-oxo-4H-chromene-2-carboxamide

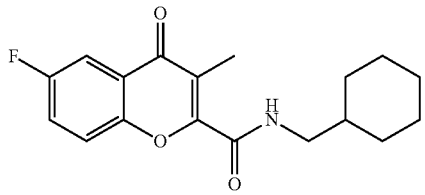 [SMILES: Cc1c(C(=O)NCC2CCCCC2)oc2ccc(F)cc2c1=O]

The compound of Example 91, was prepared following general procedure e as indicated hereinbefore in Scheme 1, for the synthesis of 2-chromone carboxamides. The product was purified by column chromatography (petroleum ether/ethyl acetate 5/1), 45% yield. $^1$H NMR (400 MHz, MeOD) δ 7.80-7.77 (m, 1H), 7.40-7.36 (m, 2H), 6.72 (s, 1H), 3.27-3.24 (m, 2H), 2.37 (s, 3H), 1.98-1.62 (m, 6H), 1.23-1.14 (m, 3H), 0.97-0.94 (m, 2H). LCMS (ESI) m/z 318 (M+H)$^+$.

Preparative Compounds and Exemplary Compounds for the Process Illustrated in Scheme 10.

Prep. 52
1-(4-fluoro-2-hydroxy-3-nitro-phenyl)ethanone

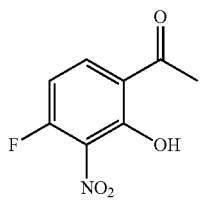

A mixture of 1-(4-fluoro-2-hydroxy-phenyl)ethanone (2332 mg, 15.13 mmol) in a pre-prepared solution of conc. sulphuric acid:water (8:2) (10 mL) was prepared at rt and cooled to 0° C. nitric acid (1634 mg, 18.16 mmol) (70%) was then added dropwise over 1 min and the mixture stirred for 30 mins at 0° C. and then poured into ice water (ca. 200 mL) and the mixture extracted with ethyl acetate (2×200 mL) and the organics dried over magnesium sulphate and concentrated under reduced pressure. The mixture was then purified by column chromatography (0-50% ethyl acetate/heptane) to afford 1-(4-fluoro-2-hydroxy-3-nitro-phenyl)ethanone (850 mg, 4.10 mmol), 27% yield as a pale yellow solid. $^1$H NMR (400 MHz, CDCl3) δ 13.29 (d, J=1.4 Hz, 1H), 7.92 (dd, J=5.8, 9.0 Hz, 1H), 6.81 (dd, J=8.9, 8.9 Hz, 1H), 2.67 (s, 3H); LCMS m/z 200 (M+H)$^+$

Prep. 53
7-Fluoro-8-nitro-4-oxo-chromene-2-carboxylate

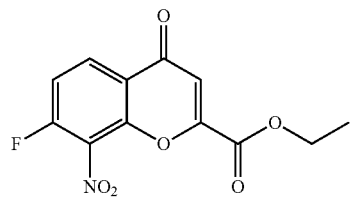

A mixture of 1-(4-fluoro-2-hydroxy-3-nitro-phenyl)ethanone (850 mg, 4.3 mmol) in ethanol (25 mL) was prepared at rt and diethyl oxalate (1559 mg, 10.67 mmol) (ca. 1.5 mL) added followed by the dropwise addition (over 5 mins) of sodium ethoxide (6076 mg, 89.29 mmol) (21% solution in ethanol) (7 mL) and the mixture stirred at rt for 2 h. The mixture was then acidified with conc. HCl (to ca. pH 1) and the mixture heated to 80° C. for 4 h. LCMS showed a 2:1 mixture of desired ester to acid. Mixture concentrated under reduced pressure to dryness, diluted with toluene (15 mL) and concentrated to dryness to remove trace water. Mixture was then suspended in ethanol (20 mL) and conc. sulphuric acid (5 mL) added and the mixture heated to 80° C. for 20 h. The mixture was then concentrated under reduced pressure, diluted with DCM (50 mL) and washed with water (2×20 mL), brine (20 mL), dried over magnesium sulphate and concentrated under reduced pressure. The mixture was then purified by PE-AX column (to remove trace acid), diluted with DCM, loaded and eluted with DCM. The mixture was then purified by column chromatography (neat DCM) to afford the desired compound ethyl 7-fluoro-8-nitro-4-oxo-chromene-2-carboxylate (480 mg, 1.54 mmol), 36% yield as a pale yellow solid. $^1$H NMR (400 MHz, CDCl3) δ 8.38 (dd, J=5.7, 9.1 Hz, 1H), 7.37 (dd, J=8.9, 8.9 Hz, 1H), 7.18 (s, 1H), 4.46 (q, J=7.1 Hz, 2H), 1.43 (t, J=7.2 Hz, 3H); LCMS m/z 282 (M+H)$^+$

Prep. 54
8-Amino-7-fluoro-4-oxo-chromene-2-carboxylate

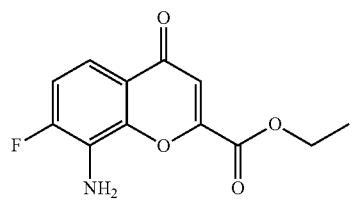 [SMILES: CCOC(=O)c1cc(=O)c2ccc(F)c([N+](=O)[O-])c2o1]

A mixture of ethyl 7-fluoro-8-nitro-4-oxo-chromene-2-carboxylate (480 mg, 1.71 mmol) in Ethanol (12 mL) was prepared at rt and ammonium chloride (457 mg, 8.53 mmol) in Water (6 mL) was added followed by iron (286 mg, 5.12 mmol) and the mixture heated to 80° C. for 4 h. TLC showed no presence of starting material and the mixture cooled to rt and filtered through a celite pad, the pad washed with ethanol (30 mL) and the filtrate concentrated under reduced pressure. The mixture was then dissolved in ethyl acetate (40 mL) and organics washed with water (20 mL), brine (20 mL), dried over magnesium sulphate and concentrated under reduced pressure. Mixture purified by column chromatography in neat DCM to afford the desired compound ethyl 8-amino-7-fluoro-4-oxo-chromene-2-carboxylate (184 mg, 0.70 mmol), 41% yield as a colourless solid. $^1$H NMR (400 MHz, CDCl3) δ 7.53 (dd, J=6.0, 8.9 Hz, 1H), 7.13 (dd, J=8.9, 10.1 Hz, 1H), 7.07 (s, 1H), 4.47 (q, J=7.2 Hz, 2H), 4.25 (s, 2H), 1.44 (t, J=7.2 Hz, 3H); LCMS m/z 252 (M+H)$^+$ Example 92

8-Amino-N-[(4,4-difluoro-1-hydroxy-cyclohexyl)methyl]-7-fluoro-4-oxo-chromene-2-carboxamide

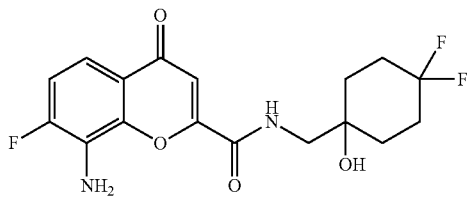 [SMILES: Nc1c(F)ccc2c(=O)cc(C(=O)NCC3(O)CCC(F)(F)CC3)oc12]

A mixture of N-1-(aminomethyl)-4,4-difluoro-cyclohexanol hydrochloride (241 mg, 1.19 mmol) in pyridine (6 mL) was prepared at rt and triethylamine (0.15 mL, 109 mg, 1.08 mmol) added and the mixture stirred for 1 h. A mixture of ethyl 8-amino-7-fluoro-4-oxo-chromene-2-carboxylate (84 mg, 0.33 mmol) in pyridine (2 mL) and DMAP (45 mg, 0.34 mmol) was stirred at rt for 1 h. The previously prepared solution of amine in pyridine was then added to the chromone DMAP mixture and the mixture stirred for 96 h at rt and monitored by LCMS to confirm presence of desired product. Mixture then concentrated under reduced pressure, dissolved in DCM (15 mL) and purified by solid phase extraction column PEAX-SCX (Acid/base) capture SPE column, eluted with DCM and then methanol to obtain the desired product 8-amino-N-[(4,4-difluoro-1-hydroxy-cyclohexyl)methyl]-7-fluoro-4-oxo-chromene-2-carboxamide (67 mg, 0.17 mmol), 51% yield as a pale yellow solid. $^1$H NMR (400 MHz, DMSO) δ 9.26 (t, J=6.4 Hz, 1H), 7.29-7.18 (m, 2H), 6.82 (s, 1H), 6.22 (s, 2H), 4.79 (s, 1H), 3.36 (d, J=6.6 Hz, 2H), 2.11-1.84 (m, 4H), 1.67-1.56 (m, 4H); LCMS m/z 371 (M+H)$^+$ Prep. 55

1-(5-Fluoro-2-hydroxy-3-nitro-phenyl)-ethanone

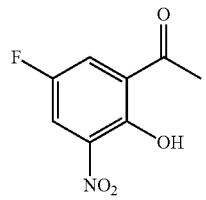

To a stirred solution of 1-(5-Fluoro-2-hydroxy-phenyl)-ethanone (10 g, 13 mmol) in acetic acid (80 ml), conc. HNO$_3$ (4.9 ml, 110 mmol) was added drop wise at 0° C. and allowed to stir at room temperature for 16 hr. After completion of starting material by TLC, the reaction mass was poured into ice cold water and solid precipitate was filtered. The solid material was washed with ice cold water, azeotroped with toluene and dried under reduced pressure to obtain 1-(5-Fluoro-2-hydroxy-3-nitro-phenyl)-ethanone (11.5 g, 89%) as yellow solid. $^1$H NMR (400 MHz, DMSO-d6): δ 12.56 (brs, 1H), 8.24 (dd, J=3.2, 8.0 Hz, 1H), 8.18 (dd, J=3.24, 8.56 Hz, 1H), 2.70 (s, 3H). LCMS m/z 198 (M−H)$^+$ Prep. 56 Ethyl 6-fluoro-8-nitro-4-oxo-4H-chromene-2-carboxylate

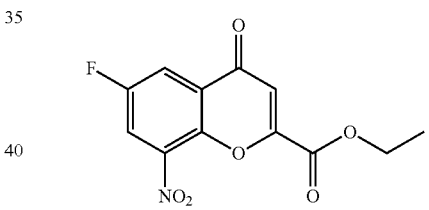

To a stirred solution of 1-(5-Fluoro-2-hydroxy-3-nitro-phenyl)-ethanone (5.0 g, 25 mmol) in DMF (120 ml) was added diethyl oxalate (8.82 ml, 63 mmol) and cooled to 0° C. 1M sol of t-BuOK in THF (100 ml, 100.43 mmol) was added drop wise at 0° C. and maintained for 2 hr. Then pH was adjusted to 5-6 with diluted HCl and extracted with ethyl acetate. The organic layer was dried over Na$_2$SO$_4$, filtered and concentrated to get the crude. The crude material was dissolved in ethanol (120 ml) and Conc HCl (8 ml) was added to it. The reaction mixture was refluxed for 16 hr. The reaction mixture was concentrated and the residue (containing some amount of DMF) was taken in ethyl acetate. The organic layer was washed with saturated sodium bicarbonate solution, water and chilled brine. The organic layer was dried over Na$_2$SO$_4$, filtered and concentrated. The crude material was purified by combi-flash column chromatography and eluted at 9% ethyl acetate-hexane to obtain ethyl 6-fluoro-8-nitro-4-oxo-4H-chromene-2-carboxylate (3.8 g, 54%). $^1$H NMR (400 MHz, DMSO-d6): δ 8.65-8.63 (m, 1H), 8.17-8.15 (m, 1H), 7.09 (s, 1H), 4.41 (q, J=6.96 Hz, 2H), 1.35 (t, J=6.92 Hz, 3H). LCMS m/z 282 (M+H)$^+$

Prep. 57 Ethyl 8-amino-6-fluoro-4-oxo-4H-chromene-2-carboxylate

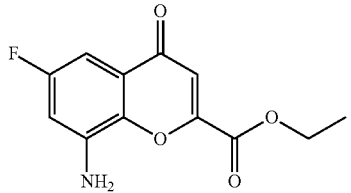 [SMILES: CCOC(=O)c1cc(=O)c2cc(F)cc([N+](=O)[O-])c2o1]

To a stirred solution of ethyl 6-fluoro-8-nitro-4-oxo-4H-chromene-2-carboxylate (3.8 g, 13.51 mmol) in ethanol (15 ml) was added a solution of NH4Cl (3.61 g, 66 mmol) in water (15 ml) followed by addition of iron powder (2.26 g, 41 mmol). The reaction mixture was heated to reflux at 90° C. for 1.5 h. After complete conversion of the starting material (checked by TLC), iron was filtered off and the filtrate was concentrated. The residue was partitioned between water and ethyl acetate. Ethyl acetate layer was washed with water and brine. Dried over $Na_2SO_4$, filtered and concentrated. The crude compound was triturated with ether-pentane mixture to obtain ethyl 8-amino-6-fluoro-4-oxo-4H-chromene-2-carboxylate (2.5 g, 74%) as yellow solid. $^1$H NMR (400 MHz, DMSO-d6): δ 6.90-6.87 (m, 2H), 6.79 (dd, J=2.92, 8.44 Hz, 1H), 5.95 (s, 2H), 4.39 (q, J=7.08 Hz, 2H), 1.36 (t, J=7.04 Hz, 3H). LCMS m/z 252 (M+H)+

Prep. 58 8-amino-6-fluoro-4-oxo-4H-chromene-2-carboxylic acid

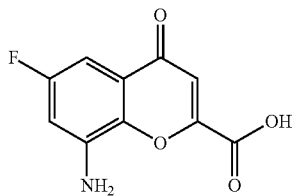 [SMILES: Nc1cc(F)cc2c(=O)cc(C(=O)O)oc12]

To a stirred solution of ethyl 8-amino-6-fluoro-4-oxo-4H-chromene-2-carboxylate (3.0 g, 12 mmol) in methanol (10 ml) was added $K_2CO_3$ (4.95 g, 36 mmol) and allowed to stir at rt for 16 h. The residue was concentrated and the crude material was poured into ice cold water. Adjusted the pH ~6 to 7 with dil HCl and extracted with ethyl acetate. The organic layer was washed with water and brine. Dried over $Na_2SO_4$, filtered and concentrated. The crude material was triturated with diethyl ether to obtain 8-amino-6-fluoro-4-oxo-4H-chromene-2-carboxylic acid (2.05 g, 77%) as brown solid. $^1$H NMR (400 MHz, DMSO-d6): δ 6.88-6.85 (m, 2H), 6.80-6.77 (m, 1H), 5.99 (brs, 2H). LCMS m/z 224 (M+H)+

Example 93 8-amino-N-[(4,4-difluoro-1-hydroxy-cyclohexyl)methyl]-6-fluoro-4-oxo-chromene-2-carboxamide

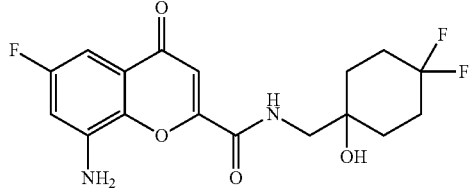 [SMILES: Nc1cc(F)cc2c(=O)cc(C(=O)NCC3(O)CCC(F)(F)CC3)oc12]

A mixture of N1-(aminomethyl)-4,4-difluoro-cyclohexanol hydrochloride (241 mg, 1.19 mmol) in pyridine (8 mL) was prepared at rt and triethylamine (0.56 mL, 409 mg, 4.04 mmol) added and the mixture stirred for 1 h. A mixture of ethyl 8-amino-7-fluoro-4-oxo-chromene-2-carboxylate (507 mg, 2.02 mmol) in pyridine (2 mL) and DMAP (272 mg, 2.22 mmol) was stirred at rt for 1 h. The previously prepared solution of amine in pyridine was then added to the chromone DMAP mixture and the mixture stirred for 96 h at RT and monitored by LCMS to confirm presence of desired product. Mixture then concentrated under reduced pressure, dissolved in DCM (15 mL) and purified by solid phase extraction column. Mixture purified through an SCX column (base capture) SPE column, eluted with DCM 20% methanol/DCM, and then methanol to obtain the desired crude product. The product was further purified by column chromatography to afford 8-amino-N-[(4,4-difluoro-1-hydroxy-cyclohexyl)methyl]-6-fluoro-4-oxo-chromene-2-carboxamide (346 mg, 0.93 mmol), 46% yield as a pale yellow solid. $^1$H NMR (400 MHz, DMSO) δ 9.18 (t, J=6.4 Hz, 1H), 6.85-6.75 (m, 3H), 6.59 (s, 2H), 4.79 (s, 1H), 3.37 (d, J=6.5 Hz, 2H), 2.08-1.91 (m, 4H), 1.64-1.53 (m, 4H); LCMS m/z 371 (M+H)+

Example 94 8-amino-N-[(4,4-difluorocyclohexyl)methyl]-6-fluoro-4-oxo-4H-chromene-2-carboxamide

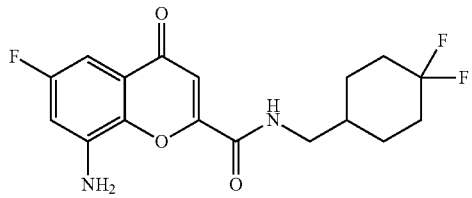 [SMILES: Nc1cc(F)cc2c(=O)cc(C(=O)NCC3CCC(F)(F)CC3)oc12]

To a stirred solution of 8-amino-6-fluoro-4-oxo-4H-chromene-2-carboxylic acid (0.15 g, 0.7 mmol) and (4,4-difluorocyclohexyl)methylamine (0.11 g, 0.7 mmol) in DMF (2 ml) were added T3P (50% in ethyl acetate, 1.3 ml, 2 mmol) and DIPEA (0.6 ml, 3.4 mmol) at room temperature. The reaction mixture was heated at 80° C. for 16 hr. Reaction mixture was poured into ice cold water and extracted with ethyl acetate. The organic layer was dried over $Na_2SO_4$, filtered and concentrated. Crude material was purified by column chromatography followed by prep HPLC (ammonium bicarbonate buffer) to obtain 8-amino-N-[(4,4- difluorocyclohexyl)methyl]-6-fluoro-4-oxo-4H-chromene-2-carboxamide (88 mg, 37%) as yellow solid. ¹H NMR (400 MHz, DMSO-d6): δ 9.22 (brs, 1H), 6.82-6.74 (m, 3H), 6.55 (brs, 2H), 3.24-3.22 (m, 2H), 2.01-1.99 (m, 2H), 1.83-1.75 (m, 5H), 1.25-1.20 (m, 2H). LCMS m/z 355 (M+H)⁺

Example 95

8-amino-N-[(3,3-difluorocyclopentyl)methyl]-6-fluoro-4-oxo-4H-chromene-2-carboxamide

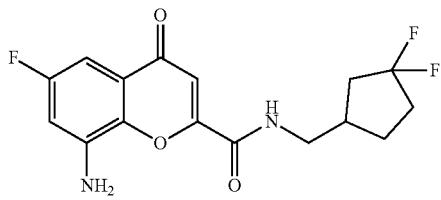 [SMILES: Nc1cc(F)cc2c(=O)cc(C(=O)NCC3CCC(F)(F)C3)oc12]

To a stirred solution of 8-amino-6-fluoro-4-oxo-4H-chromene-2-carboxylic acid (0.1 g, 0.45 mmol) in DMF (3 mL) in a pears vial EDC.HCl (0.3 g, 1.6 mmol), HOBT (0.22 g, 1.6 mmol) were added and stirred for 30 min. After 30 min Et₃N (0.32 ml, 2.2 mmol), (3,3-difluorocyclopentyl)methylamine (0.07 g, 0.54 mmol) were added and allowed to stir at rt for 48 h. Reaction mixture was poured in ice cold water and extracted with ethyl acetate. The organic layer was washed with saturated NaHCO₃ solution, water and brine. Dried over anhydrous Na₂SO₄, filtered and concentrated. Crude material was purified by preparative TLC (eluent-5% methanol in dichloromethane) to obtain 8-amino-N-[(3,3-difluorocyclopentyl)methyl]-6-fluoro-4-oxo-4H-chromene-2-carboxamide (7 mg, 5%) as a yellow solid. ¹H NMR (400 MHz, DMSO-d6): δ 9.21 (t, 1H, J=5.8 Hz), 6.83-6.74 (m, 2H), 6.81 (s, 1H), 6.53 (s, 2H), 3.36-3.29 (m, 2H), 2.50-2.40 (m, 1H), 2.26-2.00 (m, 3H), 1.92-1.82 (m, 2H), 1.58-1.49 (m, 1H). LCMS m/z 341) (M+H)⁺

Example 96

8-amino-6-fluoro-N-[(1-hydroxycyclohexyl)methyl]-4-oxo-4H-chromene-2-carboxamide

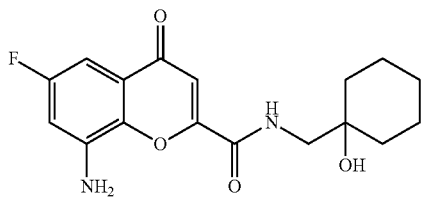

To a stirred solution of 8-amino-6-fluoro-4-oxo-4H-chromene-2-carboxylic acid ethyl ester (100 mg, 0.4 mmol) in DCM (0.5 mL) was added pyridine (1 mL), and DMAP (47 mg, 0.4 mmol). Thereafter, a solution of 1-aminomethyl-cyclohexanol (103 mg, 0.8 mmol) in DCM (0.5 mL) was added dropwise into the reaction mixture at rt. The resulting mixture was allowed to stir at rt for 16 h under argon atmosphere. Then it was concentrated under reduced pressure, the residue was diluted with water and extracted with ethyl acetate. The combined organic layer was washed with brine, dried over anhydrous Na₂SO₄, filtered and concentrated. The crude material was purified by preparative HPLC (ammonium bicarbonate buffer) to afford 8-amino-6-fluoro-N-[(1-hydroxycyclohexyl)methyl]-4-oxo-4H-chromene-2-carboxamide (25 mg, 19%) as a yellow solid. ¹H NMR (400 MHz, DMSO-d6): δ 9.05 (t, 1H, J=6.2 Hz), 6.83-6.74 (m, 2H), 6.82 (s, 1H), 6.58 (s, 2H), 4.35 (s, 1H), 3.31-3.28 (m, 2H), 1.56-1.31 (m, 9H), 1.23-1.16 (m, 1H). LCMS m/z 335 (M+H)⁺

Example 97

8-amino-6-fluoro-N-[(1-fluorocyclohexyl)methyl]-4-oxo-4H-chromene-2-carboxamide

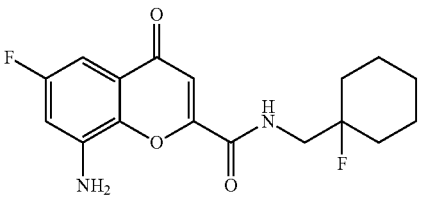 [SMILES: Nc1cc(F)cc2c(=O)cc(C(=O)NCC3(F)CCCCC3)oc12]

To a stirred solution of 8-amino-6-fluoro-4-oxo-4H-chromene-2-carboxylic acid (0.13 g, 0.6 mmol) and (1-fluorocyclohexyl)methanamine (0.115 g, 0.9 mmol) in DMF (1 ml) were added T3P (50% in ethyl acetate, 1.2 ml, 1.749 mmol) and pyridine (0.193 ml, 2.3 mmol). The reaction mass was stirred for 16 hr at rt. Reaction mixture was poured into ice cold water and extracted with ethyl acetate. The organic layer was washed with saturated NaHCO₃ solution, 1N HCl solution, water and brine. Dried over Na₂SO₄, filtered and concentrated. The crude material was purified by combi flash chromatography followed by trituration with diethyl ether and n-pentane to afford 8-amino-6-fluoro-N-[(1-fluorocyclohexyl)methyl]-4-oxo-4H-chromene-2-carboxamide (0.12 g, 61%) as yellow solid. ¹H NMR (400 MHz, DMSO-d6) δ 9.32 (t, J=6.0 Hz, 1H), 6.83-6.74 (m, 3H), 6.61 (brs, 2H), 3.53 (dd, J=6.0, 21 Hz, 2H), 1.76-1.72 (m, 2H), 1.55-1.47 (m, 7H), 1.25-1.22 (m, 1H). LCMS m/z 337 (M+H)⁺

Example 98

8-amino-6-fluoro-N-[(4-hydroxycyclohexyl)methyl]-4-oxo-chromene-2-carboxamide

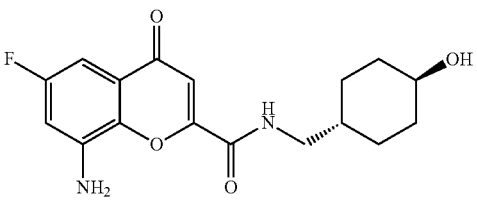 [SMILES: Nc1cc(F)cc2c(=O)cc(C(=O)NC[C@H]3CC[C@H](O)CC3)oc12]

A mixture of tert-butyl N-[(4-oxocyclohexyl)methyl]carbamate (316 mg, 1.39 mmol) in methanol (10 mL) was prepared at rt and stirred under nitrogen. Sodium borohydride (59 mg, 1.53 mmol) was then added in one portion and the mixture stirred for 45 mins. TLC (stained in KMnO4) showed no starting material and mixture concentrated under reduced pressure. The residue was dissolved in DCM (20 mL), washed with water (5 mL), organics were cloudy so brine (1 mL) added and organics filtered through a phase separator. Organics then dried over magnesium sulphate and filtrate concentrated under reduced pressure. Crude intermediate oil (Boc protected amino cyclohexanol) dissolved in DCM (10 mL) and TFA (1 mL) added to the mixture and stirred at rt for 18 h. TLC showed no presence of starting material and mixture concentrated under reduced pressure. Mixture then diluted with methanol (5 mL) and basified with 7M ammonia/methanol (to ca. pH 10) and the mixture concentrated under reduced pressure. Pure amino alcohol not isolated and used in the amidation step as a mixture of amine with ammonium salt and used without further purification.

A mixture of ethyl 8-amino-6-fluoro-4-oxo-chromene-2-carboxylate (130 mg, 0.52 mmol) in THF (6 mL) was prepared at rt and lithium hydroxide monohydrate (23 mg, 0.55 mmol) in Water (2 mL) added in one portion and the mixture stirred at rt for 1 h. LCMS (neg mode) showed a mass of 222 (M−H+) only and mixture concentrated to dryness under reduced pressure. The crude carboxylate intermediate was then dissolved in DMF (6 mL) and HBTU added and the mixture stirred at rt for 1 h. Previously prepared amino alcohol/salt mixture was suspended in DMF (3 mL) and added in one portion and the mixture stirred for 20 h at rt. Mixture was diluted with ethyl acetate (40 mL) and washed with 5% LiCl aq. (2×10 mL), brine (10 mL), organics dried over magnesium sulphate and concentrated under reduced pressure. Crude mixture was then dissolved in methanol (20 mL) and filtered through an acid capture column (SAX) and the filtrate concentrated under reduced pressure. The mixture was then purified by mass directed autopreparative HPLC to afford the desired compound 8-amino-6-fluoro-N-[(4-hydroxycyclohexyl)methyl]-4-oxo-chromene-2-carboxamide (4 mg, 0.01 mmol), 2% yield as an off-white solid. $^1$H NMR (400 MHz, MeOD) δ 7.01 (s, 1H), 6.93 (dd, J=3.0, 8.8 Hz, 1H), 6.87 (dd, J=3.0, 10.3 Hz, 1H), 3.56-3.49 (m, 1H), 3.30 (d, J=6.8 Hz, 2H), 2.02-1.96 (m, 2H), 1.90-1.83 (m, 2H), 1.70-1.61 (m, 1H), 1.33-1.22 (m, 2H), 1.16-1.05 (m, 2H) (amide NH, aniline NH2 and OH not observed); LCMS m/z 335 (M+H)$^+$ Example 99

8-amino-N-(cyclohexylmethyl)-6-fluoro-4-oxo-chromene-2-carboxamide

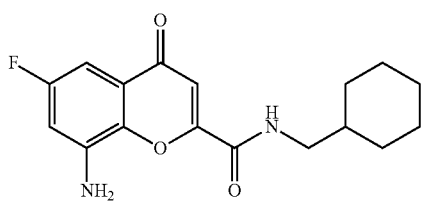 [SMILES: Nc1cc(F)cc2c(=O)cc(C(=O)NCC3CCCCC3)oc12]

To a solution of 8-amino-6-fluoro-4-oxo-4H-chromene-2-carboxylic acid (3.80 g, 15.13 mmol, 1.00 eq) in MeCN (40 mL) was added 3-methylpyridine (4.23 g, 45.39 mmol, 4.41 mL, 3.00 eq), MsCl (1.91 g, 16.64 mmol, 1.29 mL, 1.10 eq) and cyclohexylmethanamine (1.88 g, 16.64 mmol, 2.17 mL, 1.10 eq) at 0° C. The mixture was stirred at 25° C. for 1 hour. The mixture was poured into water (200 mL). The aqueous phase was extracted with ethyl acetate (200 mL×2). The combined organic phase was washed with brine (300 mL×2), dried with anhydrous Na$_2$SO$_4$, filtered and concentrated in vacuum. The residue was purified by prep-HPLC (column: Phenomenex luna C18 250*50 mm*10 um; mobile phase: [water (0.1% TFA)-ACN]; B %; 35ACN %-60ACN %, 29 MIN; 60% min). The fraction was concentrated in vacuo to afford 8-amino-N-(cyclohexylmethyl)-6-fluoro-4-oxo-chromene-2-carboxamide (1.25 g, 3.91 mmol, 26% yield) as yellow solid. $^1$H NMR (400 MHz, DMSO-d6) δ 9.16-9.13 (m, 1H), 6.83-6.74 (m, 3H), 6.56 (s, 2H), 3.19-3.16 (t, J=6.4 Hz, 1H), 1.73-1.21-1.13 (m, 3H), 0.98-0.93 (m, 2H). LCMS m/z 335 (M+H)$^+$.

Example 100

N-(cyclohexylmethyl)-6-fluoro-8-(methanesulfonamido)-4-oxo-chromene-2-carboxamide

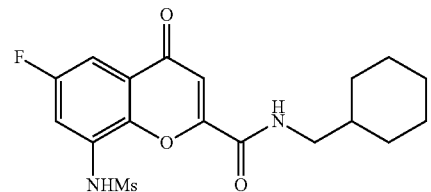

To a solution of 8-amino-N-(cyclohexylmethyl)-6-fluoro-4-oxo-chromene-2-carboxamide (50 mg, 0.1571 mmol) in DCM (1 mL) DMF (0.5 mL), DIPEA (41 mg, 0.3 mmol) was added followed by methanesulfonyl chloride (18 mg, 0.2 mmol) and the reaction mixture stirred under nitrogen at RT overnight. After that time only traces of product were detected by LCMS (basic method) thus one more equivalent of DIPEA (41 mg, 0.3 mmol) and methanesulfonyl chloride (18 mg, 0.2 mmol) were added and the reaction mixture stirred overnight and then the reaction mixture was warmed to 50° C. and stirred for further 4 h. The reaction mixture was quenched with water and extracted with EtOAc, the organic phase was then washed with NH$_4$Cl saturated solution, dried and evaporated to give a crude material that was purified by flash column chromatography eluting with 50% EtOAc in heptane. The desired fraction were concentrated to give a mixture of product and starting material. The mixture was further purified by prep HPLC to give N-(cyclohexylmethyl)-6-fluoro-8-(methanesulfonamido)-4-oxo-chromene-2-carboxamide (15 mg, 0.04 mmol), 23% yield as a yellow solid. $^1$H NMR (400 MHz, DMSO) 9.14 (1H, s), 6.83 (1H, s), 3.20 (2H, dd, J=6.5, 6.5 Hz), 3.04 (3H, s), 1.75-1.64 (6H, m), 1.58 (1H, s), 1.19 (2H, s), 1.01-0.95 (2H, m). LCMS (ESI) m/z 319 (M+H)$^+$ Further Preparatory Compounds Preparatory compound for compounds having R$^1$=OH [5-OH]: Examples 5 and 15: 8-Hydroxy-4-oxo-4H-1-benzopyran-2-carboxylic acid, commercially available from Molbase CAS 53878-47-0. Compound can also be prepared from prep 6 (5-methoxy) by method described in prep 20.

Preparatory compound for compounds having R$^3$=Cl [7-Cl]: Example 9: 7-Chloro-4-oxo-4H-1-benzopyran-2-carboxylic acid. Commercially available from Flurochem (cat no. 329037) CAS 114741-22-9;

Preparatory compound for compounds having R$^4$=Br [8-Br]: Example 11: 8-Bromo-4-oxo-4H-1-benzopyran-2-carboxylic acid, commercially available from Molbase, CAS 328058-02-2;

Preparatory compound for compounds having $R^4$=OH [8-OH]: Example 12: 8-Hydroxy-4-oxo-4H-1-benzopyran-2-carboxylic acid, commercially available from Molbase, CAS 129472-71-5;

Preparatory compound for compounds having $R^2$=CH$_3$ [6-CH$_3$]: Example 28: 6-Methyl-4-oxo-4H-1-benzopyran-2-carboxylic acid, commercially available from Aldrich, CAS 5006-44-0;

Preparatory compound for compounds having $R^2$=Br [6-Br]: Example 29: 6-Bromo-4-oxo-4H-1-benzopyran-2-carboxylic acid, commercially available from Aldrich, CAS 51484-06-1;

Preparatory compound for compounds having $R^2$=F [6-F]: Example 31, 32, 33, 35, 36, 37, 38, 40, 41, 50, 51, 52, 53, 54, 78: 6-Fluoro-4-oxo-4H-1-benzopyran-2-carboxylic acid, commercially available from Aldrich, CAS 99199-59-4;

Preparatory compound for compounds having $R^3$=F [7-F]: Example 42: 7-Fluoro-4-oxo-4H-1-benzopyran-2-carboxylic acid, commercially available from Aldrich, CAS 128942-39-2;

Preparatory compound for compounds having $R^2$=OCH$_3$ [6-OCH$_3$]: Example 49: 7-Methoxy-4-oxo-4H-1-benzopyran-2-carboxylic acid, commercially available from Molbase CAS 86277-98-7;

The preparatory starting carbamide for Examples 38 and 39, tert-butyl 1-(aminomethyl)cyclohexylcarbamate, is commercially available from Aldrich, CAS 864943-63-5;

The preparatory starting amine for Example 50, spiro[3.3]heptan-2-ylmethanamine hydrochloride, is commercially available from Enamine, CAS 1803566-88-2;

The preparatory starting amine for Example 58, 2-(tert-butoxycarbonylamino)ethyl bromide, is commercially available from Aldrich, CAS 39684-80-5;

The preparatory starting amine for Example 59, N-Boc-4-bromomethyl-piperidine, is commercially available from Aldrich, CAS 158407-04-6; and The preparatory starting amine for Example 60, 4-(2-Bromoethyl)-1-piperazinecarboxylic acid, 1,1-dimethyl-ethyl ester, is commercially available from Aldrich, CAS 655225-01-7.

The preparatory starting amine for Example 97, (1-fluorocyclohexyl)methanamine hydrochloride, is commercially available from Flurochem, CAS 1391732-86-7.

The invention claimed is:

1. A compound of formula C-III

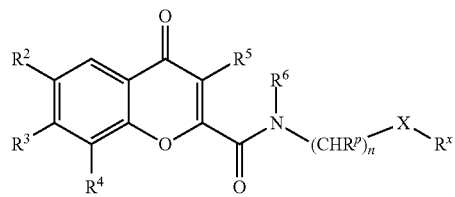

C-III wherein n is 1 or 2;
wherein X is a bond;
wherein $R^x$ is a cyclohexyl substituted by one or more groups independently selected from: OH or F, or wherein $R^x$ is selected from the group consisting of a cyclopentyl, cyclobutyl, tetrahydropyranyl, benzoxazole group, and each of the foregoing groups substituted by one or more groups independently selected from: OH, $CH_3$, or F;
wherein $R^p$ is H or $CH_3$ and wherein when $R^p$ is H, n is 1 or 2, and wherein when $R^p$ is $CH_3$, n is 1;
wherein $R^2$ is H, OH, F, Cl, Br, —$CH_3$, —$CH_2CH_3$, —$OCH_3$, or —CN;
wherein $R^3$ is H, OH, F, Cl, or —O($CH_2$)$_2NH_2$;
wherein $R^4$ is H, F, Br, OH, —$OCH_3$, —C(O)$NH_2$, —$CH_2OH$, —C(O)OH, —$NH_2$, —$NHSO_2CH_3$, —$SO_2NH_2$, or a 1H-tetrazol-5-yl group;
wherein $R^5$ is selected from H or $CH_3$;
wherein R6 is H;
with the proviso that when $R^2=R^3=R^4=R^5=R^6$=H, $R^p$ is not H or $R^x$ is not cyclohexyl;

or a veterinarily or pharmaceutically acceptable salt, hydrate, solvate, optical, geometric or tautomeric isomer, or polymorph thereof.

2. A compound of formula C-II according to claim 1

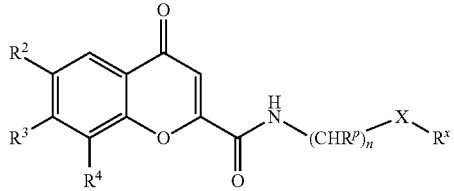

C-II wherein the compounds of formula C-II are compounds of formula C-III wherein $R^5$ and $R^6$ are both H;
wherein n is 1; X is a bond; $R^p$ is H;
wherein $R^2$ is H, OH, F, Cl, Br, —$CH_3$, —$CH_2CH_3$, —$OCH_3$, or —CN;
wherein $R^3$ is H, F, or Cl;
wherein $R^4$ is H, F, OH, —$CH_2OH$, —C(O)OH, —$NH_2$, —$NHSO_2CH_3$, or a 1H-tetrazol-5-yl group;
wherein $R^x$ is a C-linked cyclohexyl substituted by one or more groups independently selected from: OH or F, or a tetrahydropyranyl group, which is optionally substituted with one or more groups independently selected from: OH, or F;

or a veterinarily or pharmaceutically acceptable salt, hydrate, solvate, optical, geometric or tautomeric isomer or polymorph thereof.

3. A compound of formula S-I according to claim 1

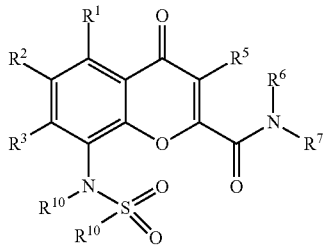

wherein the compounds of formula S-I are compounds of formula I wherein $R^4$ is an —N(HSO$_2$CH$_3$ group; and wherein $R^7$ represents an —X—$R^x$ group wherein X is represented by a —(CH$_2$)$_n$— group wherein n is 1 or 2 or by a —CH(CH$_3$)— group;
or a veterinarily or pharmaceutically acceptable salt, hydrate, solvate, optical, geometric or tautomeric isomer or polymorph thereof.

4. A compound according to claim 1, wherein the compound is Fluoro-8-hydroxy-N-((1-hydroxycyclohexyl) methyl)-4-oxo-4H-chromene-2-carboxamide;
or a veterinarily or pharmaceutically acceptable salt, hydrate, solvate, optical, geometric or tautomeric isomer or polymorph thereof.

5. A compound having the formula N-(cyclohexylmethyl)-7-fluoro-8-hydroxy-4-oxo-4H-chromene-2-carboxamide; or a veterinarily or pharmaceutically acceptable salt, hydrate, solvate, optical, geometric or tautomeric isomer or polymorph thereof.

6. A compound according to claim 1 wherein the compound is 8-fluoro-6-hydroxy-N-((1-hydroxycyclohexyl) methyl)-4-oxo-4H-chromene-2-carboxamide; or a veterinarily or pharmaceutically acceptable salt, hydrate, solvate, optical, geometric or tautomeric isomer or polymorph thereof.

7. A compound according to claim 1 having a pEC$_{50}$ for Pf 3D7 of 6 or more.

8. A compound according to claim 1 having a pIC$_{50}$ for Pf KRS1 of 6.3 or more.

9. A compound according to claim 1 having a pEC$_{50}$ for *Crytosporidium parvum* of 6 or more.

10. A pharmaceutical composition comprising a compound according to claim 1, or a pharmaceutically acceptable salt, solvate, hydrate, optical, geometric or tautomeric isomer or polymorph thereof, together with one or more pharmaceutically acceptable carriers, diluents or excipients.

11. A compound according to claim 1, wherein the compound is (6-Hydroxy-N-[(1-hydroxycyclohexyl)methyl]-4-oxo-chromene-2-carboxamide; or a veterinarily or pharmaceutically acceptable salt, hydrate, solvate, optical, geometric or tautomeric isomer or polymorph thereof.

* * * * *

SEQUENCE LISTING

<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: His Tag

<400> SEQUENCE: 1

Met Gly Ser Ser His His His His His His Gly Ser Ser
1               5                   10

<210> SEQ ID NO 2
<211> LENGTH: 382
<212> TYPE: PRT
<213> ORGANISM: Artificial Sequence
<220> FEATURE:
<223> OTHER INFORMATION: Maltose Binding protein

<400> SEQUENCE: 2

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly

```
                130                 135                 140
Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
                210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
                290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu
                370                 375                 380

<210> SEQ ID NO 3
<211> LENGTH: 9
<212> TYPE: PRT
<213> ORGANISM: Artificial Sequence
<220> FEATURE:
<223> OTHER INFORMATION: TEV Clevage site

<400> SEQUENCE: 3

Gly Glu Asn Leu Tyr Phe Gln Gly His
1               5

<210> SEQ ID NO 4
<211> LENGTH: 508
<212> TYPE: PRT
<213> ORGANISM: Artificial Sequence
<220> FEATURE:
<223> OTHER INFORMATION: Pf KRS1

<400> SEQUENCE: 4

Met Glu Val Asp Pro Arg Leu Tyr Phe Glu Asn Arg Ser Lys Phe Ile
1               5                   10                  15

Gln Asp Gln Lys Asp Lys Gly Ile Asn Pro Tyr Pro His Lys Phe Glu
                20                  25                  30

Arg Thr Ile Ser Ile Pro Glu Phe Ile Glu Lys Tyr Lys Asp Leu Gly
                35                  40                  45
```

```
Asn Gly Glu His Leu Glu Asp Thr Ile Leu Asn Ile Thr Gly Arg Ile
 50                  55                  60
Met Arg Val Ser Ala Ser Gly Gln Lys Leu Arg Phe Phe Asp Leu Val
 65                  70                  75                  80
Gly Asp Gly Glu Lys Ile Gln Val Leu Ala Asn Tyr Ser Phe His Asn
                 85                  90                  95
His Glu Lys Gly Asn Phe Ala Glu Cys Tyr Asp Lys Ile Arg Arg Gly
                100                 105                 110
Asp Ile Val Gly Ile Val Gly Phe Pro Gly Lys Ser Lys Lys Gly Glu
                115                 120                 125
Leu Ser Ile Phe Pro Lys Glu Thr Ile Leu Ser Ala Cys Leu His
    130                 135                 140
Met Leu Pro Met Lys Tyr Gly Leu Lys Asp Thr Glu Ile Arg Tyr Arg
145                 150                 155                 160
Gln Arg Tyr Leu Asp Leu Leu Ile Asn Glu Ser Ser Arg His Thr Phe
                165                 170                 175
Val Thr Arg Thr Lys Ile Ile Asn Phe Leu Arg Asn Phe Leu Asn Glu
                180                 185                 190
Arg Gly Phe Phe Glu Val Glu Thr Pro Met Met Asn Leu Ile Ala Gly
                195                 200                 205
Gly Ala Asn Ala Arg Pro Phe Ile Thr His His Asn Asp Leu Asp Leu
    210                 215                 220
Asp Leu Tyr Leu Arg Ile Ala Thr Glu Leu Pro Leu Lys Met Leu Ile
225                 230                 235                 240
Val Gly Gly Ile Asp Lys Val Tyr Glu Ile Gly Lys Val Phe Arg Asn
                245                 250                 255
Glu Gly Ile Asp Asn Thr His Asn Pro Glu Phe Thr Ser Cys Glu Phe
                260                 265                 270
Tyr Trp Ala Tyr Ala Asp Tyr Asn Asp Leu Ile Lys Trp Ser Glu Asp
                275                 280                 285
Phe Phe Ser Gln Leu Val Tyr His Leu Phe Gly Thr Tyr Lys Ile Ser
                290                 295                 300
Tyr Asn Lys Asp Gly Pro Glu Asn Gln Pro Ile Glu Ile Asp Phe Thr
305                 310                 315                 320
Pro Pro Tyr Pro Lys Val Ser Ile Val Glu Glu Ile Glu Lys Val Thr
                325                 330                 335
Asn Thr Ile Leu Glu Gln Pro Phe Asp Ser Asn Glu Thr Ile Glu Lys
                340                 345                 350
Met Ile Asn Ile Ile Lys Glu His Lys Ile Glu Leu Pro Asn Pro Pro
    355                 360                 365
Thr Ala Ala Lys Leu Leu Asp Gln Leu Ala Ser His Phe Ile Glu Asn
    370                 375                 380
Lys Tyr Asn Asp Lys Pro Phe Phe Ile Val Glu His Pro Gln Ile Met
385                 390                 395                 400
Ser Pro Leu Ala Lys Tyr His Arg Thr Lys Pro Gly Leu Thr Glu Arg
                405                 410                 415
Leu Glu Met Phe Ile Cys Gly Lys Glu Val Leu Asn Ala Tyr Thr Glu
                420                 425                 430
Leu Asn Asp Pro Phe Lys Gln Lys Glu Cys Phe Lys Leu Gln Gln Lys
                435                 440                 445
Asp Arg Glu Lys Gly Asp Thr Glu Ala Ala Gln Leu Asp Ser Ala Phe
    450                 455                 460
Cys Thr Ser Leu Glu Tyr Gly Leu Pro Pro Thr Gly Gly Leu Gly Leu
```

-continued

```
                465                 470                 475                 480
            Gly Ile Asp Arg Ile Thr Met Phe Leu Thr Asn Lys Asn Ser Ile Lys
                                485                 490                 495

Asp Val Ile Leu Phe Pro Thr Met Arg Pro Ala Asn
                            500                 505

<210> SEQ ID NO 5
<211> LENGTH: 505
<212> TYPE: PRT
<213> ORGANISM: Artificial Sequence
<220> FEATURE:
<223> OTHER INFORMATION: MtbKRS1

<400> SEQUENCE: 5

Met Ser Ala Ala Asp Thr Ala Glu Asp Leu Pro Glu Gln Phe Arg Ile
1               5                   10                  15

Arg Arg Asp Lys Arg Ala Arg Leu Leu Ala Gln Gly Arg Asp Pro Tyr
                20                  25                  30

Pro Val Ala Val Pro Arg Thr His Thr Leu Ala Glu Val Arg Ala Ala
            35                  40                  45

His Pro Asp Leu Pro Ile Asp Thr Ala Thr Glu Asp Ile Val Gly Val
        50                  55                  60

Ala Gly Arg Val Ile Phe Ala Arg Asn Ser Gly Lys Leu Cys Phe Ala
65                  70                  75                  80

Thr Leu Gln Asp Gly Asp Gly Thr Gln Leu Gln Val Met Ile Ser Leu
                85                  90                  95

Asp Lys Val Gly Gln Ala Ala Leu Asp Ala Trp Lys Ala Asp Val Asp
            100                 105                 110

Leu Gly Asp Ile Val Tyr Val His Gly Ala Val Ile Ser Ser Arg Arg
        115                 120                 125

Gly Glu Leu Ser Val Leu Ala Asp Cys Trp Arg Ile Ala Ala Lys Ser
130                 135                 140

Leu Arg Pro Leu Pro Val Ala His Lys Glu Met Ser Glu Glu Ser Arg
145                 150                 155                 160

Val Arg Gln Arg Tyr Val Asp Leu Ile Val Arg Pro Glu Ala Arg Ala
                165                 170                 175

Val Ala Arg Leu Arg Ile Ala Val Val Arg Ala Ile Arg Thr Ala Leu
            180                 185                 190

Gln Arg Arg Gly Phe Leu Glu Val Glu Thr Pro Val Leu Gln Thr Leu
        195                 200                 205

Ala Gly Gly Ala Ala Ala Arg Pro Phe Ala Thr His Ser Asn Ala Leu
    210                 215                 220

Asp Ile Asp Leu Tyr Leu Arg Ile Ala Pro Glu Leu Phe Leu Lys Arg
225                 230                 235                 240

Cys Ile Val Gly Gly Phe Asp Lys Val Phe Glu Leu Asn Arg Val Phe
                245                 250                 255

Arg Asn Glu Gly Ala Asp Ser Thr His Ser Pro Glu Phe Ser Met Leu
            260                 265                 270

Glu Thr Tyr Gln Thr Tyr Gly Thr Tyr Asp Asp Ser Ala Val Val Thr
        275                 280                 285

Arg Glu Leu Ile Gln Glu Val Ala Asp Glu Ala Ile Gly Thr Arg Gln
    290                 295                 300

Leu Pro Leu Pro Asp Gly Ser Val Tyr Asp Ile Asp Gly Glu Trp Ala
305                 310                 315                 320

Thr Ile Gln Met Tyr Pro Ser Leu Ser Val Ala Leu Gly Glu Glu Ile
```

|  | 325 |  |  |  | 330 |  |  |  |  | 335 |  |
|---|---|---|---|---|---|---|---|---|---|---|---|
| Thr | Pro | Gln | Thr | Thr | Val | Asp | Arg | Leu | Arg | Gly | Ile | Ala | Asp | Ser | Leu |
|  |  |  | 340 |  |  |  |  | 345 |  |  |  |  | 350 |  |  |
| Gly | Leu | Glu | Lys | Asp | Pro | Ala | Ile | His | Asp | Asn | Arg | Gly | Phe | Gly | His |
|  |  | 355 |  |  |  |  | 360 |  |  |  |  | 365 |  |  |  |
| Gly | Lys | Leu | Ile | Glu | Glu | Leu | Trp | Glu | Arg | Thr | Val | Gly | Lys | Ser | Leu |
|  | 370 |  |  |  |  | 375 |  |  |  |  | 380 |  |  |  |  |
| Ser | Ala | Pro | Thr | Phe | Val | Lys | Asp | Phe | Pro | Val | Gln | Thr | Thr | Pro | Leu |
| 385 |  |  |  |  | 390 |  |  |  |  | 395 |  |  |  |  | 400 |
| Thr | Arg | Gln | His | Arg | Ser | Ile | Pro | Gly | Val | Thr | Glu | Lys | Trp | Asp | Leu |
|  |  |  |  | 405 |  |  |  |  | 410 |  |  |  |  | 415 |  |
| Tyr | Leu | Arg | Gly | Ile | Glu | Leu | Ala | Thr | Gly | Tyr | Ser | Glu | Leu | Ser | Asp |
|  |  |  | 420 |  |  |  |  | 425 |  |  |  |  | 430 |  |  |
| Pro | Val | Val | Gln | Arg | Glu | Arg | Phe | Ala | Asp | Gln | Ala | Arg | Ala | Ala | Ala |
|  |  | 435 |  |  |  |  | 440 |  |  |  |  | 445 |  |  |  |
| Ala | Gly | Asp | Asp | Glu | Ala | Met | Val | Leu | Asp | Glu | Asp | Phe | Leu | Ala | Ala |
| 450 |  |  |  |  | 455 |  |  |  |  | 460 |  |  |  |  |  |
| Leu | Glu | Tyr | Gly | Met | Pro | Pro | Cys | Thr | Gly | Thr | Gly | Met | Gly | Ile | Asp |
| 465 |  |  |  |  | 470 |  |  |  |  | 475 |  |  |  |  | 480 |
| Arg | Leu | Leu | Met | Ser | Leu | Thr | Gly | Leu | Ser | Ile | Arg | Glu | Thr | Val | Leu |
|  |  |  |  | 485 |  |  |  |  | 490 |  |  |  |  | 495 |  |
| Phe | Pro | Ile | Val | Arg | Pro | His | Ser | Asn |  |  |  |  |  |  |  |
|  |  |  | 500 |  |  |  |  | 505 |  |  |  |  |  |  |  |